(12) United States Patent
Nagarathnam et al.

(10) Patent No.: US 9,181,214 B2
(45) Date of Patent: Nov. 10, 2015

(54) BICYCLIC COMPOUNDS AS MODULATORS OF GPR-119

(75) Inventors: Dhanapalan Nagarathnam, La Chaux-de-Fonds (CH); Swaroop Kumar V. S. Vakkalanka, La Chaux-de-Fonds (CH); Srikant Viswanadha, Hyderabad (IN); Gayatri S. Merikapudi, Hyderabad (IN)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 13/492,309

(22) Filed: Jun. 8, 2012

(65) Prior Publication Data

US 2013/0045986 A1   Feb. 21, 2013

Related U.S. Application Data

(60) Provisional application No. 61/543,152, filed on Oct. 4, 2011, provisional application No. 61/543,157, filed on Oct. 4, 2011.

(30) Foreign Application Priority Data

| Jun. 9, 2011 | (IN) | ............................ 1958/CHE/2011 |
| Jul. 11, 2011 | (IN) | ............................ 2352/CHE/2011 |
| Oct. 7, 2011 | (IN) | ............................ 3462/CHE2011 |
| Oct. 7, 2011 | (IN) | ............................ 3463/CHE/2011 |
| Jan. 9, 2012 | (IN) | ................................ 82/CHE/2012 |

(51) Int. Cl.
| A61K 31/454 | (2006.01) |
| A61K 31/506 | (2006.01) |
| C07D 401/04 | (2006.01) |
| C07D 401/14 | (2006.01) |
| C07D 405/04 | (2006.01) |
| C07D 413/04 | (2006.01) |
| C07D 413/14 | (2006.01) |
| C07D 417/04 | (2006.01) |
| C07D 417/14 | (2006.01) |
| C07D 498/04 | (2006.01) |

(52) U.S. Cl.
CPC ............ *C07D 401/04* (2013.01); *C07D 401/14* (2013.01); *C07D 405/04* (2013.01); *C07D 413/04* (2013.01); *C07D 413/14* (2013.01); *C07D 417/04* (2013.01); *C07D 417/14* (2013.01); *C07D 498/04* (2013.01)

(58) Field of Classification Search
CPC ......................... A61K 31/454; A61K 31/506
USPC ........................................... 546/198; 514/321
See application file for complete search history.

(56) References Cited

U.S. PATENT DOCUMENTS

| 2006/0235037 A1* | 10/2006 | Purandare et al. ............ 514/278 |
| 2009/0143353 A1 | 6/2009 | Kawakami et al. |
| 2011/0065706 A1 | 3/2011 | Birch et al. |

FOREIGN PATENT DOCUMENTS

| EP | 2404902 A1 | | 1/2012 |
| WO | WO 2007-061458 | * | 5/2007 |
| WO | WO-2008008895 A1 | | 1/2008 |
| WO | WO-2008137436 A1 | | 11/2008 |
| WO | WO 2011/075634 | * | 6/2011 |
| WO | WO-2011075634 A1 | | 6/2011 |

OTHER PUBLICATIONS

Wan et al Bioorganic and Medicinal Chemistry Letters 2009, 19, 5063-5066.*
U.S. Pat. No. 6,376,506—abstract Broka et al 2002.*
Semple, et al., Discovery of Fused Bicycic Agonists of the Orphan G-protein Coupled Receptor GPR119 with in vivo Activity in Rodent Models of Glucose Control, Bioorganic and Medicinal Chemistry Letters, Mar. 13, 2011, 21:13:3134-3141.
Wan, et al., Benzo[d]imidazole Inhibitors of Coactivator Associated Arginine Methyltransferase 1 (CARM1) hit to Lead Studies, Bioorganic and Medicinal Chemistry Letters, Jul. 10, 2009, 19:5063-5066.
International Search Report issued in PCT/US2012/041632 on Aug. 22, 2012.

* cited by examiner

*Primary Examiner* — John Mabry
(74) *Attorney, Agent, or Firm* — Blank Rome LLP

(57) ABSTRACT

The present invention relates to novel compounds of formula (A) and (B) as modulators of GPR-119, methods of preparing them, pharmaceutical compositions containing them and methods of treatment, prevention and/or amelioration of GPR-119 mediated diseases or disorders with them.

33 Claims, 2 Drawing Sheets

BICYCLIC COMPOUNDS AS MODULATORS OF GPR-119

This application claims the benefit of Indian Provisional Patent Application Nos. 1958/CHE/2011 dated 9 Jun. 2011, 2352/CHE/2011 dated 11 Jul. 2011, 3462/CHE/2011 dated 7 Oct. 2011, 3463/CHE/2011 dated 7 Oct. 2011, 82/CHE/2012 dated 9 Jan. 2012, and U.S. Provisional Patent Application Nos. 61/543,152 dated 4 Oct. 2011 and 61/543,157 dated 4 Oct. 2011, each of which is hereby incorporated by reference.

FIELD OF THE INVENTION

The present invention relates to novel compounds of formula (A) and (B) as modulators of GPR-119, methods of preparing them, pharmaceutical compositions containing them and methods of treatment, prevention and/or amelioration of GPR-119 mediated diseases or disorders with them.

BACKGROUND OF THE INVENTION

Metabolic disorders in general and in particular, obesity and diabetes are the most common human health problems in the developed world. Its estimated that in developed countries around a third of the population is at least 20% overweight. In the United States, the percentage of obese people has increased from 25% at the end of the 1970's, to 33% at the beginning the 1990's. Obesity is one of the most important risk factors for NIDDM (noninsulin-dependent diabetes mellitus) which is the result of an imbalance between caloric intake and energy expenditure, and is highly correlated with insulin resistance and diabetes in experimental animals and humans.

Obesity is a medical condition in which excess body fat has accumulated to the extent that it may have an adverse effect on health, leading to reduced life expectancy and/or increased health problems. Body mass index (BMI), a measurement which compares weight and height, defines people as overweight (pre-obese) if their BMI is between 25 and 30 kg/m$^2$, and obese when it is greater than 30 kg/m$^2$. (see Haslam D W, James W P (2005), "Obesity", *Lancet* 366 (9492): 1197-209; World Health Organization—Obesity pg 6 & 9, 2000). Obesity increases the likelihood of various diseases, particularly heart disease, type 2 diabetes, breathing difficulties during sleep, certain types of cancer, and osteoarthritis. Obesity is most commonly caused by a combination of excessive food energy intake, lack of physical activity, and genetic susceptibility, although a few cases are caused primarily by genes, endocrine disorders, medications or psychiatric illness. Evidence to support the view that some obese people eat little yet gain weight due to a slow metabolism is limited; on average obese people have a greater energy expenditure than their thin counterparts due to the energy required to maintain an increased body mass. (http://en.wikipedia.org/wiki/Obesity)

Dieting and physical exercise are the mainstays of treatment for obesity. Moreover, it is important to improve diet quality by reducing the consumption of energy-dense foods such as those high in fat and sugars, and by increasing the intake of dietary fiber. To supplement this, or in case of failure, anti-obesity drugs may be taken to reduce appetite or inhibit fat absorption. In severe cases, surgery is performed or an intragastric balloon is placed to reduce stomach volume and/or bowel length, leading to earlier satiation and reduced ability to absorb nutrients from food.

Obesity is a leading preventable cause of death worldwide, with increasing prevalence in adults and children, and authorities view it as one of the most serious public health problems of the 21st century (see Barness L A et. al., "Obesity: genetic, molecular, and environmental aspects". Am. J. Med. Genet. A 143A (24): 3016-34, 2007). Obesity is stigmatized in much of the modern world (particularly in the Western world), though it was widely perceived as a symbol of wealth and fertility at other times in history, the low- and middle income people suffer from obesity.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight.

Diabetes is one of the major causes of premature illness and death worldwide. Developing countries are on the radar with huge population especially the low- and middle income people being suffering from the said disease. The reason being, lack of sufficient diagnosis and treatment, being made available to the patients. This is reflected from the number of deaths attributable to diabetes in 2010 which shows a 5.5% increase over the estimates for the year 2007. Although 80% of type 2 diabetes is preventable by changing diet, increasing physical activity and improving the living environment. Yet, without effective prevention and control programmes, the incidence of diabetes is likely to continue rising globally.

Currently it's estimated that 285 million people, corresponding to 6.4% of the worlds adult population, is living with diabetes. The number is expected to grow to 438 million by 2030, corresponding to 7.8% of the adult population. The largest age group currently affected by diabetes is between 40-59 years. By 2030 this "record" is expected to move to the 60-79 age groups with some 196 million cases. With an estimated 50.8 million people living with diabetes, India has the world's largest diabetes population, followed by China with 43.2 million. Unless addressed, the mortality and disease burden from diabetes and other NCDs will continue to increase. WHO projects that globally, deaths caused by these health problems will increase by 17% over the next decade, with the greatest increase in low- and middle-income countries, mainly in the African (27%) and Eastern Mediterranean (25%) regions. (see: IDF, Diabetes Atlas, 4th edition)

Diabetes is a chronic disease that occurs when the pancreas does not produce enough insulin, or when the body cannot effectively use the insulin it produces. Hyperglycemia, or raised blood sugar, is a common effect of uncontrolled diabetes and over time leads to serious damage to many of the body's systems. It implicated in the development of kidney disease, eye diseases and nervous system problems. Diabetes causes about 5% of all deaths globally each year and is likely to increase by >50% in the next 10 years. Thus the pharmaceutical industry has been on a quest to characterize more promising molecular targets to satisfy stringent new criteria for anti-hyperglycaemic agents.

Type 1 diabetes, also known as insulin-dependent diabetes mellitus (IDDM), is caused by the autoimmune destruction of the insulin producing pancreatic beta-cells, and requires regular administration of exogenous insulin. Type 1 diabetes usually starts in childhood or young adulthood manifesting sudden symptoms of high blood sugar (hyperglycemia).

Type 2 diabetes, also known as non-insulin-dependent diabetes mellitus (NIDDM), manifests with an inability to adequately regulate blood-glucose levels. NIDDM may be characterized by a defect in insulin secretion or by insulin resistance. NIDDM is a genetically heterogeneous disease caused by various reasons such as genetic susceptibility to other environmental factors contributing to NIDDM, such as obesity, sedentary lifestyle, smoking, and certain drugs. NIDDM is a chronic disease resulting from defects in both insulin secretion and sensitivity. In NIDDM patients, the gradual loss of pancreatic β-cell function is a characteristic feature of disease progression that is associated with sustained hyperglycemia and poor outcome. Strategies for promoting normoglycemia have focused on enhancing glucose stimulated insulin secretion (GSIS) through the targeting of G protein-coupled receptors (GPCRs), such as the glucagon-like peptide1 (GLP-1) receptor, which have been shown to mediate this effect. In clinical therapy for NIDDM, metformin, α-glucosidase inhibitors, thiazolidines (TZDs), and sulfonylurea (SU) derivatives (SUs) are widely used as hypoglycaemic agents; however, the side effects of these compounds include hypoglycaemic episodes, weight-gain, gastrointestinal problems, and loss of therapy responsiveness.

Along with GLP-1 receptor as a major targets for the treatment of diabetes, GPR119 agonists have also been recognised as a major targets for the treatment of diabetes was discussed recently at the American Chemical Society 239$^{th}$ National Meeting (2010, San Francisco).

Further glucagon-like peptide 1 receptor agonists have shown promising therapeutic benefit over the existing therapy by way of body weight loss in type 2 diabetics, however these being injectables (Exenatide, marketed as Byetta) lack patient compliance there by limiting their usage. Other glucagon-like peptide 1 receptor agonists such as Liraglutide (Victoza), Albiglutide and Taspoglutide are also injectables.

GPR119 agonists have potential to achieve blood glucose control together with body weight loss in type 2 diabetics, similar to that of glucagon-like peptide 1 receptor agonists by way of oral route. Accordingly, oral GPR119 agonist would prove to a preferred choice of drug therapy for diabetics.

GPR119, a class-A (rhodopsin-like) G protein-coupled receptor, expressed primarily in the human pancreas and gastrointestinal tract, has attracted considerable interest as a drug target for NIDDM. The activation of GPR119 increases the intracellular accumulation of cAMP, leading to enhanced glucose-dependent insulin secretion and increased levels of the incretion hormones GLP-1 (glucagon-like peptide 1) and GIP (glucose-dependent insulinotropic peptide). (Overton H A et al. Cell Metab, 2006, 3, 167-175). In rodent models, orally available GPR119-specific agonists have been shown to attenuate blood glucose levels with a simultaneous body weight loss. (Shah U. see Curr Opin Drug Discov Devel. 2009 July; 12(4):519-32.).

In various animal models of type 2 diabetes and obesity, orally available, potent, selective, synthetic GPR119 agonists: i) lowers blood glucose without hypoglycaemia; ii) slow diabetes progression; and iii) reduce food intake and body weight.

GPR119 was first described by Fredriksson et al. (see Fredriksson R, et. al. *FEBS Lett.* 2003; 554:381-388) as a class 1 (rhodopsin-type) orphan G-protein-coupled receptor having no close primary sequence relative in the human genome. Independently, GPR119 has been studied and described in the literature under various synonyms including SNORF25 (see: Bonini et al., U.S. Pat. No. 6,221,660, U.S. Pat. No. 6,468, 756), RUP3 (Jones et al., WO 2004/065380.), GPCR2 (Takeda et al., *FEBS Lett.* 2002; 520:97-101 2002), 19AJ (see Davey et. al., Expert Opin Ther Targets. 2004; 8:165-170.2004), OSGPR116 (see. U.S. Pat. No. 7,083,933) and glucose-dependent insulinotropic receptor (Chu et al., Keystone Symposium. Diabetes: Molecular Genetics, Signalling Pathways and Integrated Physiology, Keystone, Colo., USA, 14-19 Jan. 2007, abstract 117 and abstract 230).

Early signs of GPR119 as an attractive target were established by the teachings of Hilary Overton and colleagues from (OSI) Prosidion, who found that the naturally occurring lipid-signalling agent oleoylethanolamide, was capable of reducing the food intake and weight gain in rats, and can exert its effects through the G protein-coupled receptor (GPCR) GPR119. Found predominantly in the pancreas and digestive tract in humans and mice, as well as in the rodent brain, the mysterious/unknown function of GPR119 was solved.

The demonstration that GPR119 agonists stimulate the release of GLP-1 lends further credence to these agents having an effect on body weight, since GLP-1 is known to cause gastric deceleration and increase satiety, phenomena that lead to reduced caloric intake and weight loss in both animal models and human subjects (Meier et al., Eur J Pharmacol.; 440:269-279, 2002; Zander et al., 2002; Lancet.; 359:824-830. 2002 and Nielsen L L Drug Discov Today. 10, 703-710, 2005). Possibly as a result of their effects on GLP-1 secretion, selective small-molecule GPR119 agonists inhibit gastric emptying and suppress food intake upon acute dosing to rats, with no indication of drug-induced malaise or conditioned taste aversion (Fyfe et al., *Diabetes.* 55 Suppl 1:346-P, 2006; Diabetes; 56 Suppl 1:532-P, 2007; Overton et. al., Cell Metab. 3, 167-175, 2006). The hypophagic actions of GPR119 agonists lead to reduced weight gain, fat pad masses and plasma leptin/triglyceride levels when administered sub-chronically in rodent models of obesity (Fyfe et al., *Diabetes.* 55 Suppl 1:346-P, 2006; Diabetes; 56 Suppl 1:532-P, 2007; Overton et. al., Cell Metab. 3, 167-175, 2006). The testing of potent, selective agonists for food intake and body weight effects in GPR119-deficient mouse models has not been reported so far.

There are suggesting evidence about the isoforms of GPR119 been identified in a number of mammalian species, including rats, mice, hamsters, chimpanzees, rhesus monkeys, cattle and dogs. For example see. Fredriksson et al. FEBS Lett.; 554:381-388, 2003; U.S. Pat. No. 6,221,660; U.S. Pat. No. 6,468,756 and EP 1338651-A1.

GPR 119 is thus an attractive target from a clinical perspective mainly because of GPR119 agonists are capable of lowering blood glucose without hypoglycaemia; slowing of diabetes progression; and most importantly helping in reduction of food intake and body weight.

More recently Unmesh shah et. al., in Chapter-16 Vitamins & Harmones, Volume 84, pg 415-448 (2010), and Chapter-7. Annual reports in Med Chem 44 pg 149-170 (2009) have provided additional insight about GRP119

Patent literature belonging to some of these applicants include the following patents and/or patent applications: WO2011005929A1, WO2009126245A1, WO2008005576A1, WO2008005569A2, WO2007120702A2, WO2007120689A2, WO2007035355A2, WO06127595A1, WO06083491A2, WO06076455A2, WO2006 076243A1, WO05121121A2, WO05007658A2, WO05007647A1, WO04076413A2, WO2004065380; WO2010009183A1, WO2009012277A1, WO2008137436A1, WO2008 137435A1; WO2011041154A1, WO2010008739A2, WO2009014910A2, WO2009 123992A1, WO2008083238A2; WO2010103335A1, WO2010103334A1, WO2010 103333A1, WO2010004348A1, WO2010004347A1, WO2010001166A1, WO2009 050523A1, WO2009050522A1, WO2009034388A1, WO2008081208A1, WO2008081207 A1, WO2008081206A1, WO2008081205A1, WO2008081204A1, WO2007116230A1, WO2007116229A1, WO2007003964A1, WO2007003962A2, WO2007003961A2, WO2007003960A1, WO05061489A1; WO2011061679A1, WO2011036576A1, WO2010 140092A1, WO2010128425A1, WO2010128414A1, WO2010106457A2; WO2011 062889A1, WO2011 062885A1, WO2011053688A1, WO2010114958A1, WO2010 114957A1, WO2010 075273A1, WO2010075271A1, WO2010075269A1, WO2010 009208A1, WO2010 009207A1, WO20100009195A1, WO2009143049A1, WO2009 055331A2, WO2008 130615A1, WO2008130584A1, WO2008130581A1, WO2008033465A1, WO2008 033464A2, WO2008033460A2, WO2008033456A1, WO2008033431A1, WO2011030139A1, WO2011019538A1, WO2011014520A2, WO2011008663A1, WO2011044001A1, WO2011055770A1, WO2011066137A1, WO2011078306A1, WO2011093501A1, WO2011127051A1, WO2011127106A1, WO2011128394A1, WO2011128395A1, WO2011138427A2, WO2011140160A1, WO2011140161A1, WO2011147951A1, WO2011159657A1, WO2011146335A1, WO2011145718A1, WO2011148922A1, WO2012006955A1, WO2012011707A2, WO2012025811A1, WO2012037393A1, WO2012040279A1, WO2012046249A1, WO2012045363A1, WO2012066077A1, WO2012069948A1, WO2012069917A1.

Further review and literature disclosure on GPR119 molecules have been given by Sempl, G et al., (See; Bio org. Med. Chem. Lett. (2011), doi: 10.1016/j. bmcl. 2011.03.007), Szewczyk, J. W. Et al., (See; Bio org. Med. Chem. Lett. (2011), doi:10.1016/j.bmcl. 2010.12.086), Vincent Mascitti et al., (See; Bioorganic & Medicinal Chemistry Letters 21 (2011) 1306-1309), Shigeru Yoshida et al., (See; Biochemical and Biophysical Research Communications 400 (2010) 745-751), Yulin Wu et. al., (See; Bioorganic & Medicinal Chemistry Letters 20 (2010) 2577-2581), Chu et al., (See; Endocrinology 2008 149:2038-2047), Y Ning et al., (see; British Journal of Pharmacology (2008) 155, 1056-1065), H A Overton et al., (See; British Journal of Pharmacology (2008)153, S76-S81), Carolyn Root et al., (See; Journal of Lipid Research, Volume 43, 2002, Pg 1320-1330). All of these patents and/or patent applications and literature disclosures are incorporated herein as reference in their entirety for all purposes.

Despite the advances made in the treatment of metabolic disorders and in particular in the treatment of diabetes and obesity, challenges remain in terms of the complexities of the diseases involved, and most importantly the safety concerns expected from any treatment. Accordingly, there is a need in the art for additional GPR 119 modulators with improved efficacy and safety profiles. The compounds, compositions, and pharmaceutical methods provided herein are aimed at meeting these needs.

SUMMARY OF THE INVENTION

The present invention relates to novel compounds useful as GPR-119 modulators and in particular GPR-119 agonists.

In one embodiment, the compound of the present invention has the formula (A) and (B)

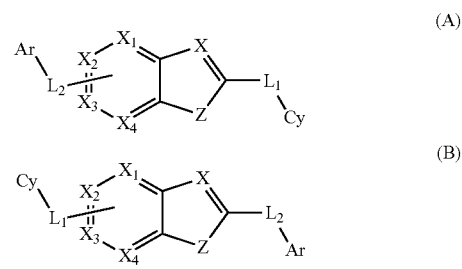

or a tautomer, stereoisomer, enantiomer, diastereomer, salt (e.g., pharmaceutically acceptable salt), prodrug (e.g., ester), or N-oxide thereof, wherein Ar is selected from substituted or unsubstituted aryl, substituted or unsubstituted heteroaryl or $Cy^1$;

$L_1$ is absent or is selected from $NR^a$, O, $S(O)_q$ or $CR^aR^b$;

$L_2$ is absent or is selected from $NR^a$, O, $S(O)_q$ or $CR^aR^b$;

$X^1$ is $CR^1$ or N; $X^2$ is $CR^2$ or N; $X^3$ is $CR^3$ or N and $X^4$ is $CR^4$ or N;

X is CR or N;

Z is NR, CO, O or $S(O)_q$;

Cy is selected from substituted or unsubstituted cycloalkyl or substituted or unsubstituted heterocyclic group;

$Cy^1$ is selected from substituted or unsubstituted cycloalkyl or substituted or unsubstituted heterocyclic group;

each occurrence of R, $R^1$, $R^2$, $R^3$ and $R^4$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, —$OR^a$, —$S(=O)_q$—$R^a$, —$NR^aR^b$, —$C(=Y)$—$R^a$, —$CR^aR^b$—C(=Y)—$R^a$, —$CR^aR^b$—Y—$CR^aR^b$-, —C(=Y)—$NR^aR^b$-, —$NR^aR^b$—C(=Y)—$NR^aR^b$-, —$S(=O)_q$—$NR^aR^b$-, —$NR^aR^b$—S(=O)_q—$NR^aR^b$-, —$NR^aR^b$—$NR^aR^b$—;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclcyalkyl, substituted or unsubstituted aryl, substituted or unsubstituted arylalkyl, substituted or unsubstituted heteroaryl, substituted or unsubstituted heteroarylalkyl, and —ONO$_2$;

each occurrence of Y is independently selected from O, S, and NR$^a$; and each occurrence of q independently represents 0, 1 or 2.

Another embodiment is a compound of the formula (A-I), (A-II), (A-III), (A-IV), (B-I), (B-II), (B-III) or (B-IV):

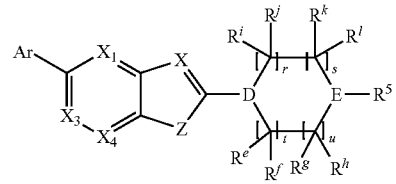
(A-I)

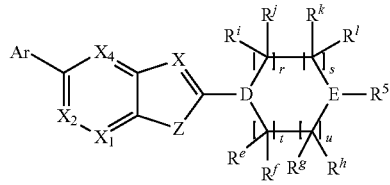
(A-II)

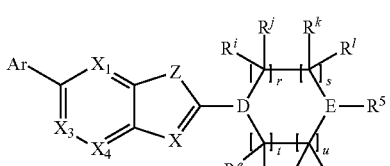
(A-III)

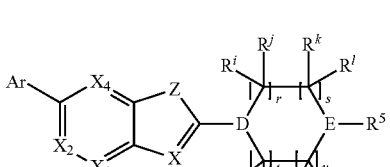
(A-IV)

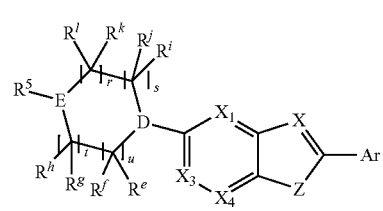
(B-I)

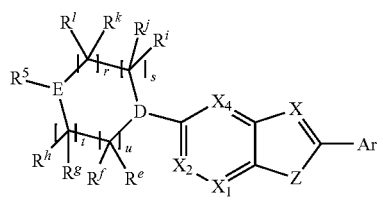
(B-II)

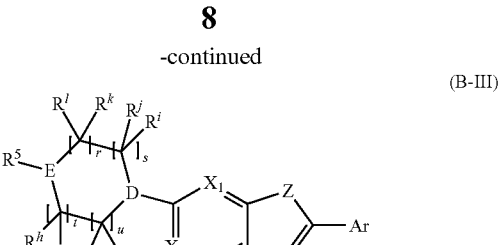
(B-III)

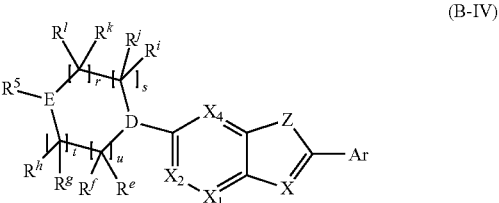
(B-IV)

or a tautomer, stereoisomer, enantiomer, diastereomer, salt (e.g., pharmaceutically acceptable salt), prodrug (e.g., ester), or N-oxide thereof, wherein Z is NR, CO, O or S(O)$_q$; wherein R and q is as defined above for compound of formula (A) or (B);

D and E are independently selected from CH or N;

R$^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, —(=N—N(R$^a$)R$^b$), —NR$^a$C(O)OR$^b$, —NR$^a$C(O)R$^b$-, —NR$^a$C(S)R$^b$—NR$^a$C(S)NR$^a$R$^b$, —SONR$^a$R$^b$-, —SO$_2$NR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$—SO$_2$R$^a$, and —ONO$_2$, wherein R$^a$ and R$^b$ are as defined in formula (A) or (B);

each occurrence of R$^e$, R$^f$, R$^g$, R$^h$, R$^i$, R$^j$, R$^k$ and R$^l$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl; or any two of R$^e$, R$^f$, R$^g$, R$^h$, R$^i$, R$^j$, R$^k$, R$^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl);

each of r, s, t and u is 0, 1 or 2 with the proviso that r+s+t+u≠0; and and all the other variables are the same as described above for the compound of formula (A) and (B), with the proviso 1. that for compound of formula (A-III), wherein Z is O or S and X$_4$ is N or CR$^4$ then Ar cannot be

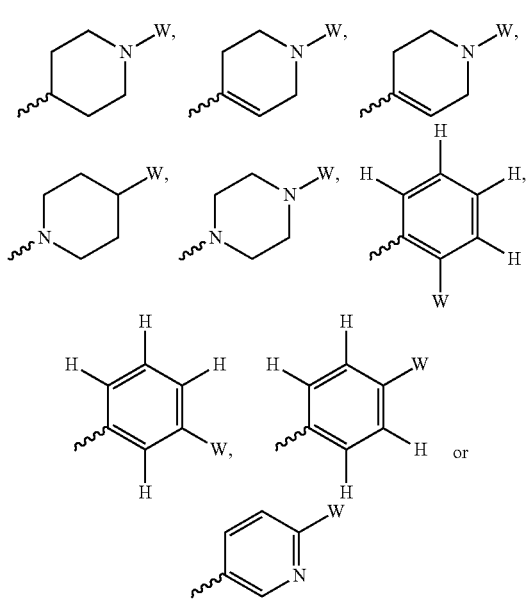

2. that for compound of formula (A-IV) wherein Z is O or S and X₁ is N or CR¹ then Ar cannot be

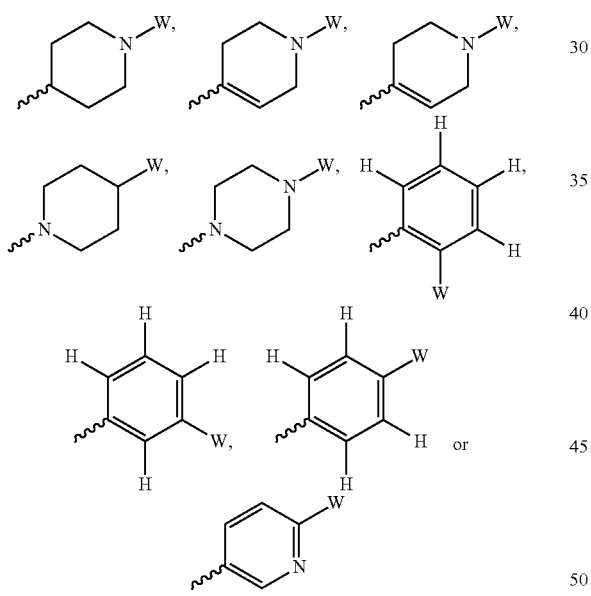

wherein
R¹ and R⁴ is as defined above for compound of formula (A)
W is $S(=O)_2-R_1$, $S(=O)_2-NR_{1a}R_1$, $-C(=O)-R_1$, $-C(=O)-O-R_1$, $-C(=O)-NR_{1a}R_1$, $-NR_{1a}-S(=O)_2-R_1$, halo, or a 4 to 10-membered optionally substituted heteroaryl, which contains 1-4 heteroatoms selected from N, O, and S;
$R_{1a}$, at each occurrence, is independently hydrogen or ($C_1$-$C_8$)alkyl; and
$R_1$ is optionally substituted ($C_1$-$C_6$)-alkyl, optionally substituted ($C_2$-$C_6$)-alkenyl, optionally substituted ($C_2$-$C_6$)-alkynyl, optionally substituted ($C_3$-$C_{12}$)-cycloalkyl, optionally substituted ($C_6$-$C_{10}$)aryl, a 4 to 10-membered optionally substituted heteroaryl, which contains 1-4 heteroatoms selected from N, O, and S; or a 4- to 10-membered heterocyclyl, which contains 1-4 heteroatoms selected from N, O, and S.

Further preferred is a compound of formula (A), (A-I), (A-II), (A-III), (A-IV), (B), (B-I), (B-II), (B-III) or (B-IV) wherein Ar is selected from

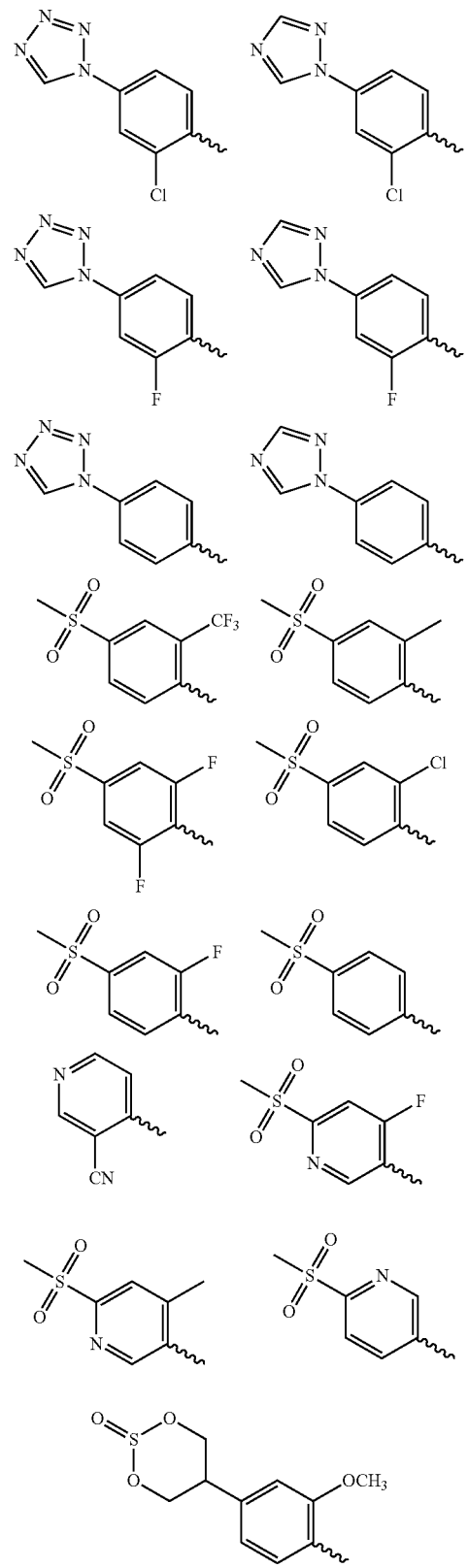

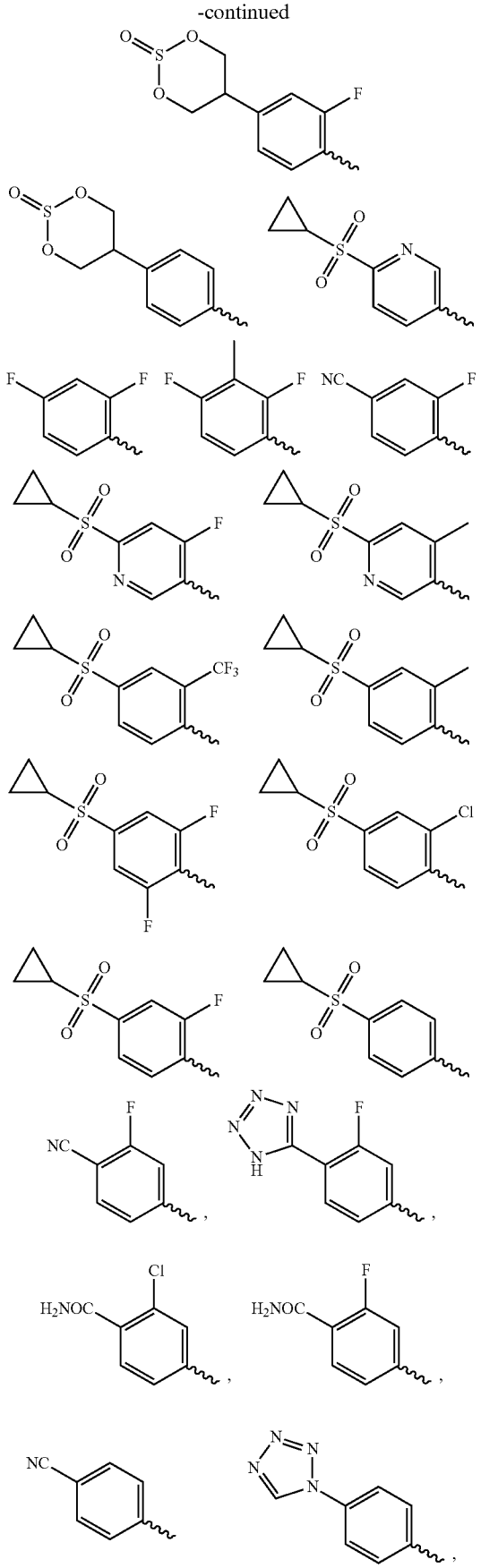
Further preferred is a compound of formula (A), (A-I), (A-II), (A-III), (A-IV), (B), (B-I), (B-II), (B-III) or (B-IV) wherein Ar is $Cy^1$.
Further preferred is a compound of formula (A), (A-I), (A-II), (A-III), (A-IV), (B), (B-I), (B-II), (B-III) or (B-IV) wherein $Cy^1$ is selected from
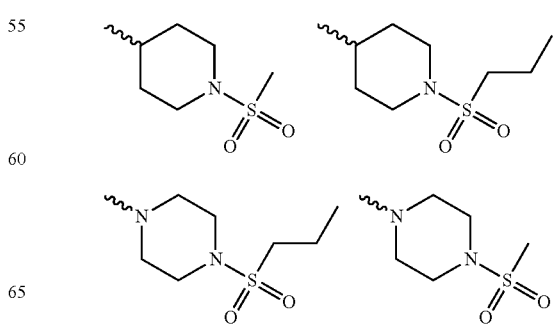

-continued

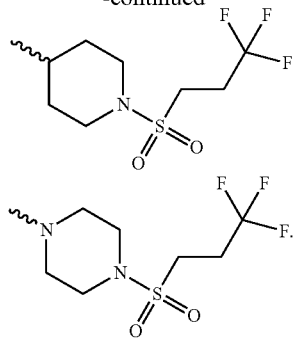

Further preferred is a compound of formula (A) or (B) wherein $L_1$ is absent.

Further preferred is a compound of formula (A) or (B) wherein $L_2$ is absent.

Further preferred is a compound of formula (A), (A-I), (A-II), (A-III), (A-IV), (B), (B-I), (B-II), (B-III) or (B-IV) wherein Z is NH or N—CH$_3$.

Further preferred is a compound of formula (A), (A-I), (A-II), (A-III), (A-IV), (B), (B-I), (B-II), (B-III) or (B-IV) wherein Z is O.

Further preferred is a compound of formula (A), (A-I), (A-II), (A-III), (A-IV), (B), (B-I), (B-II), (B-III) or (B-IV) wherein Z is S.

Further preferred is a compound of formula (A), (A-I), (A-II), (A-III), (A-IV), (B), (B-I), (B-II), (B-III) or (B-IV) wherein $X^1$ is $CR^1$ or N, wherein $R^1$ is H or Halogen.

Further preferred is a compound of formula (A), (A-II), (A-IV), (B), (B-II) or (B-IV) wherein $X^2$ is CH.

Further preferred is a compound of formula (A), (A-II), (A-IV), (B), (B-II) or (B-IV) wherein $X^3$ is CH.

Further preferred is a compound of formula (A), (A-I), (A-II), (A-III), (A-IV), (B), (B-I), (B-II), (B-III) or (B-IV) wherein $X^4$ is $CR^4$ or N, wherein $R^4$ is H or Halogen.

Further preferred is a compound of formula (A), (A-I), (A-II), (A-III), (A-IV), (B), (B-I), (B-II), (B-III) or (B-IV) wherein X is CR or N, wherein R is H, hydrogen, cyano, halogen, substituted or unsubstituted $C_{1-6}$ alkyl, substituted or unsubstituted $C_{3-6}$ cycloalkyl, and substituted or unsubstituted $C_{3-6}$ cycloalkenyl, —OR$^a$, —NR$^a$R$^b$ or —C(=Y)—R$^a$ and R$^a$, R$^b$, and Y are as defined above for compound of formula (A) or (B);

Further preferred is a compound of formula (A), (A-I), (A-II), (A-III), (A-IV), (B), (B-I), (B-II), (B-III) or (B-IV): wherein Cy is selected from

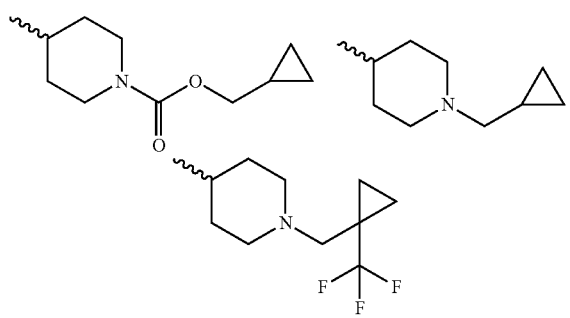

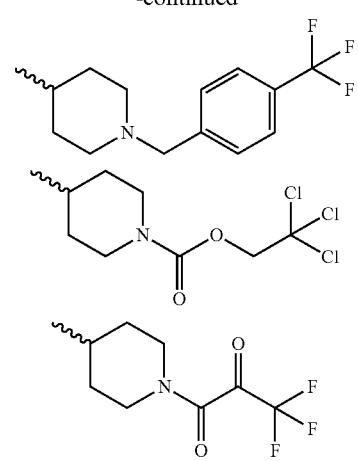

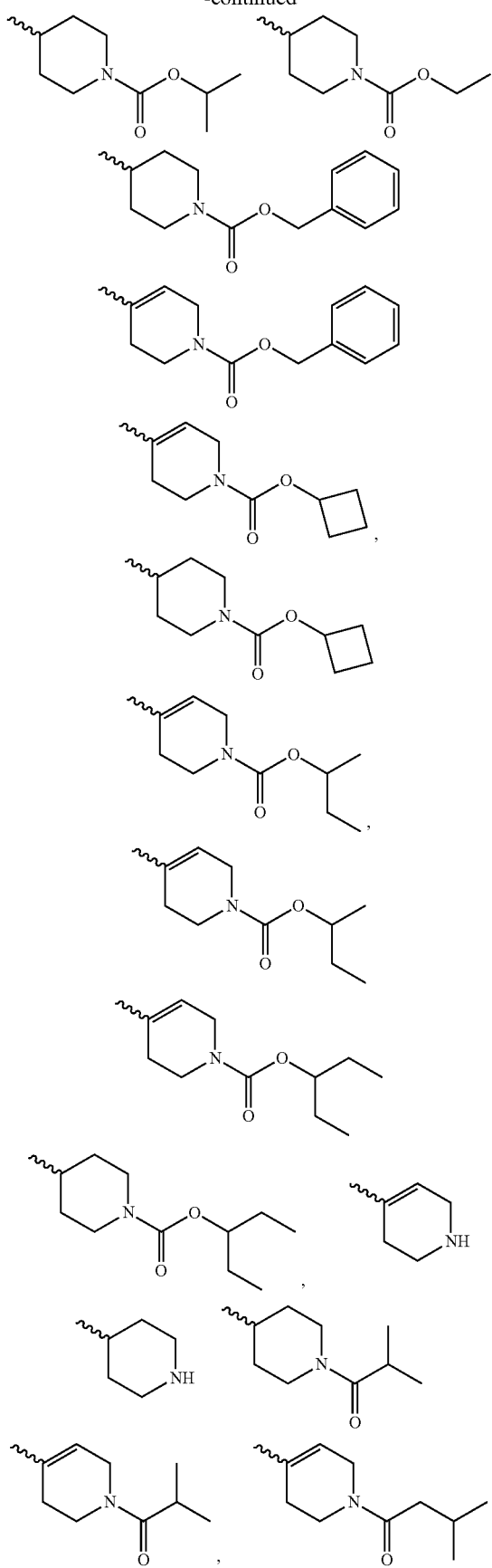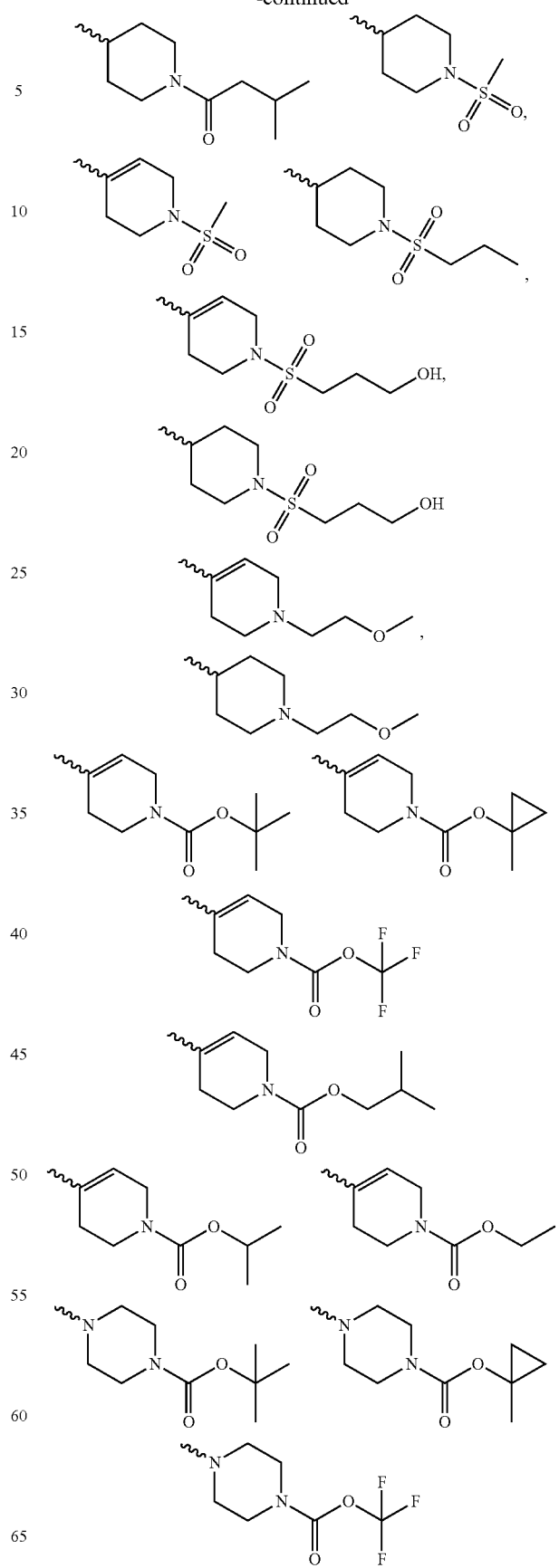

-continued
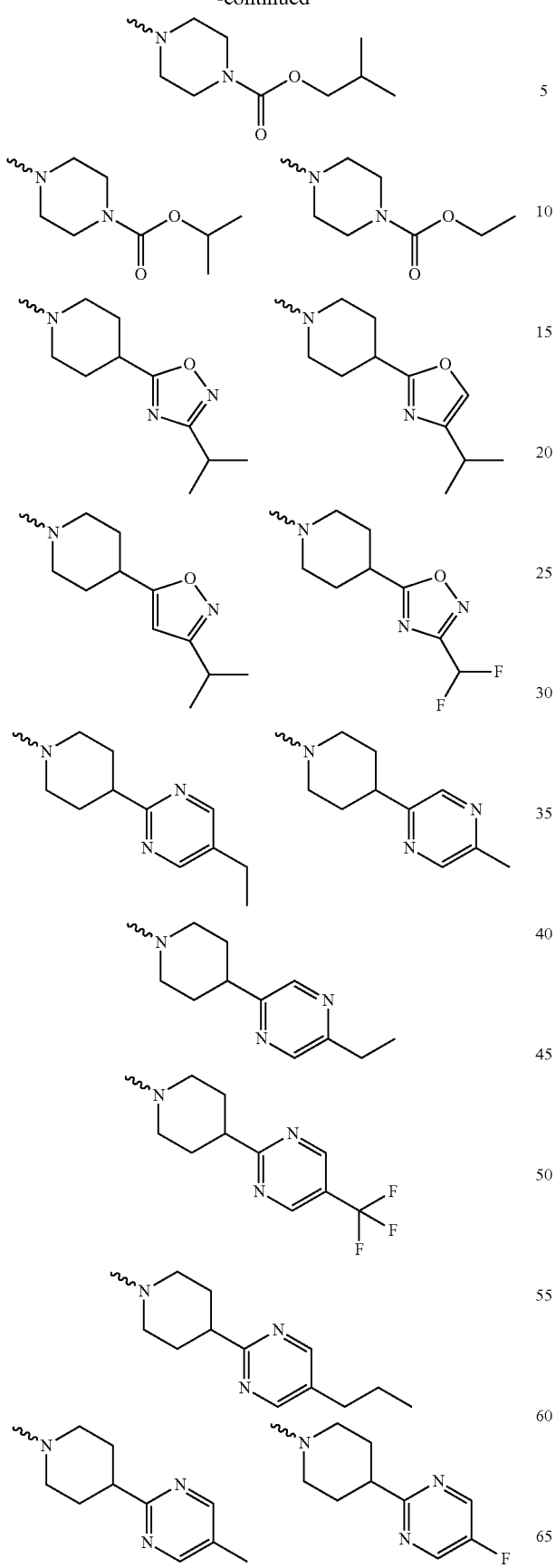
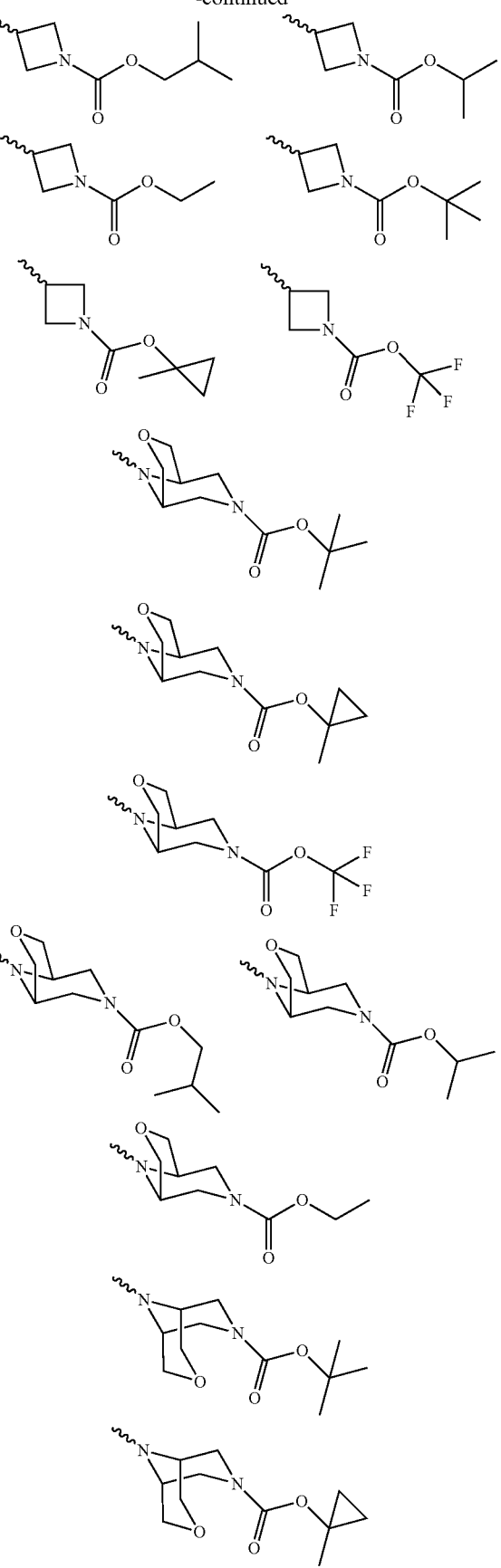

-continued
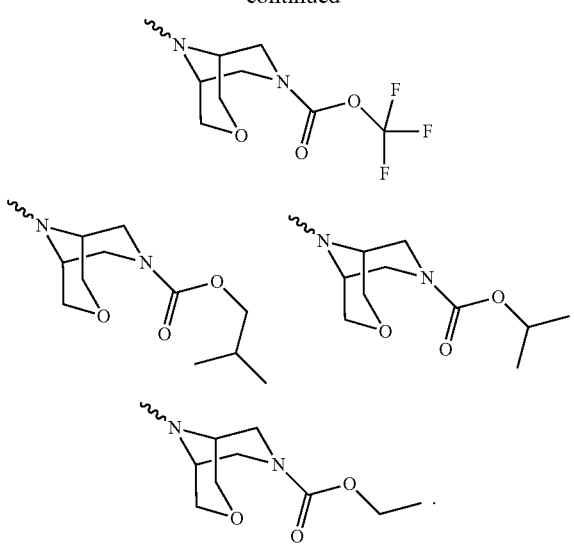
Yet another embodiment is a compound of formula (A-IA), (A-IIA), (B-IA), (B-IIA), (B-IIIA) or (B-IVA):
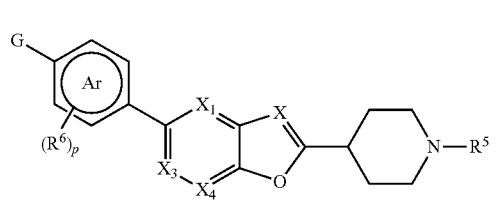
(A-IA)
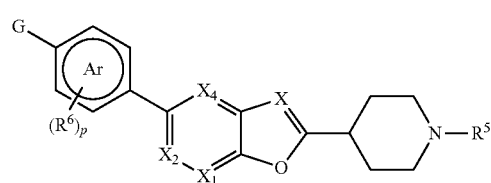
(A-IIA)
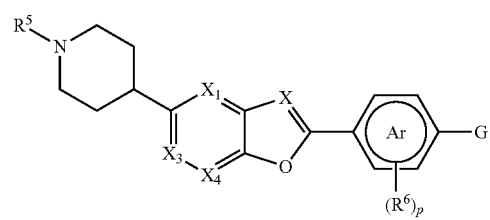
(B-IA)
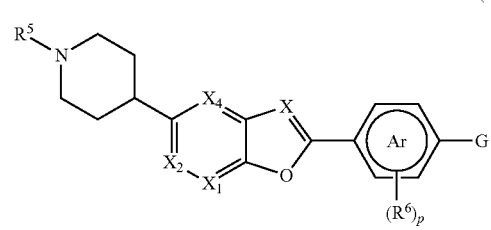
(B-IIIA)
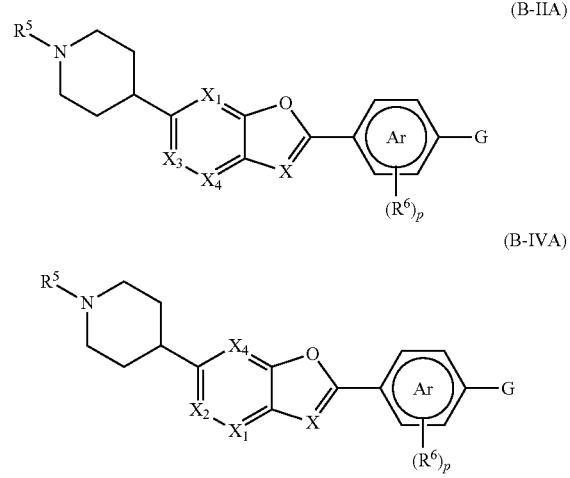
or a tautomer, stereoisomer, enantiomer, diastereomer, salt (e.g., pharmaceutically acceptable salt), prodrug (e.g., ester), or N-oxide thereof, wherein
Ar is
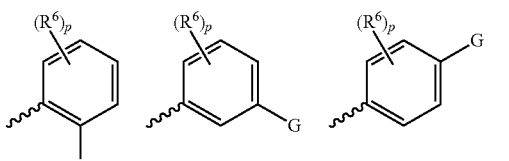
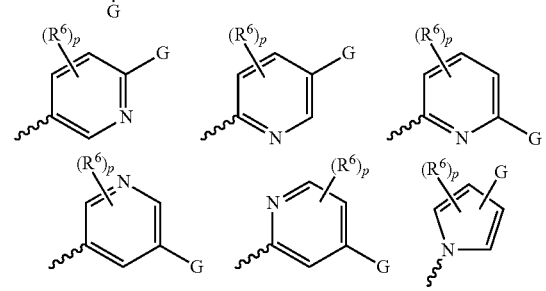
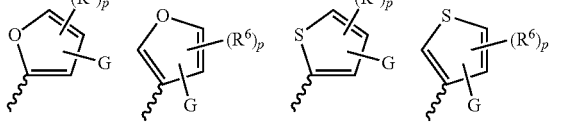
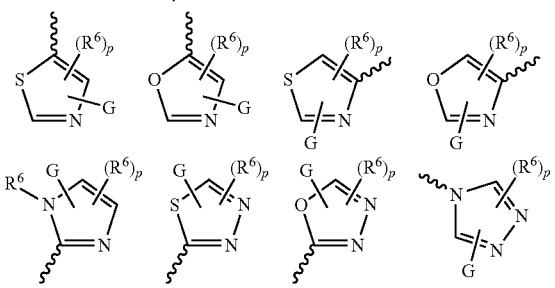

-continued

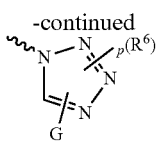

G is independently selected from

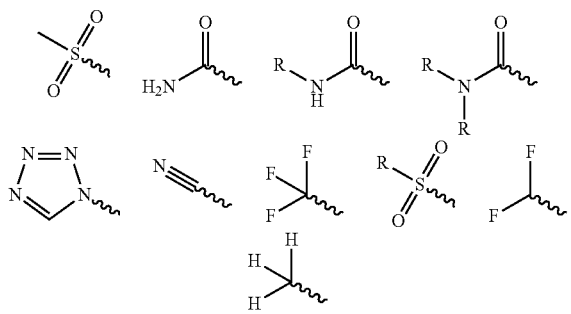

R is substituted or unsubstituted alkyl, substituted or unsubstituted alkoxy, substituted or unsubstituted alkenyl, substituted or unsubstituted alkynyl or substituted or unsubstituted cycloalkyl.

$R^6$ is selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, —(=N—N(R$^a$)R$^b$), —NR$^a$C(O)OR$^b$, —NR$^a$C(O)R$^b$-, —NR$^a$C(S)R$^b$—NR$^a$C(S)NR$^a$R$^b$, —SONR$^a$R$^b$-, —SO$_2$NR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$—SO$_2$R$^a$, and —ONO$_2$;

each occurrence of R$^a$ and R$^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two R$^a$ and/or R$^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^d$ or S;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclcyalkyl, substituted or unsubstituted aryl, substituted or unsubstituted arylalkyl, substituted or unsubstituted heteroaryl, substituted or unsubstituted heteroarylalkyl, and —ONO$_2$, p is 0, 1, 2, 3 or 4; and all the other variables ($X_1$-$X_4$, X, and $R^5$) are the same as described above for compound of formula (A), (B), (A-I), (B-I), (A-II) or (B-II).

Yet another embodiment is a compound of formula (A-IIIA) and (A-IVA)

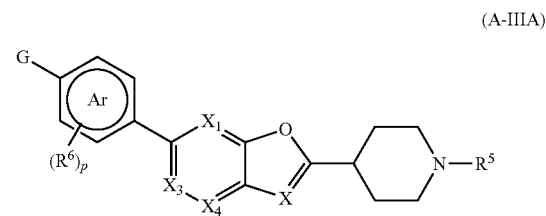

(A-IIIA)

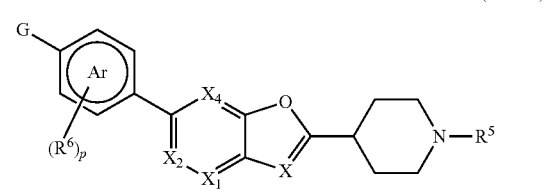

(A-IVA)

wherein the variables Ar, G, $R^6$, and p are defined as above with respect to formulas (A-MA) or (A-IVA), and all the other variables ($X_1$-$X_4$, X, and $R^5$) are the same as described above for compound of formula (A), (B), (A-I), (B-I), (A-II) or (B-II)

with the proviso 1. that for compound of formula (A-IIIA), wherein Z is O or S and $X_4$ is N or CR$^4$ then Ar-G cannot be

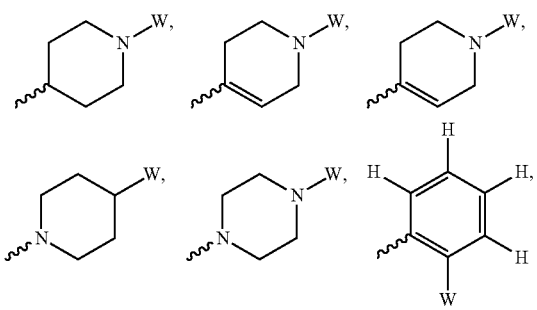

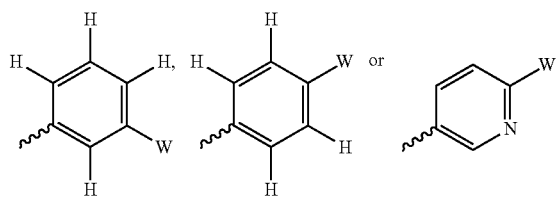

2. that for compound of formula (A-IVA) wherein Z is O or S and $X_1$ is N or CR$^1$ then Ar-G cannot be

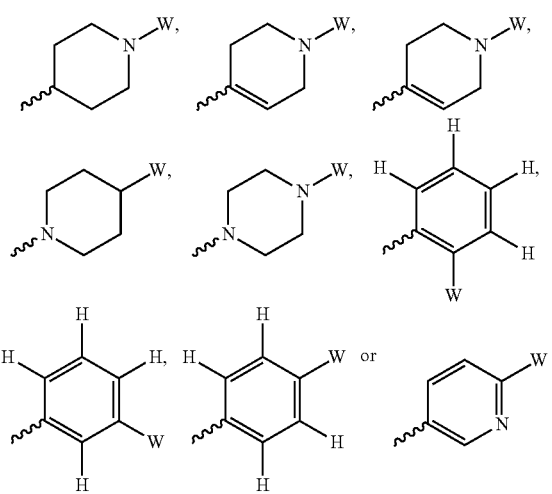

wherein
R¹ and R⁴ is as defined above for compound of formula (A)
W is S(=O)₂—R₁, S(=O)₂—NR₁ₐR₁, —C(=O)—R₁, —C(=O)—O—R₁, —C(=O)—NR₁ₐR₁, —NR₁ₐ—S(=O)₂—R₁, halo, or a 4- to 10-membered optionally substituted heteroaryl, which contains 1-4 heteroatoms selected from N, O, and S;
R₁ₐ, at each occurrence, is independently hydrogen or ($C_1$-$C_8$)alkyl;
R₁ is optionally substituted ($C_1$-$C_6$)-alkyl, optionally substituted ($C_2$-$C_6$)-alkenyl, optionally substituted ($C_2$-$C_6$)-alkynyl, optionally substituted ($C_3$-$C_{12}$)-cycloalkyl, optionally substituted ($C_6$-$C_{10}$)aryl, a 4-10-membered optionally substituted heteroaryl, which contains 1-4 heteroatoms selected from N, O, and S; or a 4- to 10-membered heterocyclo, which contains 1-4 heteroatoms selected from N, O, and S;

Further preferred is a compound of formula (A-IA), (A-IIA), (A-IIIA), (A-IVA), (B-IA), (B-IIA), (B-IIIA) or (B-IVA) wherein Ar is selected from.

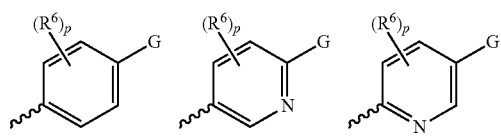

Further preferred is a compound of formula (A-IA), (A-IIA), (A-IIIA), (A-IVA), (B-IA), (B-IIA), (B-IIIA) or (B-IVA) wherein G is selected from.

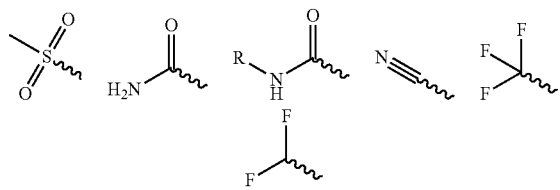

Further preferred is a compound of formula (A-IA), (A-IIA), (A-IIIA), (A-IVA), (B-IA), (B-IIA), (B-IIIA) or (B-IVA) wherein $X^1$ is $CR^1$ or N, wherein $R^1$ is H or Halogen.
Further preferred is a compound of formula (A-IIA), (A-IVA), (B-IIA) or (B-IVA) wherein $X^2$ is CH.

Further preferred is a compound of formula (A-IA), (A-IIIA), (B-IA) or (B-IIIA) wherein $X^3$ is CH.
Further preferred is a compound of formula (A-IA), (A-IIA), (A-IIIA), (A-IVA), (B-IA), (B-IIA), (B-IIIA) or (B-IVA) wherein $X^4$ is $CR^4$ or N, wherein $R^1$ is H or Halogen.
Further preferred is a compound of formula (A-IA), (A-IIA), (A-IIIA), (A-IVA), (B-IA), (B-IIA), (B-IIIA) or (B-IVA) wherein X is CH or N.
Further preferred is a compound of formula (A-IA), (A-IIA), (A-IIIA) or (A-IVA) (B-IA), (B-IIA), (B-IIIA) or (B-IVA) wherein $R^5$ is selected from

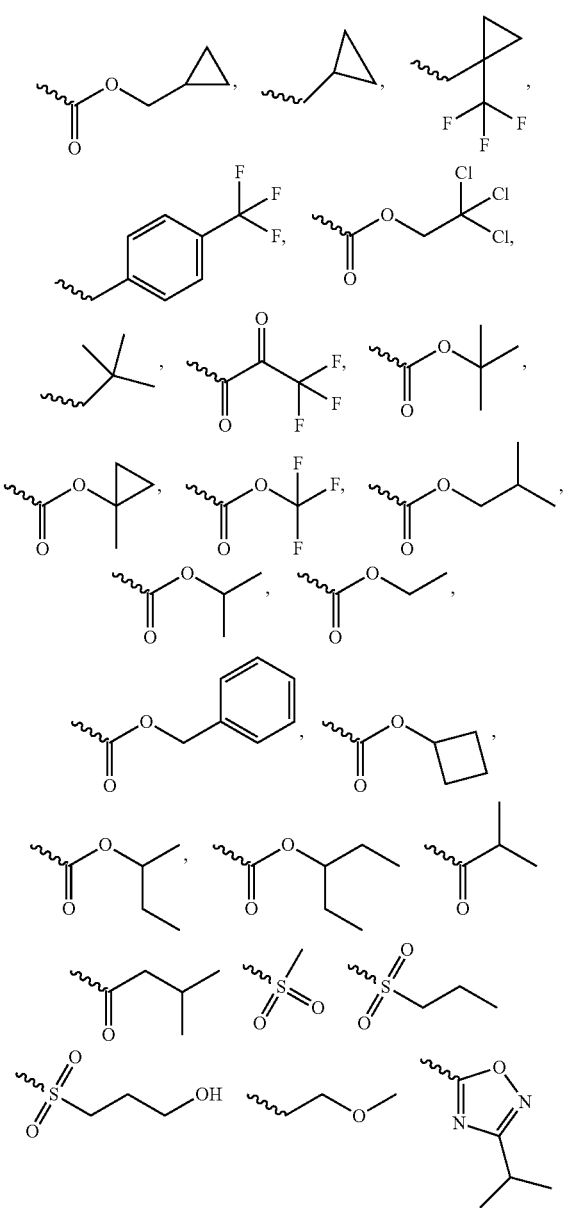

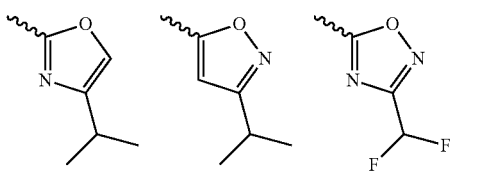

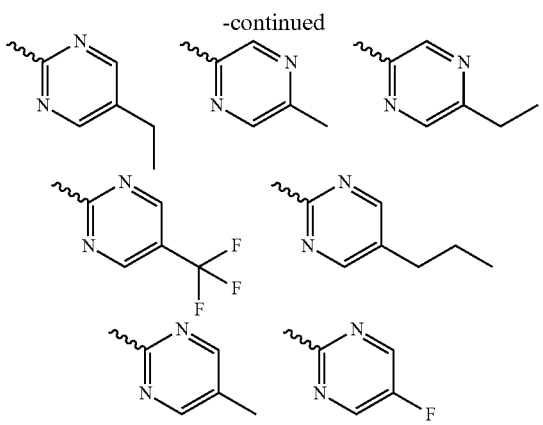

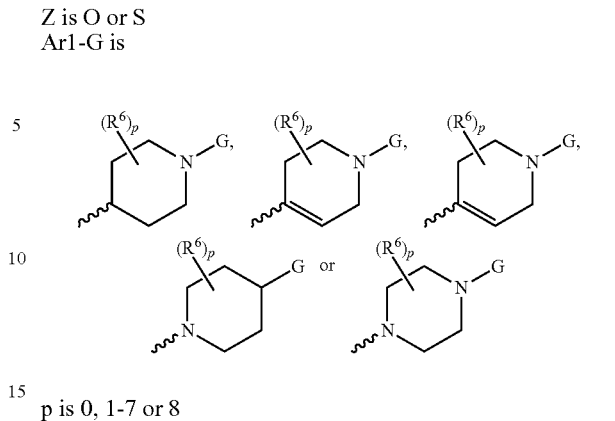

Further preferred is a compound of formula (A-IA), (A-IIA), (A-IIIA), (A-IVA), (B-IA), (B-IIA), (B-IIIA) or (B-IVA) wherein $R^5$ is BOC(—C(O)OC(CH$_3$)$_3$).

Further preferred is a compound of formula (A-IA), (A-IIA), (A-IIIA), (A-IVA) (B-IA), (B-IIA), (B-IIIA) or (B-IVA) wherein $R^5$ is —C(O)OCH(CH$_3$)$_2$.

Further preferred is a compound of formula (A-IIA) or (B-IIA) wherein $X^1$ is CH or CF.

In one preferred embodiment, X is N.

In one preferred embodiment, X is CH.

In one preferred embodiment, Z is S

In one preferred embodiment, Z is O.

Further preferred is a compound of formula (A-IA), (A-IIA), (A-IIIA), (A-IVA), (B-IA), (B-IIA), (B-IIIA) or (B-IVA) wherein p is 0 or 1.

Further preferred is a compound of formula (A-IA), (A-IIA), (A-IIIA), (A-IVA), (B-IA), (B-IIA), (B-IIIA) or (B-IVA) wherein $R^6$ is halogen, substituted or unsubstituted alkyl or —$OR^a$; wherein $R^a$ is substituted or unsubstituted alkyl.

Further preferred is a compound of formula ((A-IA), (A-IIA), (A-IIIA), (A-IVA), (B-IA), (B-IIA), (B-IIIA) or (B-IVA) wherein $R^6$ is —F, —CH$_3$, —CF$_3$ or —OCH$_3$.

Yet another embodiment is a compound of formula (A-IB) and (A-IIB):

(A-IB)

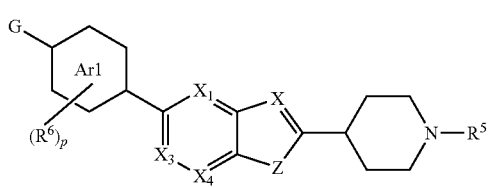

(A-IIB)

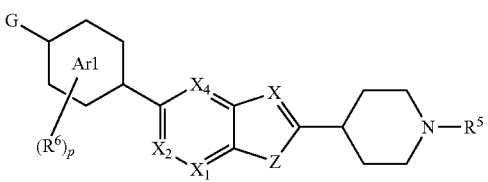

or a tautomer, stereoisomer, enantiomer, diastereomer, salt (e.g., pharmaceutically acceptable salt), prodrug (e.g., ester), or N-oxide thereof, wherein Z is O or S Ar1-G is

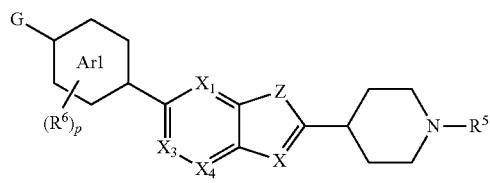

p is 0, 1-7 or 8 and all the variables ($R^6$, $X_1$-$X_4$, X, and $R^5$) are the same as described above Yet another embodiment is a compound of formula (A-IIIB) and (A-IVB):

(A-IIIB)

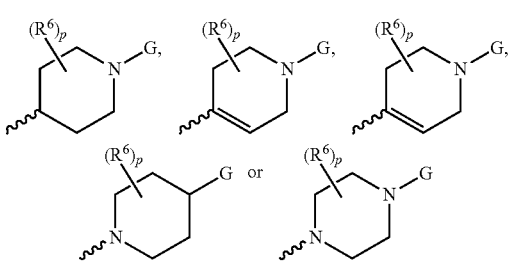

(A-IVB)

or a tautomer, stereoisomer, enantiomer, diastereomer, salt (e.g., pharmaceutically acceptable salt), prodrug (e.g., ester), or N-oxide thereof, wherein Z is O or S Ar1-G is

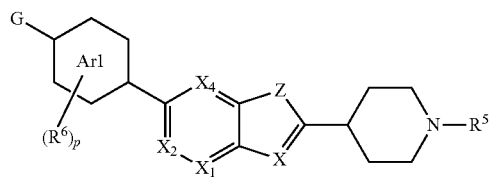

p is 0, 1-7 or 8 and all the variables ($R^6$, X, —$X_4$, X, and $R^5$) are the same as described above.

1. that for compound of formula (A-IIIB), wherein Z is O or S and $X_4$ is N or $CR^4$ then Ar1-G cannot be

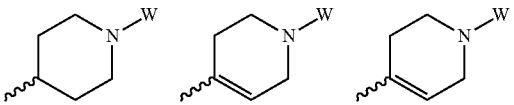

-continued

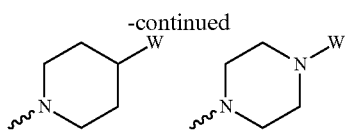

2. that for compound of formula (A-IVB) wherein Z is O or S and $X_1$ is N or $CR^1$ then Ar1-G cannot be

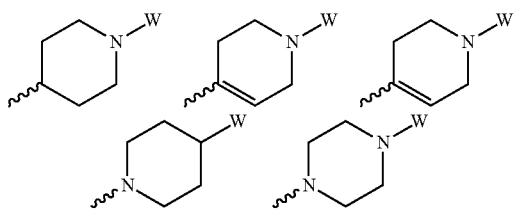

wherein
$R^1$ and $R^4$ is as defined above for compound of formula (A)
W is $S(=O)_2-R_1$, $S(=O)_2-NR_{1a}R_1$, $-C(=O)-R_1$, $-C(=O)-O-R_1$, $-C(=O)-NR_{1a}R_1$, $-NR_{1a}-S(=O)_2-R_1$, halo, or a 4 to 10-membered optionally substituted heteroaryl, which contains 1-4 heteroatoms selected from N, O, and S;
$R_{1a}$, at each occurrence, is independently hydrogen or $(C_1-C_8)$alkyl; and
$R_1$ is optionally substituted $(C_1-C_6)$-alkyl, optionally substituted $(C_2-C_6)$-alkenyl, optionally substituted $(C_2-C_6)$-alkynyl, optionally substituted $(C_3-C_{12})$-cycloalkyl, optionally substituted $(C_6-C_{10})$aryl, a 4 to 10-membered optionally substituted heteroaryl, which contains 1-4 heteroatoms selected from N, O, and S; or a 4 to 10-membered heterocyclo, which contains 1-4 heteroatoms selected from N, O, and S.

Yet another embodiment is a compound of formula (A-V):

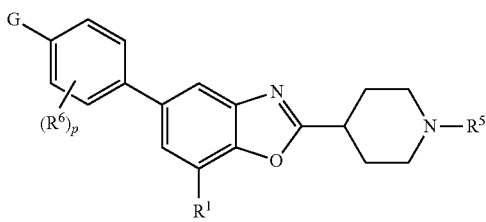

or a pharmaceutically acceptable salt thereof, wherein
$R^1$ is hydrogen or F;
$R^5$ is as defined above;
G is selected from $-SO_2R^a$, $-C(O)R^aR^b$, $C_1-C_4$ alkyl substituted with one or more halogens, and a tetrazole of the formula

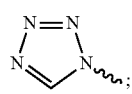

each occurrence of $R^6$ is independently halogen;
each occurrence of $R^a$ and $R^b$ is independently hydrogen or unsubstituted or substituted $C_1-C_6$ alkyl; and
p is 0, 1, 2 or 3.

In one preferred embodiment of the compound of formula (A-V), $R^5$ is selected from $-COO-R^a$ and $-SO_2-R^a$ (wherein $R^a$ is an unsubstituted $C_1-C_4$ alkyl, $C_1-C_4$ alkyl with one or more halogens, or $C_3-C_6$ cycloalkyl).

In a preferred embodiment of the compound of formula (A-V), G is selected from $-SO_2R^a$ (where $R^a$ is an unsubstituted $C_1-C_4$ alkyl), $-C(O)R^aR^b$ (where $R^a$ and $R^b$ are independently selected from hydrogen and a $C_1-C_4$ alkyl optionally substituted with one or more halogen), a $C_1-C_2$ alkyl substituted with one or more halogens, and a tetrazole of the formula above.

Yet another embodiment is a compound of formula (B-V):

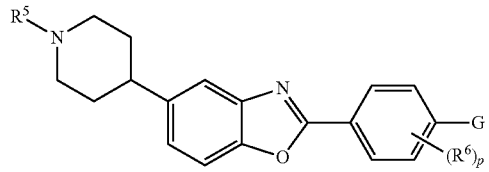

or a pharmaceutically acceptable salt thereof, wherein
$R^5$ is as defined above;
G is selected from $-SO_2R^a$;
each occurrence of $R^6$ is independently halogen;
each occurrence of $R^a$ is independently hydrogen or unsubstituted or substituted $C_1-C_6$ alkyl; and
p is 0, 1, 2 or 3.

In one preferred embodiment of the compound of formula (B-V), $R^5$ is $-COO-R^a$ where $R^a$ is an unsubstituted or substituted $C_1-C_6$ alkyl. More preferably, $R^a$ is an unsubstituted $C_1-C_6$ alkyl, such as an unsubstituted $C_1-C_4$ alkyl.

In a preferred embodiment of the compound of formula (B-V), G is selected from $-SO_2R^a$ where $R^a$ is an unsubstituted $C_1-C_4$ alkyl, such as methyl.

In a preferred embodiment of the compound of formula (B-V), p is 1 and $R^6$ is fluorine. More preferably, the fluorine is at a position ortho the benzo[d]oxazole group.

Representative compounds of the present invention include those specified below (including Table 1 and Table 2) and pharmaceutically acceptable salts thereof. The present invention should not be construed to be limited to them.

1. 2-[1-(5-Ethylpyrimidin-2-yl)piperidin-4-yl]-5-[2-fluoro-4-(methylsulfonyl)phenyl]-1H-benzo[d]imidazole:
2. Tert-butyl 4-{5-[2-fluoro-4-(methylsulfonyl)phenyl]-1H-benzo[d]imidazol-2-yl}piperidine-1-carboxylate:
3. 2-[1-(5-ethylpyrimidin-2-yl)piperidin-4-yl]-5-[2-fluoro-4-(methylsulfonyl)phenyl]benzo[d]oxazole:
4. Tert-butyl 4-{5-[2-fluoro-4-(methylsulfonyl)phenyl]benzo[d]oxazol-2-yl}piperidine-1-carboxylate:
5. Tert-butyl 4-{5-[2-fluoro-4-(methylsulfonyl)phenyl]-1-methyl-1H-benzo[d]imidazol-2-yl}piperidine-1-carboxylate:
6. Tert-butyl 4-{6-[2-fluoro-4-(methylsulfonyl)phenyl]benzo[d]oxazol-2-yl}piperidine-1-carboxylate:
7. Isopropyl 4-{5-[2-fluoro-4-(methylsulfonyl)phenyl]benzo[d]oxazol-2-yl}piperidine-1-carboxylate:
8. Tert-butyl 4-{7-fluoro-5-[2-fluoro-4-(methylsulfonyl)phenyl]benzo[d]oxazol-2-yl}piperidine-1-carboxylate:
9. Tert-butyl 4-[5-(4-cyanophenyl)benzo[d]oxazol-2-yl]piperidine-1-carboxylate:
10. Tert-butyl 4-{5-[3-fluoro-4-(methylsulfonyl)phenyl]benzo[d]oxazol-2-yl}piperidine-1-carboxylate:
11. Tert-butyl 4-{5-[4-(1H-tetrazol-1-yl)phenyl]benzo[d]oxazol-2-yl}piperidine-1-carboxylate:
12. Tert-butyl 4-{5-[2-fluoro-4-(1H-tetrazol-1-yl)phenyl]benzo[d]oxazol-2-yl}piperidine-1-carboxylate:

13. Tert-butyl 4-{5-[4-(trifluoromethyl)phenyl]benzo[d]oxazol-2-yl}piperidine-1-carboxylate:
14. Isopropyl 4-{5-[2-fluoro-4-(1H-tetrazol-1-yl)phenyl]benzo[d]oxazol-2-yl}piperidine-1-carboxylate:
15. Tert-butyl 4-{5-[3-fluoro-4-(1H-tetrazol-1-yl)phenyl]benzo[d]oxazol-2-yl}piperidine-1-carboxylate:
16. 2-[1-(5-ethylpyrimidin-2-yl)piperidin-4-yl]-5-[2-fluoro-4-(1H-tetrazol-1-yl)phenyl]benzo[d]oxazole:
17. Tert-butyl 4-[5-(4-cyano-3-fluorophenyl)benzo[d]oxazol-2-yl]piperidine-1-carboxylate:
18. Isopropyl 4-{5-[3-fluoro-4-(1H-tetrazol-1-yl)phenyl]benzo[d]oxazol-2-yl}piperidine-1-carboxylate:
19. Tert-butyl 4-{5-[3-fluoro-4-(1H-tetrazol-5-yl)phenyl]benzo[d]oxazol-2-yl}piperidine-1-carboxylate:
20. Tert-butyl 4-[5-(4-carbamoyl-3-chlorophenyl)benzo[d]oxazol-2-yl]piperidine-1-carboxylate:
21. Tert-butyl 4-[5-(4-carbamoyl-3-fluorophenyl)benzo[d]oxazol-2-yl]piperidine-1-carboxylate:
22. Tert-butyl 4-[5-(3-fluoro-4-isopropoxyphenyl)benzo[d]oxazol-2-yl]piperidine-1-carboxylate:
23. Cyclobutyl 4-{5-[2-fluoro-4-(1H-tetrazol-1-yl)phenyl]benzo[d]oxazol-2-yl}piperidine-1-carboxylate:
24. Sec-butyl 4-{5-[2-fluoro-4-(1H-tetrazol-1-yl)phenyl]benzo[d]oxazol-2-yl}piperidine-1-carboxylate:
25. Pentan-3-yl 4-{5-[2-fluoro-4-(1H-tetrazol-1-yl)phenyl]benzo[d]oxazol-2-yl}piperidine-1-carboxylate:
26. 5-[2-fluoro-4-(1H-tetrazol-1-yl)phenyl]-2-(piperidin-4-yl)benzo[d]oxazole:
27. Isopropyl 4-{5-[4-(trifluoromethyl)phenyl]benzo[d]oxazol-2-yl}piperidine-1-carboxylate:
28. Isopropyl 4-[5-(4-formylphenyl)benzo[d]oxazol-2-yl]piperidine-1-carboxylate:
29. Isopropyl 4-{5-[4-(difluoromethyl)phenyl]benzo[d]oxazol-2-yl}piperidine-1-carboxylate:
30. Isopropyl 4-[5-(4-carbamoyl-3-chlorophenyl)benzo[d]oxazol-2-yl]piperidine-1-carboxylate:
31. Isopropyl 4-[5-(4-carbamoyl-3-fluorohenyl)benzo[d]oxazol-2-yl]piperidine-1-carboxylate:
32. 1-{4-[5-(2-fluoro-4-(1H-tetrazol-1-yl)phenyl)benzo[d]oxazol-2-yl]piperidin-1-yl}-2-methylpropan-1-one:
33. Isopropyl 4-{6-[4-(difluoromethyl)phenyl]benzo[d]oxazol-2-yl}piperidine-1-carboxylate:
34. 6-{2-[1-(isopropoxycarbonyl)piperidin-4-yl]benzo[d]oxazol-5-yl}nicotinic acid:
35. 5-[2-fluoro-4-(1H-tetrazol-1-yl)phenyl]-2-[1-(methylsulfonyl)piperidin-4-yl]benzo[d]oxazole:
36. Isopropyl 4-[5-(5-carbamoylpyridin-2-yl)benzo[d]oxazol-2-yl]piperidine-1-carboxylate:
37. Isopropyl 4-[5-(4-carbamoyl-2-fluorophenyl)benzo[d]oxazol-2-yl]piperidine-1-carboxylate:
38. Isopropyl 4-[5-(4-carbamoyl-2-chlorophenyl)benzo[d]oxazol-2-yl]piperidine-1-carboxylate:
39. 2-Fluoro-4-{2-[1-(3-methylbutanoyl)piperidin-4-yl]benzo[d]oxazol-5-yl}benzamide:
40. 1-{4-[5-(2-fluoro-4-(1H-tetrazol-1-yl)phenyl]benzo[d]oxazol-2-yl]piperidin-1-yl}-3-methylbutan-1-one:
41. 5-[2-fluoro-4-(1H-tetrazol-1-yl)phenyl]-2-[1-(2-methoxyethyl)piperidin-4-yl]benzo[d]oxazole:
42. Isopropyl 4-{5-[3-fluoro-4-(methylcarbamoyl)phenyl]benzo[d]oxazol-2-yl}piperidine-1-carboxylate:
43. 2-Fluoro-4-[2-(1-isobutyrylpiperidin-4-yl)benzo[d]oxazol-5-yl]benzamide:
44. Isopropyl 4-[6-(4-carbamoyl-3-fluorophenyl)benzo[d]oxazol-2-yl]piperidine-1-carboxylate:
45. Isopropyl 4-{5-[3-fluoro-4-(2-hydroxyethylcarbamoyl)phenyl]benzo[d]oxazol-2-yl}piperidine-1-carboxylate:
46. Isopropyl 4-{5-[3-fluoro-4-(isopropylcarbamoyl)phenyl]benzo[d]oxazol-2-yl}piperidine-1-carboxylate:
47. Isopropyl 4-{5-[4-(N-methylsulfamoyl)phenyl]benzo[d]oxazol-2-yl}piperidine-1-carboxylate:
48. Isopropyl 4-{5-[6-(methylcarbamoyl)pyridin-3-yl]benzo[d]oxazol-2-yl}piperidine-1-carboxylate:
49. Isopropyl 4-{5-[3-methyl-4-(methylcarbamoyl)phenyl]benzo[d]oxazol-2-yl}piperidine-1-carboxylate:
50. Isopropyl 4-{5-[4-(cyclopropylcarbamoyl)-3-fluorophenyl]benzo[d]oxazol-2-yl}piperidine-1-carboxylate:
51. 2-Fluoro-4-{2-[1-(5-fluoropyrimidin-2-yl)piperidin-4-yl]benzo[d]oxazol-5-yl}benzamide:
52. Tert-butyl 4-[5-(4-carbamoyl-3-fluorophenyl)benzofuran-2-yl]-5,6-dihydropyridine-1(2H)-carboxylate:
53. 2-fluoro-4-{2-[1-(propylsulfonyl)piperidin-4-yl]benzo[d]oxazol-5-yl}benzamide:
56. Tert-butyl 4-{2-[2-fluoro-4-(methylsulfonyl)phenyl]-1H-benzo[d]imidazol-5-yl}-5,6-dihydropyridine-1(2H)-carboxylate;
57. Tert-butyl 4-{2-[2-fluoro-4-(methylsulfonyl)phenyl]-1H-benzo[d]imidazol-5-yl}piperidine-1-carboxylate;
58. 5-[1(5-ethylpyrimidin-2-yl)piperidin-4-yl]-2-[2-fluoro-4-(methylsulfonyl)phenyl]-1H-benzo[d]imidazole;
59. Tert-butyl 4-{2-[2-fluoro-4-(methylsulfonyl)phenyl]benzo[d]oxazol-5-yl}-5,6-dihydropyridine-1(2H)-carboxylate;
60. Tert-butyl 4-{2-[2-fluoro-4-(methylsulfonyl)phenyl]benzo[d]oxazol-5-yl}piperidine-1-carboxylate;
61. 2-[2-fluoro-4-(methylsulfonyl)phenyl]-5-(piperidin-4-yl)benzo[d]oxazole 2,2,2-trifluoro acetate;
62. 5-[1(5-ethylpyrimidin-2-yl)piperidin-4-yl]-2-[2-fluoro-4-(methylsulfonyl)phenyl]benzo[d]oxazole.
63. Tert-butyl 4-{7-fluoro-2-[2-fluoro-4-(methylsulfonyl)phenyl]benzo[d]oxazol-5-yl}piperidine-1-carboxylate:
64. Isopropyl 4-{2-[2-fluoro-4-(methylsulfonyl)phenyl]benzo[d]oxazol-5-yl}piperidine-1-carboxylate:
65. Tert-butyl 4-{2-[2-fluoro-4-(methylsulfonyl)phenyl]benzo[d]thiazol-6-yl}-5,6-dihydropyridine-1(2H)-carboxylate:
66. Tert-butyl 4-{2-[2-fluoro-4-(methylsulfonyl)phenyl]benzo[d]thiazol-5-yl}-5,6-dihydropyridine-1(2H)-carboxylate:
67. Tert-butyl 4-{2-[2-fluoro-4-(methylsulfonyl)phenyl]benzo[d]oxazol-6-yl}piperidine-1-carboxylate:
68. Tert-butyl 4-{2-[2-fluoro-4-(methylsulfonyl)phenyl]benzo[d]thiazol-5-yl}piperidine-1-carboxylate:
69. Ethyl 4-{2-[2-fluoro-4-(methylsulfonyl)phenyl]benzo[d]oxazol-5-yl}piperidine-1-carboxylate:
70. Tert-butyl 4-{2-[4-(trifluoromethyl)phenyl]benzo[d]oxazol-5-yl}piperidine-1-carboxylate:
71. Isopropyl 4-{2-[2-fluoro-4-(methylsulfonyl)phenyl]benzo[d]oxazol-6-yl}piperidine-1-carboxylate:
72. Ethyl 4-{2-[2-fluoro-4-(methylsulfonyl)phenyl]benzo[d]oxazol-6-yl}piperidine-1-carboxylate:
73. Ethyl 4-{2-[2-fluoro-4-(methylsulfonyl)phenyl]benzo[d]oxazol-6-yl}piperidine-1-carboxylate:
74. Benzyl 4-{2-[2-fluoro-4-(methylsulfonyl)phenyl]benzo[d]oxazol-5-yl}piperidine-1-carboxylate:
75. Isobutyl 4-{2-[2-fluoro-4-(methylsulfonyl)phenyl]benzo[d]oxazol-5-yl}piperidine-1-carboxylate:
76. Isopropyl 4-{2-[2-fluoro-4-(methylsulfonyl)phenyl]benzo[d]thiazol-6-yl}piperidine-1-carboxylate:
77. Isopropyl 4-{2-[4-(trifluoromethyl)phenyl]benzo[d]oxazol-5-yl}piperidine-1-carboxylate:
78. Isopropyl 4-(2-p-tolylbenzo[d]oxazol-6-yl)piperidine-1-carboxylate:

79. 3-{4-[2-(2-fluoro-4-(methylsulfonyl)phenyl)benzo[d]oxazol-5-yl]-5,6-dihydropyridin-1(2H)-ylsulfonyl}propan-1-ol:
80. 3-{4-[2-(2-fluoro-4-(methylsulfonyl)phenyl)benzo[d]oxazol-5-yl]piperidin-1-ylsulfonyl}propan-1-ol:
81. 3-{4-[2-(2-fluoro-4-(methylsulfonyl)phenyl)benzo[d]oxazol-5-yl]piperidin-1-ylsulfonyl}propan-1-ol:
82. Tert-butyl 4-[2-(4-carbamoyl-3-fluorophenyl)benzo[d]oxazol-5-yl]piperidine-1-carboxylate:
83. 2-[2-fluoro-4-(methylsulfonyl)phenyl]-5-[4-(3-isopropyl-1,2,4-oxadiazol-5-yl)piperidin-1-yl]benzo[d]oxazole:
84. Tert-butyl 4-{2-[4-(trifluoromethyl)phenyl]benzo[d]oxazol-6-yl}piperidine-1-carboxylate
85. Isopropyl 4-{2-[2-fluoro-4-(methylsulfonyl)phenyl]benzo[d]oxazol-5-yl}piperazine-1-carboxylate:
86. Tert-butyl 4-{2-[4-(trifluoromethyl)phenyl]oxazolo[5,4-b]pyridin-6-yl}-5,6-dihydropyridine-1(2H)-carboxylate:
87. Tert-butyl 4-{2-[4-(trifluoromethyl)phenyl]oxazolo[5,4-b]pyridin-6-yl}piperidine-1-carboxylate:

TABLE-1

| Example | Structure |
|---------|-----------|
| 1 | 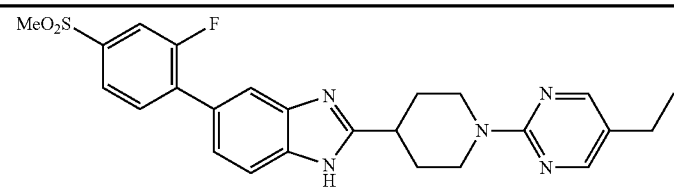 |
| 2 | 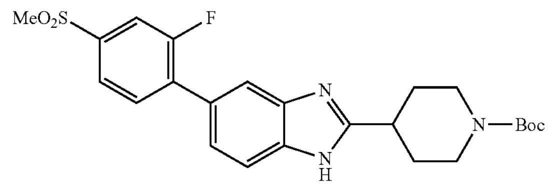 [SMILES: CC(C)(C)OC(=O)N1CCC(c2nc3cc(-c4ccc(S(C)(=O)=O)cc4F)ccc3[nH]2)CC1] |
| 3 | 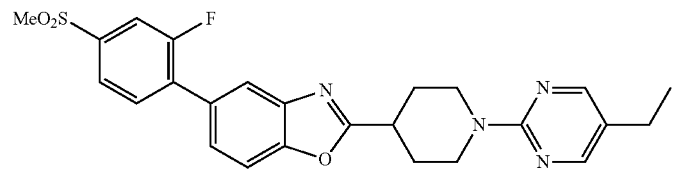 [SMILES: CCc1cnc(N2CCC(c3nc4cc(-c5ccc(S(C)(=O)=O)cc5F)ccc4o3)CC2)nc1] |
| 4 | 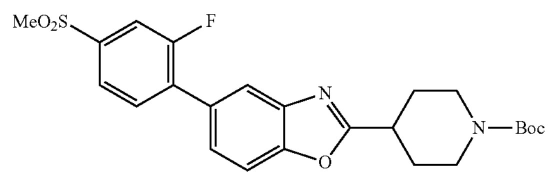 [SMILES: CC(C)(C)OC(=O)N1CCC(c2nc3cc(-c4ccc(S(C)(=O)=O)cc4F)ccc3o2)CC1] |
| 5 | (tentative) |
| 6 | 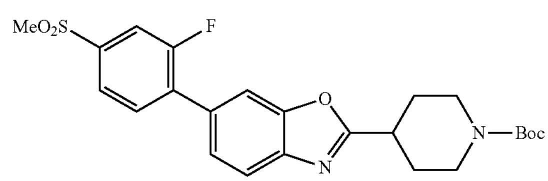 [SMILES: CC(C)(C)OC(=O)N1CCC(c2nc3ccc(-c4ccc(S(C)(=O)=O)cc4F)cc3o2)CC1] |
| 7 | 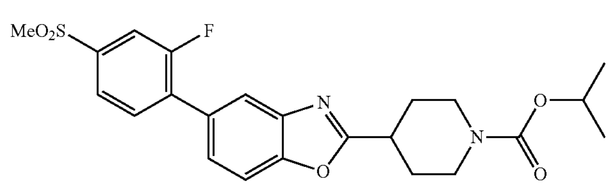 [SMILES: CC(C)OC(=O)N1CCC(c2nc3cc(-c4ccc(S(C)(=O)=O)cc4F)ccc3o2)CC1] |

TABLE-1-continued

| Example | Structure |
|---|---|
| 8 | 5-(4-(methylsulfonyl)-2-fluorophenyl)-7-fluoro-2-(1-Boc-piperidin-4-yl)benzo[d]oxazole |
| 9 | 5-(4-cyanophenyl)-2-(1-Boc-piperidin-4-yl)benzo[d]oxazole |
| 10 | 5-(4-(methylsulfonyl)-3-fluorophenyl)-2-(1-Boc-piperidin-4-yl)benzo[d]oxazole |
| 11 | 5-(4-(1H-tetrazol-1-yl)phenyl)-2-(1-Boc-piperidin-4-yl)benzo[d]oxazole |
| 12 | 5-(4-(1H-tetrazol-1-yl)-2-fluorophenyl)-2-(1-Boc-piperidin-4-yl)benzo[d]oxazole |
| 13 | 5-(4-(trifluoromethyl)phenyl)-2-(1-Boc-piperidin-4-yl)benzo[d]oxazole |
| 14 | 5-(4-(1H-tetrazol-1-yl)-2-fluorophenyl)-2-(1-isopropoxycarbonyl-piperidin-4-yl)benzo[d]oxazole |

TABLE-1-continued

| Example | Structure |
|---|---|
| 15 | 5-(4-(1H-tetrazol-1-yl)-3-fluorophenyl)-2-(1-Boc-piperidin-4-yl)benzo[d]oxazole |
| 16 | 5-(4-(1H-tetrazol-1-yl)-2-fluorophenyl)-2-(1-(5-ethylpyrimidin-2-yl)piperidin-4-yl)benzo[d]oxazole |
| 17 | 5-(4-cyano-3-fluorophenyl)-2-(1-Boc-piperidin-4-yl)benzo[d]oxazole |
| 18 | isopropyl 4-(5-(4-(1H-tetrazol-1-yl)-3-fluorophenyl)benzo[d]oxazol-2-yl)piperidine-1-carboxylate |
| 19 | 5-(4-(1H-tetrazol-5-yl)-3-fluorophenyl)-2-(1-Boc-piperidin-4-yl)benzo[d]oxazole |
| 20 | 4-(2-(1-Boc-piperidin-4-yl)benzo[d]oxazol-5-yl)-2-chlorobenzamide |
| 21 | 4-(2-(1-Boc-piperidin-4-yl)benzo[d]oxazol-5-yl)-2-fluorobenzamide |

TABLE-1-continued

| Example | Structure |
|---|---|
| 22 | 5-(3-fluoro-4-isopropoxyphenyl)-2-(1-Boc-piperidin-4-yl)benzoxazole |
| 23 | cyclobutyl 4-(5-(2-fluoro-4-(1H-tetrazol-1-yl)phenyl)benzoxazol-2-yl)piperidine-1-carboxylate |
| 24 | sec-butyl 4-(5-(2-fluoro-4-(1H-tetrazol-1-yl)phenyl)benzoxazol-2-yl)piperidine-1-carboxylate |
| 25 | pentan-3-yl 4-(5-(2-fluoro-4-(1H-tetrazol-1-yl)phenyl)benzoxazol-2-yl)piperidine-1-carboxylate |
| 26 | 5-(2-fluoro-4-(1H-tetrazol-1-yl)phenyl)-2-(piperidin-4-yl)benzoxazole |
| 27 | isopropyl 4-(5-(4-(trifluoromethyl)phenyl)benzoxazol-2-yl)piperidine-1-carboxylate |

TABLE-1-continued

| Example | Structure |
|---------|-----------|
| 28 | 4-formylphenyl benzoxazole-2-yl piperidine-1-carboxylic acid isopropyl ester |
| 29 | 4-(difluoromethyl)phenyl benzoxazole-2-yl piperidine-1-carboxylic acid isopropyl ester |
| 30 | 2-chloro-4-(benzoxazol-5-yl)benzamide piperidine-1-carboxylic acid isopropyl ester |
| 31 | 2-fluoro-4-(benzoxazol-5-yl)benzamide piperidine-1-carboxylic acid isopropyl ester |
| 32 | 4-(tetrazol-1-yl)-2-fluorophenyl benzoxazole-2-yl piperidine 1-(2-methylpropanoyl) |
| 33 | 4-(difluoromethyl)phenyl benzoxazole-2-yl piperidine-1-carboxylic acid isopropyl ester |
| 34 | 6-(benzoxazol-5-yl)nicotinic acid piperidine-1-carboxylic acid isopropyl ester |

TABLE-1-continued

| Example | Structure |
|---|---|
| 35 | (1-tetrazolyl-2-fluorophenyl)-benzoxazol-2-yl-piperidine-N-SO₂Me |
| 36 | (5-carbamoylpyridin-2-yl)-benzoxazol-2-yl-piperidine-N-C(O)O-iPr |
| 37 | (4-carbamoyl-2-fluorophenyl)-benzoxazol-2-yl-piperidine-N-C(O)O-iPr |
| 38 | (4-carbamoyl-2-chlorophenyl)-benzoxazol-2-yl-piperidine-N-C(O)O-iPr |
| 39 | (4-carbamoyl-3-fluorophenyl)-benzoxazol-2-yl-piperidine-N-C(O)-CH₂CH(CH₃)₂ |
| 40 | (1-tetrazolyl-2-fluorophenyl)-benzoxazol-2-yl-piperidine-N-C(O)-CH₂CH(CH₃)₂ |
| 41 | (1-tetrazolyl-2-fluorophenyl)-benzoxazol-2-yl-piperidine-N-CH₂CH₂-OMe |

TABLE-1-continued
| Example | Structure |
|---|---|
| 42 | 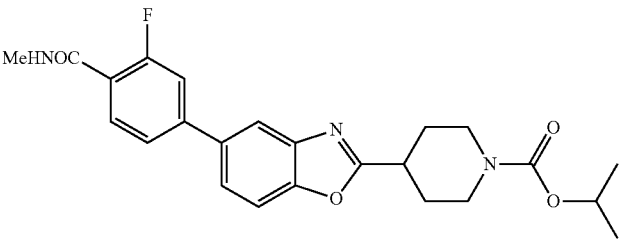 |
| 43 | 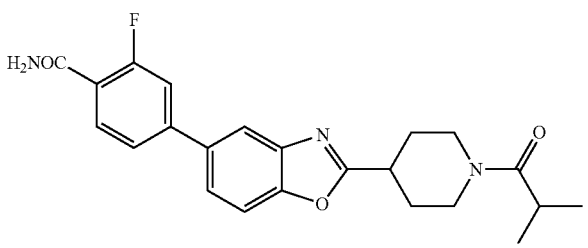 [SMILES: CC(C)C(=O)N1CCC(c2nc3cc(-c4ccc(C(N)=O)c(F)c4)ccc3o2)CC1] |
| 44 | 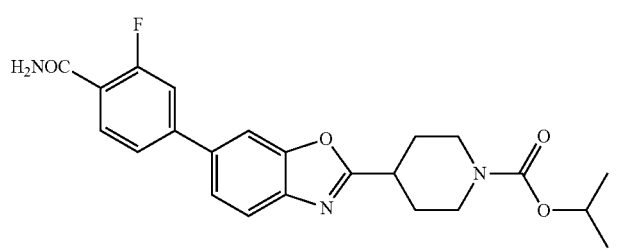 [SMILES: CC(C)OC(=O)N1CCC(c2nc3ccc(-c4ccc(C(N)=O)c(F)c4)cc3o2)CC1] |
| 45 | 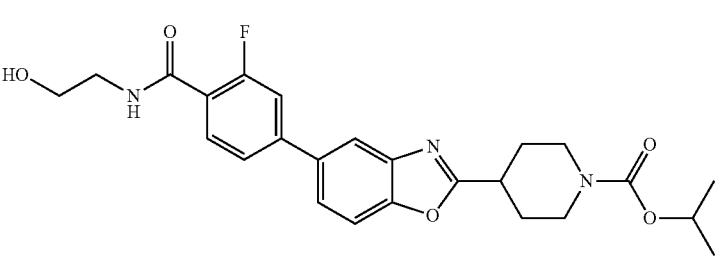 [SMILES: CC(C)OC(=O)N1CCC(c2nc3cc(-c4ccc(C(=O)NCCO)c(F)c4)ccc3o2)CC1] |
| 46 | 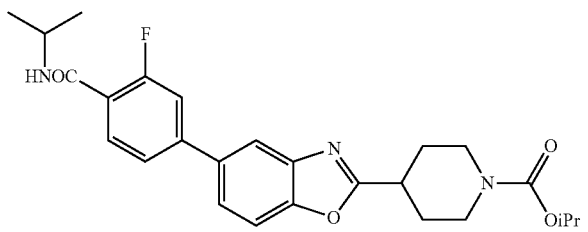 |
| 47 | 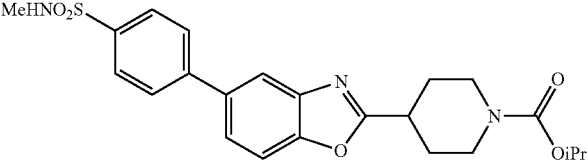 |
| 48 | 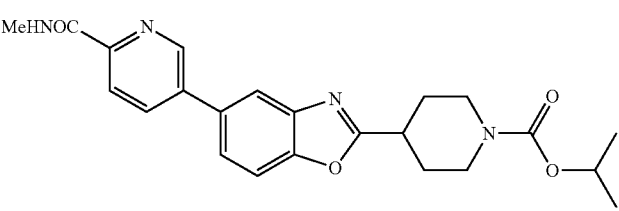 |

TABLE-1-continued
| Example | Structure |
|---|---|
| 49 | 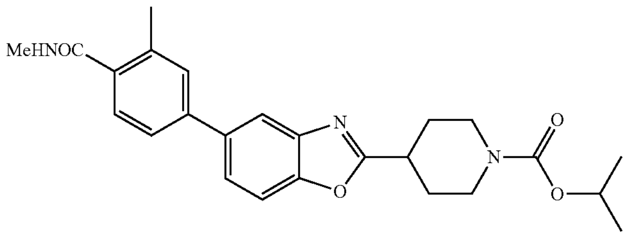 |
| 50 | 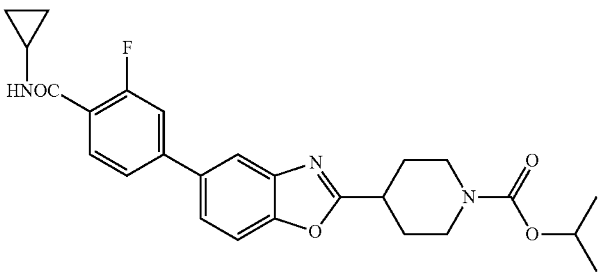 |
| 51 | 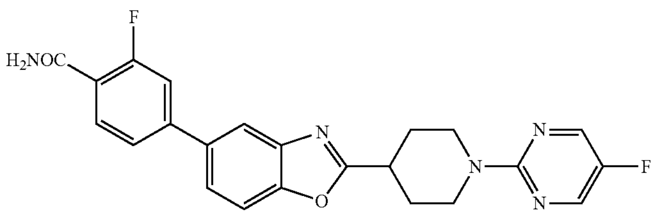 [SMILES: NC(=O)c1ccc(-c2ccc3oc(C4CCN(c5ncc(F)cn5)CC4)nc3c2)cc1F] |
| 52 | 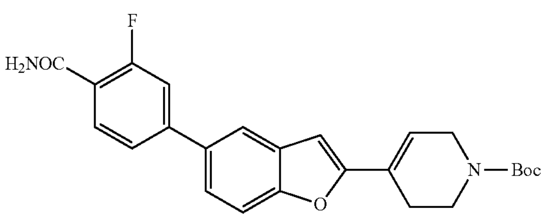 [SMILES: CC(C)(C)OC(=O)N1CC=C(c2cc3cc(-c4ccc(C(N)=O)c(F)c4)ccc3o2)CC1] |
| 53 | 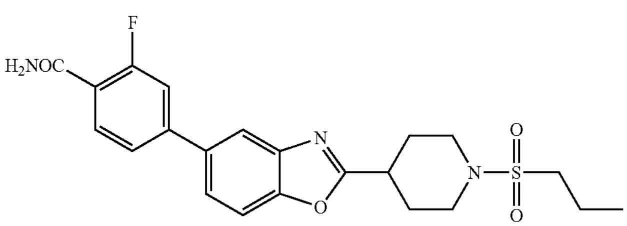 [SMILES: CCCS(=O)(=O)N1CCC(c2nc3cc(-c4ccc(C(N)=O)c(F)c4)ccc3o2)CC1] |
TABLE-2
| 56 | 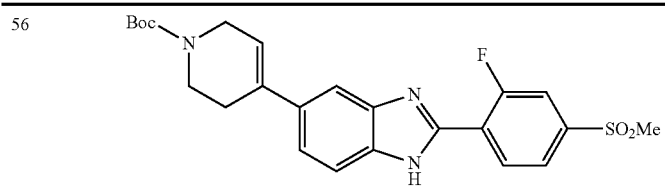 |

TABLE-2-continued
| 57 | 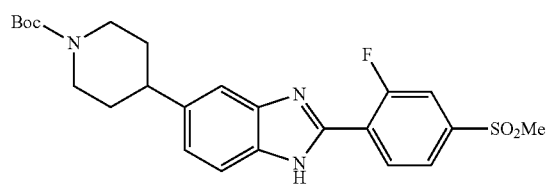 [SMILES: CC(C)(C)OC(=O)N1CCC(c2ccc3[nH]c(-c4ccc(S(C)(=O)=O)cc4F)nc3c2)CC1] |
| 58 | 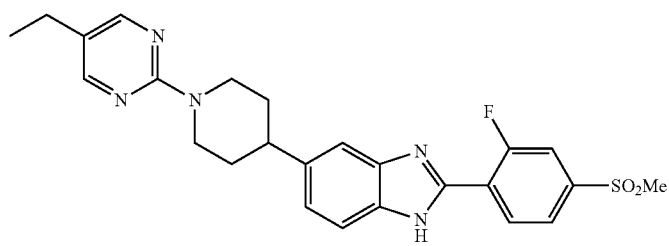 [SMILES: CCc1cnc(N2CCC(c3ccc4[nH]c(-c5ccc(S(C)(=O)=O)cc5F)nc4c3)CC2)nc1] |
| 59 | 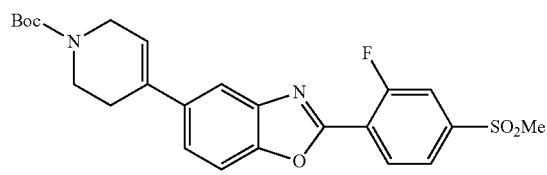 [SMILES: CC(C)(C)OC(=O)N1CC=C(c2ccc3oc(-c4ccc(S(C)(=O)=O)cc4F)nc3c2)CC1] |
| 60 | 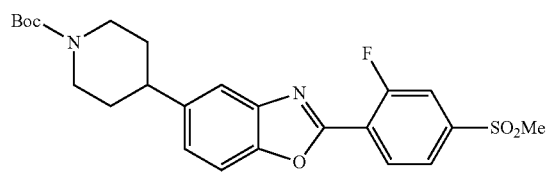 |
| 61 | 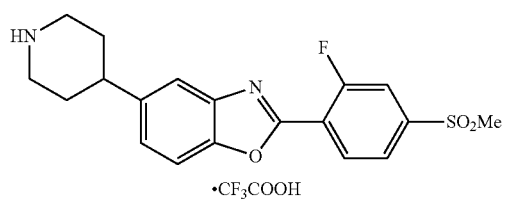 |
| 62 | 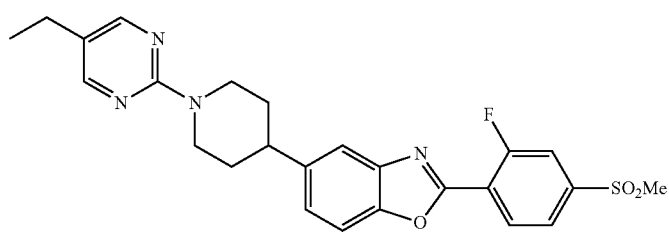 [SMILES: CCc1cnc(N2CCC(c3ccc4oc(-c5ccc(S(C)(=O)=O)cc5F)nc4c3)CC2)nc1] |
| 63 | 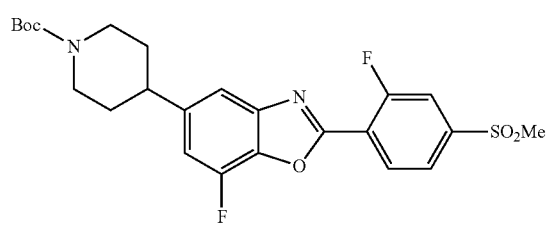 [SMILES: CC(C)(C)OC(=O)N1CCC(c2cc(F)c3oc(-c4ccc(S(C)(=O)=O)cc4F)nc3c2)CC1] |

TABLE-2-continued
| | |
|---|---|
| 64 | 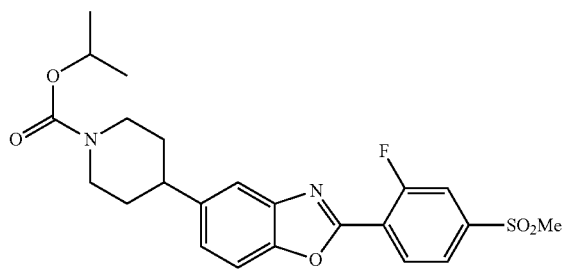 [SMILES: CC(C)OC(=O)N1CCC(c2ccc3oc(-c4ccc(S(C)(=O)=O)cc4F)nc3c2)CC1] |
| 65 | 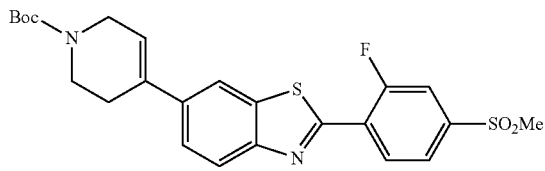 [SMILES: CC(C)(C)OC(=O)N1CC=C(c2ccc3nc(-c4ccc(S(C)(=O)=O)cc4F)sc3c2)CC1] |
| 66 | 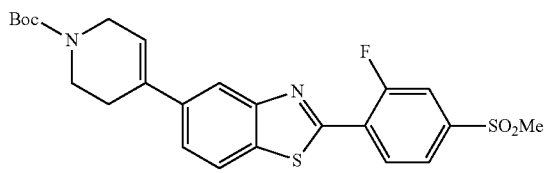 [SMILES: CC(C)(C)OC(=O)N1CC=C(c2ccc3sc(-c4ccc(S(C)(=O)=O)cc4F)nc3c2)CC1] |
| 67 | 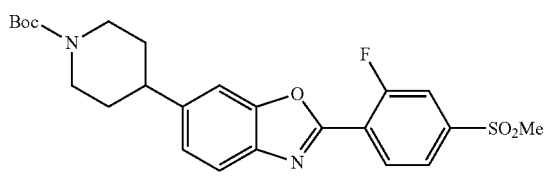 [SMILES: CC(C)(C)OC(=O)N1CCC(c2ccc3nc(-c4ccc(S(C)(=O)=O)cc4F)oc3c2)CC1] |
| 68 | 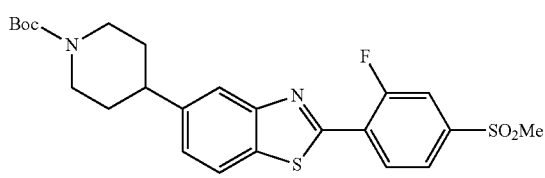 |
| 69 | 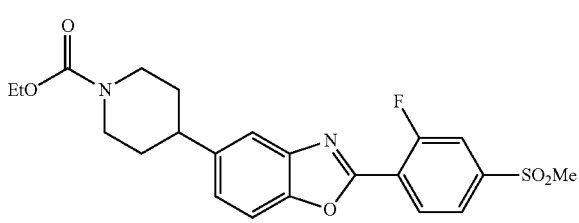 [SMILES: CCOC(=O)N1CCC(c2ccc3oc(-c4ccc(S(C)(=O)=O)cc4F)nc3c2)CC1] |
| 70 | 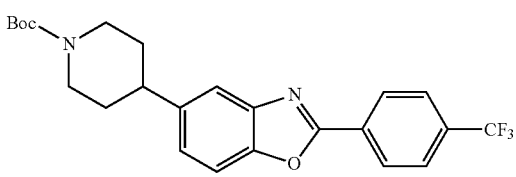 [SMILES: CC(C)(C)OC(=O)N1CCC(c2ccc3oc(-c4ccc(C(F)(F)F)cc4)nc3c2)CC1] |
| 71 | 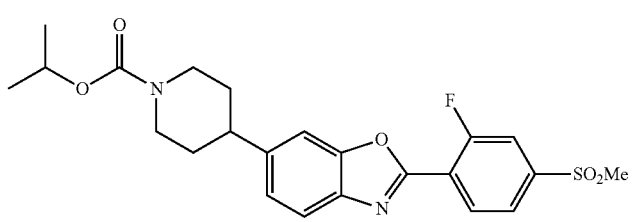 [SMILES: CC(C)OC(=O)N1CCC(c2ccc3nc(-c4ccc(S(C)(=O)=O)cc4F)oc3c2)CC1] |

TABLE-2-continued
| 72 | 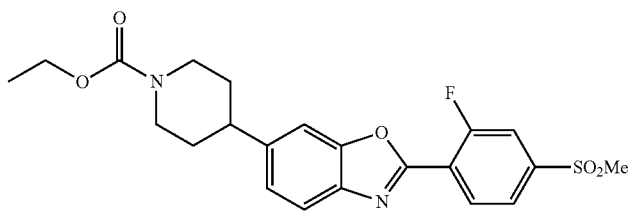 [SMILES: CCOC(=O)N1CCC(c2ccc3nc(-c4ccc(S(C)(=O)=O)cc4F)oc3c2)CC1] |
| 73 | 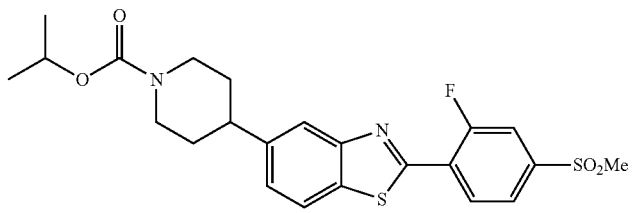 [SMILES: CC(C)OC(=O)N1CCC(c2ccc3sc(-c4ccc(S(C)(=O)=O)cc4F)nc3c2)CC1] |
| 74 | 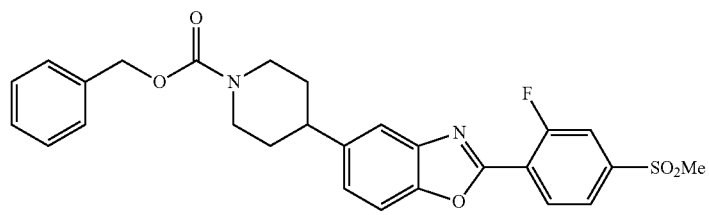 [SMILES: CS(=O)(=O)c1ccc(-c2nc3cc(C4CCN(C(=O)OCc5ccccc5)CC4)ccc3o2)c(F)c1] |
| 75 | 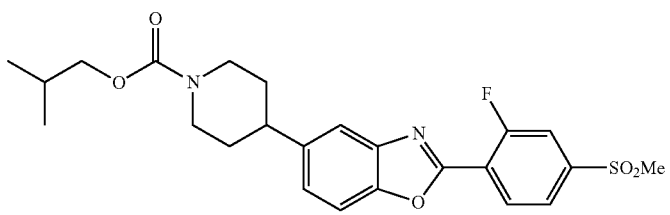 [SMILES: CC(C)COC(=O)N1CCC(c2ccc3oc(-c4ccc(S(C)(=O)=O)cc4F)nc3c2)CC1] |
| 76 | 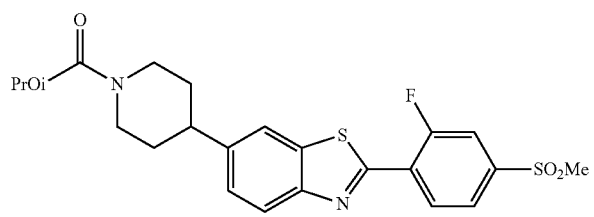 |
| 77 | 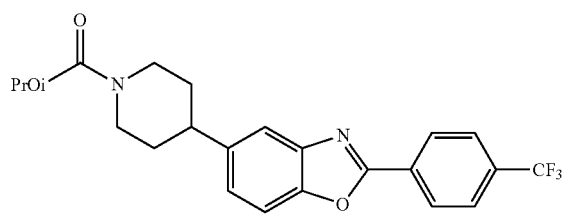 |
| 78 | 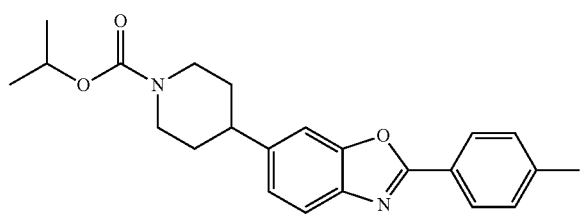 [SMILES: Cc1ccc(-c2nc3ccc(C4CCN(C(=O)OC(C)C)CC4)cc3o2)cc1] |

TABLE-2-continued
| 79 | 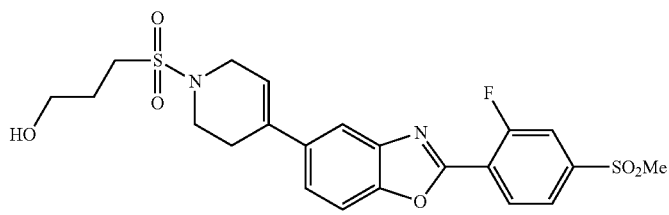 [SMILES: CS(=O)(=O)c1ccc(-c2nc3cc(C4=CCN(S(=O)(=O)CCCO)CC4)ccc3o2)c(F)c1] |
| 80 | 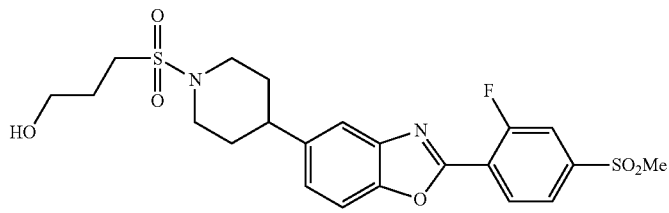 |
| 81 | 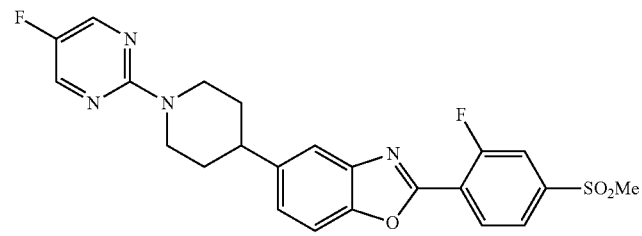 [SMILES: CS(=O)(=O)c1ccc(-c2nc3cc(C4CCN(c5ncc(F)cn5)CC4)ccc3o2)c(F)c1] |
| 82 | 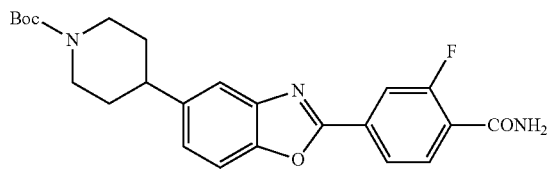 [SMILES: CC(C)(C)OC(=O)N1CCC(c2ccc3oc(-c4ccc(C(N)=O)c(F)c4)nc3c2)CC1] |
| 83 | 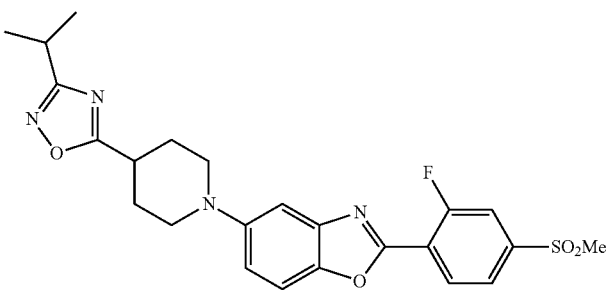 [SMILES: CC(C)c1noc(C2CCN(c3ccc4oc(-c5ccc(S(C)(=O)=O)cc5F)nc4c3)CC2)n1] |
| 84 | 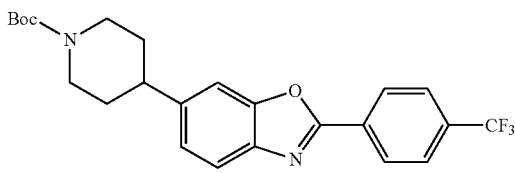 [SMILES: CC(C)(C)OC(=O)N1CCC(c2ccc3nc(-c4ccc(C(F)(F)F)cc4)oc3c2)CC1] |
| 85 | 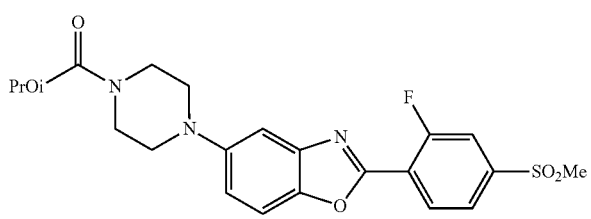 |

TABLE-2-continued

| 86 | 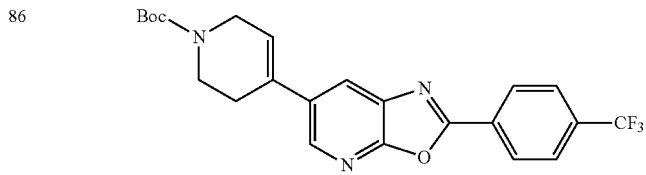 |
| 87 | 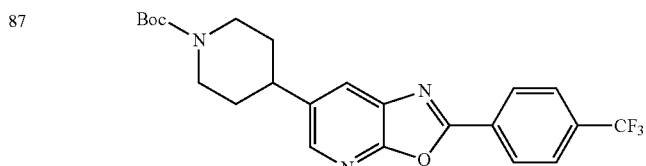 |

Yet another embodiment of the present invention is a method for treating a GPR119 receptor related disorder by administering to a subject in need of such treatment an effective amount of at least one compound of the present invention, such as a compound of formula (A), (A-I), (A-II), (A-III), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB) (B-IIB), (B-IIIB), (B-IVB), or (B-V) as defined above.

Yet another embodiment of the present invention is a method for treating a GPR119 receptor related disorder by administering to a subject in need of such treatment an effective amount of at least one compound of the present invention, such as a compound of formula (A), (A-I), (A-II), (A-III), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), or (B-V) as defined above, in combination (simultaneously or sequentially) with at least one other therapeutic agent. In a preferred embodiment, the GPR119 receptor related disorder is a metabolic disorder and in particular the metabolic disorder is diabetes and/or obesity.

More particularly, the compounds of formula (A), (A-I), (A-II), (A-III), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), and (B-V) as defined above can be administered for the treatment, prevention and/or amelioration of GPR119 receptor associated diseases or disorders including, but not limited to, diabetes and other metabolic disorders or diseases.

Yet another embodiment of the present invention pertains to the use of a compound of the present invention, such as a compound of formula (A), (A-I), (A-II), (A-M), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), or (B-V) as defined above, or a composition thereof in the manufacture of a medicament for modulating the activity of a GPR 119 receptor.

More particularly, the present invention pertains to the use of a compound of the present invention, such as a compound of formula (A), (A-I), (A-II), (A-III), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), or (B-V) as defined above, or a composition thereof in the manufacture of a medicament for agonizing a GPR 119 receptor The compounds of the present invention, such as the compounds of formula (A), (A-I), (A-II), (A-III), (A-IV), (A-IA), (A-IIA), (A-IIIA), (A-IVA), (A-IB) (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB). (B-IVB), and (B-V) as defined above are useful in the treatment of a variety of metabolic disorders including, but not limited to, diabetes mellitus, type 1 diabetes, type 2 diabetes, inadequate glucose tolerance, impaired glucose tolerance, insulin resistance, hyperglycemia, hyperlipidemia, hypertriglyceridemia, hypercholesterolemia, dyslipidemia, atherosclerosis, stroke, syndrome X, hypertension, pancreatic beta-cell insufficiency, enteroendocrine cell insufficiency, glucosuria, metabolic acidosis, cataracts, diabetic nephropathy, diabetic neuropathy, peripheral neuropathy, diabetic coronary artery disease, diabetic cerebrovascular disease, diabetic peripheral vascular disease, diabetic retinopathy, metabolic syndrome, a condition related to diabetes mellitus, myocardial infarction, learning impairment, memory impairment, a neurodegenerative disorder, a condition ameliorated by increasing a blood GLP-1 level in an individual with a neurodegenerative disorder, excitotoxic brain damage caused by severe epileptic seizures, Alzheimer's disease, Parkinson's disease, Huntington's disease, prion-associated disease, stroke, motor-neuron disease, traumatic brain injury, spinal cord injury, obesity, delayed wound healing, abnormal heart function, myocardial ischemia, low HDL, high LDL, non-cardiac ischemia, vascular restenosis, pancreatitis, neurodegenerative disease, lipid disorders, cognitive impairment and dementia, bone disease, HIV protease associated lipodystrophy and glaucoma.

More particularly, the compounds of the present invention, such as the compounds of formula (A), (A-I), (A-II), (A-III), (A-IV), (A-IA), (A-IIA), (A-IIIA), (A-IVA), (A-IB), (A-IIB), (A-IIIB), (A-IVB), (A-V), (B), (B-I), (B-II), (B-III), (B-IV), (B-IA), (B-IIA), (B-IIIA), (B-IVA), (B-IB) (B-IIB), (B-IIIB), (B-IVB), and (B-V) as defined above can be administered for the treatment of metabolic-related disorder selected from the group consisting of type 2 diabetes, hyperglycemia, hyperinsulinemia, hyperlipidemia, hypertriglyceridemia, insulin resistance, type 1 diabetes, idiopathic type 1 diabetes (type Ib), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, coronary heart disease, vascular restenosis, restenosis, restenosis after angioplasty, peripheral vascular disease, claudication, intermittent claudication, cell death associated with myocardial infarction (e.g. necrosis and apoptosis), dyslipidemia, postprandial lipemia, conditions of impaired glucose tolerance (IGT), impaired glucose metabolism, conditions of impaired glucose metabolism, conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, ischemic stroke, transient ischemic attacks, stroke, erectile dysfunction, skin and connective tissue disorders, foot ulcerations, ulcerative colitis, endothelial dysfunction, and impaired vascular compliance.

More particularly, the compounds of the present invention, such as the compounds of formula (A), (A-I), (A-II), (A-III), (A-IV), (A-IA), (A-IIA), (A-IIIA), (A-IVA), (A-IB) (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), and (B-V) as defined above can be administered for the treatment of type 2 diabetes, hyperglycemia, hyperlipidemia, hypertriglyceridemia, type 1 diabetes, dyslipidemia, and syndrome X.

The invention further provides a pharmaceutical composition comprising one or more compounds of the present invention together with a pharmaceutically acceptable carrier. The pharmaceutical composition may further comprise one or more of the active ingredients identified above, such as other anti-cancer agents. In one embodiment, the pharmaceutical composition includes a therapeutically effective amount of one or more compounds of the present invention, such as at least one compound of formula (A), (A-I), (A-II), (A-III), (A-IV), (A-IA), (A-IIA), (A-IIIA), (A-IVA), (A-IB) (A-IIB), (A-IIIB), (A-IVB), (A-V), (B), (B-I), (B-II), (B-III), (B-IV), (B-IA), (B-IIA), (B-IIIA), (B-IVA), (B-IB), (B-IIB), (B-IIIB), (B-IVB), or (B-V) as defined above.

Yet another embodiment is a method of treating metabolic disorder in a subject in need thereof by administering a therapeutically effective amount of a compound of the present invention. For example, the compounds of the present invention are effective for treating diabetes (e.g., type II diabetes) and/or obesity.

DETAILED DESCRIPTION

Figure 1:
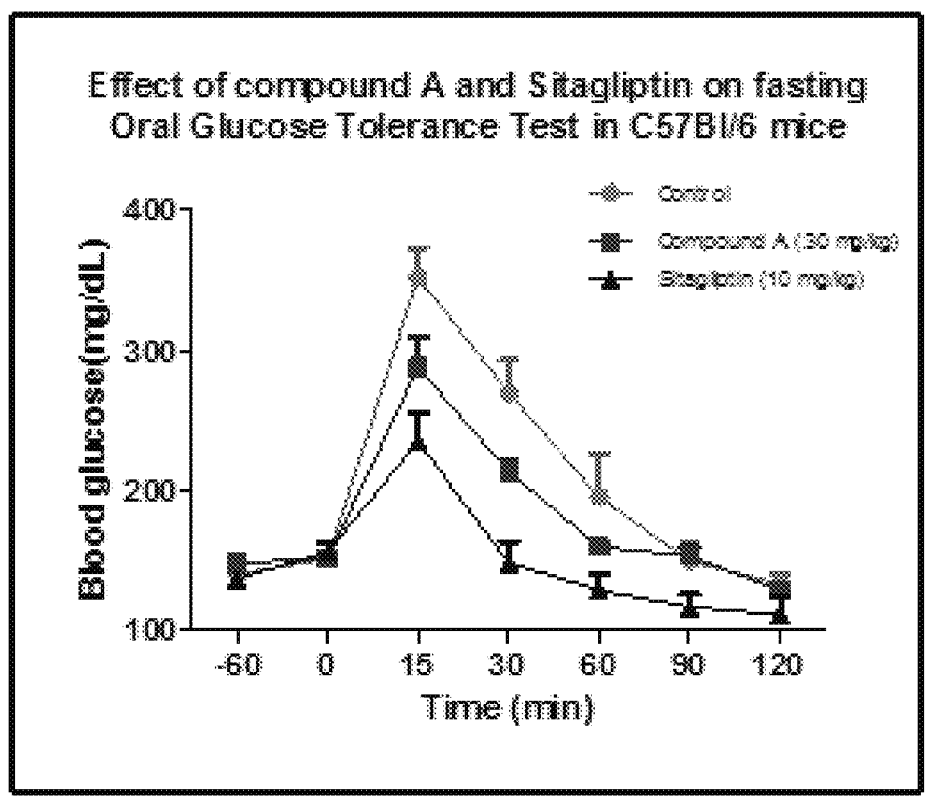
FIG. 1 is a graph of blood glucose over time in C57BI/6J mice according to the oral glucose tolerance test (Biological Assay Procedure E) before and after oral administration of vehicle (control), compound A (Example 64@ 30 mg/kg), or sitagliptin (10 mg/kg @ 10 mg/kg).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. Accordingly, all combinations of uses and medical indications described herein specifically embraced by the present invention just as if each and every subcombination of uses and medical indications was individually and explicitly recited herein.

As used herein the following definition shall apply unless otherwise indicated. Further many of the groups defined herein can be optionally substituted. The listing of substituents in the definition is exemplary and is not to be construed to limit the substituents defined elsewhere in the specification.

The term 'alkyl' refers to a straight or branched hydrocarbon chain radical consisting solely of carbon and hydrogen atoms, containing no unsaturation, having, unless otherwise indicated, from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term substituted or unsubstituted $(C_{1-4})$alkyl refers to an alkyl group as defined above having up to 4 carbon atoms, and the term substituted or unsubstituted $(C_{1-6})$alkyl refers to an alkyl group as defined above having up to 6 carbon atoms.

The term "alkenyl" refers to an aliphatic hydrocarbon group containing a carbon-carbon double bond and which may be a straight or branched or branched chain having, unless otherwise indicated, 2 to about 10 carbon atoms, e.g., ethenyl, 1-propenyl, 2-propenyl (allyl), iso-propenyl, 2-methyl-1-propenyl, 1-butenyl, and 2-butenyl.

The term substituted or unsubstituted $(C_{2-6})$ alkenyl refers to an alkenyl group as defined above having up to 6 carbon atoms.

The term "alkynyl" refers to a straight or branched chain hydrocarbyl radicals having at least one carbon-carbon triple bond, and having, unless otherwise indicated, in the range of 2 up to 12 carbon atoms (with radicals having in the range of about 2 up to 10 carbon atoms presently being preferred) e.g., ethynyl, propynyl, and butynyl.

The term substituted or unsubstituted $(C_{2-6})$ alkynyl refers to an alkynyl group as defined above having up to 6 carbon atoms.

The term "alkoxy" denotes an alkyl group as defined above attached via an oxygen linkage to the rest of the molecule. Representative examples of these groups are —$OCH_3$ and —$OC_2H_5$. The term "substituted alkoxy" refers to an alkoxy group where the alkyl constituent is substituted (i.e., —O-(substituted alkyl) wherein the term "substituted alkyl" is the same as defined above for "alkyl". For example "alkoxy" refers to the group —O-alkyl, including, unless otherwise indicated, from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl" denotes a non-aromatic mono or multicyclic ring system of, unless otherwise indicated, 3 to about 12 carbon atoms such as cyclopropyl, cyclobutyl, cyclopentyl, and cyclohexyl. Examples of multicyclic cycloalkyl groups include perhydronapththyl, adamantyl and norbornyl groups, bridged cyclic groups, and spirirobicyclic groups, e.g., sprio (4,4) non-2-yl.

The term "$C_{3-8}$ cycloalkyl" refers to a cycloalkyl group as defined above having up to 8 atoms.

The term "cycloalkylalkyl" refers to a cyclic ring-containing radical containing, unless otherwise indicated, in the range of 3 up to about 8 carbon atoms directly attached to an alkyl group which are then attached to the main structure at any carbon from alkyl group that results in the creation of a stable structure such as cyclopropylmethyl, cyclobuyylethyl, and cyclopentylethyl.

The term "$C_{3-6}$ cycloalkylalkyl" refers to a cycloalkylalkyl group as defined above having up to 6 atoms.

The term "cycloalkenyl" refers to cyclic ring-containing radicals containing, unless otherwise indicated, in the range of 3 up to about 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from alkyl group that results in the creation of a stable structure The term "$C_{3-6}$ cycloalkenyl" refers to a cycloalkenyl group as defined above having up to 6 atoms.

The term "aryl" refers to aromatic radicals having, unless otherwise indicated, in the range of 6 up to 20 carbon atoms such as phenyl, naphthyl, tetrahydronapthyl, indanyl, and biphenyl.

The term "arylalkyl" refers to an aryl group as defined above directly bonded to an alkyl group as defined above. e.g., —$CH_2C_6H_5$ and —$C_2H_5C_6H_5$.

The term "heterocyclic ring" refers to a non-aromatic 3 to 15 member ring radical which, consists of carbon atoms and at least one heteroatom selected from the group consisting of nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl" refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl" refers to heteroaryl ring radical as defined above directly bonded to an alkyl group. The heteroarylalkyl radical may be attached to the main structure at any carbon atom from alkyl group that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure.

The term "cyclic ring" refers to a cyclic ring containing, unless otherwise indicated, 3 to 10 carbon atoms.

The term "substituted" unless otherwise specified, refers to substitution with any one or any combination of the following substituents and may be the same or different which one or more are selected from the groups such as hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocycyl, substituted or unsubstituted heterocyclcyalkyl, substituted or unsubstituted aryl, substituted or unsubstituted arylalkyl, substituted or unsubstituted heteroaryl, substituted or unsubstituted heteroarylalkyl, —COOR', —C(O)R', —C(S)R', —C(O)NR' R", —C(O)ONR'R", —NR'R", —NR'CONR'R", —N(R')SOR", —N(R')SO$_2$R", —(=N—N(R')R"), —NR'C(O)OR", —NR'R", —NR'C(O)R"—, —NR'C(S)R"—NR'C(S)NR"R'", —SONR'R"—, —SO$_2$NR'R"—, —OR', —OR' C(O)NR"R'", —OR'C(O)OR"—, —OC(O)R', —OC(O)NR'R", —R'NR"C(O)R'", —R'OR", —R'C(O)OR", —R'C(O)NR'R'", —R'C(O)R", —R'OC(O)R", —SR', —SOR', —SO$_2$R', —ONO$_2$ wherein R', R" and R'" in each of the above groups can independently be hydrogen, hydrogen, hydroxy, halogen, carboxyl, cyano, nitro, oxo (=O), thio (=S), imino (=NR'), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocycyl, substituted or unsubstituted heterocyclcyalkyl, substituted or unsubstituted aryl, substituted or unsubstituted arylalkyl, substituted or unsubstituted heteroaryl, or substituted or unsubstituted heteroarylalkyl, or any two of R', R" and R'" may be joined to form a substituted or unsubstituted saturated or unsaturated 3-10 membered ring, which may optionally include heteroatoms which may be the same or different and are selected from O, NR$^X$ or S or form oxo (=O), thio (=S) or imino (=NR', where R' is defined above). The substituents in the aforementioned "substituted" groups cannot be further substituted. For example, when the substituent on "substituted alkyl" is "substituted aryl", the substituent on "substituted aryl" cannot be "substituted alkenyl". Substitution or the combinations of substituents envisioned by this invention are preferably those that result in the formation of a stable or chemically feasible compound. The term stable as used herein refers to the compounds or the structure that are not substantially altered when subjected to conditions to allow for their isolation, production, detection and preferably their recovery, purification and incorporation into a pharmaceutical composition.

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" refer to haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl) ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

The term "stereoisomer" refers to compounds, which have identical chemical composition, but differ with regard to arrangement of the atoms and the groups in space. These include enantiomers, diastereomers, geometrical isomers, atropisomer or conformational isomers.

All the stereoisomers of compounds described herein are within the scope of this invention. Racemic mixtures are also encompassed within the scope of this invention. Therefore, single stereochemical isomers as well enantiomeric, diastereoisomeric and geometric (or conformational) mixtures of the present compounds fall within the scope of the invention.

Certain of the compounds described herein contain one or more asymmetric centers and can thus give rise to enantiomers, diastereomers, and other stereoisomeric forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For the instance the non-limiting example of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as MeI and (Me)$_2$SO$_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The term "agonist" generally refers to a moiety that interacts and activates a receptor, such as, the GPR119 receptor and initiates a physiological or pharmacological response characteristic of that receptor. For example, when moieties activate the intracellular response upon binding to the receptor, or enhance GTP binding to membranes.

The term "contact or contacting" refers to bringing the indicated moieties together, whether in an in vitro system or an in vivo system. Thus, "contacting" a GPR 119 receptor with a compound of the invention includes the administration of a compound of the present invention to an individual, preferably a human, having a GPR 119 receptor, as well as, for example, introducing a compound of the invention into a sample containing a cellular or more purified preparation containing a GPR 119 receptor.

The term "hydrate" as used herein means a compound of the invention or a salt thereof, that further includes a stoichiometric or non-stoichiometric amount of water bound by non-covalent intermolecular forces.

The terms "in need of treatment" and "in need thereof," when referring to treatment are used interchangeably to refer to a judgment made by a caregiver (e.g. physician, nurse, or nurse practitioner in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by the compounds of the invention. Accordingly, the compounds of the invention can be used in a protective or preventive manner; or compounds of the invention can be used to alleviate, inhibit or ameliorate the disease, condition or disorder.

The term "modulate or modulating" refers to an increase or decrease in the amount, quality, response or effect of a particular activity, function or molecule.

The term "pharmaceutical composition" refers to a composition comprising at least one active ingredient, including but not limited to, salts, solvates, and hydrates of compounds of the present invention whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "solvate" as used herein means a compound of the invention or a salt, thereof, that further includes a stoichiometric or non-stoichiometric amount of a solvent bound by non-covalent intermolecular forces. Preferred solvents are volatile, non-toxic, and/or acceptable for administration to humans in trace amounts.

Abbreviations, unless otherwise indicated, used herein have their conventional meaning within the chemical and biological arts.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including, but not limited to, disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the subject, notwithstanding that the subject may still be afflicted with the underlying disorder. For prophylactic benefit, the compositions may be administered to a subject at risk of developing a particular disease, or to a subject reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "individual" or "subject" is intended to mean any animal, including mammals, preferably mice, rats, other rodents, rabbits, dogs, cats, swine, cattle, sheep, horses, or primates and most preferably humans. In another embodiment, the individual is a human and in certain embodiments, the human is an infant, child, adolescent or adult. In one embodiment, the individual is at risk for developing a GPR119-related disorder. In one embodiment, the individual is at risk for developing a metabolic-related disease or disorder. Individuals who are at risk include, but are not limited to, those with hereditary history of a metabolic-related disease or disorder, or those in a state of physical health which puts them at risk for a metabolic-related disease or disorder. In another embodiment, the individual has been determined, by the care-giver or someone acting under the guidance of the care-giver, to have a metabolic-related disease or disorder.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

Method of Treatment

In addition to the foregoing beneficial uses for compounds of the present invention as disclosed herein, compounds of the invention are useful in the treatment of additional diseases. Without limitation, these include the following.

The most significant pathologies in type 2 diabetes are impaired insulin signaling at its target tissues ("insulin resistance") and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling.

Physiological signaling systems which function in this manner are well-characterized and include the gut peptides GLP1, GIP and PACAP. These hormones act via their cognate G-protein coupled receptor to stimulate the production of cAMP in pancreatic β-cells. The increased cAMP does not appear to result in stimulation of insulin release during the fasting or preprandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including GPR119, would also stimulate the release of endogenous insulin and consequently promote normoglycemia in type 2 diabetes.

It is also established that increased cAMP, for example as a result of GLP-1 stimulation, promotes β-cell proliferation, inhibits β-cell death and thus improves islet mass. This positive effect on β-cell mass is expected to be beneficial in both type 2 diabetes, where insufficient insulin is produced, and type 1 diabetes, where β-cells are destroyed by an inappropriate autoimmune response.

Some β-cell GPCRs, including GPR119, are also present in the hypothalamus where they modulate hunger, satiety, decrease food intake, controlling or decreasing weight and energy expenditure. Hence, given their function within the hypothalamic circuitry, agonists or inverse agonists of these receptors mitigate hunger, promote satiety and therefore modulate weight.

It is also well-established that metabolic diseases exert a negative influence on other physiological systems. Thus, there is often the co-development of multiple disease states (e.g. type 1 diabetes, type 2 diabetes, inadequate glucose tolerance, insulin resistance, hyperglycemia, hyperlipidemia, hypertriglyceridemia, hypercholesterolemia, dyslipidemia, obesity or cardiovascular disease in "syndrome X") or diseases which clearly occur secondary to diabetes mellitus (e.g. kidney disease, peripheral neuropathy). Thus, it is expected that effective treatment of the diabetic condition will in turn be of benefit to such interconnected disease states.

In some embodiments of the present invention the metabolic-related disorder is selected from type 2 diabetes, hyperglycemia, hyperinsulinemia, hyperlipidemia, hypertriglyceridemia, insulin resistance, type 1 diabetes, idiopathic type 1 diabetes (type Ib), latent autoimmune diabetes in adults (LADA), early-onset type 2 diabetes (EOD), youth-onset atypical diabetes (YOAD), maturity onset diabetes of the young (MODY), malnutrition-related diabetes, gestational diabetes, cardiovascular disease, coronary heart disease, vascular restenosis, restenosis, restenosis after angioplasty, peripheral vascular disease, claudication, intermittent claudication, cell death associated with myocardial infarction (e.g. necrosis and apoptosis), dyslipidemia, post-prandial lipemia, conditions of impaired glucose tolerance (IGT), impaired glucose metabolism, conditions of impaired glucose metabolism, conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, angina pectoris, thrombosis, atherosclerosis, ischemic stroke, transient ischemic attacks, stroke, erectile dysfunction, skin and connective tissue disorders, foot ulcerations, ulcerative colitis, endothelial dysfunction, and impaired vascular compliance.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

The invention also relates to a method of treating diabetes in a mammal that comprises administering to said mammal a therapeutically effective amount of a compound of the present invention.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, Crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditis, Ostheoarthritis, uveoretinitis, pemphigus, polyarthritis, primary biliary cirrhosis, reiter's syndrome, takayasu's arteritis, temporal arteritis, warm autoimmune hemolytic anemia, Wegener's granulomatosis, alopecia universalis, chagas[1] disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention. Examples of cardiovascular conditions include, but are not limited to, atherosclerosis, restenosis, vascular occlusion and carotid obstructive disease.

The invention further provides methods of modulating GPR119 activity by contacting a GPR119 receptor with an amount of a compound of the invention sufficient to modulate the activity of the GPR119. Modulate can be inhibiting or activating GPR119 activity. In some embodiments, the invention provides methods of agonizing GPR119 activity by contacting a GRP119 receptor with an amount of a compound of the invention sufficient to activate the activity of the GPR119 receptor. In some embodiments, the invention provides methods of agonising in a solution by contacting said solution with an amount of a compound of the invention sufficient to activate the activity of the GPR119 receptor in said solution. In some embodiments, the invention provides methods of agonizing GPR119 activity in a cell by contacting said cell with an amount of a compound of the invention sufficient to activate the activity of GPR119 receptor in said cell. In some embodiments, the invention provides methods of agonizing GPR119 activity in a tissue by contacting said tissue with an amount of a compound of the invention sufficient to activate the activity of GPR119 receptor in said tissue. In some embodiments, the invention provides methods of agonizing GPR119 activity in a organism by contacting said organism with an amount of a compound of the invention sufficient to activate the activity of GPR119 receptor in said organism. In some embodiments, the invention provides methods of agonizing GPR119 activity in a animal by contacting said animal with an amount of a compound of the invention sufficient to activate the activity of GPR119 receptor in said animal. In some embodiments, the invention provides methods of agonizing GPR119 activity in a mammal by contacting said mammal with an amount of a compound of the invention sufficient to activate the activity of GPR119 receptor in said mammal. In some embodiments, the invention provides methods of agonizing GPR119 activity in a human by contacting said human with an amount of a compound of the invention sufficient to activate the activity of GPR119 receptor in said human.

Combination Treatment

The present invention also provides methods for combination therapies in which is an agent known to modulate other pathways, or other components of the same pathway, or even overlapping sets of target enzymes or receptors are used in combination with a compound of the present invention. In one aspect, such therapy includes but is not limited to the combination of the subject compound with other agents such as known antidiabetic, anti-obesity agents or any other agents use for the treatment of metabolic disorders to provide a synergistic or additive therapeutic effect.

In the context of the present invention, a compound as described herein or a pharmaceutical composition thereof can be utilized for modulating the activity of GPR 119 receptor related diseases, conditions and/or disorders as described herein. Examples of modulating the activity of GPR1 19 receptor related diseases include the treatment of metabolic related disorders. Metabolic related disorders include, but are not limited to, hyperlipidemia, type 1 diabetes, type 2 diabetes, and conditions associated therewith, such as, but not limited to coronary heart disease, ischemic stroke, restenosis after angioplasty, peripheral vascular disease, claudication, intermittent claudication, cell death associated with myocardial infarction (e.g. necrosis and apoptosis), dyslipidemia, post-prandial lipemia, conditions of impaired glucose tolerance (IGT), conditions of impaired fasting plasma glucose, metabolic acidosis, ketosis, arthritis, obesity, osteoporosis, hypertension, congestive heart failure, left ventricular hypertrophy, peripheral arterial disease, diabetic retinopathy, macular degeneration, cataract, diabetic nephropathy, glomerulosclerosis, chronic renal failure, diabetic neuropathy, metabolic syndrome, syndrome X, premenstrual syndrome, coronary heart disease, angina pectoris, thrombosis, atherosclerosis, myocardial infarction, transient ischemic attacks, stroke, vascular restenosis, hyperglycemia, hyperinsulinemia, hyperlipidemia, hypertriglyceridemia, insulin resistance, impaired glucose metabolism, conditions of impaired glucose tolerance, conditions of impaired fasting plasma glucose, obesity, erectile dysfunction, skin and connective tissue disorders, foot ulcerations, ulcerative colitis, endothelial dysfunction and impaired vascular compliance. In some embodiments, metabolic related disorders include type 1 diabetes, type 2 diabetes, inadequate glucose tolerance, insulin resistance, hyperglycemia, hyperlipidemia, hypertriglyceridemia, hypercholesterolemia, dyslipidemia and syndrome X. Other examples of modulating the activity of GPR1 19 receptor related diseases include the treatment of obesity and/or overweight by decreasing food intake, inducing satiation (i.e., the feeling of fullness), controlling weight gain, decreasing body weight and/or affecting metabolism such that the recipient loses weight and/or maintains weight.

While a compound of the invention can be administered as the sole active pharmaceutical agent (i.e., mono-therapy), the compound can also be used in combination with one or more pharmaceutical agents (i.e., combination-therapy) either administered together or separately for the treatment of the diseases/conditions/disorders described herein. Therefore, another aspect of the present invention includes methods of treatment of a metabolic related disorder, including a weight related disorder, such as obesity, comprising administering to an individual in need of prophylaxis and/or treatment a therapeutically effective amount of a compound of the present invention in combination with one or more additional pharmaceutical agent as described herein.

Suitable pharmaceutical agents that can be used in combination with the compounds of the present invention include anti-obesity agents such as apolipoprotein-B secretion/microsomal triglyceride transfer protein (apo-B/MTP) inhibitors, MCR-4 agonists, cholescystokinin-A (CCK-A) agonists, serotonin and norepinephrine reuptake inhibitors (for example, sibutramine), sympathomimetic agents, β3 adrenergic receptor agonists, dopamine agonists (for example, bromocriptine), melanocyte-stimulating hormone receptor analogues, cannabinoid 1 receptor antagonists [for example, SR141716: N-(piperidin-1-yi)-5-(4-chlorophenyl)-1-(2,4-dichlorophenyl)-4-methyl-1H-pyrazole-3-carboxamide], melanin concentrating hormone antagonists, leptons (the OB protein), leptin analogues, leptin receptor agonists, galanin antagonists, lipase inhibitors (such as tetrahydrolipstatin, i.e., Orlistat), anorectic agents (such as a bombesin agonist), Neuropeptide-Y antagonists, thyromimetic agents, dehydroepiandrosterone or an analogue thereof, glucocorticoid receptor agonists or antagonists, orexin receptor antagonists, urocortin binding protein antagonists, glucagon-like peptide-1 receptor agonists, ciliary neutrotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or reverse agonists, neuromedin U receptor agonists, noradrenergic anorectic agents (for example, phentermine, mazindol and the like) and appetite suppressants (for example, bupropion).

Other anti-obesity agents, including the agents set forth infra, are well known, or will be readily apparent in light of the instant disclosure, to one of ordinary skill in the art.

It is understood that the scope of combination-therapy of the compounds of the present invention with other anti-obesity agents, anorectic agents, appetite suppressant and related agents is not limited to those listed above, but includes in principle any combination with any pharmaceutical agent or pharmaceutical composition useful for the treatment of overweight and obese individuals.

It is understood that the scope of combination-therapy of the compounds of the present invention with other pharmaceutical agents is not limited to those listed herein, supra or infra, but includes in principle any combination with any pharmaceutical agent or pharmaceutical composition useful for the treatment of diseases, conditions or disorders that are linked to metabolic related disorders.

Some embodiments of the present invention include methods of treatment of a disease, disorder, condition or complication thereof as described herein, comprising administering to an individual in need of such treatment a therapeutically effective amount or dose of a compound of the present invention in combination with at least one pharmaceutical agent selected from the group consisting of: sulfonylureas (for example, glyburide, glipizide, glimepiride and other sulfonylureas known in the art), meglitinides (for example, repaglinide, nateglinide and other meglitinides known in the art), biguanides (for example, biguanides include phenformin, metformin, buformin, and biguanides known in the art), α-glucosidase inhibitors [for example, acarbose, N-(1,3-dihydroxy-2-propyl)valiolamine (generic name; voglibose), miglitol, and α-glucosidase inhibitors known in the art], peroxisome proliferators-activated receptor-γ (i.e., PPAR-γ) agonists (for example, rosiglitazone, pioglitazone, tesaglitazar, netoglitazone, GW-409544, GW-501516 and PPAR-γ agonists known in the art), insulin, insulin analogues, HMG-CoA reductase inhibitors (for example, rosuvastatin, pravastatin and its sodium salt, simvastatin, lovastatin, atorvastatin, fluvastatin, cerivastatin, rosuvastatin, pitavastatin, BMS's "superstatin", and HMG-CoA reductase inhibitors known in the art), cholesterol-lowering drugs (for example, fibrates that include: bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art; bile acid sequestrants which include: cholestyramine, colestipol and the like; and niacin), antiplatelet agents (for example, aspirin and adenosine diphosphate receptor antagonists that include: clopidogrel, ticlopidine and the like), angiotensin-converting enzyme inhibitors (for example, captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art), angiotensin II receptor antagonists [for example, losartan (and the potassium salt form)], angiotensin II receptor antagonists known in the art, adiponectin, squalene synthesis inhibitors (for example, (S)-α-[bis[2,2-dimethyl-1-oxopropoxy)methoxy]phosphinyl]-3-phenoxybenzenebutanesulfonic acid, mono potassium salt (BMS-188494) and squalene synthesis inhibitors known in the art), and the like. In some embodiments, compounds of the present invention and the pharmaceutical agents are administered separately. In further embodiments, compounds of the present invention and the pharmaceutical agents are administered together.

Suitable pharmaceutical agents that can be used in conjunction with compounds of the present invention include, but not limited to, amylin agonists (for example, pramlintide), insulin secretagogues (for example, GLP-I agonists; exendin-4; insulinotropin (NN2211); acyl CoA cholesterol acetyltransferase inhibitors (for example, ezetimibe, eflucimibe, and like compounds), cholesterol absorption inhibitors (for example, ezetimibe, pamaqueside and like compounds), cholesterol ester transfer protein inhibitors (for example, CP-529414, JTT-705, CETi-I, and like compounds), microsomal triglyceride transfer protein inhibitors (for example, implitapide, and like compounds), cholesterol modulators (for example, NO-1886, and like compounds), bile acid modulators (for example, GT103-279 and like compounds), insulin signaling pathway modulators, like inhibitors of protein tyrosine phosphatases (PTPases), non-small molecule mimetic compounds and inhibitors of glutamine-fructose-6-phosphate amidotransferase (GFAT), compounds influencing a dysregulated hepatic glucose production, like inhibitors of glucose-6-phosphatase (GOPase), inhibitors of fructose-1,6-bisphosphatase (F-1,6-BPase), inhibitors of glycogen phosphorylase (GP), glucagon receptor antagonists and inhibitors of phosphoenolpyruvate carboxykinase (PEPCK), pyruvate dehydrogenase kinase (PDHK) inhibitors, insulin sensitivity enhancers, insulin secretion enhancers, inhibitors of gastric emptying, $\alpha_2$-adrenergic antagonists, retinoid X receptor (PvXR) agonists, and dipeptidyl peptidase-4 (DPP-IV) inhibitors.

In accordance with the present invention, the combination can be used by mixing the respective active components, a compound of the present invention and pharmaceutical agent, either all together or independently with a physiologically acceptable carrier, excipient, binder, diluent, etc., as described herein above, and administering the mixture or mixtures either orally or non-orally as a pharmaceutical composition. When a compound or a mixture of compounds of the present invention are administered as a combination therapy with another active compound the therapeutic agents can be formulated as separate pharmaceutical compositions given at the same time or at different times; or the compound or a mixture of compounds of the present invention and the therapeutic agent(s) can be formulated together as a single unit dosage.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The methods in accordance with the invention may include administering a GPR 119 agonist with one or more other agents that either enhance the activity of the agonist or compliment its activity or use in treatment. Such additional factors and/or agents may produce an augmented or even synergistic effect when administered with a GPR 119 agonist, or minimize side effects.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Representative compounds of the present invention include those specified above in Table 1 and pharmaceutically acceptable salts thereof. The present invention also includes the intermediate compounds discussed in the examples and elsewhere in the specification as well as their salts. The present invention should not be construed to be limited to them.

General Method of Preparation of Compounds of the Invention

The compounds of the present invention may be prepared by the following processes. Unless otherwise indicated, the variables (e.g. Z, X, $X_1$, $X_2$, $X_3$, $X_4$, Cy, L and Ar) when used in the below formulae are to be understood to present those groups described above in relation to formula (A) and (B).

Scheme 1:

This scheme provides a method for the preparation of a compound of formula (A) wherein $L_2$ is absent, NH or O, X is N, Z is NR or O and other variables such as Cy, $X_1$, $X_2$, $X_3$, $X_4$, and are the same as described above in relation to formula (A). $L_2$ is shown as L in the scheme below.

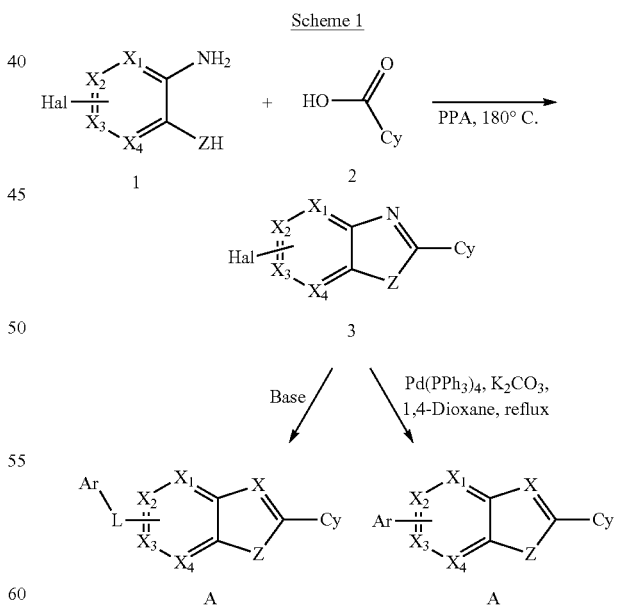

A compound of formula (1) wherein Hal represent halogen and Z is NH or O can be coupled with a compound of formula (2) in the presence of a suitable poly phosphoric acid at a sufficiently high temperature to give a compound of (3). The compound of formula (3) can then be coupled with a compound of formula Ar—B(OH)$_2$ in the presence of a catalyst, such as Palladium tetrakis triphenylphosphine, and a suitable base, such as potassium carbonate, to give the desired compounds of formula (A), i.e wherein L is absent, X is N, Z is O or NR and other variables are the same as described above in relation to formula (A).

Similarly, the corresponding compound of formula (3) can be coupled with a compound of the formula Ar—NH$_2$ or Ar—OH in the presence of a suitable base, such as potassium carbonate, to give the desired compounds of formula (A), wherein L is NH or O, X is N, Z is O or NR and other variables are the same as described above in relation to formula (A).

Illustration:

A compound of formula (1a) wherein Hal represents halogen can be coupled with a compound of formula (2a) in the presence of a suitable poly phosphoric acid at a sufficiently high temperature to give a compound of formula (3a). The compound of formula (3a) can then be coupled with a compound of formula R$^5$-Lg (where Lg represents a leaving group) in the presence of a suitable base such as diisopropyl amine to give a compound of formula (4). The compound of formula (4) can then be coupled with a compound of formula Ar—B(OH)$_2$ in the presence of a catalyst, such as Palladium

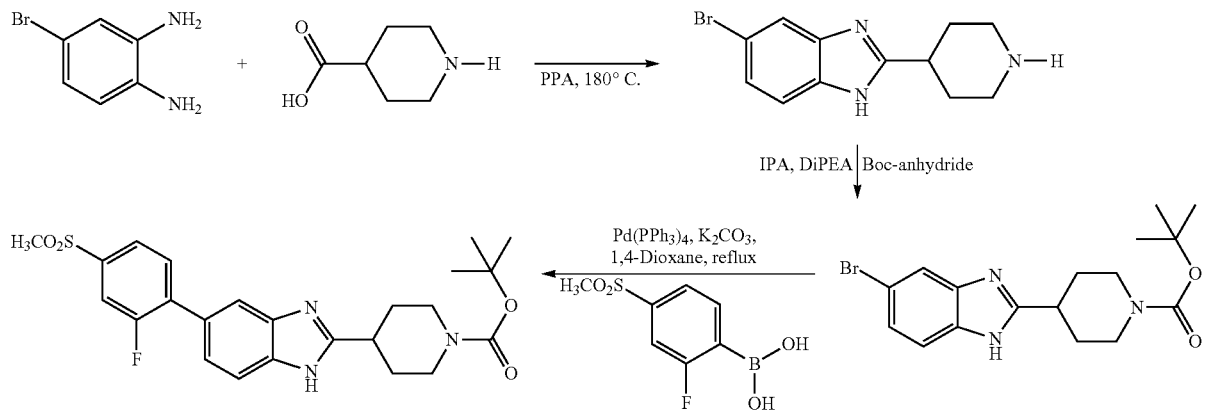

Scheme 2:

This scheme provides a method for the preparation of a compound of formula (A-I) wherein L$_1$ and L$_2$ are absent, X is N, Z is O, D is CH, E is N and other variables such as R$^{e-l}$, X$_1$, X$_3$ and X$_4$ are the same as described above in relation to formula (A-I).

tetrakis triphenylphosphine, and a suitable base, such as potassium carbonate, to give the desired compounds of formula (A-I), where X is N, Z is O, D is CH, E is N and other variables are the same as described above in relation to formula (A-I).

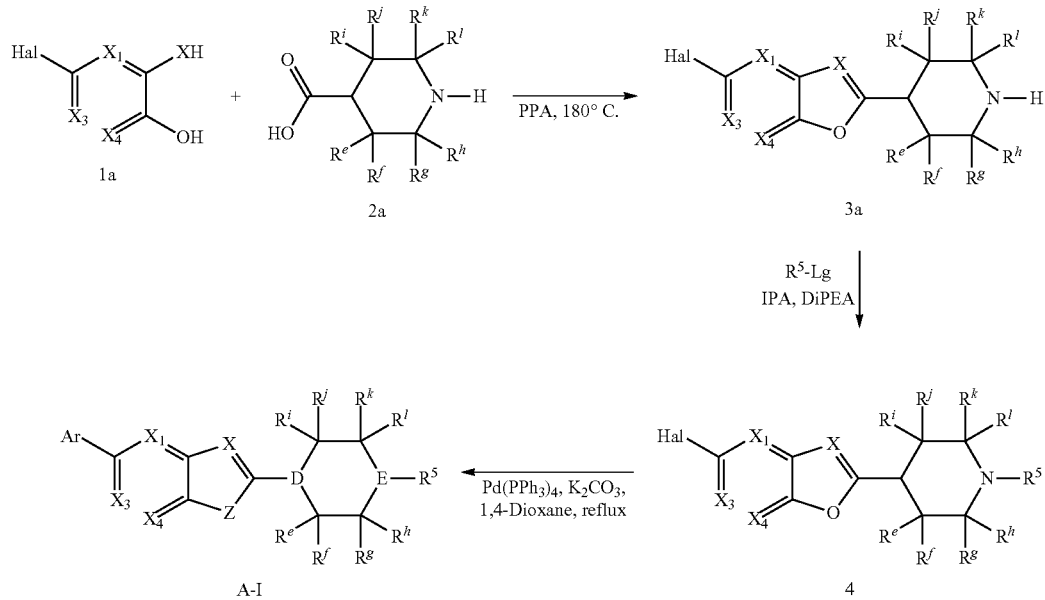

Illustration:

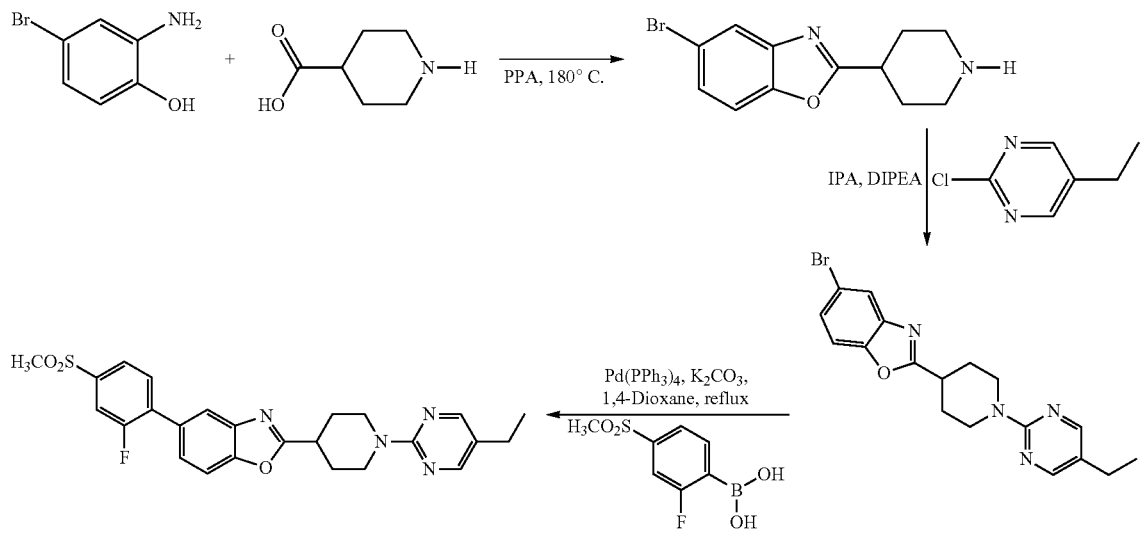

Scheme 3:

This scheme provides a method for the preparation of a compound of formula (A-II) wherein $L_1$ and $L_2$ are absent, X is N, Z is O, D is CH, E is N and other variables such as $R^{e-l}$, $X_1$, $X_2$ and $X_4$ are the same as described above in relation to formula (A-II)

Scheme 3

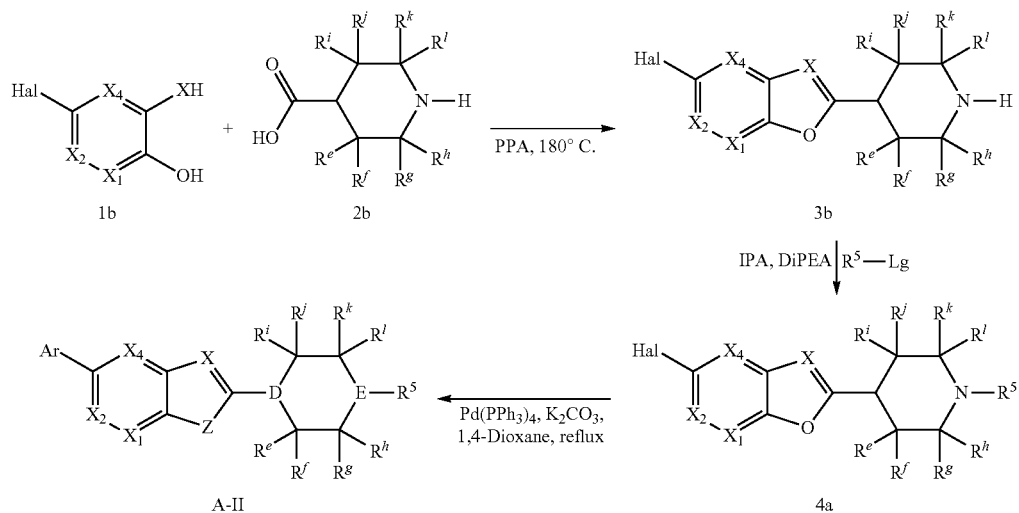

A compound of formula (1b) wherein Hal represent halogen and Z is NH or O can be coupled with a compound of formula (2b) in the presence of a suitable poly phosphoric acid at a sufficiently high temperature to give a compound of formula (3b). The compound of formula (3b) can then be coupled with a compound of formula $R^5$-Lg (where Lg is a leaving group) in the presence of a suitable base such as diisopropyl amine to give the compound of formula (4a). The compound of formula (4a) can then be coupled with a compound of formula Ar—B(OH)$_2$ in the presence of a catalyst, such as Palladium tetrakis triphenylphosphine, and a suitable base, such as potassium carbonate, to give the desired compounds of formula (A-II), X is N, Z is O, D is CH, E is N and other variables are the same as described above in relation to formula (A-II).

Scheme 3A:

This scheme provides a method for the preparation of a compound of formula (A-II) wherein $L_1$ and $L_2$ are absent, X is CH, Z is O, D is CH, E is N and other variables such as $R^{e-l}$, $X_1$, $X_2$ and $X_4$ are the same as described above in relation to formula (A-II).

Scheme 3A

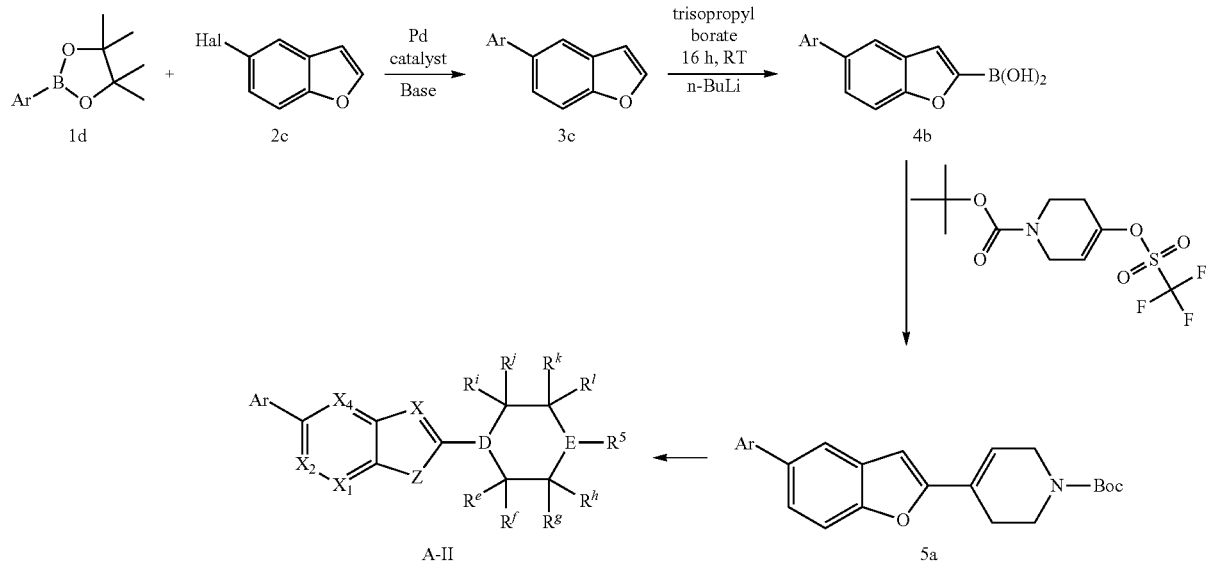

A compound of formula (1d) can be coupled with a compound of formula (2c) in the presence of catalyst, such as Palladium tetrakis triphenylphosphine, and a suitable base, such as potassium carbonate, to give a compound of (3c). The compound of formula (3c) can then be lithiated followed by treatment with triisopropyl borate to give the compound of formula (4b). The compound of formula (4b) can then be coupled with a compound of formula (4c) to give a compound of formula (5a) which can then be reduced using suitable reducing agent to give the desired compounds of formula (A-II) wherein X is C, Z is O, D is CH, E is N and all the other variables are the same as described above in relation to formula (A-II).

Illustration:

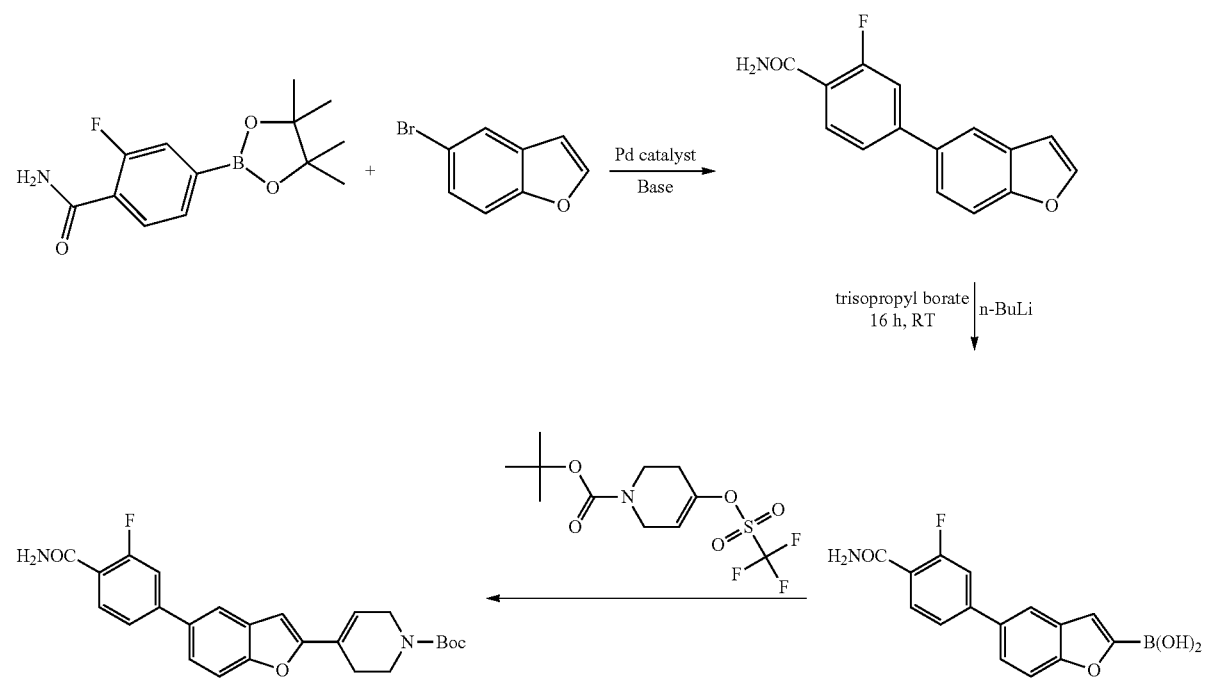

Scheme 4:

This scheme provides a method for the preparation of compound of formula (B) wherein $L_1$ is absent, NH or O, X is N, Z is NR or O, $L_2$ is absent and other variables such as Ar, Cy, $X_1$, $X_2$, $X_3$ and $X_4$ are the same as described above in relation to formula (B).

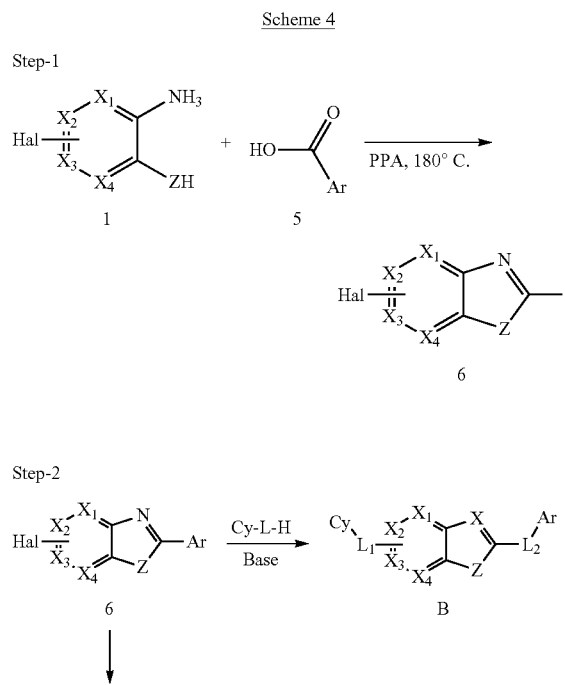

A compound of formula (1) wherein Hal represent halogen and Z is NH or O can be coupled with a compound of formula (5) in the presence of poly phosphoric acid at a sufficiently high temperature to give a compound of formula (6). The compound of formula (6) can then be coupled with a compound of formula Cy-NH$_2$ or Cy-OH in the presence of a suitable base, such as potassium carbonate, to give the desired compounds of formula (B) wherein $L_1$ is NH or O, X is N, Z is O or NR and other variables are the same as described above in relation to formula (B). Alternately, the compound of formula (6) can be converted to compound of formula (6a) using 4,4,4',4',5,5,5',5'-octamethyl-2,2'-bi(1,3,2-dioxaborolane) under Suzuki coupling conditions. The compound of formula (6a) can then be coupled with a compound of formula Cy-Lg (wherein Lg is an leaving group) in the presence of a catalyst, such as Palladium tetrakis triphenylphosphine, and a suitable base, such as potassium carbonate, to give the desired compounds of formula (B), i.e wherein $L_1$ is absent, X is N, Z is O or NR and other variables are the same as described above in relation to formula (B).

Illustration:

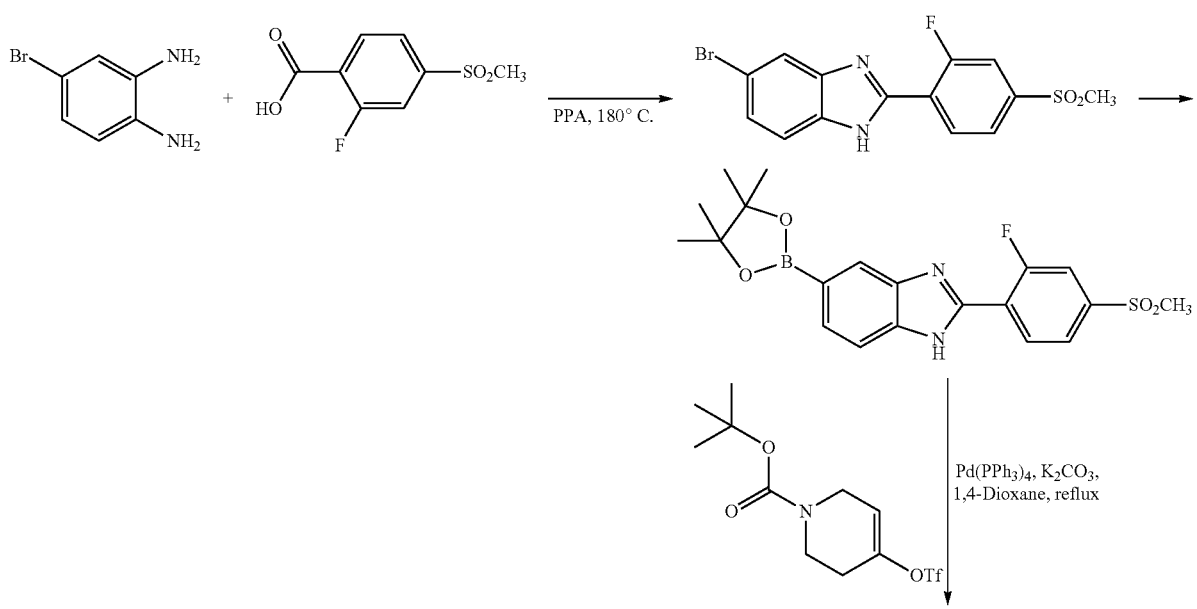

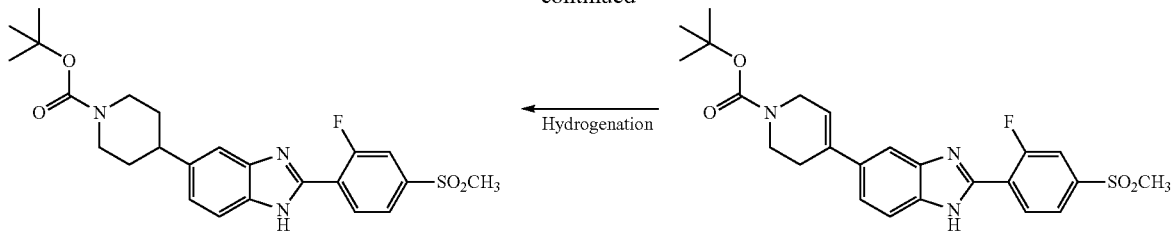

Scheme 5:
This scheme provides a method for the preparation of a compound of formula (B-I) wherein $L_1$ and $L_2$ are absent, X is N, D is CH, E is N, Z is O and other variables such as $R^{e-l}$, $X_1$, $X_3$ and $X_4$ are the same as described above in relation to formula (B-I).

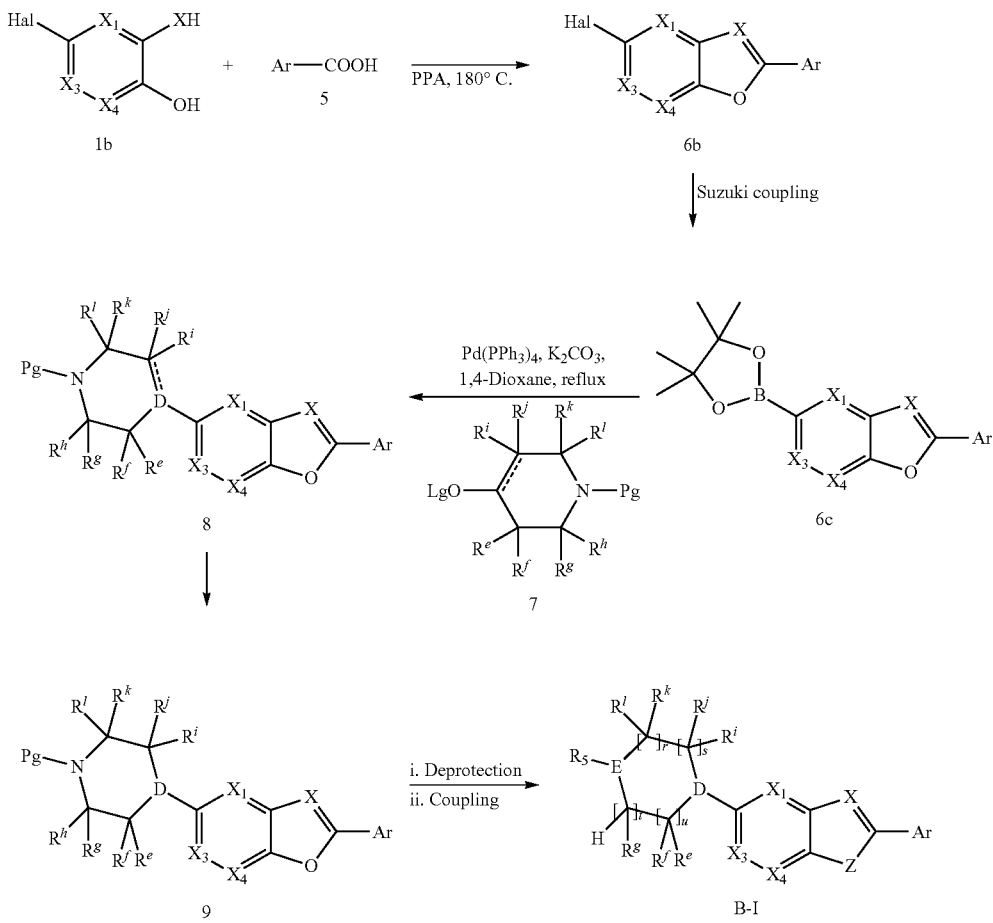

A compound of formula (1b) wherein Hal represents halogen can be coupled with a compound of formula (5) in the presence of poly phosphoric acid at a sufficiently high temperature to give a compound of formula (6b). The compound of formula (6b) can then be converted to a compound of formula (6c) using Suzuki coupling. The compound of formula (6c) can then be coupled with a compound of formula (7) (wherein Pg is a protecting group) using palladium tetrakis triphenylphosphine and a suitable base, such as potassium carbonate, to provide a compound of formula (8). The compound of formula (8) can then be subjected to hydrogenation to give the compound of formula (9). The compound of formula (9) can then be de-protected followed by coupling with a compound of formula $R^5$-Lg wherein Lg is a leaving group to give the desired compounds of formula (B-I).

Illustration:
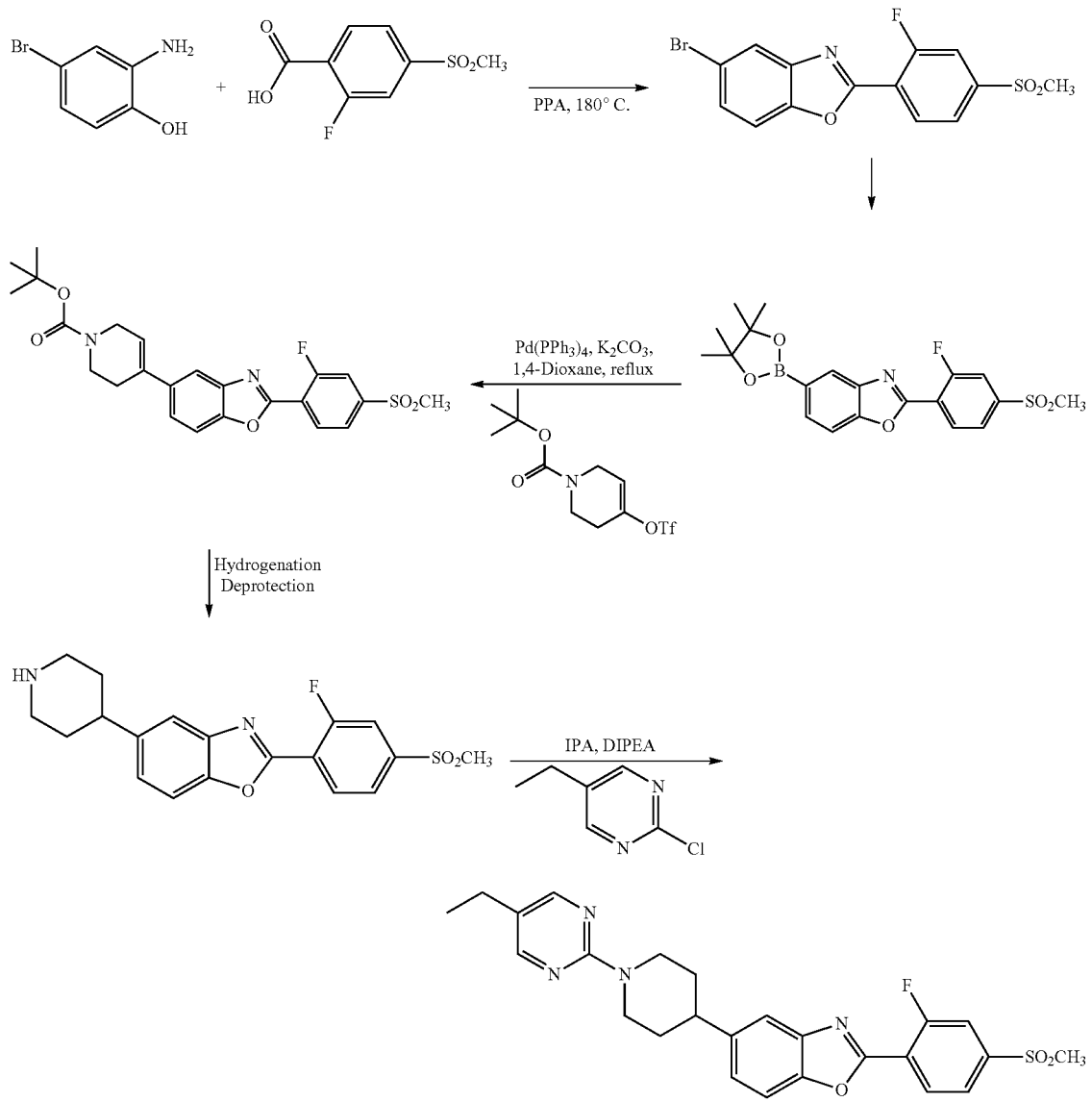
Scheme 6:
This scheme provides a method for the preparation of a compound of formula (B-II) wherein $L_1$ and $L_2$ are absent, X is N, D is CH, E is N, Z is O and other variables such as $R_{e-1}$, $X_1$, $X_2$ and $X_4$ are the same as described above in relation to formula (B-II).
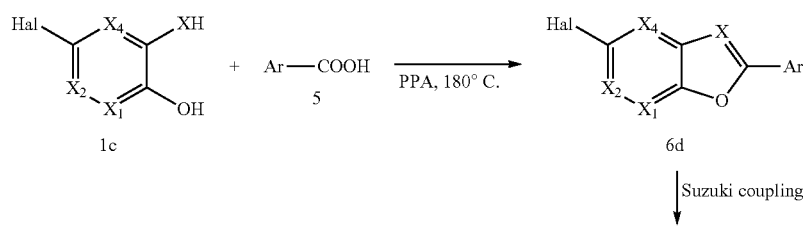

-continued
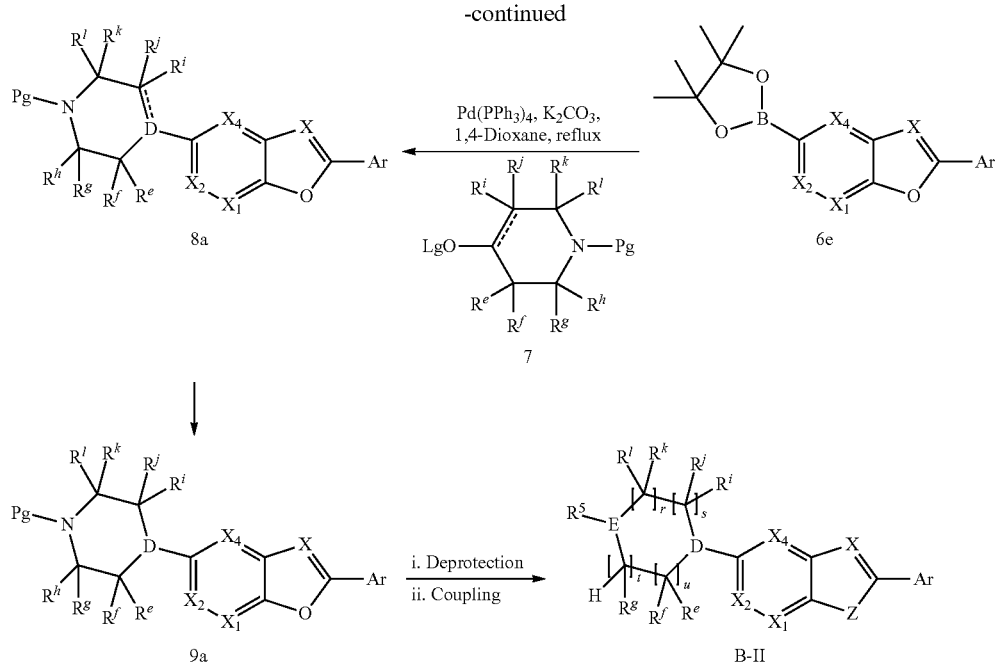
Illustration:
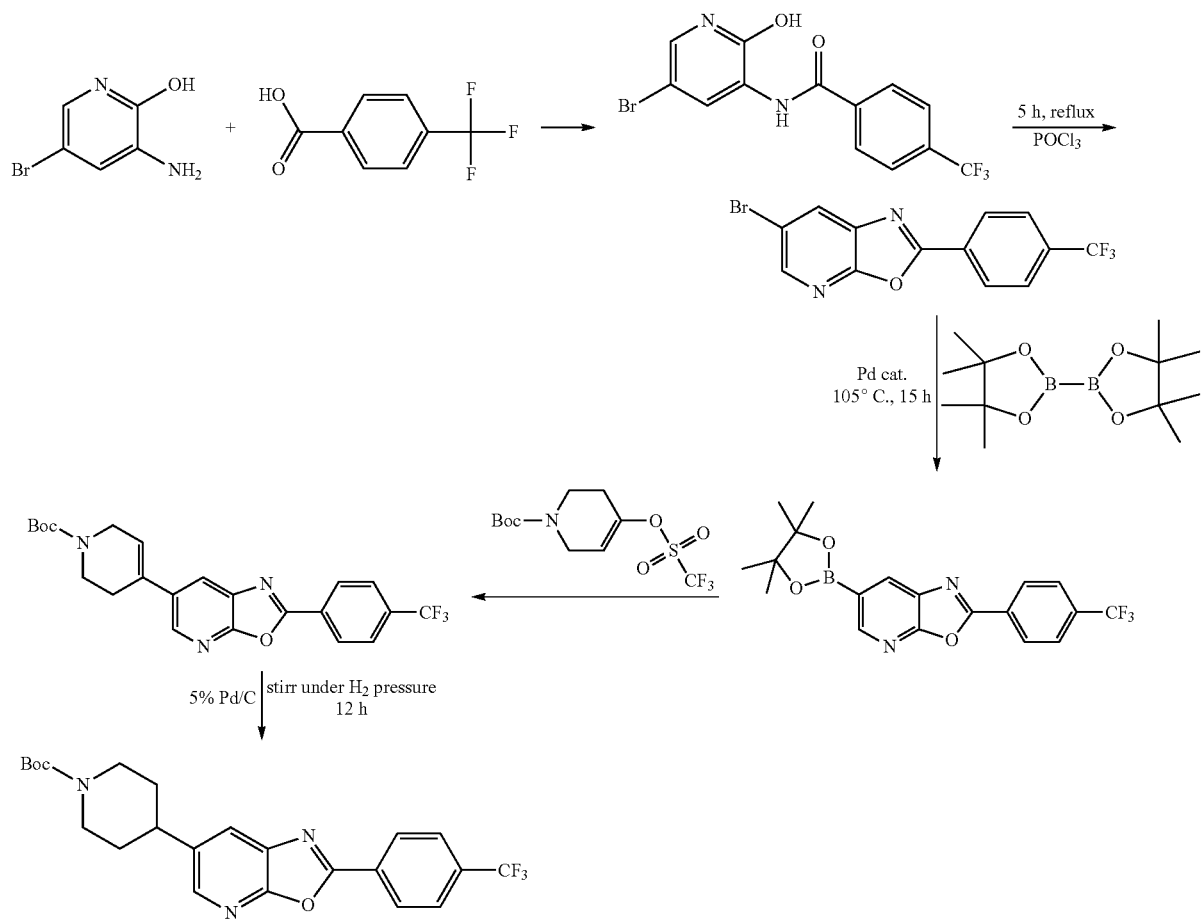

A compound of formula (1c) wherein Hal represents halogen can be coupled with a compound of formula (5) in the presence of a suitable poly phosphoric acid at sufficiently high temperature to give a compound of formula (6d). The compound of formula (6d) can then be converted to compound of formula (6e) using Suzuki coupling. The compound of formula (6e) can then be coupled with a compound of formula (7) using palladium tetrakis triphenylphosphine and a suitable base, such as potassium carbonate, to provide a compound of formula (8a). The compound of formula (8a) can then be subjected to hydrogenation to give the compound of formula (9a). The compound of formula (9a) can then be de-protected followed by coupling with a compound of formula $R^5$-Lg wherein Lg is a leaving group to give the desired compounds of formula (B-II).

Similar methodologies with certain modifications as known to those skilled in the art can be used to synthesize compounds of formula (A), (A-I), (A-II), (A-III), (A-IV), (A-IA), (A-IIA), (A-IIIA), (A-IVA), (A-IB) (A-IIB), (A-IIIB), (A-IVB), (A-V), (B), (B-I), (B-II), (B-III), (B-IV), (B-IA), (B-IIA), (B-IIIA), (B-IVA), (B-IB) (B-IIB), (B-IIIB), (B-IVB), and (B-V) wherein all the variables are to be understood to present those groups described above in relation to formula (A) or (B) using suitable intermediates and reagents.

EXPERIMENTAL

Unless otherwise mentioned, work-up refers to distribution of a reaction mixture between the aqueous and organic phases indicated within parenthesis, separation and drying over $Na_2SO_4$ of the organic layer and evaporating the solvent to give a residue. Unless otherwise stated, purification refers to column chromatography using silica gel as the stationary phase and a mixture of petroleum ether (boiling at 60-80° C.) and ethyl acetate or dichloromethane and methanol of suitable polarity as the mobile phases. RT generally refers to ambient temperature (25-28° C.).

Intermediates

TABLE-3

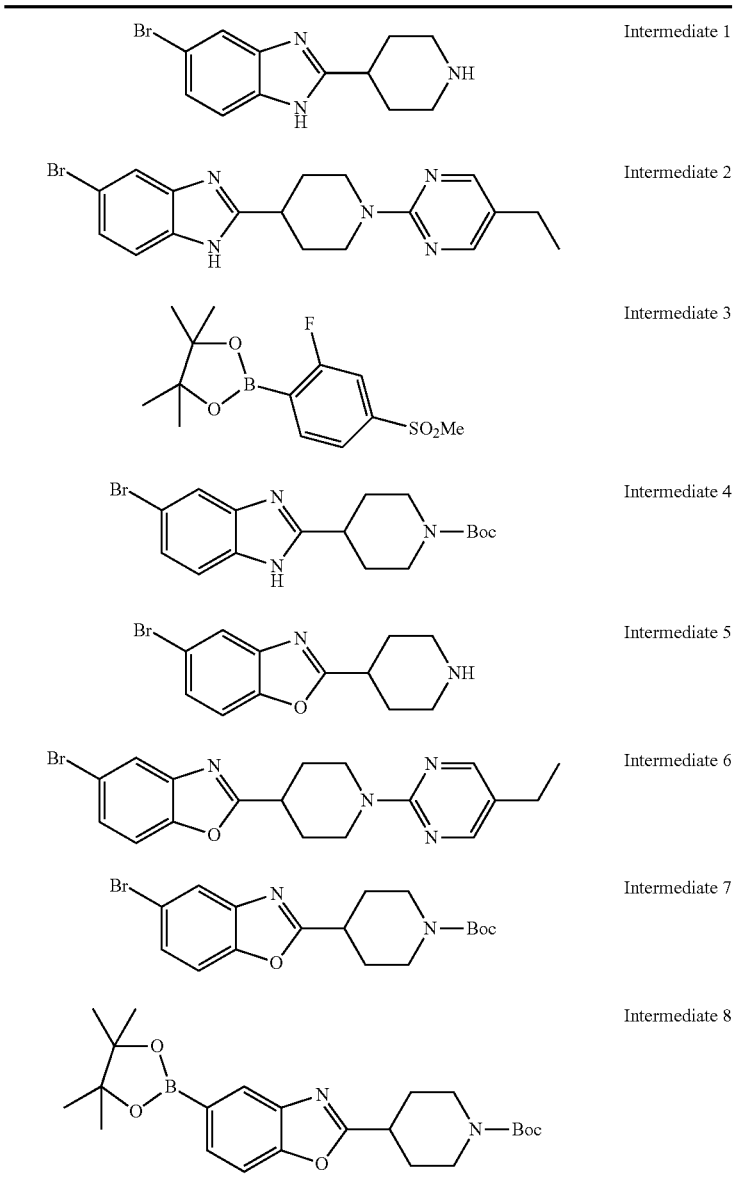

TABLE-3-continued
| | |
|---|---|
| 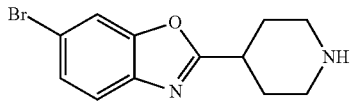 | Intermediate 9 |
| 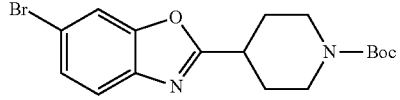 [SMILES: CC(C)(C)OC(=O)N1CCC(c2nc3ccc(Br)cc3o2)CC1] | Intermediate 10 |
| 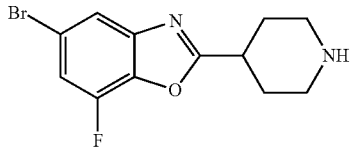 [SMILES: Fc1cc(Br)cc2nc(C3CCNCC3)oc12] | Intermediate 11 |
| 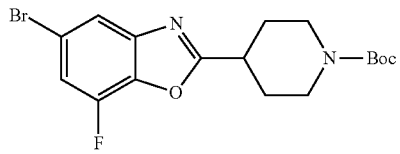 [SMILES: CC(C)(C)OC(=O)N1CCC(c2nc3cc(Br)cc(F)c3o2)CC1] | Intermediate 12 |
| 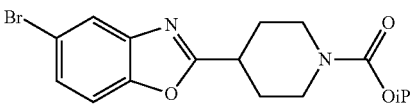 | Intermediate 13 |
| 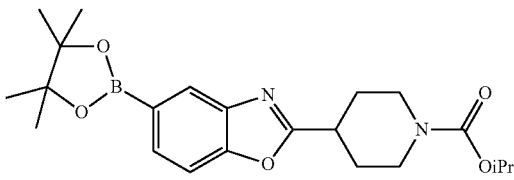 [SMILES: CC(C)OC(=O)N1CCC(c2nc3cc(B4OC(C)(C)C(C)(C)O4)ccc3o2)CC1] | Intermediate 14 |
| 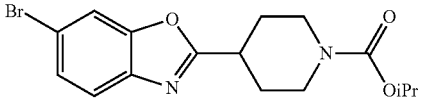 [SMILES: CC(C)OC(=O)N1CCC(c2nc3ccc(Br)cc3o2)CC1] | Intermediate 15 |
| 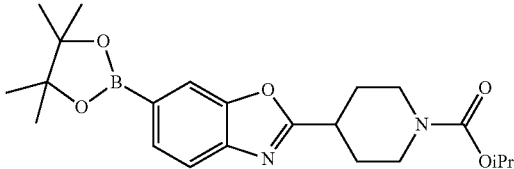 [SMILES: CC(C)OC(=O)N1CCC(c2nc3ccc(B4OC(C)(C)C(C)(C)O4)cc3o2)CC1] | Intermediate 16 |
| 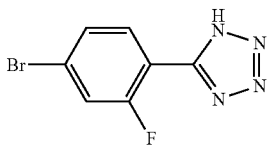 [SMILES: Fc1cc(Br)ccc1-c1nnn[nH]1] | Intermediate 17 |
| 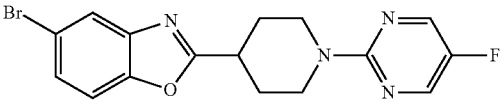 [SMILES: Fc1cnc(N2CCC(c3nc4cc(Br)ccc4o3)CC2)nc1] | Intermediate 18 |
| 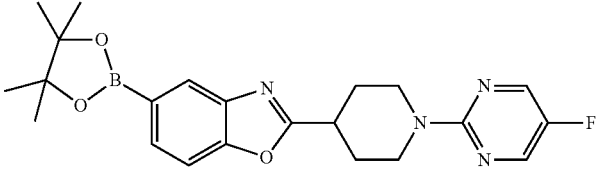 [SMILES: CC1(C)OB(c2ccc3oc(C4CCN(c5ncc(F)cn5)CC4)nc3c2)OC1(C)C] | Intermediate 19 |

TABLE-3-continued
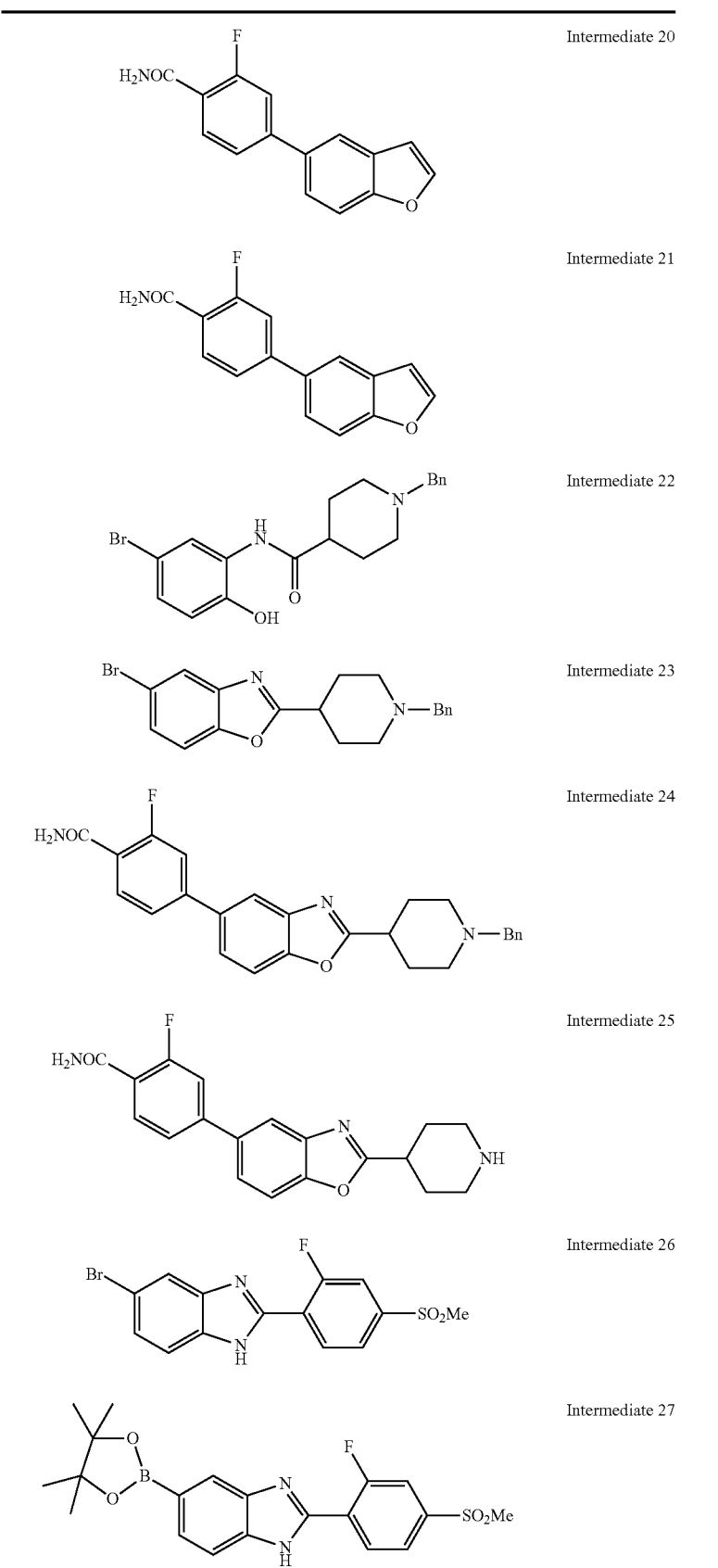
| | |
|---|---|
| | Intermediate 20 |
| | Intermediate 21 |
| | Intermediate 22 |
| | Intermediate 23 |
| | Intermediate 24 |
| | Intermediate 25 |
| | Intermediate 26 |
| | Intermediate 27 |

TABLE-3-continued
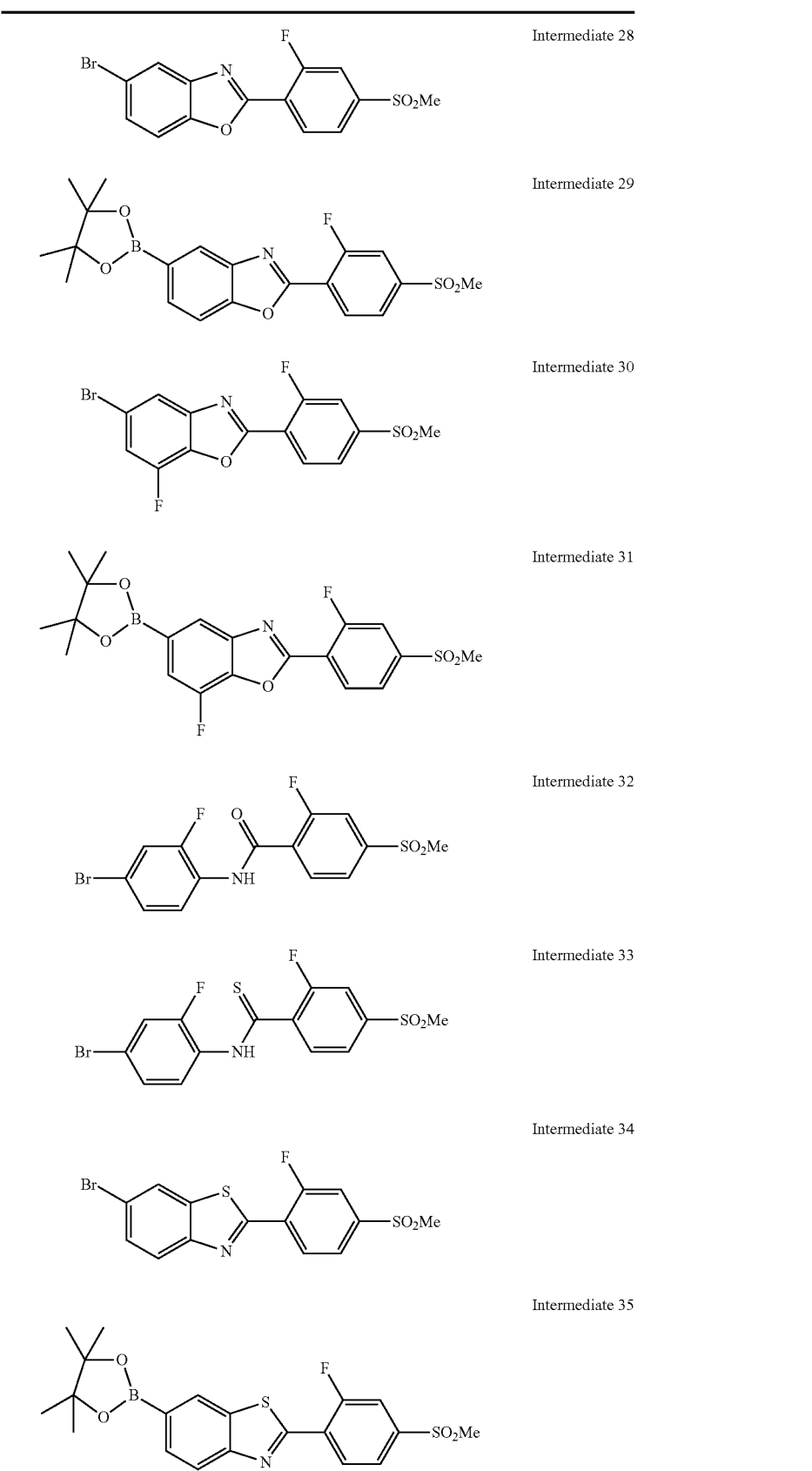
Intermediate 28
Intermediate 29
Intermediate 30
Intermediate 31
Intermediate 32
Intermediate 33
Intermediate 34
Intermediate 35

TABLE-3-continued
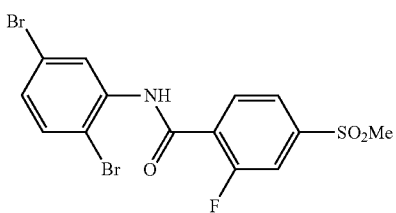 [SMILES: CS(=O)(=O)c1ccc(C(=O)Nc2cc(Br)ccc2Br)c(F)c1]
Intermediate 36
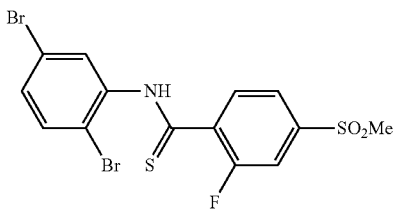
Intermediate 37
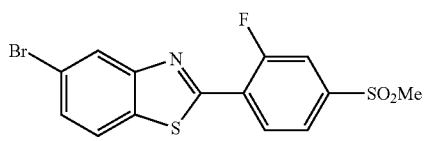 [SMILES: CS(=O)(=O)c1ccc(-c2nc3cc(Br)ccc3s2)c(F)c1]
Intermediate 38
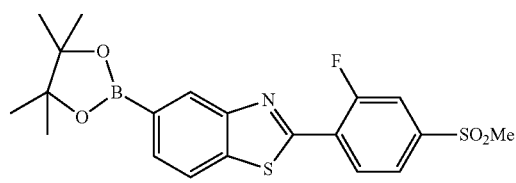 [SMILES: CC1(C)OB(c2ccc3sc(-c4ccc(S(C)(=O)=O)cc4F)nc3c2)OC1(C)C]
Intermediate 39
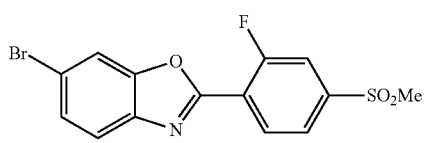
Intermediate 40
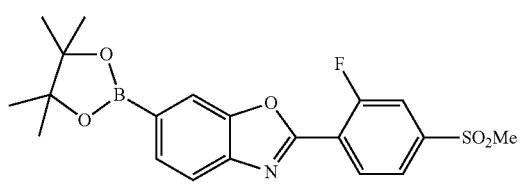 [SMILES: CC1(C)OB(c2ccc3nc(-c4ccc(S(C)(=O)=O)cc4F)oc3c2)OC1(C)C]
Intermediate 41
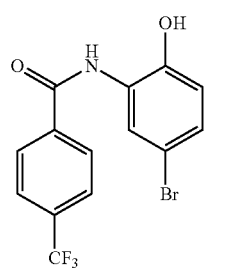 [SMILES: O=C(Nc1cc(Br)ccc1O)c1ccc(C(F)(F)F)cc1]
Intermediate 42
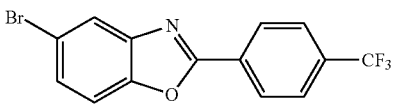 [SMILES: FC(F)(F)c1ccc(-c2nc3cc(Br)ccc3o2)cc1]
Intermediate 43

TABLE-3-continued
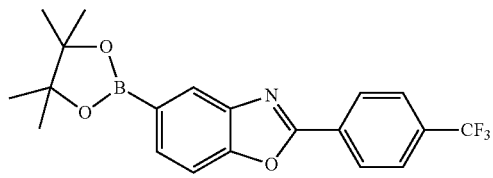 [SMILES: CC1(C)OB(c2ccc3oc(-c4ccc(C(F)(F)F)cc4)nc3c2)OC1(C)C] Intermediate 44
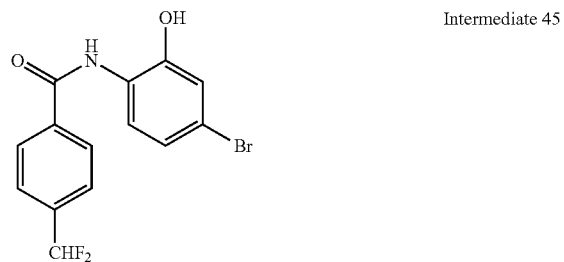 Intermediate 45
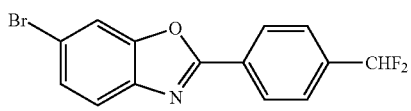 Intermediate 46
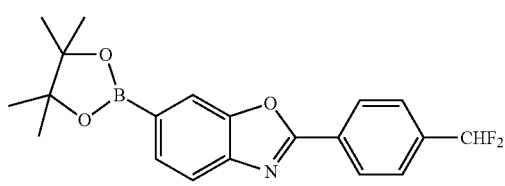 [SMILES: CC1(C)OB(c2ccc3nc(-c4ccc(C(F)F)cc4)oc3c2)OC1(C)C] Intermediate 47
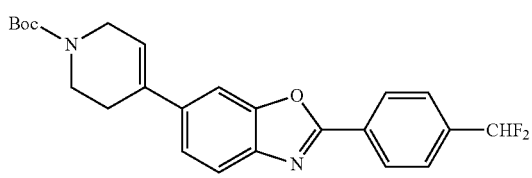 [SMILES: CC(C)(C)OC(=O)N1CC=C(c2ccc3nc(-c4ccc(C(F)F)cc4)oc3c2)CC1] Intermediate 48
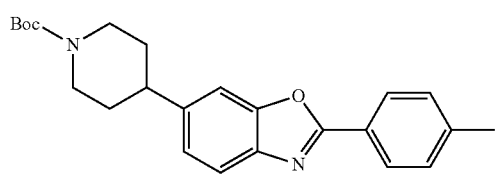 [SMILES: Cc1ccc(-c2nc3ccc(C4CCN(C(=O)OC(C)(C)C)CC4)cc3o2)cc1] Intermediate 49
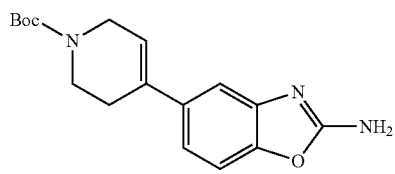 [SMILES: CC(C)(C)OC(=O)N1CC=C(c2ccc3oc(N)nc3c2)CC1] Intermediate 50
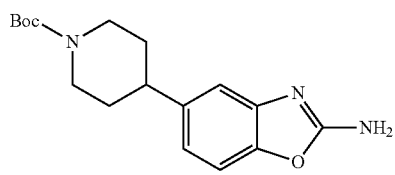 [SMILES: CC(C)(C)OC(=O)N1CCC(c2ccc3oc(N)nc3c2)CC1] Intermediate 51
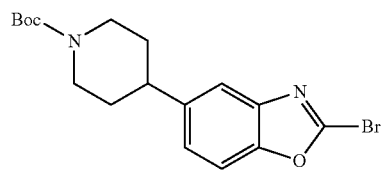 [SMILES: CC(C)(C)OC(=O)N1CCC(c2ccc3oc(Br)nc3c2)CC1] Intermediate 52

TABLE-3-continued

| | |
|---|---|
| 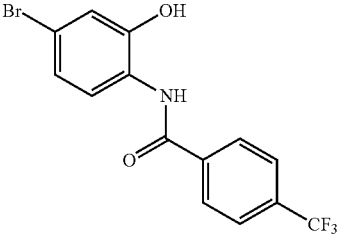 [SMILES: O=C(Nc1ccc(Br)cc1O)c1ccc(C(F)(F)F)cc1] | Intermediate 53 |
| 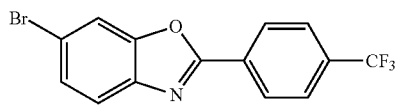 | Intermediate 54 |
| 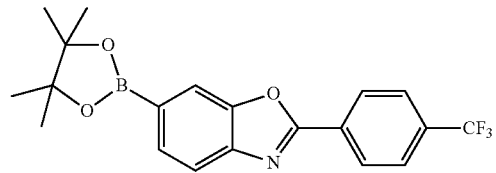 [SMILES: CC1(C)OB(c2ccc3nc(-c4ccc(C(F)(F)F)cc4)oc3c2)OC1(C)C] | Intermediate 55 |
| 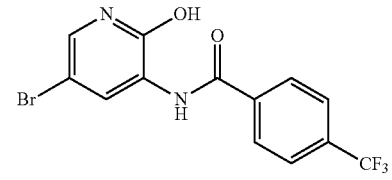 [SMILES: O=C(Nc1cc(Br)cnc1O)c1ccc(C(F)(F)F)cc1] | Intermediate 56 |
| 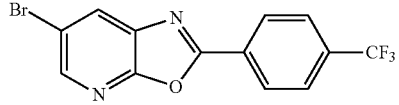 [SMILES: FC(F)(F)c1ccc(-c2nc3cc(Br)cnc3o2)cc1] | Intermediate 57 |
| 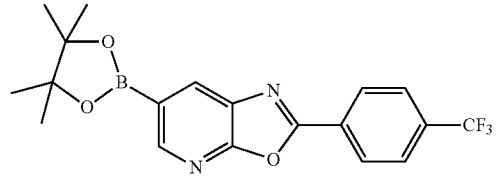 [SMILES: CC1(C)OB(c2cnc3oc(-c4ccc(C(F)(F)F)cc4)nc3c2)OC1(C)C] | Intermediate 58 |

Intermediate 1: 5-Bromo-2-(piperidin-4-yl)-1H-benzo[d]imidazole 4-bromobenzene-1,2-diamine (1.43 g, 7.64 mmol) and piperidine-4-carboxylic acid (0.99 g, 7.64 mmol) were dissolved in polyphosphoric acid (20 g). This mixture was heated at 190° C. for three and half hours. Reaction mixture cooled to rt and diluted with water (100 ml). Aqueous layer basified with sodium hydroxide pellets to pH 14. Solid was filtered, washed with methanol and dried to obtain the title compound (1 g) as a dark brown solid.

Intermediate 2: 5-Bromo-2-(1-(5-ethylpyrimidin-2-yl)piperidin-4-yl)-1H-benzo[d]imidazole Intermediate 1 (500 mg, 1.69 mmol) and 2-chloro-5-ethylpyrimidine (264 mg, 1.86 mmol) were dissolved in propan-2-ol (25 ml). To this mixture N,N-Diisopropylethyl amine (1.8 ml, 10.1 mmol) added and stirred at 90° C. for 12 h. After completion of the reaction, propan-2-ol was removed to obtain the crude. Crude was purified by combiflash using a mixture of AcOET and Petether (40:60) as eluent to afford the titled compound (0.2 g) as a pale-yellow solid.

Intermediate 3: 2-[2-Fluoro-4-(methylsulfonyl)phenyl]-4,4,5,5-tetramethyl-1,3,2-dioxaborolane 1-bromo-2-fluoro-4-(methylsulfonyl)benzene (900 mg, 3.5 mmol), 4,4,4',4',5,5,5',5'-octamethyl-2,2'-bi(1,3,2-dioxaborolane) (1.15 g, 4.5 mmol) and potassium acetate (1.13 g, 11.48 mmol) were dissolved in dioxane (30 ml) under $N_2$ atmosphere. This mixture was degassed with nitrogen for 30 mins and added Pd(dppf)$_2$Cl$_2$.CH$_2$Cl$_2$ (85 mg, 0.1 mmol). This mixture stirred at 105° C. for 12 h. Reaction mixture diluted with water and work up (AcOEt/H$_2$O) afforded the crude. Crude was purified by combiflash using a mixture of AcOEt and Petether (20:80) to afford the titled compound (900 mg) as a white solid. $^1$H-NMR (δ ppm, CDCl$_3$, 400 MHz): 7.97-7.92 (m, 1H), 7.70 (dd, J 1.4, 7.7, 1H), 7.60 (dd, J 1.2, 8.1, 1H), 3.05 (s, 3H), 1.37 (s, 12H).

Intermediate 4: Tert-butyl 4-(5-bromo-1H-benzo[d]imidazol-2-yl)piperidine-1-carboxylate Intermediate 1 (200 mg, 0.68 mmol) was dissolved in DCM (40 ml) and added TEA (0.2 ml, 0.68 mmol). Reaction mixture cooled to 0° C. and added di-tert-butyl dicarbonate (0.2 ml, 0.68 mmol). Reaction mixture stirred at 0° C. for 2 h. After completion of the reaction, reaction mixture washed with water, DCM layer dried over $Na_2SO_4$ and removal of DCM afforded the crude. Crude was purified by combiflash using AcOEt and Petether (35:65) as eluent to afford the titled compound (60 mg) as a brown solid.

Intermediate 5: 5-Bromo-2-(piperidin-4-yl)benzo[d]oxazole 2-amino-4-bromophenol (1.2 g, 5.8 mmol) and piperidine-4-carboxylic acid (0.74 g, 5.8 mmol) were dissolved in polyphosphoric acid (30 g). This mixture was heated at 190° C. for three and half hours. Reaction mixture cooled to rt and diluted with water (100 ml). Aqueous layer basified with sodium hydroxide pellets to pH 9. Work up (AcOEt/$H_2O$) followed removal of AcOEt afforded the titled compound (0.8 g) as a pale-yellow gummy solid.

Intermediate 6: 5-Bromo-2-[1-(5-ethylpyrimidin-2-yl)piperidin-4-yl]benzo[d]oxazole Intermediate 5 (800 mg, 2.85 mmol) and 2-chloro-5-ethylpyrimidine (447 mg, 3.14 mmol) were dissolved in propan-2-ol (25 ml). To this mixture N,N-Diisopropylethyl amine (3.1 ml, 17.12 mmol) added and stirred at 90° C. for 12 h. After completion of the reaction, propan-2-ol was removed to obtain the crude. Crude was purified by combiflash using a mixture of AcOEt and Petether (8:92) as eluent to afford the titled compound (80 mg) as a pale-yellow solid. $^1$H-NMR (δ ppm, $CDCl_3$, 400 MHz): 8.19 (s, 2H), 7.81 (s, 1H), 7.41 (dd, J 1.6, 8.6, 1H), 7.35 (d, J 8.6, 1H), 4.72 (d, J 13.6, 2H), 3.27-3.11 (m, 3H), 2.47 (q, J 7.6, 2H), 2.21 (dd, J 2.6, 13.1, 2H), 2.02-1.90 (m, 2H), 1.19 (t, J 7.6, 3H).

Intermediate 7: Tert-butyl 4-(5-bromobenzo[d]oxazol-2-yl)piperidine-1-carboxylate Intermediate 5 (500 mg, 1.78 mmol) was dissolved in DCM (30 ml) and added TEA (180 mg, 1.78 mmol). Reaction mixture cooled to 0° C. and added di-tert-butyl dicarbonate (388 mg, 1.78 mmol). Reaction mixture stirred at 0° C. for 1 h. After completion of the reaction, reaction mixture washed with water, DCM layer dried over $Na_2SO_4$ and removal of DCM afforded the crude. Crude was purified by combiflash using AcOEt and Petether (8:92) as eluent to afford the titled compound (150 mg) as an off-white solid.

Intermediate 8: tert-butyl 4-(5-(4,4,5,5-tetramethyl-1,3,2-dioxaborolan-2-yl)benzo[d]oxazol-2-yl)piperidine-1-carboxylate Intermediate 7 (1.8 g, 6.6 mmol), 4,4,4',4',5,5,5',5'-octamethyl-2,2'-bi(1,3,2-dioxaborolane) (2.2 g, 8.6 mmol) and potassium acetate (2.1 g, 21.8 mmol) were dissolved in dioxane (20 ml) under $N_2$ atmosphere. This mixture was degassed with nitrogen for 30 mins and added $Pd(dppf)_2Cl_2.CH_2Cl_2$ (210 mg, 0.26 mmol). Reaction mixture was stirred at 105° C. for 12 h. Reaction mixture diluted with water and work up (AcOEt/$H_2O$) afforded the crude. Crude was purified by combiflash using a mixture of AcOEt and Petether (10:90) as eluent to afford the titled compound (1.3 g) as a brown solid.

Intermediate 9: 6-bromo-2-(piperidin-4-yl)benzo[d]oxazole 2-amino-5-bromophenol (1.3 g, 6.9 mmol) and isonipecotic acid (893 mg, 6.91 mmol) were dissolved in polyphosphoric acid (39 g). This mixture was heated to 190° C. for 3 h. After 3 h, reaction mixture cooled to rt and basified with 10% aqueous NaOH solution to pH 8. Work up (EtOAc/$H_2O$) followed by removal of EtOAc afforded the title compound (500 mg) as a black solid. It was used in the next step without further purification.

Intermediate 10: tert-butyl 4-(6-bromobenzo[d]oxazol-2-yl)piperidine-1-carboxylate Intermediate 9 (500 mg, 1.77 mmol) was dissolved in DCM (20 mol), cooled to 0° C. and added TEA (0.25 ml, 1.77 mmol). To this mixture $(Boc)_2O$ (0.4 ml, 1.77 mmol) was added and stirred at rt for 3 h. At this stage, reaction mixture diluted with water and extracted with DCM. DCM removed on rotavapour to obtain the crude. Crude was purified by combiflash using EtOAc and Petether (7.5%) as eluent to obtain the title compound (500 mg). $^1$H-NMR (δ ppm, $CDCl_3$, 400 MHz): 7.65 (d, J 1.6, 1H), 7.53 (d, J 8.4, 1H), 7.43 (dd, J 1.7, 8.4, 1H), 4.13 (d, J 9.9, 2H), 3.17-3.05 (m, 1H), 2.97 (t, J 12.6, 2H), 2.20-2.08 (m, 2H), 1.96-1.82 (m, 2H), 1.47 (s, 9H).

Intermediate 11: 5-bromo-7-fluoro-2-(piperidin-4-yl)benzo[d]oxazole 2-amino-4-bromo-6-fluorophenol (1.7 g, 8.24 mmol) and isonipecotic acid (1.06 g, 8.24 mmol) were dissolved in polyphosphoric acid (28 g). This mixture was heated to 195° C. for 3 h. After 3 h, reaction mixture cooled to rt and basified with aqueous NaOH solution to pH 14. Solid that obtained was filtered and dried to obtain the title compound (1.3 g) as a brown solid.

Intermediate 12: Tert-butyl 4-(5-bromo-7-fluorobenzo[d]oxazol-2-yl)piperidine-1-carboxylate Intermediate 11 (1.3 g, 4.36 mmol) was dissolved in DCM (40 mol), cooled to 0° C. and added TEA (1.2 ml, 8.72 mmol). To this mixture $(Boc)_2O$ (950 mg, 4.36 mmol) was added and stirred at rt for 3 h. At this stage reaction mixture diluted with water and extracted with DCM. DCM removed on rotavapour to obtain the crude. Crude was purified by combiflash using EtOAc and Petether (10:90) as eluent to obtain the title compound (200 mg) as a brick brown solid.

Intermediate 13: Isopropyl 4-(5-bromobenzo[d]oxazol-2-yl)piperidine-1-carboxylate Intermediate 5 (980 mg, 3.31 mmol) was dissolved in DCM (50 mol) and added TEA (0.45 ml, 3.31 mmol). Reaction mixture cooled to 0° C., isopropylchloro formate (2.7 ml, 6.62 mmol) was added and stirred the reaction mixture for 3 h at rt. Work up (DCM/$H_2O$) followed by column purification on 60-120 mesh silica gel using EtOAc and Petether (15:85) as eluent afforded the titled compound (500 mg) as a pale-red solid.

Intermediate 14: Isopropyl 4-(5-(4,4,5,5-tetramethyl-1,3,2-dioxaborolan-2-yl)benzo[d]oxazol-2-yl)piperidine-1-carboxylate Intermediate 7 (0.35 g, 0.95 mmol), 4,4,4',4',5,5,5',5'-octamethyl-2,2'-bi(1,3,2-dioxaborolane) (0.31 g, 1.23 mmol) and potassium acetate (0.3 g, 3.14 mmol) were dissolved in dioxane (20 ml) under $N_2$ atmosphere. This mixture was degassed with nitrogen for 30 mins and added $Pd(dppf)_2Cl_2.CH_2Cl_2$ (31 mg, 0.04 mmol). Reaction mixture was stirred at 105° C. for 12 h. Reaction mixture diluted with water and work up (AcOEt/$H_2O$) afforded the crude. Crude was purified by combiflash using a gradient mixture of AcOEt and Petether (20:80) as eluent to afford the titled compound (0.3 g) as a pale-red solid.

Intermediate 15: Isopropyl 4-(6-bromobenzo[d]oxazol-2-yl)piperidine-1-carboxylate Intermediate 9 (1.3 g, 4.4 mmol) was dissolved in DCM (50 mol) and added TEA (1.22 ml, 8.8 mmol). Reaction mixture cooled to 0° C., isopropylchloro formate (2.6 ml, 6.6 mmol) was added and stirred the reaction mixture for 3 h at rt. Work up (DCM/$H_2O$) followed by purification on combiflash using gradient mixture of EtOAc and Petether (15:85) as eluent afforded the titled compound (510 mg) as a brown viscous liquid.

Intermediate 16: Isopropyl 4-(6-(4,4,5,5-tetramethyl-1,3,2-dioxaborolan-2-yl)benzo[d]oxazol-2-yl)piperidine-1-carboxylate Intermediate 15 (0.51 g, 1.4 mmol), 4,4,4',4',5,5,5',5'-octamethyl-2,2'-bi(1,3,2-dioxaborolane) (0.45 g, 1.8 mmol) and potassium acetate (0.4 g, 4.2 mmol) were dissolved in dioxane (20 ml) under $N_2$ atmosphere. This mixture was degassed with nitrogen for 30 mins and added $Pd(dppf)_2Cl_2.CH_2Cl_2$ (45 mg, 0.05 mmol). Reaction mixture was stirred at 105° C. for 12 h. Reaction mixture diluted with water and work up (AcOEt/$H_2O$) afforded the crude. Crude was purified by combiflash using a gradient mixture of AcOEt and Petether (15:85) as eluent to afford the titled compound (0.36 g) as a brown viscous liquid.

Intermediate 17: 5-(4-bromo-2-fluorophenyl)-1H-tetrazole

2-Fluoro-4-bromobenzonitrile (300 mg, 1.5 mmol) dissolved in EtOH, added sodium azide (320 mg, 4.9 mmol), Zinc chloride (240 mg, 1.8 mmol). This mixture was stirred refluxed for 38 h. Work up (EtOAc/$H_2O$) afforded the crude. Crude was washed with petether to obtain the titled compound (120 mg) as a white solid. $^1$H-NMR (δ ppm, DMSO-$d_6$, 400 MHz): 7.89-7.79 (m, 1H), 7.59 (dd, J 1.6, 10.04, 1H), 7.45 (dd, J 1.8, 8.3, 1H).

Intermediate 18: 5-Bromo-2-[1-(5-fluoropyrimidin-2-yl)piperidin-4-yl]benzo[d]oxazole Intermediate 5 (1 g, 3.4 mmol) and 2-Chloro-5-fluoropyrimidine was dissolved in isopropanol (20 ml) and added N,N-diisopropylethyl amine (2.4 ml). This mixture was stirred at 90° C. for 90 mins. Isopropanol was removed on rotavapour to obtain a residue. Work up (EtOAc/$H_2O$) followed by purification on combiflash using a gradient mixture of EtOAc and Petether (7:93) as eluent afforded the titled compound as a pink solid.

Intermediate 19: 2-[1-(5-Fluoropyrimidin-2-yl)piperidin-4-yl]-5-(4,4,5,5-tetramethyl-1,3,2-dioxaborolan-2-yl)benzo[d]oxazole Intermediate 18 (0.28 g, 1.74 mmol), 4,4,4',4',5,5,5',5'-octamethyl-2,2'-bi(1,3,2-dioxaborolane) (0.24 g, 1.0 mmol) and potassium acetate (0.22 g, 2.2 mmol) were dissolved in dioxane (20 ml) under $N_2$ atmosphere. This mixture was degassed with nitrogen for 30 mins and added $Pd(dppf)_2Cl_2.CH_2Cl_2$ (24 mg, 0.03 mmol). Reaction mixture was stirred at 105° C. for 12 h. Reaction mixture diluted with water and work up (AcOEt/$H_2O$) afforded the crude. Crude was purified by column chromatography on 60-120 mesh silica gel using a gradient mixture of AcOEt and Petether (8:92) as eluent to afford the titled compound (0.15 g) as a pink solid.

Intermediate 20: 4-(Benzofuran-5-yl)-2-fluorobenzamide

Following the general procedure-1 the titled compound (200 mg) was obtained from 5-Bromobenzofuran (200 mg, 1 mmol) and 2-fluoro-4-(4,4,5,5-tetramethyl-1,3,2-dioxaborolan-2-yl)benzamide (320 mg, 1.2 mmol) as a brown solid. $^1$HNMR (δ ppm, DMSO-$d_6$, 400 MHz): 8.05 (d, J 2.2, 2H), 8.02 (bs, 1H), 7.76-7.72 (m, 1H), 7.70-7.65 (m, 3H), 7.64-7.58 (m, 3H), 7.01 (d, J 1.9, 1H).

Intermediate 21: 5-(4-carbamoyl-3-fluorophenyl)benzofuran-2-ylboronic acid

Intermediate 20 (100 mg 0.4 mmol) was dissolved in THF (10 ml) and this mixture was cooled to −78° C. under $N_2$ atmosphere. n-BuLi (0.5 ml, 1.3 mmol) was added to the above mixture and stirred at same temperature for 20 mins Reaction mixture warmed to 0° C. and stirred for 2 hrs. After that trisopropyl borate (88 mg, 0.47 mmol) was added and stirred the reaction for 16 h at rt. Reaction mass quenched with 2N HCl worked it up (EtOAC/$H_2O$) to afford the titled compound (110 mg) as a crude. It was used in the next step without further purification.

Intermediate 22: 1-Benzyl-N-(5-bromo-2-hydroxyphenyl)piperidine-4-carboxamide 1-Benzylpiperidine-4-carboxylic acid (29 g, 0.13 mol) dissolved in DCM (300 ml), cooled to 0° C. and added oxalyl chloride (17.3 ml, 0.2 mol). Catalytic amount of DMF was added to this mixture and stirred at rt for 2 h. After 2 h, DCM removed on rotavapour and co-distilled the residue two times with DCM to obtain 1-benzylpiperidine-4-carbonyl chloride quantitatively. 2-Amino-4-bromophenol (23 g, 0.12 mol) dissolved in DCM and added pyridine (11.5 g, 0.15 mol) under nitrogen atmosphere. This mixture stirred at rt for 30 mins and added 1-benzylpiperidine-4-carbonyl chloride (29 g, 0.12 mol) in DCM (100 ml). After continuing stirring at rt for 2 h, DCM was removed on the rotavapour to obtain the titled compound (47.6 g), which was used in the next step without further purification.

Intermediate 23: 2-(1-Benzylpiperidin-4-yl)-5-bromobenzo[d]oxazole

Intermediate 22 (47.6 g, 0.122 mol) was dissolved in xylene (500 ml) and added p-Toluenesulphonic acid (46 g, 0.24 mol). This mixture was refluxed for 20 h under a deanstark condenser. Xylene was removed and pH of the residue was adjusted to 9 using aq NaHCO$_3$ solution. Work up (EtOAc/H$_2$O) afforded the crude. Crude was purified by column on 60-120 mesh silicagel using a gradient mixture of EtOAc and Petether (10:90) as eluent to afford the titled compound (11 g) as brown solid.

Intermediate 24: 4-(2-(1-benzylpiperidin-4-yl)benzo[d]oxazol-5-yl)-2-fluorobenzamide Following the general procedure-3, the titled compound (4.8 g) was prepared from intermediate 23 (6 g, 16.2 mmol) and 2-fluoro-4-(4,4,5,5-tetramethyl-1,3,2-dioxaborolan-2-yl)benzamide (4.7 g, 17.8 mmol) as a brown solid.

Intermediate 25: 2-Fluoro-4-(2-(piperidin-4-yl)benzo[d]oxazol-5-yl)benzamide

Intermediate 24 (100 mg, 0.23 mmol) dissolved in MeOH (10 ml) and added Pd/C (100 mg). This mixture was stirred under 60 Psi hydrogen atmosphere in an autoclave for 16. After 16 h, reaction mass filtered through celite and celite was washed with MeOH. MeOH was removed on rotavapour to obtain the titled compound (80 mg) as an off-white solid.

Intermediate 26: 5-Bromo-2-[2-fluoro-4-(methylsulfonyl)phenyl]-1H-benzo[d]Imidazole 4-bromobenzene-1,2-diamine (1.75 g, 9.39 mmol) and 2-fluoro-4-(methylsulfonyl)benzoic acid (2 g, 9.39 mmol) were dissolved in polyphosphoric acid (70 g). This mixture was heated at 195° C. for three and half hours. Reaction mixture cooled to rt and diluted with ice water (100 ml). Aqueous layer basified with sodium hydroxide pellets to pH 9. Work up (EtOAc/H$_2$O) followed by removal of EtOAc afforded the crude. Crude was purified on combiflash with a gradient mixture of EtOAc and Petether (33:67) to obtain the titled compound (1.5 g) as an off-white solid.

Intermediate 27: 2-[2-Fluoro-4-(methylsulfonyl)phenyl]-5-(4,4,5,5-tetramethyl-1,3,2-dioxaborolan-2-yl)-1H-benzo[d]imidazole Intermediate 26 (1.5 g, 4.1 mmol), 4,4,4',4',5,5,5',5'-octamethyl-2,2'-bi(1,3,2-dioxaborolane) (1.34 g, 5.3 mmol) and potassium acetate (1.32 g, 13.5 mmol) were dissolved in dioxane (60 ml) under N$_2$ atmosphere. This mixture was degassed with nitrogen for 30 mins and added Pd(dppf)$_2$Cl$_2$.CH$_2$Cl$_2$ (133 mg, 0.16 mmol). This mixture stirred at 105° C. for 12 h. Reaction mixture diluted with water and work up (AcOEt/H$_2$O) afforded the crude. Crude was purified by combiflash using a mixture of AcOEt and Petether (33:67) to afford the titled compound (880 mg) as an off-white solid.

Intermediate 28: 5-Bromo-2-[2-fluoro-4-(methylsulfonyl)phenyl]benzo[d]oxazole

2-Amino-4-bromophenol (1.77 g, 9.4 mmol) and 2-fluoro-4-(methylsulfonyl)benzoic acid (2 g, 9.4 mmol) were dissolved in polyposphoric acid (60 g). This mixture was heated at 195° C. for three and half hours. Reaction mixture cooled to rt and diluted with ice water (100 ml). Aqueous layer basified with sodium hydroxide pellets to pH 9. Work up (EtOAc/H$_2$O) followed by evaporation of EtOAc afforded the crude. Crude was purified on combiflash with a gradient mixture of EtOAc and Petether (33:67) to obtain the titled compound (2.8 g) as an off-white solid.

Intermediate 29: 2-[2-Fluoro-4-(methylsulfonyl)phenyl]-5-(4,4,5,5-tetramethyl-1,3,2-dioxaborolan-2-yl)benzo[d]oxazole Intermediate 28 (2.8 g, 7.6 mmol) 4,4,4',4',5,5,5',5'-octamethyl-2,2'-bi(1,3,2-dioxaborolane) (2.5 g, 9.9 mmol) and potassium acetate (2.46 g, 25.08 mmol) were dissolved in dioxane (150 ml) under N$_2$ atmosphere. This mixture was degassed with nitrogen for 30 mins and added Pd(dppf)$_2$Cl$_2$.CH$_2$Cl$_2$ (248 mg, 0.3 mmol). This mixture stirred at 105° C. for 12 h. Reaction mixture diluted with water and work up (AcOEt/H$_2$O) afforded the crude. Crude was purified by combiflash using a gradient mixture of AcOEt and Petether (33:67) to afford the titled compound (1 g) as an off-white solid.

Intermediate 30: 5-Bromo-7-fluoro-2-[2-fluoro-4-(methylsulfonyl)phenyl]benzo[d]oxazole 2-Amino-4-bromo-6-fluorophenol (2.6 g, 9.7 mmol) and 2-fluoro-4-(methylsulfonyl)benzoic acid (2.1 g, 9.7 mmol) were dissolved in polyposphoric acid (63.5 g). This mixture was heated at 195° C. for three and half hours. Reaction mixture cooled to rt and diluted with ice water (100 ml). Aqueous layer basified with sodium hydroxide pellets to pH 9. Work up (EtOAc/H$_2$O) followed by evaporation of EtOAc afforded the crude. Crude (3.1 g) was used in the next step without further purification.

Intermediate 31: 7-Fluoro-2-[2-fluoro-4-(methylsulfonyl)phenyl]-5-(4,4,5,5-tetramethyl-1,3,2-dioxaborolan-2-yl)benzo[d]oxazole Intermediate 30 (1.5 g, 3.87 mmol) 4,4,4',4',5,5,5',5'-octamethyl-2,2'-bi(1,3,2-dioxaborolane) (1.28 g, 5 mmol) and potassium acetate (1.25 g, 12.8 mmol) were dissolved in dioxane (20 ml) under N$_2$ atmosphere. This mixture was degassed with nitrogen for 30 mins and added Pd(dppf)$_2$Cl$_2$.CH$_2$Cl$_2$ (126 mg, 0.15 mmol). This mixture stirred at 105° C. for 12 h. Reaction mixture diluted with water and work up (AcOEt/H$_2$O) afforded the crude. Crude was purified by combiflash using a gradient mixture of AcOEt and Petether (18:82) as eluent to afford the titled compound (620 mg) as an off-white solid.

Intermediate 32: N-(4-Bromo-2-fluorophenyl)-2-fluoro-4-(methylsulfonyl)benzamide 2-Fluoro-4-(methylsulfonyl)benzoic acid (2 g, 9.2 mmol) dissolved in DCM (10 ml), cooled to 0° C. and added oxalyl chloride (1.2 ml, 13.8 mmol). Catalytic amount of DMF was added to this mixture and stirred at rt for 30 mins. After 30 mins, DCM removed on rotavapour and co-distilled the residue two times with DCM to obtain 2-fluoro-4-(methylsulfonyl)benzoyl chloride quantitatively. 4-Bromo-2-fluoroaniline (1.4 g, 7.37 mmol) dissolved in DCM and added Pyridine (0.7 g, 8.84 mmol) under nitrogen atmosphere. This mixture stirred at rt for 30 mins and added 2-fluoro-4-(methylsulfonyl)benzoyl chloride (2.08 g, 8.84 mmol). After continuing stifling at rt for 15 mins, reaction mixture diluted with water and extracted with DCM. DCM layer washed with aq. NaHCO$_3$ and DCM removed on rotavapour to obtain the solid. Solid was triturated with Et$_2$O and Petether mixture (4:1) to obtain the titled compound (1 g) as a brown solid.

Intermediate 33: N-(4-Bromo-2-fluorophenyl)-2-fluoro-4-(methylsulfonyl)benzothioamide Intermediate 32 (1 g, 2.56 mmol) dissolved in toluene (10 ml) and added P$_2$S$_5$ (0.57 g, 2.56 mmol). This mixture was refluxed for 18 h. Toluene removed on rotavapour to obtain the crude. Crude was purified by column chromatography on 60-120 mesh silicagel using EtOAc and Petether (20:80) as eluent to afford the title compound (500 mg) as a yellow solid. $^1$H-NMR (δ ppm, DMSO-d$_6$, 400 MHz): 11.02 (s, 1H), 7.92-7.85 (m, 2H), 7.69 (dd, J 1.6, 8.1, 1H), 7.63 (dd, J 1.6, 9, 1H), 7.33-7.27 (m, 2H), 3.02 (s, 3H).

Intermediate 34: 6-Bromo-2-[2-fluoro-4-(methylsulfonyl)phenyl]benzo[d]thiazole

Intermediate 33 (600 mg, 1.47 mmol) dissolved in DMF (7 ml) and added Na$_2$CO$_3$ (156 mg, 1.47 mmol). This mixture stirred at 110° C. for 17 h. Work up (EtOAc/H$_2$O) afforded the crude. Crude was triturated with Petether and dried to obtain the titled compound (360 mg) as a white solid. $^1$H-NMR (δ ppm, CDCl$_3$, 400 MHz): 8.71-8.65 (m, 1H), 8.13 (d, J 1.9, 1H), 8.01 (d, J 8.7, 1H), 7.91-7.83 (m, 2H), 7.66 (dd, J 1.9, 8.7, 1H), 3.12 (s, 3H).

Intermediate 35: 2-[2-Fluoro-4-(methylsulfonyl)phenyl]-6-(4,4,5,5-tetramethyl-1,3,2-dioxaborolan-2-yl)benzo[d]thiazole Intermediate 34 (360 mg, 0.94 mmol) 4,4,4',4',5,5,5',5'-octamethyl-2,2'-bi(1,3,2-dioxaborolane) (300 mg, 1.2 mmol) and potassium acetate (300 mg, 1.2 mmol) were dissolved in dioxane (10 ml) under N$_2$ atmosphere. This mixture was degassed with nitrogen for 30 mins and added Pd(dppf)$_2$Cl$_2$.CH$_2$Cl$_2$ (30 mg, 0.04 mmol). This mixture stirred at 105° C. for 12 h. Reaction mixture diluted with water and work up (AcOEt/H$_2$O) afforded the crude. Crude was purified by combiflash using a mixture of AcOEt and Petether (12:88) as eluent to afford the titled compound (300 mg) as an off-white solid. $^1$H-NMR (δ ppm, CDCl$_3$, 400 MHz): 8.74-8.69 (m, 1H), 8.46 (s, 1H), 8.14 (d, J 8.2, 1H), 7.97 (dd, J 1, 8.2, 1H), 7.91-7.83 (m, 2H), 3.12 (s, 3H), 1.38 (s, 12H).

Intermediate 36: N-(2,5-Dibromophenyl)-2-fluoro-4-(methylsulfonyl)benzamide

2-Fluoro-4-(methylsulfonyl)benzoic acid (1 g, 4.6 mmol) dissolved in DCM (15 ml), cooled to 0° C. and added oxalyl chloride (0.6 ml, 6.9 mmol). Catalytic amount of DMF was added to this mixture and stirred at rt for 30 mins. After 30 mins, DCM removed on rotavapour and co-distilled the residue two times with DCM to obtain 2-fluoro-4-(methylsulfonyl)benzoyl chloride quantitatively. 2,5-Dibromoaniline (0.9 g, 3.59 mmol) dissolved in DCM (10 ml) and added Pyridine (0.34 g, 4.30 mmol) under nitrogen atmosphere. This mixture stirred at rt for 30 mins and added 2-fluoro-4-(methylsulfonyl)benzoyl chloride (1.01 g, 3.59 mmol). After continuing stirring at rt for 15 mins, reaction mass diluted with water and extracted with DCM. DCM layer washed with aq. NaHCO$_3$ and DCM removed on rotavapour to obtain the solid. Solid was triturated with Et$_2$O and Petether mixture (4:1) to obtain the titled compound (1.6 g) as a brown solid. $^1$H-NMR (δ ppm, DMSO-d$_6$, 400 MHz): 10.34 (s, 1H), 8.34-7.99 (m, 1H), 7.98-7.93 (m, 2H), 7.92-7.89 (m, 1H), 7.68 (d, J 8.6, 1H), 7.43 (dd, J 2.4, 8.6, 1H), 3.33 (s, 3H).

Intermediate 37: N-(2,5-Dibromophenyl)-2-fluoro-4-(methylsulfonyl)benzothioamide Intermediate 36 (1.5 g, 3.34 mmol) dissolved in toluene (20 ml) and added P$_{2S5}$ (0.74 g, 3.34 mmol). This mixture was refluxed for 18 h. Toluene removed on rotavapour to obtain the crude. Crude was purified by column chromatography on 60-120 mesh silicagel using EtOAc and Petether (20:80) as eluent to afford the title compound (480 mg) as a yellow solid. $^1$H-NMR (δ ppm, DMSO-d$_6$, 400 MHz): 12.26 (s, 1H), 7.94-7.83 (m, 3H), 7.78-7.72 (m, 2H), 7.55 (dd, J 2.3, 8.6, 1H), 3.32 (s, 3H).

Intermediate 38: 5-Bromo-2-[2-fluoro-4-(methylsulfonyl)phenyl]benzo[d]thiazole

Intermediate 37 (0.48 g, 1.03 mmol) dissolved in N-Methylpyrrolidinone (0.97 ml) and added NaH (52 mg, 2.2 mmol). This mixture was stirred at 140° C. for 3 h. Reaction mixture cooled to rt and diluted with water to obtain the solid. Solid was filtered and dried to obtain the crude. Crude was purified on column chromatography using 60-120 mesh silicagel and DCM as eluent to afford the titled compound (260 mg) as a white solid. $^1$H-NMR (δ ppm, CDCl$_3$, 400 MHz): 8.71-8.66 (m, 1H), 8.32 (d, J 1.7, 1H), 7.92-7.83 (m, 3H), 7.59 (dd, J 1.8, 8.6, 1H), 3.13 (s, 3H).

Intermediate 39: 2-[2-Fluoro-4-(methylsulfonyl)phenyl]-5-(4,4,5,5-tetramethyl-1,3,2-dioxaborolan-2-yl)benzo[d]thiazole Intermediate 38 (360 mg, 0.94 mmol) 4,4,4',4',5,5,5',5'-octamethyl-2,2'-bi(1,3,2-dioxaborolane) (220 mg, 0.88 mmol) and potassium acetate (220 mg, 2.2 mmol) were dissolved in dioxane (10 ml) under N$_2$ atmosphere. This mixture was degassed with nitrogen for 30 mins and added Pd(dppf)$_2$Cl$_2$.CH$_2$Cl$_2$ (22 mg, 0.03 mmol). This mixture stirred at 105° C. for 12 h. Reaction mixture diluted with water and work up (AcOEt/H$_2$O) afforded the crude. Crude was purified by combiflash using a mixture of AcOEt and Petether (12:88) as eluent to afford the titled compound (230 mg) as a yellow solid. $^1$H-NMR (δ ppm, CDCl$_3$, 400 MHz): 8.73-8.67 (m, 1H), 8.62 (s, 1H), 7.98 (d, J 8, 1H), 7.90-7.81 (m, 3H), 3.12 (s, 3H), 1.39 (s, 12H).

Intermediate 40: 6-Bromo-2-[2-fluoro-4-(methylsulfonyl)phenyl]benzo[d]oxazole 2-amino-5-bromophenol (1.72 g, 9.2 mmol) and 2-fluoro-4-(methylsulfonyl)benzoic acid (2 g, 9.2 mmol) were dissolved in polyposphoric acid (30 g). This mixture was heated at 195° C. for three and half hours. Reaction mixture cooled to rt and diluted with ice water (100 ml). Aqueous layer basified with sodium hydroxide pellets to pH 9. Solid that formed was filtered and dried to obtain the crude. Crude was purified by combiflash using a gradient mixture of EtOAc and Petether (1:3) as eluent to afford the titled compound (450 mg) as a dark brown solid.

Intermediate 41: 2-[2-fluoro-4-(methylsulfonyl)phenyl]-6-(4,4,5,5-tetramethyl-1,3,2-dioxaborolan-2-yl)benzo[d]oxazole Intermediate 40 (1.5 g, 4.1 mmol) 4,4,4',4',5,5,5',5'-octamethyl-2,2'-bi(1,3,2-dioxaborolane) (1.35 g, 5.29 mmol) and potassium acetate (1.32 g, 13.45 mmol) were dissolved in dioxane (10 ml) under N$_2$ atmosphere. This mixture was degassed with nitrogen for 30 mins and added Pd(dppf)$_2$Cl$_2$.CH$_2$Cl$_2$ (133 mg, 0.16 mmol). This mixture stirred at 105° C. for 12 h. Reaction mixture diluted with water and work up (AcOEt/H$_2$O) afforded the crude. Crude was purified by combiflash using a gradient mixture of AcOEt and Petether (1:3) as eluent to afford the titled compound (500 mg) as a pink solid.

Intermediate 42: N-(5-Bromo-2-hydroxyphenyl)-4-(trifluoromethyl)benzamide 4-(Trifluoromethyl)benzoic acid (1 g, 5.3 mmol) dissolved in DCM (10 ml), cooled to 0° C. and added oxalyl chloride (0.7 ml, 7.9 mmol). Catalytic amount of DMF was added to this mixture and stirred at rt for 30 mins. After 30 mins, DCM removed on rotavapour and co-distilled the residue two times with DCM to obtain 4-(trifluoromethyl)benzoyl chloride quantitatively. 2-Amino-4-bromophenol (0.8 g, 4.25 mmol) dissolved in DCM (20 ml) and added Pyridine (0.4 ml, 5.1 mmol) under nitrogen atmosphere. This mixture stirred at rt for 30 mins and added 4-(trifluoromethyl)benzoyl chloride (1.06 g, 5.1 mmol). After continuing stirring at rt for 15 mins, reaction mass diluted with water and extracted with DCM. DCM layer washed with aq. NaHCO$_3$ and DCM removed on rotavapour to obtain the solid. Solid was triturated with Et$_2$O and Petether mixture (4:1) to obtain the titled compound (1 g) as a brown solid. $^1$H-NMR (δ ppm, DMSO-d$_6$, 400 MHz): 10.15 (bs, 1H), 9.75 (s, 1H), 8.13 (d, J 8.1, 2H), 7.92-7.87 (m, 3H), 7.20 (dd, J 2.5, 8.6, 1H), 6.88 (d, J 8.6, 1H).

Intermediate 43: 5-bromo-2-[4-(trifluoromethyl)phenyl]benzo[d]oxazole

Intermediate 42 (1 g, 2.77 mmol) was dissolved in 1,4-Dioxane and added Phosphorus oxychloride (0.76 ml, 8.3 mmol). This mixture was refluxed for 2 h. 1,4-Dioxane removed on rotavapour to obtain the residue. Residue was washed with water to obtain solid. Solid was filtered and dried to obtain the titled compound (630 mg) as an off-white solid. $^1$H-NMR (δ ppm, CDCl$_3$, 400 MHz): 8.35 (d, J 8.2, 2H), 7.93 (d, J 1.5, 1H), 7.79 (d, J 8.3, 2H), 7.52-7.49 (m, 2H).

Intermediate 44: 5-(4,4,5,5-Tetramethyl-1,3,2-dioxaborolan-2-yl)-2-(4-(trifluoromethyl)phenyl)benzo[d]oxazole Intermediate 43 (630 mg, 1.84 mmol), 4,4,4',4',5,5,5',5'-octamethyl-2,2'-bi(1,3,2-dioxaborolane) (600 mg, 2.4 mmol) and potassium acetate (590 mg, 6.1 mmol) were dissolved in 1,4-dioxane (10 ml) under N$_2$ atmosphere. This mixture was degassed with nitrogen for 30 mins and added Pd(dppf)$_2$Cl$_2$.CH$_2$Cl$_2$ (60 mg, 0.08 mmol). This mixture stirred at 105° C. for 12 h. Reaction mixture diluted with water and work up (AcOEt/H$_2$O) afforded the crude. Crude was purified by combiflash using a mixture of AcOEt and Petether (8:92) as eluent to afford the titled compound (400 mg) as a yellow solid. $^1$H-NMR (δ ppm, CDCl$_3$, 400 MHz): 8.38 (d, J 8.1, 2H), 8.25 (s, 1H), 7.86 (dd, J 1, 7.9, 1H), 7.78 (d, J 8.3, 2H), 7.59 (d, J 8.6, 1H), 1.38 (s, 12H).

Intermediate 45: N-(4-Bromo-2-hydroxyphenyl)-4-(difluoromethyl)benzamide 4-(difluoromethyl)benzoic acid (0.7 g, 4 mmol) dissolved in DCM (20 ml), cooled to 0° C. and added oxalyl chloride (0.8 g, 6.1 mmol). Catalytic amount of DMF was added to this mixture and stirred at rt for 30 mins. After 30 mins, DCM removed on rotavapour and co-distilled the residue two times with DCM to obtain 4-(difluoromethyl)benzoyl chloride quantitatively. 2-Amino-5-bromophenol (0.64 g, 3.4 mmol) dissolved in DCM (20 ml) and added Pyridine (0.32 ml, 4.1 mmol) under nitrogen atmosphere. This mixture stirred at rt for 30 mins and added 4-(difluoromethyl)benzoyl chloride (0.77 g, 4.1 mmol). After continuing stirring at rt for 15 mins, reaction mass diluted with water and extracted with DCM. DCM layer washed with aq. NaHCO$_3$ and DCM removed on rotavapour to obtain the solid. Solid was triturated with Et$_2$O and Petether mixture (4:1) to obtain the titled compound (0.5 g) as a yellow solid. $^1$H-NMR (δ ppm, DMSO-d$_6$, 400 MHz): 10.27 (s, 1H), 9.62 (s, 1H), 8.07 (d, J 8.2, 2H), 7.71 (d, J 8.2, 2H), 7.61 (d, J 8.5, 1H), 7.12 (t, J 55.7, 1H), 7.07 (d, J 2.2, 1H), 7.03-6.94 (m, 1H).

Intermediate 46: 6-Bromo-2-[4-(difluoromethyl)phenyl]benzo[d]oxazole

N-(4-Bromo-2-hydroxyphenyl)-4-(difluoromethyl)benzamide (0.5 g, 1.5 mmol) was dissolved in 1,4-Dioxane (10 ml) and added Phosphorus oxychloride (0.4 ml, 4.4 mmol). This mixture was refluxed for 2 h. 1,4-Dioxane removed on rotavapour to obtain the residue. Residue was washed with water to obtain solid. Solid was purified by column on 60-120 mesh silica gel using DCM as eluent to obtain the titled compound (130 mg) as an off-white solid. $^1$H-NMR (δ ppm, CDCl$_3$, 400 MHz): 8.28 (d, J 8.4, 2H), 7.74 (d, J 1.7, 1H), 7.65-7.58 (m, 3H), 7.46 (dd, J 1.8, 8.4, 1H), 6.68 (t, J 56.2, 1H).

Intermediate 47: 2-[4-(Difluoromethyl)phenyl]-6-(4,4,5,5-tetramethyl-1,3,2-dioxaborolan-2-yl)benzo[d]oxazole Intermediate 46 (130 mg, 0.4 mmol) 4,4,4',4',5,5,5',5'-octamethyl-2,2'-bi(1,3,2-dioxaborolane) (130 mg, 0.52 mmol) and potassium acetate (110 mg, 1.2 mmol) were dissolved in 1,4-dioxane (15 ml) under N$_2$ atmosphere. This mixture was degassed with nitrogen for 30 mins and added Pd(dppf)$_2$Cl$_2$.CH$_2$Cl$_2$ (13 mg, 0.02 mmol). This mixture stirred at 105° C. for 4 h. Reaction mixture diluted with water and work up (AcOEt/H$_2$O) afforded the crude. Crude was purified by combiflash using a mixture of AcOEt and Petether (8:92) as eluent to afford the titled compound (100 mg) as a yellow solid.

Intermediate 48: Tert-butyl 4-{2-[4-(difluoromethyl)phenyl]benzo[d]oxazol-6-yl}-5,6-dihydropyridine-1(2H)-carboxylate Following the general procedure-2, the titled compound was prepared from intermediate 47 (0.1 g, 0.27 mmol) and tert-butyl 4-(trifluoromethylsulfonyloxy)-5,6-dihydropyridine-1(2H)-carboxylate (89 mg, 0.27 mmol) as an off-white solid. $^1$H-NMR (δ ppm, CDCl$_3$, 400 MHz): 8.34 (d, J 8.4, 2H), 7.72 (d, J 8.4, 1H), 7.67 (d, J 8.2, 2H), 7.58 (d, J 1.4, 1H), 7.43 (dd, J 1.6, 8.4, 1H), 6.72 (t, J 56.2, 1H), 6.12 (bs, 1H), 4.12 (d, J 2.7, 2H), 3.68 (t, J 5.6, 2H), 2.60 (bs, 2H), 1.50 (s, 9H).

Intermediate 49: tert-butyl 4-(2-p-tolylbenzo[d]oxazol-6-yl)piperidine-1-carboxylate Intermediate 48 (45 mg, 0.14 mmol) dissolved in MeOH (10 ml) and added Pd/C (5%) (100 mg). This mixture was stirred under 60 Psi hydrogen pressure for 15 h in an autoclave. After completion of the reaction, reaction mixture filtered through a bed of celite and celite was washed with MeOH. Combined MeOH layers were removed on rotavapour to obtain the residue. Residue was triturated with petether to obtain the titled compound (40 mg) as an off-white solid. MS (m/z): 393.2 [M+H]$^+$.

Intermediate 50: Tert-butyl 4-(2-aminobenzo[d]oxazol-5-yl)-5,6-dihydropyridine-1(2H)-carboxylate 5-Bromobenzo[d]oxazol-2-amine (824 mg, 3.9 mmol) and tert-butyl 4-(trifluoromethylsulfonyloxy)-5,6-dihydropyridine-1(2H)-carboxylate (1.8 g, 5.8 mmol), Potassium fluoride (674 mg, 11.61 mmol) were dissolved in DMF under $N_2$ atmosphere. This mixture was purged with $N_2$ for 30 mins Pd(dppf)2Cl2.CH$_2$Cl$_2$ (252 mg, 0.3 mmol) was added to the above mixture and again purged with $N_2$ for 30 mins. The reaction mixture was stirred at 90° C. for 12 h. Work up (EtOAc/H$_2$O) followed by column purification on combiflash using a gradient mixture of EtOAc and Petether (1:1) as eluent afforded the titled compound (550 mg) as an off-white solid. $^1$H-NMR (δ ppm, DMSO-d$_6$, 400 MHz): 7.38-7.36 (m, 2H), 7.26-7.22 (m, 2H), 7.02 (d, J 7.9, 1H), 6.05 (s, 1H), 4.01-3.90 (m, 2H), 3.49-3.55 (m, 2H), 2.50-2.40 (m, 2H), 1.50 (s, 9H).

Intermediate 51: Tert-butyl 4-(2-aminobenzo[d]oxazol-5-yl)piperidine-1-carboxylate Intermediate 50 (550 mg, 0.14 mmol) dissolved in MeOH (25 ml) and added Pd/C (5%) (700 mg). This mixture was stirred under 80 Psi hydrogen pressure for 12 h in an autoclave. After completion of the reaction, reaction mixture filtered through a bed of celite and celite was washed with MeOH. MeOH was removed on rotavapour to obtain the residue. Residue was triturated with petether to obtain the titled compound (400 mg) as an off-white solid.

Intermediate 52: Tert-butyl 4-(2-bromobenzo[d]oxazol-5-yl)piperidine-1-carboxylate Intermediate 51 (400 mg, 1.3 mmol) was dissolved in acetonitrile (50 ml) and added CuBr$_2$ (563 mg, 2.5 mmol). This mixture stirred at rt for 15 mins Tert-Butyl nitrite (259 mg, 2.5 mmol) was added to the above mixture for 5 mins and stirred at 45° C. for 2 h. Work up (DCM/H$_2$O) followed by purification on combiflash using a gradient mixture of EtOAc and Petether (1:3) as eluent afforded the titled compound (130 mg) as an off-white solid. $^1$H-NMR (δ ppm, CDCl$_3$, 400 MHz): 8.28 (bs, 1H), 7.41 (s, 1H), 6.91 (s, 1H), 4.35-4.19 (m, 2H), 3.21-3.10 (m, 1H), 2.85 (t, J 11.3, 2H), 1.90-1.80 (m, 2H), 1.60-1.40 (m, 11H).

Intermediate 53: N-(4-bromo-2-hydroxyphenyl)-4-(trifluoromethyl)benzamide 4-(Trifluoromethyl)benzoic acid (0.8 g, 4.2 mmol) dissolved in DCM (20 ml), cooled to 0° C. and added oxalyl chloride (0.8 g, 6.1 mmol). Catalytic amount of DMF was added to this mixture and stirred at rt for 30 mins. After 30 mins, DCM removed on rotavapour and co-distilled the residue two times with DCM to obtain 4-(trifluoromethyl)benzoyl chloride quantitatively. 2-Amino-5-bromophenol (0.71 g, 3.8 mmol) dissolved in DCM (20 ml) and added Pyridine (0.32 ml, 4.1 mmol) under nitrogen atmosphere. This mixture stirred at rt for 30 mins and added 4-(trifluoromethyl)benzoyl chloride (0.88 g, 4.2 mmol). After continuing stirring at rt for 15 mins, reaction mass diluted with water and extracted with DCM. DCM layer washed with aq. NaHCO$_3$ and DCM removed on rotavapour to obtain the solid. Solid was triturated with Et$_2$O and Petether mixture (4:1) to obtain the titled compound (0.6 g) as a yellow solid.

Intermediate 54: 6-bromo-2-(4-(trifluoromethyl)phenyl)benzo[d]oxazole

Intermediate 53 (940 mg, 2.6 mmol) was dissolved in xylene (25 ml) and added p-Toluenesulphonic acid (991 mg, 5.22 mmol). This mixture was refluxed to 160° C. for 12 h under a dean-stork condenser. Xylene removed from the reaction mixture and basified the residue with aq. NaHCO$_3$ (30 ml). Work up (EtOAc/H$_2$O) followed by purification with combiflash using a gradient mixture of EtOAc and Petether (5:95) as eluent to afford the titled compound (650 mg) as an Off-White solid.

Intermediate 55: 6-(4,4,5,5-tetramethyl-1,3,2-dioxaborolan-2-yl)-2-[4-(trifluoromethyl)phenyl]benzo[d]oxazole Intermediate 54 (630 mg, 1.84 mmol) 4,4,4',4',5,5,5',5'-octamethyl-2,2'-bi(1,3,2-dioxaborolane) (600 mg, 2.4 mmol) and potassium acetate (590 mg, 3.3 mmol) were dissolved in 1,4-dioxane (30 ml) under $N_2$ atmosphere. This mixture was degassed with nitrogen for 30 mins and added Pd(dppf)$_2$Cl$_2$.CH$_2$Cl$_2$ (60 mg, 0.074 mmol). This mixture stirred at 105° C. for 17 h. Reaction mixture diluted with water and work up (AcOEt/H$_2$O) afforded the crude. Crude was purified by combiflash using a mixture of AcOEt and Petether (20:80) as eluent to afford the titled compound (420 mg) as an off-white solid. $^1$H-NMR (δ ppm, CDCl$_3$, 400 MHz): 8.39 (d, J 8.1, 2H), 8.05 (s, 1H), 7.84 (dd, J 0.8, 8, 1H), 7.82-7.76 (m, 3H), 1.38 (s, 12H).

Intermediate 56: N-(5-bromo-2-hydroxypyridin-3-yl)-4-(trifluoromethyl)benzamide 4-(Trifluoromethyl)benzoic acid (2.45 g, 12.9 mmol) dissolved in DCM (30 ml), cooled to 0° C. and added oxalyl chloride (3.4 ml, 38.6 mmol). Catalytic amount of DMF was added to this mixture and stirred at rt for 30 mins. After 30 mins, DCM removed on rotavapour and co-distilled the residue two times with DCM to obtain 4-(trifluoromethyl)benzoyl chloride quantitatively. 2-Hydroxy-3-amino-5-bromopyridine (2.4 g, 11.1 mmol) dissolved in DCM (15 ml) and added Pyridine (1.74 g, 22 mmol) under nitrogen atmosphere. This mixture stirred at rt for 30 mins and added 4-(trifluoromethyl)benzoyl chloride (2.4 g, 13.3 mmol). After continuing stirring at rt for 30 mins, reaction mass diluted with water and extracted with DCM. DCM removed on rotavapour to obtain the crude. Crude was purified on column using 60-120 mesh silica gel and a gradient mixture of MeOH and DCM (2:98) as eluent to afford the titled compound (2.1 g) as a brown solid. $^1$H-NMR (δ ppm, DMSO-d$_6$, 400 MHz): 12.43 (bs, 1H), 9.58 (s, 1H), 8.37 (d, J 2.6, 1H), 8.09 (d, J 8.2, 2H), 7.91 (d, J 8.2, 2H), 7.48 (d, J 2.6, 1H).

Intermediate 57: 6-bromo-2-(4-(trifluoromethyl)phenyl)oxazolo[5,4-b]pyridine

Intermediate 56 (2.1 g, 5.4 mmol) was dissolved in Dioxane (30 ml) and added POCl$_3$ (1.5 ml). This mixture was refluxed for 5 h. After 5 h, dioxane was removed on rotavapour to obtain the residue. Work up (EtOAc/H$_2$O) of the residue afforded the crude. Crude was purified by column on 60-120 mesh silica gel using DCM as eluent to afford the titled compound (1.2 g). ¹H-NMR (δ ppm, CDCl₃, 400 MHz): 8.46 (d, J 2.1, 1H), 8.41 (d, J 8.2, 2H), 8.24 (d, J 2.1, 1H), 7.83 (d, J 8.2, 2H).

Intermediate 58: 6-(4,4,5,5-tetramethyl-1,3,2-dioxaborolan-2-yl)-2-[4-(trifluoromethyl)phenyl]oxazolo [5,4-b]pyridine Intermediate 57 (1.2 g, 3.5 mmol) 4,4,4',4',5,5,5',5'-octamethyl-2,2'-bi(1,3,2-dioxaborolane) (973 mg, 3.8 mmol) and potassium acetate (1.03 g, 10.5 mmol) were dissolved in 1,4-dioxane (40 ml) under N₂ atmosphere. This mixture was degassed with nitrogen for 30 mins and added Pd(dppf)₂Cl₂.CH₂Cl₂ (113 mg, 0.14 mmol). This mixture stirred at 105° C. for 15 h. Reaction mixture diluted with water and work up (AcOEt/H₂O) afforded the crude. Crude was purified by combiflash using a gradient mixture of AcOEt and Petether (5:95) as eluent to afford the titled compound (1.2 g) as an off-white solid. ¹H-NMR (δ ppm, CDCl₃, 400 MHz): 8.77 (d, J 1.5, 1H), 8.46 (d, J 1.5, 1H), 8.41 (d, J 8.1, 2H), 7.80 (d, J 8.1, 2H), 1.38 (s, 12H).

General Procedure-1 for Suzuki Coupling:

Aryl bromide (1 eq.) was dissolved in Dioxane and water (5:1) and added arylboronic acid (1.3 eq), Pd(PPh₃)₄ (0.08 eq) and Na₂CO₃ (3.3 eq). Reaction mixture degassed with N₂ for 30 mins and refluxed until both the starting materials disappeared. Work-up (H₂O/AcOEt) and purification gave the desired product.

General Procedure-2 for Suzuki Coupling:

Aryl bromide (1 eq), arylboronic acid (1 eq.), Sodium carbonate (3 eq) dissolved in DMF and water (4:1) and degassed with N₂ for 15 mins. To this mixture Pd(dppf)₂Cl₂.CH₂Cl₂ (0.08 eq) was added and degassed again with N₂ for 15 mins. This mixture was irradiated in micro wave for 105 mins, at 80° C. Work-up (H₂O/AcOEt) and purification gave the desired product.

General Procedure-3 for Suzuki Coupling:

Same as General Procedure-2 except that KF was used instead of Na₂CO₃

General Procedure-4 for Suzuki Coupling:

Same as General Procedure-2 except that Dioxane was used instead of DMF.

Example 1

2-[1-(5-Ethylpyrimidin-2-yl)piperidin-4-yl]-5-[2-fluoro-4-(methylsulfonyl)phenyl]-1H-benzo[d]imidazole Following the General Procedure-1, the titled compound (25 mg) was prepared from Intermediate 2 (80 mg, 0.199 mmol) and Intermediate 3 (79 mg, 0.26 mmol) as a yellow solid. M.P.: 186.5-190° C. ¹H-NMR (δ ppm, DMSO-d₆, 400 MHz): 12.41 (d, J 4, 1H), 8.26 (s, 2H), 7.90-7.80 (m, 3H), 7.79-7.50 (m, 2H), 7.40-7.32 (m, 1H), 4.66 (d, J 13.1, 2H), 3.29 (s, 3H), 3.21 (t, J 8.3, 1H), 3.09 (t, J 11.7, 2H), 2.43 (q, J 7.73, 2H), 2.06 (d, J 12.5, 2H), 1.82-1.71 (m, 2H), 1.13 (t, J 7.5, 3H).

Example 2

Tert-butyl 4-{5-[2-fluoro-4-(methylsulfonyl)phenyl]-1H-benzo[d]imidazol-2-yl}piperidine-1-carboxylate Following the General Procedure-1, the titled compound (40 mg) was prepared from Intermediate 4 (100 mg, 0.25 mmol) and Intermediate 3 (98 mg, 0.33 mmol) as a yellow solid. M.P.: 88-92° C. ¹H-NMR (δ ppm, DMSO-d₆, 400 MHz): 12.39 (s, 1H), 7.89-7.81 (m, 3H), 7.69-7.58 (m, 2H), 7.40-7.32 (m, 1H), 4.01 (d, J 12.5, 2H), 3.30 (s, 3H), 3.12-3.05 (m, 1H), 3.00-2.88 (m, 2H), 2.00 (d, J 11.8, 2H), 1.76-1.55 (m, 2H), 1.41 (s, 9H).

Example 3

2-[1-(5-ethylpyrimidin-2-yl)piperidin-4-yl]-5-[2-fluoro-4-(methylsulfonyl)phenyl]benzo[d]oxazole Following the General Procedure-1, the titled compound (30 mg) was prepared from Intermediate 6 (80 mg, 0.21 mmol) and Intermediate 3 (80 mg, 0.27 mmol) as an off-white solid. M.P.: 247-250° C. ¹H-NMR (δ ppm, CDCl₃, 400 MHz): 8.20 (s, 2H), 7.86 (s, 1H), 7.80 (m, 1H), 7.79-7.74 (m, 1H), 7.66 (t, J 7.5, 1H), 7.59 (d, J 8.4, 1H), 7.50 (d, J 8.5, 1H), 4.75 (d, J 13.4, 2H), 3.35-3.15 (m, 3H), 3.11 (s, 3H), 2.47 (q, J 7.6, 2H), 2.31-2.22 (m, 2H), 2.09-1.94 (m, 2H), 1.20 (t, J 7.6, 3H).

Example 4 tert-butyl 4-{5-[2-fluoro-4-(methylsulfonyl)phenyl] benzo[d]oxazol-2-yl}piperidine-1-carboxylate Following the General Procedure-1, the titled compound (40 mg) was prepared from Intermediate 7 (150 mg, 0.4 mmol) and Intermediate 3 (154 mg, 0.51 mmol) as an off-white solid. M.P.: 144-147° C. ¹H-NMR (δ ppm, CDCl₃, 400 MHz): 7.87 (s, 1H), 7.82 (d, J 8, 1H), 7.77 (dd, J 1.4, 9.4, 1H), 7.67 (t, J 7.5, 1H), 7.59 (d, J 8.4, 1H), 7.50 (d, J 8.5, 1H), 4.15 (d, J 7.7, 2H), 3.22-3.10 (m, 4H), 3.00 (t, J 11.3, 2H), 2.21-2.12 (m, 2H), 2.00-1.88 (m, 2H), 1.48 (s, 9H).

Example 5

Tert-butyl 4-{5-[2-fluoro-4-(methylsulfonyl)phenyl]-1-methyl-1H-benzo[d]imidazol-2-yl}piperidine-1-carboxylate Tert-butyl 4-{5-[2-fluoro-4-(methylsulfonyl)phenyl]-1H-benzo[d]imidazol-2-yl}piperidine-1-carboxylate (85 mg, 0.17 mmol) dissolved in THF (15 ml) and cooled to 0° C. Sodium hydride (9 mg, 0.342 mmol) added to the above mixture and stirred at the same temperature for 30 mins. To this mixture methyl iodide (48 mg, 0.342 mmol) added at same temperature and stirred the reaction mixture at rt for 3 h. Reaction mixture diluted with ice and worked up (EtOAc/H₂O). Crude was purified by column chromatography on 60-120 mesh silica gel using EtOAc:Petether (3:1) as eluent to afford the title compound (50 mg) as an orange solid. M.P.: 85-88° C. ¹H-NMR (δ ppm, CDCl₃, 400 MHz): 7.85-7.75 (m, 2H), 7.73-7.64 (m, 2H), 7.56-7.51 (m, 1H), 7.50-7.45 (m, 1H), 4.39-4.21 (m, 2H), 3.82 (s, 3H), 3.11 (s, 3H), 3.10-3.00 (m, 2H), 3.00-2.88 (m, 2H), 2.05-1.93 (m, 3H), 1.48 (s, 9H).

Example 6

Tert-butyl 4-{6-[2-fluoro-4-(methylsulfonyl)phenyl] benzo[d]oxazol-2-yl}piperidine-1-carboxylate Following the General Procedure-1, the titled compound (21 mg) was prepared from Intermediate 10 (100 mg, 0.26 mmol) and Intermediate 3 (102 mg, 0.34 mmol) as an off-white solid. M.P.: 174-178.3° C. ¹H-NMR (δ ppm, CDCl₃, 400 MHz): 7.85-7.75 (m, 3H), 7.73-7.64 (m, 2H), 7.50 (d, J 8.2, 1H), 4.15 (d, J 12.4, 2H), 3.20-3.10 (m, 4H), 3.0 (t, J 12.5, 2H), 2.20-2.12 (m, 2H), 2.00-1.85 (m, 2H), 1.48 (s, 9H).

Example 7

Isopropyl 4-{5-[2-fluoro-4-(methylsulfonyl)phenyl]benzo[d]oxazol-2-yl}piperidine-1-carboxylate Tert-butyl 4-{5-[2-fluoro-4-(methylsulfonyl)phenyl]benzo[d]oxazol-2-yl}piperidine-1-carboxylate (200 mg, 0.42 mmol) dissolved in DCM and added Trifluoroacetic acid (0.75 ml). This mixture was stirred at rt for 2 h. DCM removed from the reaction mixture to obtain 5-(2-fluoro-4-(methylsulfonyl)phenyl)-2-(piperidin-4-yl)benzo[d]oxazole 2,2,2-trifluoroacetate (190 mg). 5-(2-fluoro-4-(methylsulfonyl)phenyl)-2-(piperidin-4-yl)-benzo[d]oxazole 2,2,2-trifluoroacetate (190 mg, 0.39 mmol) was dissolved in DCM (20 ml) and added TEA (0.43 ml, 3.12 mmol). This mixture stirred at rt for 30 mins and added isopropyl chloroformate in toluene (0.095 g, 0.78 mmol). After 1 h, reaction mass diluted with water and extracted with DCM. Removal of DCM afforded crude. Crude was purified by combiflash using a mixture of EtOAc and Petether (35:65) as eluent to afford the titled compound (120 mg) as a pale-yellow solid. M.P.: 96.5-101.2° C. $^1$H-NMR ($\delta$ ppm, CDCl$_3$, 400 MHz): 7.87 (s, 1H), 7.81 (dd, J 1.7, 8, 1H), 7.80-7.75 (m, 1H), 7.67 (t, J 7.5, 1H), 7.59 (d, J 8.4, 1H), 7.50 (d, J 8.5, 1H), 4.94 (septet, J 6.2, 1H), 4.19 (d, J 10.9, 2H), 3.22-3.13 (m, 1H), 3.12 (s, 3H), 3.04 (t, J 10.9, 2H), 2.22-2.14 (m, 2H), 2.00-1.88 (m, 2H), 1.26 (d, J 6.2, 6H).

Example 8

Tert-butyl 4-{7-fluoro-5-[2-fluoro-4-(methylsulfonyl)phenyl]benzo[d]oxazol-2-yl}piperidine-1-carboxylate Following the General Procedure-1, the titled compound (50 mg) was prepared from Intermediate 12 (200 mg, 0.50 mmol) and Intermediate 3 (151 mg, 0.50 mmol) as an off-white solid. M.P.: 155.3-158.4° C. $^1$H-NMR ($\delta$ ppm, CDCl$_3$, 400 MHz): 7.82 (dd, J 1.8, 8.1, 1H), 7.78 (dd, J 1.7, 9.4, 1H), 7.69-7.63 (m, 2H), 7.29 (td, 1.3, 10.6, 1H), 4.16 (d, J 11.2, 2H), 3.22-3.16 (m, 1H), 3.11 (s, 3H), 3.00 (t, J 13.3, 2H), 2.21-2.14 (m, 2H), 2.00-1.88 (m, 2H), 1.48 (s, 9H).

Example 9

Tert-butyl 4-[5-(4-cyanophenyl)benzo[d]oxazol-2-yl]piperidine-1-carboxylate

Following the General Procedure-1, the titled compound (45 mg) was prepared from Intermediate 7 (140 mg, 0.37 mmol) and 4-Cyanophenylboronic acid (53 mg, 0.37 mmol) as an off-white solid. M.P.: 137.3-141.2° C. $^1$H-NMR ($\delta$ ppm, CDCl$_3$, 400 MHz): 7.88 (d, 1.4, 1H), 7.74 (dd, J 1.8, 8.5, 2H), 7.69 (dd, J 1.8, 8.5, 2H), 7.58 (d, J 8.5, 1H), 7.53 (dd, J 1.8, 8.5, 2H), 4.15 (d, J 10.4, 2H), 3.20-3.10 (m, 1H), 3.00 (t, J 11.2, 2H), 2.20-2.12 (m, 2H), 2.00-1.85 (m, 2H), 1.48 (s, 9H).

Example 10

Tert-butyl 4-{5-[3-fluoro-4-(methylsulfonyl)phenyl]benzo[d]oxazol-2-yl}piperidine-1-carboxylate Following the General Procedure-1, the titled compound (30 mg) was prepared from Intermediate 8 (100 mg, 0.23 mmol) and 4-bromo-2-fluoro-1-(methylsulfonyl)benzene (70 mg, 0.37 mmol) as an off-white solid. M.P.: 174.3-177.5° C. $^1$H-NMR ($\delta$ ppm, CDCl$_3$, 400 MHz): 8.03 (t, J 7.9, 1H), 7.88 (d, J 1.6, 1H), 7.61-7.51 (m, 3H), 7.46 (dd, J 1.6, 11.1, 1H), 4.15 (d, J 11.2, 2H), 3.26 (s, 3H), 3.20-3.11 (m, 1H), 3.00 (t, J 12.2, 2H), 2.20-2.12 (m, 2H), 1.98-1.84 (m, 2H), 1.48 (s, 9H).

Example 11

Tert-butyl 4-{5-[4-(1H-tetrazol-1-yl)phenyl]benzo[d]oxazol-2-yl}piperidine-1-carboxylate Following the General Procedure-1, the titled compound (80 mg) was prepared from Intermediate 8 (200 mg, 0.47 mmol) and 1-(4-bromophenyl)-1H-tetrazole (100 mg, 0.44 mmol) as a brown solid. M.P.: 207-211° C. $^1$H-NMR ($\delta$ ppm, CDCl$_3$, 400 MHz): 9.02 (s, 1H), 7.91 (d, J 1.2, 1H), 7.82-7.79 (m, 4H), 7.62-7.55 (m, 2H), 4.16 (d, J 10.6, 2H), 3.21-3.12 (m, 1H), 3.00 (t, J 12.3, 2H), 2.20-2.14 (m, 2H), 2.00-1.88 (m, 2H), 1.48 (s, 9H).

Example 12

Tert-butyl 4-{5-[2-fluoro-4-(1H-tetrazol-1-yl)phenyl]benzo[d]oxazol-2-yl}piperidine-1-carboxylate Following the General Procedure-1, the titled compound (10 mg) was prepared from Intermediate 8 (200 mg, 0.47 mmol) and 1-(4-bromo-3-fluorophenyl)-1H-tetrazole (110 mg, 0.45 mmol) as a brown solid. M.P.: 203-207° C. $^1$H-NMR ($\delta$ ppm, CDCl$_3$, 400 MHz): 9.04 (s, 1H), 7.88 (s, 1H), 7.71-7.58 (m, 4H), 7.52 (td, 1.6, 8.4, 1H), 4.16 (d, J 10.8, 2H), 3.21-3.12 (m, 1H), 3.00 (t, J 12.2, 2H), 2.21-2.13 (m, 2H), 2.00-1.85 (m, 2H), 1.48 (s, 9H).

Example 13

Tert-butyl 4-{5-[4-(trifluoromethyl)phenyl]benzo[d]oxazol-2-yl}piperidine-1-carboxylate Following the General Procedure-1, the titled compound (40 mg) was prepared from Intermediate 7 (150 mg, 0.4 mmol) and 4-(trifluoromethyl)phenylboronic acid (74 mg, 0.39 mmol) as an off-white solid. M.P.: 166-169° C. $^1$H-NMR ($\delta$ ppm, CDCl$_3$, 400 MHz): 7.88 (d, J 1.2, 1H), 7.73-7.67 (m, 4H), 7.59-7.52 (m, 2H), 4.15 (d, J 10, 2H), 3.20-3.10 (m, 1H), 3.00 (t, J 11.6, 2H), 2.21-2.12 (m, 2H), 1.99-1.86 (m, 2H), 1.48 (s, 9H).

Example 14

Isopropyl 4-{5-[2-fluoro-4-(1H-tetrazol-1-yl)phenyl]benzo[d]oxazol-2-yl}piperidine-1-carboxylate Tert-butyl 4-{5-[2-fluoro-4-(1H-tetrazol-1-yl)phenyl]benzo[d]oxazol-2-yl}piperidine-1-carboxylate (120 mg, 0.26 mmol) dissolved in DCM and added Trifluoroacetic acid (0.5 ml). This mixture was stirred at rt for 2 h. DCM removed from the reaction mixture to obtain 5-(2-fluoro-4-(1H-tetrazol-1-yl)phenyl)-2-(piperidin-4-yl)benzo[d]oxazole 2,2,2-trifluoroacetate (150 mg). 5-(2-fluoro-4-(1H-tetrazol-1-yl)phenyl)-2-(piperidin-4-yl)benzo[d]oxazole 2,2,2-trifluoroacetate (70 mg, 0.17 mmol) was dissolved in DCM (15 ml) and added TEA (0.2 ml, 1.4 mmol). This mixture stirred at rt for 30 mins and added isopropyl chloroformate in toluene (42 mg, 0.34 mmol). After 1 h, reaction mass diluted with water and extracted with DCM. Removal of DCM afforded crude. Crude was purified by combiflash using a mixture of EtOAc and Petether (35:65) as eluent to afford the titled compound (30 mg) as an off-white solid. M.P.: 168-171° C. $^1$H-NMR (δ ppm, CDCl$_3$, 400 MHz): 9.03 (s, 1H), 7.88 (s, 1H), 7.68 (t, J 8.2, 1H), 7.64-7.58 (m, 3H), 7.54-7.50 (m, 1H), 4.95 (septet, J 6.2, 1H), 4.20 (d, J 11.2, 2H), 3.22-3.14 (m, 1H), 3.04 (t, J 11.2, 2H), 2.22-2.15 (m, 2H), 2.00-1.88 (m, 2H), 1.26 (d, J 6.2, 6H).

Example 15

Tert-butyl 4-{5-[3-fluoro-4-(1H-tetrazol-1-yl)phenyl]benzo[d]oxazol-2-yl}piperidine-1-carboxylate Following the General Procedure-3, the titled compound (22 mg) was prepared from Intermediate 8 (100 mg, 0.23 mmol) and 1-(4-bromo-2-fluorophenyl)-1H-tetrazole (56 mg, 0.23 mmol) as a pale-yellow solid. M.P.: 154-159° C. $^1$H-NMR (δ ppm, CDCl$_3$, 400 MHz): 9.14 (d, J 2.5, 1H), 8.04 (t, J 7.8, 1H), 7.91 (d, J 3.9, 1H), 7.64-7.54 (m, 4H), 4.16 (d, J 10, 2H), 3.21-3.13 (m, 1H), 3.01 (t, J 11.9, 2H), 2.21-2.12 (m, 2H), 2.00-1.87 (m, 2H), 1.48 (s, 9H).

Example 16

2-[1-(5-ethylpyrimidin-2-yl)piperidin-4-yl]-5-[2-fluoro-4-(1H-tetrazol-1-yl)phenyl]benzo[d]oxazole Tert-butyl 4-{5-[2-fluoro-4-(1H-tetrazol-1-yl)phenyl]benzo[d]oxazol-2-yl}piperidine-1-carboxylate (120 mg, 0.26 mmol) dissolved in DCM (15 ml) and added Trifluoroacetic acid (0.5 ml). This mixture was stirred at rt for 2 h. DCM removed from the reaction mixture to obtain 5-[2-fluoro-4-(1H-tetrazol-1-yl)phenyl]-2-(piperidin-4-yl)benzo[d]oxazole 2,2,2-trifluoroacetate (150 mg). 5-[2-fluoro-4-(1H-tetrazol-1-yl)phenyl]-2-(piperidin-4-yl)benzo[d]oxazole 2,2,2-trifluoroacetate (70 mg, 0.15 mmol) was dissolved in IPA (10 ml), added DiPEA (0.25 ml, 1.2 mmol) and stirred at rt for 30 mins 2-Chloro-5-ethyl piperidine was added to the above reaction mixture and heated the reaction mixture to 90° C. for overnight. After completion of the reaction, work-up (EtOAc/H$_2$O) followed by purification on combiflash using the gradient mixture of ethyl acetate and petether (1:1) as eluent afforded the titled compound (20 mg) as an off-white solid. M.P.: 188-192° C. $^1$H-NMR (δ ppm, CDCl$_3$, 400 MHz): 9.03 (s, 1H), 8.20 (s, 2H), 7.88 (s, 1H), 7.68 (t, J 8.2, 1H), 7.65-7.58 (m, 3H), 7.54-7.49 ((m, 1H), 4.80-4.70 (m, 2H), 3.33-3.23 (m, 1H), 3.22 (t, J 14, 2H), 2.48 (q, J 7.6, 2H), 2.30-2.22 (m, 2H), 2.07-1.95 (m, 2H), 1.20 (t, J 7.6, 3H).

Example 17

Tert-butyl 4-[5-(4-cyano-3-fluorophenyl)benzo[d]oxazol-2-yl]piperidine-1-carboxylate Following the General Procedure-2, the titled compound (70 mg) was prepared from Intermediate 8 (150 mg, 0.35 mmol) and 4-bromo-2-fluorobenzonitrile (70 mg, 0.35 mmol) as a white solid. M.P.: 138-142° C. $^1$H-NMR (δ ppm, CDCl$_3$, 400 MHz): 7.87 (d, J 1.6, 1H), 7.72-7.68 (m, 1H), 7.59 (d, J 8.5, 1H), 7.53-7.42 (m, 3H), 4.15 (d, J 10.6, 2H), 3.20-3.11 (m, 1H), 3.00 (t, J 11.8, 2H), 2.2-2.12 (m, 2H), 1.98-1.86 (m, 2H), 1.56 (S, 9H).

Example 18

Isopropyl 4-{5-[3-fluoro-4-(1H-tetrazol-1-yl)phenyl]benzo[d]oxazol-2-yl}piperidine-1-carboxylate Tert-butyl 4-{5-[3-fluoro-4-(1H-tetrazol-1-yl)phenyl]benzo[d]oxazol-2-yl}piperidine-1-carboxylate (120 mg, 0.26 mmol) dissolved in DCM (15 ml) and added Trifluoroacetic acid (0.5 ml). This mixture was stirred at rt for 2 h. DCM removed from the reaction mixture to obtain 5-[3-fluoro-4-(1H-tetrazol-1-yl)phenyl]-2-(piperidin-4-yl)benzo[d]oxazole 2,2,2-trifluoroacetate (120 mg). 5-[3-fluoro-4-(1H-tetrazol-1-yl)phenyl]-2-(piperidin-4-yl)benzo[d]oxazole 2,2,2-trifluoroacetate (120 mg, 0.25 mmol) was dissolved in DCM (15 ml) and added TEA (0.27 ml, 2 mmol). This mixture stirred at rt for 30 mins and added isopropyl chloroformate in toluene (61 mg, 0.34 mmol). After 1 h, reaction mass diluted with water and extracted with DCM. Removal of DCM afforded crude. Crude was purified by combiflash using a mixture of EtOAc and Petether (35:65) as eluent to afford the titled compound (20 mg) as an off-white solid. M.P.: 187-191° C. $^1$H-NMR (δ ppm, CDCl$_3$, 400 MHz): 9.14 (d, J 2.6, 1H), 8.02 (t, J 8.2, 1H), 7.90 (d, J 1.4, 1H), 7.63-7.55 (m, 4H), 4.95 (septet, J 6.2, 1H), 4.20 (d, J 11.2, 2H), 3.22-3.14 (m, 1H), 3.04 (t, J 11.4, 2H), 2.18 (d, J 10.8, 2H), 2.00-1.88 (m, 2H), 1.26 (d, J 6.2, 6H).

Example 19

Tert-butyl 4-{5-[3-fluoro-4-(1H-tetrazol-5-yl)phenyl]benzo[d]oxazol-2-yl}piperidine-1-carboxylate Following the General Procedure-2, the titled compound (6 mg) was prepared from Intermediate 8 (150 mg, 0.35 mmol) and intermediate 17 (85 mg, 0.35 mmol) as a brown solid. M.P.: 163-167° C. $^1$H-NMR (δ ppm, CDCl$_3$, 400 MHz): 8.15 (s, 1H), 8.11 (t, J 8, 1H), 7.86 (d, J 12.2, 1H), 7.82-7.77 (m, 3H), 3.95 (d, J 13.4, 2H), 3.42-3.35 (m, 1H), 3.05-2.92 (m, 2H), 2.14-2.06 (m, 2H), 1.76-1.64 (m, 2H), 1.41 (s, 9H).

Example 20

Tert-butyl 4-[5-(4-carbamoyl-3-chlorophenyl)benzo[d]oxazol-2-yl]piperidine-1-carboxylate Following the General Procedure-2, the titled compound (25 mg) was prepared from Intermediate 7 (150 mg, 0.4 mmol) and 2-chloro-4-(4,4,5,5-tetramethyl-1,3,2-dioxaborolan-2-yl)benzamide (110 mg, 0.4 mmol) as a brown solid. M.P.: 169-171° C. $^1$H-NMR (δ ppm, DMSO-d$_6$, 400 MHz): 8.03 (s, 1H), 7.87 (bs, 1H), 7.82-7.75 (m, 2H), 7.73-7.66 (m, 2H), 7.59 (bs, 1H), 7.52 (d, J 7.9, 1H), 3.94 (d, J 12.9, 2H), 3.30-3.22 (m, 1H), 3.08-2.92 (m, 2H), 2.09 (d, J 10.6, 2H), 1.75-1.63 (m, 2H), 1.40 (s, 9H).

Example 21

Tert-butyl 4-[5-(4-carbamoyl-3-fluorophenyl)benzo[d]oxazol-2-yl]piperidine-1-carboxylate Following the General Procedure-3, the titled compound (25 mg) was prepared from Intermediate 8 (150 mg, 0.35 mmol) and 4-bromo-2-fluorobenzamide (77 mg, 0.35 mmol) as a white solid. M.P.: 202-206° C. $^1$H-NMR (δ ppm, DMSO-d$_6$, 400 MHz): 8.22 (t, J 8.3, 1H), 7.89 (s, 1H), 7.59-7.49 (m, 3H), 7.37 (dd, J 1.6, 13.24, 1H), 6.71 (d, J 9.5, 1H), 5.85 (s, 1H), 4.15 (d, J 10.7, 2H), 3.20-3.10 (m, 1H), 3.00 (t, J 11.8, 2H), 2.20-2.12 (m, 2H), 1.99-1.85 (m, 2H), 1.48 (s, 9H).

Example 22

Tert-butyl 4-[5-(3-fluoro-4-isopropoxyphenyl)benzo[d]oxazol-2-yl]piperidine-1-carboxylate Following the General Procedure-3, the titled compound (25 mg) was prepared from Intermediate 8 (150 mg, 0.35 mmol) and 4-bromo-2-fluoro-1-isopropoxybenzene (81 mg, 0.35 mmol) as a white solid. M.P.: 124-128° C. $^1$H-NMR ($\delta$ ppm, $CDCl_3$, 400 MHz): 7.81 (d, J 1.4, 1H), 7.53-7.45 (m, 2H), 7.35-7.27 (m, 2H), 7.05 (t, J 8.6, 1H), 4.58 (septet, J 6.1, 1H), 4.15 (d, J 10.4, 2H), 3.20-3.10 (m, 1H), 2.99 (t, J 11.7, 2H), 2.15 (dd, J 2.8, 13.4, 2H), 1.97-1.86 (m, 2H), 1.56 (s, 9H), 1.39 (d, J 6.1, 6H).

Example 23

Cyclobutyl 4-{5-[2-fluoro-4-(1H-tetrazol-1-yl)phenyl]benzo[d]oxazol-2-yl}piperidine-1-carboxylate Tert-butyl 4-{5-[2-fluoro-4-(1H-tetrazol-1-yl)phenyl]benzo[d]oxazol-2-yl}piperidine-1-carboxylate (300 mg, 0.65 mmol) dissolved in DCM (15 ml) and added Trifluoroacetic acid (1.5 ml). This mixture was stirred at rt for 2 h. DCM removed from the reaction mixture to obtain 5-[2-fluoro-4-(1H-tetrazol-1-yl)phenyl]-2-(piperidin-4-yl)benzo[d]oxazole 2,2,2-trifluoroacetate (300 mg). 5-[2-fluoro-4-(1H-tetrazol-1-yl)phenyl]-2-(piperidin-4-yl)benzo[d]oxazole 2,2,2-trifluoroacetate (150 mg, 0.31 mmol) was dissolved in DMF (2.6 ml) and added N,N-Carbonyl diimidazole (101 mg, 0.63 mmol) and stirred at rt for 1 h. To this mixture added cyclobutanol (0.05 ml, 0.63 mmol) and TEA (0.13 ml, 0.94 mmol) and stirred at 60° C. for overnight. Work up (EtOAc/$H_2O$) and purification of the crude by combiflash with gradient mixture of ethyl acetate and petether (1:1) as eluent afforded the titled compound (25 mg) as an off-white solid. M.P.: 165-169° C. $^1$H-NMR ($\delta$ ppm, $CDCl_3$, 400 MHz): 9.04 (s, 1H), 7.88 (s, 1H), 7.72-7.58 (m, 4H), 7.55-7.50 (m, 1H), 4.96 (septet, J 7.8, 1H), 4.20 (d, J 12.4, 2H), 3.22-3.13 (m, 1H), 3.06 (t, J 9.8, 2H), 2.40-2.30 (m, 2H), 2.24-2.15 (m, 2H), 2.15-2.02 (m, 2H), 2.00-1.90 (m, 2H), 1.78 (q, J 10, 2H).

Example 24

Sec-butyl 4-{5-[2-fluoro-4-(1H-tetrazol-1-yl)phenyl]benzo[d]oxazol-2-yl}piperidine-1-carboxylate Tert-butyl 4-{5-[2-fluoro-4-(1H-tetrazol-1-yl)phenyl]benzo[d]oxazol-2-yl}piperidine-1-carboxylate (250 mg, 0.54 mmol) dissolved in DCM (15 ml) and added Trifluoroacetic acid (1 ml). This mixture was stirred at rt for 2 h. DCM removed from the reaction mixture to obtain 5-[2-fluoro-4-(1H-tetrazol-1-yl)phenyl]-2-(piperidin-4-yl)benzo[d]oxazole 2,2,2-trifluoro acetate (260 mg). 5-[2-fluoro-4-(1H-tetrazol-1-yl)phenyl]-2-(piperidin-4-yl)benzo[d]oxazole 2,2,2-trifluoroacetate (150 mg, 0.31 mmol) was dissolved in DMF (2.6 ml) and added N,N-Carbonyl diimidazole (101 mg, 0.63 mmol) and stirred at rt for 1 h. To this mixture added 2-butanol (46 mg, 0.63 mmol) and TEA (0.13 ml, 0.94 mmol) and stirred at 60° C. for overnight. Work up (EtOAc/$H_2O$) and purification of the crude by combiflash with gradient mixture of ethyl acetate and petether (1:1) as eluent afforded the titled compound (30 mg) as an off-white solid. M.P.: 118-122° C. $^1$H-NMR ($\delta$ ppm, $CDCl_3$, 400 MHz): 9.03 (s, 1H), 7.88 (s, 1H), 7.72-7.58 (m, 4H), 7.55-7.50 (m, 1H), 4.82-4.73 (m, 1H), 4.21 (d, J 12.7, 2H), 3.24-3.13 (m, 1H), 3.06 (t, J 11.6, 2H), 2.19 (d, J 10.9, 2H), 2.00-1.88 (m, 2H), 1.69-1.50 (m, 2H), 1.24 (d, J 6.2, 3H), 0.92 (t, J 7.4, 3H).

Example 25

Pentan-3-yl 4-{5-[2-fluoro-4-(1H-tetrazol-1-yl)phenyl]benzo[d]oxazol-2-yl}piperidine-1-carboxylate Tert-butyl 4-{5-[2-fluoro-4-(1H-tetrazol-1-yl)phenyl]benzo[d]oxazol-2-yl}piperidine-1-carboxylate (250 mg, 0.54 mmol) dissolved in DCM (15 ml) and added Trifluoroacetic acid (1 ml). This mixture was stirred at rt for 2 h. DCM removed from the reaction mixture to obtain 5-[2-fluoro-4-(1H-tetrazol-1-yl)phenyl]-2-(piperidin-4-yl)benzo[d]oxazole 2,2,2-trifluoroacetate (260 mg). 5-[2-fluoro-4-(1H-tetrazol-1-yl)phenyl]-2-(piperidin-4-yl)benzo[d]oxazole 2,2,2-trifluoroacetate (150 mg, 0.31 mmol) was dissolved in DMF (2.6 ml) and added N,N-Carbonyl diimidazole (101 mg, 0.63 mmol) and stirred at rt for 1 h. To this mixture added 3-pentanol (46 mg, 0.63 mmol) and TEA (0.13 ml, 0.94 mmol) and stirred at 60° C. for overnight. Work up (EtOAc/$H_2O$) and purification of the crude by combiflash with gradient mixture of ethyl acetate and petether (1:1) as eluent afforded the titled compound (20 mg) as an off-white solid. M.P.: 114-117° C. $^1$H-NMR ($\delta$ ppm, $CDCl_3$, 400 MHz): 9.03 (s, 1H), 7.88 (s, 1H), 7.72-7.58 (m, 4H), 7.54-7.50 (m, 1H), 4.69 (quintet, J 6, 1H), 4.23 (d, J 13.5, 2H), 3.25-3.15 (m, 1H), 3.07 (t, J 11.9, 2H), 2.21-2.17 (m, 2H), 2.02-1.88 (m, 2H), 1.65-1.50 (m, 4H), 0.91 (t, J 7.4, 6H).

Example 26

5-[2-fluoro-4-(1H-tetrazol-1-yl)phenyl]-2-(piperidin-4-yl)benzo[d]oxazole

5-[2-fluoro-4-(1H-tetrazol-1-yl)phenyl]-2-(piperidin-4-yl)benzo[d]oxazole 2,2,2-trifluoroacetate (50 mg) was dissolved in DCM (15 ml) and added TEA (0.3 ml). This mixture stirred for 3 h at rt. Work up (DCM/$H_2O$) followed by purification of the crude by preparative TLC using MeOH and DCM (1:5) as eluent afforded the titled compound (15 mg) as an off-white solid. M.P.: 148-151° C. $^1$H-NMR ($\delta$ ppm, DMSO-$d_6$, 400 MHz): 10.17 (s, 1H), 8.03 (d, J 9.6, 1H), 7.95-7.79 (m, 4H), 7.58 (d, J 8.5, 1H), 3.22-3.13 (m, 1H), 3.07 (d, J 12.4, 2H), 2.70 (t, J 11.2, 2H), 2.06 (d, J 11.1, 2H), 1.82-1.70 (m, 2H).

Example 27

Isopropyl 4-{5-[4-(trifluoromethyl)phenyl]benzo[d]oxazol-2-yl}piperidine-1-carboxylate Following the General Procedure-1, the titled compound (100 mg) was prepared from Intermediate 13 (200 mg, 0.54 mmol) and 4-(trifluoromethyl)phenylboronic acid (124 mg, 0.65 mmol) as an off-white solid. M.P.: 123-126° C. $^1$H-NMR ($\delta$ ppm, $CDCl_3$, 400 MHz): 7.88 (d, J 1, 1H), 7.72-7.68 (m, 4H), 7.60-7.53 (m, 2H), 4.95 (septet, J 6.3, 1H), 4.20 (d, J 13.3, 2H), 3.22-3.12 (m, 1H), 3.04 (t, J 11.3, 2H), 2.17 (dd, J 2.6, 13.2, 2H), 2.00-1.88 (m, 2H), 1.26 (d, J 6.2, 6H).

Example 28

Isopropyl 4-[5-(4-formylphenyl)benzo[d]oxazol-2-yl]piperidine-1-carboxylate

Following the General Procedure-1, the titled compound (100 mg) was prepared from Intermediate 13 (270 mg, 0.73 mmol) and 4-formylphenylboronic acid (132 mg, 0.88 mmol) as an off-white solid. M.P.: 167-170° C. $^1$H-NMR (δ ppm, CDCl$_3$, 400 MHz): 10.07 (S, 1H), 7.96 (dd, J 1.7, 6.6, 2H), 7.93 (s, 1H), 7.76 (d, J 8.2, 2H), 7.58 (s, 2H), 4.95 (septet, J 6.2, 1H), 4.20 (d, J 11.1, 2H), 3.22-3.13 (m, 1H), 3.04 (t, J 11.3, 2H), 2.18 (dd, J 2.8, 13.3, 2H).

Example 29

Isopropyl 4-{5-[4-(difluoromethyl)phenyl]benzo[d]oxazol-2-yl}piperidine-1-carboxylate Isopropyl 4-[5-(4-formylphenyl)benzo[d]oxazol-2-yl]piperidine-1-carboxylate (100 mg, 0.25 mmol) dissolved in DCM and added DAST (123 mg, 0.76 mmol) and stirred the reaction mixture at 55° C. Work up (DCM/H$_2$O) followed by purification on combiflash with a gradient mixture of EtOAc and Petether (1:4) as eluent afforded the titled compound (35 mg) as an off-white solid. M. P.: 151-154° C. $^1$H-NMR (δ ppm, CDCl$_3$, 400 MHz): 7.88 (s, 1H), 7.68 (d, J 8.2, 2H), 7.60 (d, J 8.2, 2H), 7.58-7.52 (m, 2H), 6.70 (t, J 56.5, 1H), 4.95 (septet, J 6.2, 1H), 4.19 (d, J 11.1, 2H), 3.21-3.13 (m, 1H), 3.04 (t, J 11.4, 2H), 2.17 (d, J 10.4, 2H), 2.00-1.88 (m, 2H), 1.26 (d, J 6.2, 6H).

Example 30

Isopropyl 4-[5-(4-carbamoyl-3-chlorophenyl)benzo[d]oxazol-2-yl]piperidine-1-carboxylate Following the General Procedure-2, the titled compound (30 mg) was prepared from Intermediate 13 (150 mg, 0.41 mmol) and 2-chloro-4-(4,4,5,5-tetramethyl-1,3,2-dioxaborolan-2-yl)benzamide (110 mg, 0.41 mmol) as a pale-yellow solid. M.P.: 178-181° C. $^1$H-NMR (δ ppm, DMSO-d$_6$, 400 MHz): 8.04 (d, J 1.7, 1H), 7.88 (bs, 1H), 7.80 (d, J 1.7, 1H), 7.77 (d, J 8.5, 1H), 7.73-7.68 (m, 2H), 7.62-7.58 (m, 1H), 7.52 (d, J 8, 1H), 4.78 (septet, J 6.2, 1H), 3.97 (d, J 13.2, 2H), 3.34-3.24 (m, 1H), 3.10-3.00 (m, 2H), 2.15-2.05 (m, 2H), 1.75-1.65 (m, 2H), 1.19 (d, J 6.2, 6H).

Example 31

Isopropyl 4-[5-(4-carbamoyl-3-fluorohenyl)benzo[d]oxazol-2-yl]piperidine-1-carboxylate Following the General Procedure-2, the titled compound (30 mg) was prepared from Intermediate 14 (300 mg, 0.72 mmol) and 4-bromo-2-fluorobenzamide (157 mg, 0.72 mmol) as an off-white solid. M.P.: 184-187° C. $^1$H-NMR (δ ppm, DMSO-d$_6$, 400 MHz): 8.08 (d, J 1.4, 1H), 7.80-7.72 (m, 3H), 7.70-7.62 (m, 4H), 4.78 (septet, 6.2, 1H), 3.97 (d, J 13.4, 2H), 3.33-3.25 (m, 1H), 3.10-2.98 (m, 2H), 2.15-2.07 (m, 2H), 1.76-1.64 (m, 2H), 1.19 (d, J 6.2, 6H).

Example 32

1-{4-[5-(2-fluoro-4-(1H-tetrazol-1-yl)phenyl)benzo[d]oxazol-2-yl]piperidin-1-yl}-2-methylpropan-1-one Tert-butyl 4-{5-[2-fluoro-4-(1H-tetrazol-1-yl)phenyl]benzo[d]oxazol-2-yl}piperidine-1-carboxylate (100 mg, 0.22 mmol) dissolved in DCM (25 ml) and added trifluoroacetic acid (0.4 ml). This mixture stirred at rt for 3 h. After completion of the reaction, DCM removed on rotavapour and residue was co-distilled with ether to obtain 5-[2-fluoro-4-(1H-tetrazol-1-yl)phenyl]-2-(piperidine-4-yl)benzo[d]oxazole 2,2,2-trifluoroacetate (100 mg). 5-[2-fluoro-4-(1H-tetrazol-1-yl)phenyl]-2-(piperidin-4-yl)benzo[d]oxazole 2,2,2-trifluoroacetate (100 mg, 0.21 mmol) was dissolved in DMF (3 ml) and added isobutyric acid (202 mg, 0.23 mmol), EDC.HCl (99 mg, 0.52 mmol), HOBt (33 mg, 0.25 mmol) and TEA (0.23 ml, 1.7 mmol). After completion of the reaction, work up (EtOAc/H$_2$O) followed by purification on combiflash using the gradient mixture of EtOAc and Petether (65:35) as eluent afforded the titled compound (20 mg) as a brown solid. M.P.: 190-194° C. $^1$H-NMR (δ ppm, CDCl$_3$, 400 MHz): 9.04 (s, 1H), 7.88 (s, 1H), 7.68 (t, J 8.2, 1H), 7.67-7.59 (m, 2H), 7.52 (td, J 1.6, 8.4, 1H), 4.58 (d, J 12.1, 1H), 4.04 (d, J 13.2, 1H), 3.35-3.22 (m, 2H), 2.96 (t, J 12, 1H), 2.85 (septet, J 6.8, 1H), 2.30-2.18 (m, 2H), 2.05-1.72 (m, 2H), 1.16 (d, J 6.8, 6H).

Example 33

Isopropyl 4-{6-[4-(difluoromethyl)phenyl]benzo[d]oxazol-2-yl}piperidine-1-carboxylate Following the General Procedure-1, Isopropyl 4-[6-(4-formylphenyl)benzo[d]oxazol-2-yl]piperidine-1-carboxylate (140 mg) was prepared from Intermediate 15 (300 mg, 0.82 mmol) and 4-formylphenylboronic acid (146 mg, 0.98 mmol) as an off-white solid. Isopropyl 4-[6-(4-formylphenyl)benzo[d]oxazol-2-yl]piperidine-1-carboxylate (100 mg, 0.25 mmol) was dissolved in DCM (5 ml) and added DAST (0.1 ml, 0.76 mmol). This mixture stirred at reflux for 2 h. Work up (DCM/H$_2$O) followed by the purification of the crude on combiflash using gradient mixture of EtOAc and Petether (1:4) as eluent afforded the titled compound (35 mg) as an off-white solid. M. P.: 149-153° C. MS (m/z): 415.1 [M+H]$^+$.

Example 34

6-{2-[1-(isopropoxycarbonyl)piperidin-4-yl]benzo[d]oxazol-5-yl}nicotinic acid Following the General Procedure-2, Methyl 6-{2-(1-(isopropoxycarbonyl)piperidin-4-yl)-benzo[d]oxazol-5-yl]nicotinate (50 mg) was prepared from Intermediate 14 (400 mg, 0.97 mmol) and methyl 6-chloronicotinate (166 mg, 0.97 mmol) as a brown solid. Methyl 6-{2-(1-(isopropoxycarbonyl)piperidin-4-yl)-benzo[d]oxazol-5-yl]nicotinate (35 mg, 0.08 mmol) was dissolved in MeOH (5 ml) and added K$_2$CO$_3$ (22 mg, 0.17 mmol). This mixture was stirred at reflux for overnight. MeOH removed on rotavapour and pH adjusted to 6 using acetic acid to obtain a solid. Solid was filtered and dried to obtain the titled compound (20 mg) as a grey solid. M. P.: 239-242° C. MS (m/z): 410.4 [M+H]$^+$.

Example 35

5-[2-fluoro-4-(1H-tetrazol-1-yl)phenyl]-2-[1-(methylsulfonyl)piperidin-4-yl]benzo[d]oxazole 5-[2-fluoro-4-(1H-tetrazol-1-yl)-phenyl]-2-(piperidin-4-yl)benzo[d]oxazole 2,2,2-trifluoroacetate (30 mg, 0.06 mmol) was dissolved in DCM (5 ml) and added TEA (60 mg, 0.6 mmol) and stirred the mixture at rt for 30 mins. To this mixture added methanesulphonyl chloride (14 mg, 0.12 mmol) and stirred at rt for 2 h. Work up (DCM/H$_2$O) followed by purification on combiflash using a gradient mixture of EtOAc and Petether (7:3) as eluent afforded the titled compound (17 mg) as a brown solid. M. P.: 209-212° C. MS (m/z): 443.2 [M+H]$^+$.

Example 36

Isopropyl 4-[5-(5-carbamoylpyridin-2-yl)benzo[d] oxazol-2-yl]piperidine-1-carboxylate Following the General Procedure-3, the titled compound (40 mg) was prepared from Intermediate 14 (250 mg, 0.6 mmol) and 6-chloronicotinamide (94 mg, 0.6 mmol) as an off-white solid. M.P.: 227-230° C. MS (m/z): 409.1 [M+H]$^+$.

Example 37

Isopropyl 4-[5-(4-carbamoyl-2-fluorophenyl)benzo [d]oxazol-2-yl]piperidine-1-carboxylate Following the General Procedure-3, the titled compound (80 mg) was prepared from Intermediate 14 (200 mg, 0.48 mmol) and 4-bromo-3-fluorobenzamide (105 mg, 0.48 mmol) as an off-white solid. M.P.: 194-197° C. MS (m/z): 426.0 [M+H]$^+$.

Example 38

Isopropyl 4-[5-(4-carbamoyl-2-chlorophenyl)benzo [d]oxazol-2-yl]piperidine-1-carboxylate Following the General Procedure-3, the titled compound (80 mg) was prepared from Intermediate 14 (200 mg, 0.48 mmol) and 4-bromo-3-chlorobenzamide (105 mg, 0.48 mmol) as a brown solid. M.P.: 178-182° C. MS (m/z): 442.0 [M+H]$^+$.

Example 39

2-Fluoro-4-{2-[1-(3-methylbutanoyl)piperidin-4-yl] benzo[d]oxazol-5-yl}benzamide Tert-butyl 4-[5-(4-carbamoyl-3-fluorophenyl)benzo[d] oxazol-2-yl]piperidine-1-carboxylate (140 mg, 0.32 mmol) dissolved in DCM (25 ml) and added trifluoroacetic acid (1 ml). This mixture stirred at rt for 3 h. After completion of the reaction, DCM removed on rotavapour and residue was co-distilled with ether to obtain 2-fluoro-4-(2-(piperidin-4-yl)-benzo[d]oxazol-5-yl)-benzamide 2,2,2-trifluoroacetate (140 mg). 2-Fluoro-4-(2-(piperidin-4-yl)-benzo[d]oxazol-5-yl)-benzamide 2,2,2-trifluoroacetate (140 mg, 0.31 mmol) was dissolved in DMF (5 ml) and added isovaleric acid (34.6 mg, 0.34 mmol), EDC.HCl (147 mg, 0.77 mmol), HOBt (50 mg, 0.37 mmol) and TEA (0.4 ml, 2.47 mmol). After completion of the reaction, water added to the reaction mixture to obtain solid. Solid was filtered and washed with ether to obtain the titled compound (20 mg) as a brown solid. M.P.: 186-190° C. MS (m/z): 424.1 [M+H]$^+$.

Example 40

1-{4-[5-(2-fluoro-4-(1H-tetrazol-1-yl)phenyl]benzo [d]oxazol-2-yl]piperidin-1-yl}-3-methylbutan-1-one 5-[2-fluoro-4-(1H-tetrazol-1-yl)-phenyl]-2-(piperidin-4-yl)benzo[d]oxazole 2,2,2-trifluoroacetate (140 mg, 0.29 mmol) was dissolved in DMF (4 ml) and added isovaleric acid (38 mg, 0.37 mmol), EDC.HCl (147 mg, 0.73 mmol), HOBt (47 mg, 0.35 mmol) and TEA (88 mg, 0.88 mmol). After completion of the reaction, work up (EtOAc/H$_2$O) followed by purification of crude on combiflash using a gradient mixture of EtOAc and Petether (7:3) as eluent afforded the titled compound (100 mg) as a pale-yellow solid. M.P.: 168-172° C. MS (m/z): 449.1 [M+H]$^+$.

Example 41

5-[2-fluoro-4-(1H-tetrazol-1-yl)phenyl]-2-[1-(2-methoxyethyl)piperidin-4-yl]benzo[d]oxazole 5-[2-fluoro-4-(1H-tetrazol-1-yl)-phenyl]-2-(piperidin-4-yl)-benzo[d]oxazole 2,2,2-trifluoroacetate (30 mg, 0.06 mmol) was dissolved in DMF (2 ml) and added K$_2$CO$_3$ (40 mg, 0.29 mmol) and stirred the mixture at rt for 15 mins. To this mixture added 2-methoxyethyl methanesulfonate (45 mg, 0.29 mmol) and stirred at rt for 17 h. Work up (EtOAc/H$_2$O) followed by purification by column chromatography on 60-120 mesh silicagel using a gradient mixture of DCM and MeOH (98:2) as eluent afforded the titled compound (90 mg) as a brown solid (15 mg). M.P.: 148-152° C. MS (m/z): 423.3 [M+H]$^+$.

Example 42

Isopropyl 4-{5-[3-fluoro-4-(methylcarbamoyl)phe-nyl]benzo[d]oxazol-2-yl}piperidine-1-carboxylate Following the General Procedure-3, the titled compound (80 mg) was prepared from Intermediate 14 (200 mg, 0.54 mmol) and 4-bromo-2-fluoro-N-methylbenzamide (200 mg, 0.54 mmol) as a brown solid. M.P.: 116-120° C. MS (m/z): 440.3 [M+H]$^+$.

Example 43

2-Fluoro-4-[2-(1-isobutyrylpiperidin-4-yl)benzo[d] oxazol-5-yl]benzamide

Tert-butyl 4-[5-(4-carbamoyl-3-fluorophenyl)benzo[d] oxazol-2-yl]piperidine-1-carboxylate (190 mg, 0.32 mmol) dissolved in DCM (40 ml) and added trifluoroacetic acid (1.5 ml). This mixture stirred at rt for 3 h. After completion of the reaction, DCM removed on rotavapour and residue was co-distilled with ether to obtain 2-fluoro-4-(2-(piperidin-4-yl)-benzo[d]oxazol-5-yl)-benzamide 2,2,2-trifluoroacetate (190 mg). 2-Fluoro-4-(2-(piperidin-4-yl)-benzo[d]oxazol-5-yl)-benzamide 2,2,2-trifluoroacetate (190 mg, 0.42 mmol) was dissolved in DMF (7 ml) and added isobutyric acid (47 mg, 0.46 mmol), EDC.HCl (200 mg, 1.04 mmol), HOBt (70 mg, 0.5 mmol) and TEA (0.7 ml, 3.3 mmol). After completion of the reaction, water added to the reaction mixture to obtain solid. Solid was filtered and washed with ether to obtain the titled compound (120 mg) as a brown solid. M.P.: 193-196° C. MS (m/z): 410.2 [M+H]$^+$.

Example 44

Isopropyl 4-[6-(4-carbamoyl-3-fluorophenyl)benzo [d]oxazol-2-yl]piperidine-1-carboxylate Following the General Procedure-3, the titled compound (55 mg) was prepared from Intermediate 16 (360 mg, 0.87 mmol) and 4-bromo-2-fluorobenzamide (190 mg, 0.87 mmol) as an off-white solid. M.P.: 178-181° C. MS (m/z): 425.45 [M+H]$^+$.

Example 45

Isopropyl 4-{5-[3-fluoro-4-(2-hydroxyethylcarbamoyl)phenyl]benzo[d]oxazol-2-yl}piperidine-1-carboxylate Following the General Procedure-3, the titled compound (65 mg) was prepared from Intermediate 14 (200 mg, 0.54 mmol) and 4-bromo-2-fluoro-N-(2-hydroxyethyl)benzamide (110 mg, 0.43 mmol) as a brown solid. M.P.: 145-147° C. MS (m/z): 470.4 [M+H]$^+$

Example 46

Isopropyl 4-{5-[3-fluoro-4-(isopropylcarbamoyl)phenyl]benzo[d]oxazol-2-yl}piperidine-1-carboxylate Following the General Procedure-3, the titled compound (45 mg) was prepared from Intermediate 13 (200 mg, 0.54 mmol) and 3-fluoro-4-(isopropylcarbamoyl)phenylboronic acid (120 mg, 0.54 mmol) as a grey solid. M.P.: 147-150° C. MS (m/z): 468.4 [M+H]$^+$.

Example 47

Isopropyl 4-{5-[4-(N-methylsulfamoyl)phenyl]benzo[d]oxazol-2-yl}piperidine-1-carboxylate Following the General Procedure-3, the titled compound (35 mg) was prepared from Intermediate 13 (200 mg, 0.54 mmol) and 4-(N-methylsulfamoyl)phenylboronic acid (120 mg, 0.54 mmol) as a white solid. M.P.: 179-181° C. MS (m/z): 458.3 [M+H]$^+$.

Example 48

Isopropyl 4-{5-[6-(methylcarbamoyl)pyridin-3-yl]benzo[d]oxazol-2-yl}piperidine-1-carboxylate Following the General Procedure-1, the titled compound (20 mg) was prepared from Intermediate 13 (300 mg, 0.82 mmol) and N-methyl-5-(4,4,5,5-tetramethyl-1,3,2-dioxaborolan-2-yl)picolinamide (256 mg, 0.98 mmol) as a brown solid. M.P.: 158-161° C. MS (m/z): 423.5 [M+H]$^+$.

Example 49

Isopropyl 4-{5-[3-methyl-4-(methylcarbamoyl)phenyl]benzo[d]oxazol-2-yl}piperidine-1-carboxylate Following the General Procedure-3, the titled compound (30 mg) was prepared from Intermediate 13 (250 mg, 0.68 mmol) and N,2-dimethyl-4-(4,4,5,5-tetramethyl-1,3,2-dioxaborolan-2-yl)benzamide (187 mg, 0.68 mmol) as an off-white solid. M.P.: 151-154° C. MS (m/z): 436.5 [M+H]$^+$.

Example 50

Isopropyl 4-{5-[4-(cyclopropylcarbamoyl)-3-fluorophenyl]benzo[d]oxazol-2-yl}piperidine-1-carboxylate Following the General Procedure-3, the titled compound (20 mg) was prepared from Intermediate 14 (250 mg, 0.61 mmol) and 4-bromo-N-cyclopropyl-2-fluorobenzamide (156 mg, 0.61 mmol) as an off-white solid. M.P.: 162-165° C. MS (m/z): 466.3 [M+H]$^+$.

Example 51

2-Fluoro-4-{2-[1-(5-fluoropyrimidin-2-yl)piperidin-4-yl]benzo[d]oxazol-5-yl}benzamide Following general procedure-3 and using DMF as solvent titled compound (40 mg) was obtained from intermediate 19 (150 mg, 0.35 mmol) and 4-bromo-2-fluorobenzamide (77 mg, 0.35 mmol) as a brown solid. M.P.: 226-229° C. MS (m/z): 436.5 [M+H]$^+$.

Example 52

Tert-butyl 4-[5-(4-carbamoyl-3-fluorophenyl)benzofuran-2-yl]-5,6-dihydropyridine-1(2H)-carboxylate Following the general procedure-4, the titled compound (370 mg) was obtained from intermediate 21 (1.5 g, 5.02 mmol) and tert-butyl 4-(trifluoromethylsulfonyloxy)-5,6-dihydropyridine-1(2H)-carboxylate (1.99 g, 6 mmol) as a white solid. M.P.: 189-191° C. $^1$H-NMR (δ ppm, DMSO-d$_6$, 400 MHz): 7.95 (s, 1H), 7.77-7.71 (m, 1H), 7.69-7.58 (m, 6H), 6.91 (s, 1H), 6.50 (s, 1H), 4.10-4.05 (m, 2H), 3.56 (t, J 5.5, 2H), 3.30-3.20 (m, 2H), 1.42 (s, 9H).

Example 53

2-fluoro-4-{2-[1-(propylsulfonyl)piperidin-4-yl]benzo[d]oxazol-5-yl}benzamide

Intermediate 25 (80 mg, 0.24 mmol) was dissolved in DCM (10 ml) and added TEA (35 mg, 0.35 mmol). This mixture was stirred at rt for 15 mins Reaction mixture cooled to 0° C. and added propane-1-sulphonylchloride (33 mg, 0.23 mmol). Reaction mixture stirred at rt for 2 h. Work up (DCM/H$_2$O) afforded the crude product. Crude was purified by column chromatography on 60-120 mesh silica gel using a gradient mixture of EtOAC and Petether (70:30) as eluent to afford the titled compound (8 mg) as a white solid. M.P.: 222-225° C. $^1$H-NMR NMR (δ ppm, DMSO-d$_6$, 400 MHz): 8.09 (d, J 1.3, 1H), 7.82-7.72 (m, 3H), 7.71-7.61 (m, 4H), 3.67-3.58 (m, 2H), 3.30-3.22 (m, 2H), 3.09-2.99 (m, 2H), 2.25-2.16 (m, 2H), 1.92-1.79 (m, 2H), 1.69 (hextet, J 7.6, 2H), 0.98 (t, J 7.4, 3H).

Example 56

Tert-butyl 4-{2-[2-fluoro-4-(methylsulfonyl)phenyl]-1H-benzo[d]imidazol-5-yl}-5,6-dihydropyridine-1(2H)-carboxylate 2-[2-fluoro-4-(methylsulfonyl)phenyl]-5-(4,4,5,5-tetramethyl-1,3,2-dioxa borolan-2-yl)-1H-benzo[d]imidazole (880 mg, 2.12 mmol), tert-butyl 4-(trifluoromethylsulfonyloxy)-5,6-dihydropyridine-1(2H)-carboxylate (700 mg, 2.12 mmol) and sodium carbonate (1.13 g, 11.48 mmol) were dissolved in DMF (20 ml) under N$_2$ atmosphere. This mixture was degassed with nitrogen for 30 mins and added Pd(dppf)$_2$Cl$_2$.CH$_2$Cl$_2$ (138 mg, 0.17 mmol). This mixture stirred at 80° C. for 90 mins in microwave. Reaction mixture diluted with water and work up (AcOEt/H$_2$O) afforded the crude. Crude was purified by combiflash using a mixture of AcOEt and Petether (35:65) to afford the titled compound (240 mg) as an off-white solid. ¹H-NMR (δ ppm, DMSO-d₆, 400 MHz): 12.80 (s, 1H), 8.49 (t, J 7.5, 1H), 8.02 (d, J 10.4, 1H), 7.92 (d, J 8.2, 1H), 7.88-7.67 (m, 1H), 7.66-7.54 (m, 1H), 7.48-7.39 (m, 1H), 6.18 (bs, 1H), 4.02 (bs, 2H), 3.57 (bs, 2H), 3.34 (s, 3H), 2.60-2.55 (m, 2H), 1.43 (s, 9H).

Example 57

Tert-butyl 4-{2-[2-fluoro-4-(methylsulfonyl)phenyl]-1H-benzo[d]imidazol-5-yl}piperidine-1-carboxylate Example 56 (240 mg, 0.51 mmol) was dissolved in MeOH (25 ml) and added 10% Pd/C (100 mg). This mixture was stirred in an auto clave under hydrogen atmosphere at 55 psi for 14 h. After 14 h, reaction mass filtered through a pad of celite and celite washed thoroughly with methanol. Methanol removed on rotavapour to obtain the titled compound (200 mg) as an off-white solid. M.P.: 208-211.5° C. ¹H-NMR (δ ppm, DMSO-d₆, 400 MHz): 12.71 (s, 1H), 8.47 (t, J 7.7, 1H), 8.01 (d, J 10.4, 1H), 7.91 (dd, J 1.4, 8.2, 1H), 7.65-7.40 (m, 2H), 7.30-7.24 (m, 1H), 4.08 (d, J 11.1, 2H), 3.33 (s, 3H), 2.92-2.74 (m, 3H), 1.81 (d, J 12.2, 2H), 1.54 (d, J 10.4, 2H), 1.42 (s, 9H).

Example 58

5-[1-(5-ethylpyrimidin-2-yl)piperidin-4-yl]-2-[2-fluoro-4-(methylsulfonyl)phenyl]-1H-benzo[d]imidazole Example 57 (150 mg, 0.3 mmol) dissolved in DCM (12 ml) and added TFA (0.45 ml). This mixture stirred at rt for 3 h. After 3 h, DCM removed on rotavapour and co-distilled with DCM to obtain 2-[2-fluoro-4-(methylsulfonyl)phenyl]-5-(piperidin-4-yl)-1H-benzo[d]imidazole 2,2,2-trifluoroacetate (150 mg). 2-[2-fluoro-4-(methylsulfonyl)phenyl]-5-(piperidin-4-yl)-1H-benzo[d]imidazole 2,2,2-trifluoroacetate (150 mg, 0.4 mmol) and 2-chloro-5-ethylpyrimidine (60 mg, 0.4 mmol) were dissolved in propan-2-ol (10 ml) and added DiPEA (0.6 ml, 3.2 mmol). This mixture was refluxed at 90° C. for 12 h. After 12 h, propan-2-ol removed on rotavapor to obtain the residue. Residue was purified on combiflash using Ethyl acetate and Petether (1:1) as eluent to afford the titled compound (50 mg) as a white solid. M.P.: 220-223.5° C. ¹H-NMR (δ ppm, DMSO-d₆, 400 MHz): 12.69 (d, J 12.8, 1H), 8.49-8.45 (m, 1H), 8.24 (s, 2H), 8.00 (dd, J 1.5, 10.4, 1H), 7.91 (d, J 8.3, 1H), 7.67-7.56 (m, 1H), 7.55-7.40 (m, 1H), 7.22-7.12 (m, 1H), 4.80 (d, J 12.6, 2H), 3.33 (s, 3H), 2.97-2.91 (m, 3H), 2.43 (q, J 7.5, 2H), 1.89 (d, J 12.4, 2H), 1.69-1.54 (m, 2H), 1.13 (t, J 7.6, 3H).

Example 59

Tert-butyl 4-{2-[2-fluoro-4-(methylsulfonyl)phenyl]benzo[d]oxazol-5-yl}-5,6-dihydropyridine-1(2H)-carboxylate 2-[2-fluoro-4-(methylsulfonyl)phenyl]-5-(4,4,5,5-tetramethyl-1,3,2-dioxa borolan-2-yl)benzo[d]oxazole (50 mg, 0.12 mmol), tert-butyl 4-(trifluoromethylsulfonyloxy)-5,6-dihydropyridine-1(2H)-carboxylate (39 mg, 0.12 mmol) and sodium carbonate (38 mg, 0.36 mmol) were dissolved in DMF (2 ml) under N₂ atmosphere. This mixture was degassed with nitrogen for 30 mins and added Pd(dppf)₂Cl₂.CH₂Cl₂ (10 mg, 0.009 mmol). This mixture stirred at 80° C. for 90 mins in microwave. Reaction mixture diluted with water and work up (AcOEt/H₂O) afforded the crude. Crude was purified by combiflash using a mixture of AcOEt and Petether (27:73) to afford the titled compound (25 mg) as an off-white solid. M.P.: 149-151° C. ¹H-NMR (δ ppm, CDCl₃, 400 MHz): 8.47 (t, J 7.4, 1H), 7.93-7.80 (m, 3H), 7.65-7.57 (m, 1H), 7.53-7.45 (m, 1H), 6.20-6.02 (m, 1H), 4.12 (bs, 2H), 3.68 (t, J 5.3, 2H), 3.13 (s, 3H), 2.65-2.55 (m, 2H), 1.50 (s, 9H).

Example 60

Tert-butyl 4-{2-[2-fluoro-4-(methylsulfonyl)phenyl]benzo[d]oxazol-5-yl}piperidine-1-carboxylate Example 59 (300 mg, 0.64 mmol) was dissolved in MeOH (25 ml) and added 10% Pd/C (100 mg). This mixture was stirred in an auto clave under hydrogen atmosphere at 55 psi for 14 h. After 14 h, reaction mass filtered through a pad of celite and celite washed thoroughly with methanol. Methanol removed on rotavapour to obtain the titled compound (200 mg) as an off-white solid. M.P.: 168-171° C. ¹H-NMR (δ ppm, CDCl₃, 400 MHz): 8.46 (t, J 7.1, 1H), 7.87 (t, J 7.6, 2H), 7.69 (s, 1H), 7.57 (d, J 8.4, 1H), 7.30 (d, J 7.7, 1H), 4.35-4.20 (m, 2H), 3.13 (s, 3H), 2.90-2.75 (m, 3H), 1.90 (d, J 12.6, 2H), 1.63-1.74 (m, 2H), 1.49 (s, 9H).

Example 61

2-[2-fluoro-4-(methylsulfonyl)phenyl]-5-(piperidin-4-yl)benzo[d]oxazole 2,2,2-trifluoroacetate Example 60 (170 mg, 0.36 mmol) dissolved in DCM (15 ml) and added TFA (0.6 ml). This mixture stirred at rt for 3 h. After 3 h, DCM removed on rotavapour and co-distilled with DCM to obtain 2-[2-fluoro-4-(methylsulfonyl)phenyl]-5-(piperidin-4-yl)benzo[d]oxazole 2,2,2-trifluoroacetate (180 mg). M.P.: 223-227° C. ¹H-NMR (δ ppm, DMSO-d₆, 400 MHz): 8.61 (bs, 1H), 8.47 (t, J 7.6, 1H), 8.39 (bs, 1H), 8.07 (d, J 10, 1H), 7.98 (d, J 8.1, 1H), 7.83 (d, J 8.4, 1H), 7.74 (s, 1H), 7.39 (d, J 8.3, 1H), 3.45-3.33 (m, 5H), 3.10-2.98 (m, 3H), 2.02 (d, J 12.9, 2H), 1.93-1.80 (m, 2H).

Example 62

5-[1-(5-ethylpyrimidin-2-yl)piperidin-4-yl]-2-[2-fluoro-4-(methylsulfonyl)phenyl]benzo[d]oxazole Example 61 (150 mg, 0.31 mmol) and 2-chloro-5-ethylpyrimidine (48 mg, 0.34 mmol) were dissolved in propan-2-ol (20 ml) and added DiPEA (0.4 ml, 2.45 mmol). This mixture was refluxed at 90° C. for 12 h. After 12 h, propan-2-ol removed on rotavapor to obtain the residue. Residue was purified on combiflash using Ethyl acetate and Petether (35:65) as eluent to afford the titled compound (30 mg) as a white solid. M.P.: 190-194° C. ¹H-NMR (δ ppm, CDCl₃, 400 MHz): 8.49-8.43 (m, 1H), 8.20 (s, 2H), 7.90-7.84 (m, 2H), 7.71 (s, 1H), 7.57 (d, J 8.4, 1H), 7.33 (d, J 7.6, 1H), 4.91 (d, J 13.3, 2H), 3.13 (s, 3H), 3.05-2.90 (m, 3H), 2.48 (q, J 7.5, 2H), 2.00 (d, J 13, 2H), 1.83-1.70 (m, 2H), 1.20 (t, J 7.6, 3H).

Example 63

Tert-butyl 4-{7-fluoro-2-[2-fluoro-4-(methylsulfonyl)phenyl]benzo[d]oxazol-5-yl}piperidine-1-carboxylate Following the general procedure-1 Tert-butyl 4-{7-fluoro-2-[2-fluoro-4-(methylsulfonyl)phenyl]benzo[d]oxazol-5-yl}-5,6-dihydropyridine-1(2H)-carboxylate (180 mg)

obtained from intermediate 31 (600 mg, 1.38 mmol) and tert-butyl 4-(trifluoromethylsulfonyloxy)-5,6-dihydropyridine-1(2H)-carboxylate (456 mg, 1.38 mmol). Tert-butyl 4-{7-fluoro-2-[2-fluoro-4-(methylsulfonyl)phenyl]benzo[d]oxazol-5-yl}-5,6-dihydropyridine-1(2H)-carboxylate (150 mg, 0.30 mmol) dissolved in MeOH and added Pd/C (71 mg). This mixture was stirred in an auto clave in hydrogen atmosphere at 55 Psi for 12 h. Reaction mixture filtered through celite and washed the cetile with MeOH. Methanol was removed on rotavapour to obtain the titled compound (100 mg) as a brown solid. M.P.: 188-192.4° C. $^1$H-NMR (δ ppm, CDCl$_3$, 400 MHz): 8.47 (t, J 7.12, 1H), 7.89 (t, J 7.6, 2H), 7.49 (s, 1H), 7.07 (d, J 11.2, 1H), 4.28 (bs, 2H), 3.13 (s, 3H), 2.90-2.72 (m, 3H), 1.95-1.85 (m, 2H), 1.72-1.56 (m, 2H). 1.49 (s, 9H).

Example 64

Isopropyl 4-{2-[2-fluoro-4-(methylsulfonyl)phenyl]benzo[d]oxazol-5-yl}piperidine-1-carboxylate Example 61 (100 mg, 0.20 mmol) was dissolved in DCM (10 ml) and added TEA (1.4 ml). This mixture was stirred at rt for 30 mins Isopropyl chloroformate in toluene (50 mg, 0.41 mmol) added to the above mixture and stirred at rt for 1 h. Reaction mixture diluted with water and extracted with DCM. DCM removed on rotavapour to obtain the crude. Crude was purified by combiflash with EA and Petehter (35:65) as eluent to afford the title compound (50 mg) as an off-white solid. M.P.: 151.4-156.5° C. $^1$H-NMR (δ ppm, 400 MHz): 8.47 (t, J 7.8, 1H), 8.05 (d, J 10.3, 1H), 7.97 (dd, J 1.5, 8.2, 1H), 7.78-7.74 (m, 2H), 7.42 (d, J 8.6, 1H), 4.79 (heptet, J 6.2, 1H), 4.12 (d, J 11.6, 2H), 3.29 (s, 3H), 2.95-2.80 (m, 3H), 1.86-1.77 (m, 2H), 1.65-1.55 (m, 2H), 1.20 (d, J 6.2, 6H).

Example 65

Tert-butyl 4-{2-[2-fluoro-4-(methylsulfonyl)phenyl]benzo[d]thiazol-6-yl}-5,6-dihydropyridine-1(2H)-carboxylate Following the general procedure-1, the titled compound (140 mg) was obtained from intermediate 35 (300 mg, 0.69 mmol) and tert-butyl 4-(trifluoromethylsulfonyloxy)-5,6-dihydropyridine-1(2H)-carboxylate (230 mg, 0.69 mmol) as a brown solid. M.P.: 159.9-163.5° C. $^1$H-NMR (δ ppm, CDCl$_3$, 400 MHz): 8.68 (t, J 6.9, 1H), 8.09 (d, J 8.6, 1H), 7.94 (d, J 1.3, 1H), 7.90-7.82 (m, 2H), 7.88 (d, J 1.7, 8.2, 1H), 6.18 (s, 1H), 4.13 (d, J 2.3, 2H), 3.69 (t, J 5.6, 2H), 3.12 (s, 3H), 2.62 (bs, 2H), 1.50 (s, 9H).

Example 66

Tert-butyl 4-{2-[2-fluoro-4-(methylsulfonyl)phenyl]benzo[d]thiazol-5-yl}-5,6-dihydropyridine-1(2H)-carboxylate Following the general procedure-1, the titled compound (120 mg) was obtained from intermediate 39 (230 mg, 0.53 mmol) and tert-butyl 4-(trifluoromethylsulfonyloxy)-5,6-dihydropyridine-1(2H)-carboxylate (175 mg, 0.53 mmol) as an yellow solid. M.P.: 170-174.8° C. $^1$H-NMR (δ ppm, CDCl$_3$, 400 MHz): 8.71-8.67 (m, 1H), 8.13 (d, J 1.3, 1H), 7.95-7.82 (m, 3H), 7.55 (dd, J 1.7, 8.5, 1H), 6.19 (s, 1H), 4.14 (d, J 2.6, 2H), 3.70 (t, J 5.6, 2H), 3.12 (s, 3H), 2.70-2.60 (m, 2H), 1.51 (s, 9H).

Example 67

Tert-butyl 4-{2-[2-fluoro-4-(methylsulfonyl)phenyl]benzo[d]oxazol-6-yl}piperidine-1-carboxylate Following the general procedure-1 Tert-butyl 4-{2-[2-fluoro-4-(methylsulfonyl)phenyl]benzo[d]oxazol-6-yl}-5,6-dihydropyridine-1(2H)-carboxylate (35 mg) obtained from intermediate 41 (400 mg, 0.96 mmol) and tert-butyl 4-(trifluoromethylsulfonyloxy)-5,6-dihydropyridine-1(2H)-carboxylate (318 mg, 0.961 mmol). Tert-butyl 4-{2-[2-fluoro-4-(methylsulfonyl)phenyl]benzo[d]oxazol-6-yl}-5,6-dihydropyridine-1(2H)-carboxylate (50 mg, 0.11 mmol) dissolved in MeOH and added Pd/C (30 mg). This mixture was stirred in an auto clave under hydrogen atmosphere at 55 Psi for 12 h. Reaction mixture filtered through celite and washed the cetile with MeOH. Methanol was removed on rotavapour to obtain the crude. Crude was purified by combiflash using EtOAc and Petether (38:62) as eluent to obtain titled compound (18 mg) as an off-white solid. M.P.: 166.2-169.3° C. $^1$H-NMR (δ ppm, CDCl$_3$, 400 MHz): 8.48-8.46 (m, 1H), 7.91-7.83 (m, 2H), 7.78 (d, J 8.3, 1H), 7.49 (s, 1H), 7.33-7.25 (m, 1H), 4.35-4.20 (m, 2H), 3.13 (s, 3H), 2.90-2.75 (m, 3H), 1.95-1.85 (m, 2H), 1.75-1.60 (m, 2H), 1.49 (s, 9H).

Example 68

{2-[2-fluoro-4-(methylsulfonyl)phenyl]benzo[d]thiazol-5-yl}piperidine-1-carboxylate Tert-butyl 4-{2-[2-fluoro-4-(methylsulfonyl)phenyl]benzo[d]thiazol-5-yl}piperidine-1-carboxylate (30 mg, 0.06 mmol) dissolved in MeOH and added Pd/C (30 mg). This mixture was stirred in an auto clave under hydrogen atmosphere at 55 Psi for 87 h. Reaction mixture filtered through celite and washed the cetile with MeOH. Methanol was removed on rotavapour to obtain the crude. Crude was purified by combiflash using EtOAc and Petether (20:80) as eluent to obtain titled compound (12 mg) as a pale-yellow solid. M.P.: 173.3-178.1° C. $^1$H-NMR (δ ppm, CDCl$_3$, 400 MHz): 8.71-8.65 (m, 1H), 7.99 (s, 1H), 7.93-7.82 (m, 3H), 7.35 (dd, J 1.5, 8.3, 1H), 4.35-4.20 (m, 2H), 3.12 (s, 3H), 2.91-2.79 (m, 3H), 1.96-1.88 (m, 2H), 1.80-1.68 (m, 2H), 1.50 (s, 9H).

Example 69

Ethyl 4-{2-[2-fluoro-4-(methylsulfonyl)phenyl]benzo[d]oxazol-5-yl}piperidine-1-carboxylate 2-[2-fluoro-4-(methylsulfonyl)phenyl]-5-(piperidin-4-yl)benzo[d]oxazole 2,2,2-trifluoroacetate (80 mg, 0.16 mmol) dissolved in DCM (10 ml) and added TEA (0.12 ml, 0.8 mmol). This mixture was stirred at rt for 30 mins Ethylchloro formate (35 mg, 0.33 mmol) was added to the above mixture and stirred at rt for 30 mins Reaction mixture extracted with DCM. DCM removed on rotavapour to obtain the crude. Crude was purified by combiflash using EtOAc and Petether (38:62) as eluent to afford the titled compound (20 mg) as an off-white solid. M.P.: 145-148° C. $^1$H-NMR (δ ppm, CDCl$_3$, 400 MHz): 8.49-8.44 (m, 1H), 7.90-7.84 (m, 2H), 7.69 (d, J 1.2, 1H), 7.58 (d, J 8.5, 1H), 7.30 (dd, J 1.6, 8.5, 1H), 4.40-

4.28 (m, 2H), 4.17 (q, J 7.1, 2H), 3.13 (s, 3H), 2.95-2.79 (m, 3H), 1.96-1.88 (m, 2H), 1.75-1.65 (m, 2H), 1.29 (t, J 7.1, 3H).

Example 70

Tert-butyl 4-{2-[4-(trifluoromethyl)phenyl]benzo[d]oxazol-5-yl}piperidine-1-carboxylate Following the general procedure-1, Tert-butyl 4-{2-[4-(trifluoromethyl)phenyl]benzo[d]oxazol-5-yl}-5,6-dihydropyridine-1(2H)-carboxylate (90 mg) obtained from intermediate 44 (200 mg, 0.51 mmol) and Tert-butyl 4-(trifluoromethylsulfonyloxy)-5,6-dihydropyridine-1(2H)-carboxylate (170 mg, 0.511 mmol). Tert-butyl 4-{2-[4-(trifluoromethyl)phenyl]benzo[d]oxazol-5-yl}-5,6-dihydropyridine-1(2H)-carboxylate (90 mg, 0.2 mmol) dissolved in MeOH (30 ml) and added Pd/C (90 mg). This mixture was stirred in an auto clave in hydrogen atmosphere at 55 Psi for 12 h. Reaction mixture filtered through celite and washed the cetile with MeOH. Methanol was removed on rotavapour to obtain the crude. Crude was triturated with Petether and EtOAc (1:1) to obtain the titled compound (50 mg) as an off-white solid. M.P.: 161-164° C. $^1$H-NMR (δ ppm, 400 MHz): 8.36 (d, J 8.2, 2H), 7.78 (d, J 8.4, 2H), 7.63 (d, J 1.5, 1H), 7.53 (d, J 8.4, 1H), 7.26-7.20 (m, 1H), 4.34-4.20 (m, 2H), 2.90-2.75 (m, 3H), 1.93-1.84 (m, 2H), 1.74-1.62 (m, 2H), 1.49 (s, 9H).

Example 71

Isopropyl 4-{2-[2-fluoro-4-(methylsulfonyl)phenyl]benzo[d]oxazol-6-yl}piperidine-1-carboxylate Tert-butyl 4-{2-[2-fluoro-4-(methylsulfonyl)phenyl]benzo[d]oxazol-6-yl}piperidine-1-carboxylate (270 mg, 5.7 mmol) dissolved in THF (5 ml) and added Et$_2$O.HCl (10 ml). Reaction mixture stirred at rt for 3 h. Ether removed on rotavapour to obtain crude. Crude was triturated with ether to obtain 2-[2-fluoro-4-(methylsulfonyl)phenyl]-6-(piperidin-4-yl)-benzo[d]oxazole hydrochloride (225 mg). 2-[2-fluoro-4-(methylsulfonyl)phenyl]-6-(piperidin-4-yl)-benzo[d]oxazole hydrochloride (70 mg, 0.17 mmol) was dissolved in DCM (5 ml) and added TEA (0.11 ml, 0.85 mmol). This mixture stirred at rt for 30 mins and added isopropylchloro formate in toluene (42 mg, 0.34 mmol). After 30 mins reaction mixture quenched with water and extracted with DCM. DCM removed on rotavapour to obtain the crude. Crude was purified by combiflash using EtOAC and Petether (1:3) as eluent to afford the titled compound (30 mg) as a white solid. M.P.: 170.3-174.3° C. $^1$H-NMR (δ ppm, CDCl$_3$, 400 MHz): 8.47-8.44 (m, 1H), 7.90-7.83 (m, 2H), 7.78 (d, J 8.3, 1H), 7.49 (s, 1H), 7.28 (dd. J 1.5, 8.3, 1H), 4.96 (septet, J 6.2, 1H), 4.40-4.28 (m, 2H), 3.13 (s, 3H), 2.92-2.80 (m, 3H), 1.96-1.88 (m, 2H), 1.75-1.62 (m, 2H), 1.28 (d, J 6.2, 6H).

Example 72

Ethyl 4-{2-[2-fluoro-4-(methylsulfonyl)phenyl]benzo[d]oxazol-6-yl}piperidine-1-carboxylate 2-[2-fluoro-4-(methyl sulfonyl)phenyl]-6-(piperidin-4-yl)benzo[d]oxazole hydrochloride (70 mg, 0.17 mmol) from Example 71 was dissolved in DCM (10 ml) and added TEA (0.12 ml, 0.83 mmol). This mixture stirred at rt for 30 mins and added Ethylchloro formate (35 mg, 0.34 mmol). After 30 mins reaction mixture quenched with water and extracted with DCM. DCM removed on rotavapour to obtain the crude. Crude was purified by combiflash using EtOAc and Petether (1:3) as eluent to afford the titled compound (30 mg) as a white solid. M.P.: 153.5-157.5° C. $^1$H-NMR (δ ppm, CDCl$_3$, 400 MHz): 8.49-8.43 (m, 1H), 7.90-7.82 (m, 2H), 7.78 (d, J 8.3, 1H), 7.49 (s, 1H), 7.28 (dd, J 1.4, 8.3, 1H), 4.42-4.28 (m, 2H), 4.17 (q, J 7.1, 2H), 3.13 (s, 3H), 2.95-2.80 (m, 3H), 1.96-1.88 (m, 2H), 1.75-1.65 (m, 2H), 1.29 (t, J 7.1, 3H).

Example 73

Ethyl 4-{2-[2-fluoro-4-(methylsulfonyl)phenyl]benzo[d]oxazol-6-yl}piperidine-1-carboxylate Tert-butyl 4-{2-[2-fluoro-4-(methylsulfonyl)phenyl]benzo[d]thiazol-5-yl}piperidine-1-carboxylate (130 mg, 0.27 mmol) dissolved in DCM (5 ml) and added TFA (0.5 ml). Reaction mixture stirred at rt for 3 h. DCM removed on rotavapour to obtain crude. Crude was triturated with ether to obtain 2-[2-fluoro-4-(methylsulfonyl)phenyl]-5-(piperidin-4-yl)benzo[d]thiazole 2,2,2-trifluoroacetate (150 mg). 2-[2-fluoro-4-(methylsulfonyl)phenyl]-5-(piperidin-4-yl)benzo[d]thiazole 2,2,2-trifluoroacetate (105 mg, 0.21 mmol) was dissolved in DCM (20 ml) and added TEA (0.23 ml, 1.66 mmol). This mixture stirred at rt for 30 mins and added isopropylchloro formate in toluene (51 mg, 0.42 mmol). After 30 mins reaction mixture quenched with water and extracted with DCM. DCM removed on rotavapour to obtain the crude. Crude was purified by combiflash using EtOAc and Petether (1:3) as eluent to afford the titled compound (60 mg) as a grey solid. M.P.: 174-177° C. $^1$H-NMR (δ ppm, CDCl$_3$, 400 MHz): 8.71-8.65 (m, 1H), 8.00 (d, J 1.2, 1H), 7.93-7.81 (m, 3H), 7.35 (dd, J 1.6, 8.4, 1H), 4.96 (septet, J 6.2, 1H), 4.40-4.22 (m, 2H), 3.12 (s, 3H), 2.95-2.82 (m, 3H), 2.0-1.90 (m, 2H), 1.80-1.64 (m, 2H), 1.28 (d, J 6.3, 6 H).

Example 74

Benzyl 4-{2-[2-fluoro-4-(methylsulfonyl)phenyl]benzo[d]oxazol-5-yl}piperidine-1-carboxylate 2-[2-fluoro-4-(methylsulfonyl)phenyl]-5-(piperidin-4-yl)benzo[d]oxazole 2,2,2-trifluoroacetate (Example 61) (70 mg, 0.14 mmol) dissolved in DCM (10 ml) and added TEA (0.1 ml, 0.72 mmol). This mixture stirred at rt for 30 mins and added benzyl carbonochloridate in toluene (48 mg, 0.28 mmol). After 30 mins reaction mixture quenched with water and extracted with DCM. DCM removed on rotavapour to obtain the crude. Crude was purified by combiflash using EtOAc and Petether (1:2) as eluent to afford the titled compound (30 mg) as an off-white solid. M.P.: 172-175° C. $^1$H-NMR (δ ppm, CDCl$_3$, 400 MHz): 8.49-8.43 (m, 1H), 7.90-7.84 (m, 2H), 7.68 (d, J 1.4, 1H), 7.57 (d, J 8.5, 1H), 7.42-7.22 (m, 6H), 5.17 (s, 2H), 4.42-4.25 (bs, 2H), 3.13 (s, 3H), 3.00-2.78 (m, 3H), 2.00-1.88 (m, 2H), 1.80-1.65 (m, 2H).

Example 75

Isobutyl 4-{2-[2-fluoro-4-(methylsulfonyl)phenyl]benzo[d]oxazol-5-yl}piperidine-1-carboxylate 2-[2-fluoro-4-(methylsulfonyl)phenyl]-5-(piperidin-4-yl)benzo[d]oxazole 2,2,2-trifluoroacetate (Example 61) (140 mg, 0.29 mmol), isobutanol (42 mg, 0.58 mmol), N,N-Carbonyl diimidazole (82 mg, 0.50 mmol) and TEA (0.2 ml, 1.26 mmol) were dissolved in DMF (2.4 ml). Reaction mixture heated to 60° C. for 18 h. Work up (EtOAc/H$_2$O) followed by purification of the crude by column chromatography on 60-120 mesh silica gel using EtOAc and Petether as eluent to afford the titled compound as a white solid. M.P.: 169-173° C. $^1$H-NMR ($\delta$ ppm, CDCl$_3$, 400 MHz): 8.49-8.43 (m, 1H), 7.83-7.90 (m, 2H), 7.69 (d, J 1.4, 1H), 7.58 (d, J 8.5, 1H), 7.30 (dd, J 1.7, 8.5, 1H) 4.42-4.26 (m, 2H), 3.90 (d, J 6.7, 2H), 3.13 (s, 3H), 3.00-2.78 (m, 3H), 2.00-1.88 (m, 3H), 1.80-1.65 (m, 2H), 0.96 (d, J 6.7, 6H).

Example 76

Isopropyl 4-{2-[2-fluoro-4-(methylsulfonyl)phenyl]benzo[d]thiazol-6-yl}piperidine-1-carboxylate Tert-butyl 4-{2-[2-fluoro-4-(methylsulfonyl)phenyl]benzo[d]thiazol-5-yl}piperidine-1-carboxylate (190 mg, 0.38 mmol) dissolved in DCM, cooled to 0° C., trifluoroacetic acid (0.8 ml) was added and stirred the reaction mixture at rt for 3 h. DCM and trifluoroacetic acid was removed on rotavapour to obtain the crude. Crude was washed with petether to obtain 2-[2-fluoro-4-(methylsulfonyl)phenyl]-6-(piperidin-4-yl)benzo[d]thiazole (190 mg) as an off-white solid. 2-[2-fluoro-4-(methylsulfonyl)phenyl]-6-(piperidin-4-yl)benzo[d]thiazole (190 mg, 0.38 mmol) dissolved in DCM (20 ml). To this mixture added TEA (0.3 g, 3 mmol) and stirred the reaction mixture at rt for 30 mins. Reaction mixture cooled to 0° C. and added isopropylchloro formate (92 mg, 0.75 mmol). This mixture was stirred at rt for 30 mins. Work up (DCM/H$_2$O) followed by evaporation of the DCM on rotavapour afforded crude. Crude was triturated with diethyl ether and dried on high vacuum to afford the titled compound (60 mg) as a white solid. M.P.: 163-166° C. $^1$H-NMR ($\delta$ ppm, CDCl$_3$, 400 MHz):

Example 77

Isopropyl 4-{2-[4-(trifluoromethyl)phenyl]benzo[d]oxazol-5-yl}piperidine-1-carboxylate Tert-butyl 4-{2-[4-(trifluoromethyl)phenyl]benzo[d]oxazol-5-yl}-5,6-dihydropyridine-1(2H)-carboxylate (80 mg, 0.17 mmol) dissolved in DCM (15 ml), cooled to 0° C., trifluoroacetic acid (0.1 ml) was added and stirred the reaction mixture at rt for 3 h. DCM and trifluoroacetic acid was removed on rotavapour to obtain the crude. Crude was washed with petether to obtain 5-(piperidin-4-yl)-2-(4-(trifluoromethyl)phenyl)benzo[d]oxazole 2,2,2-trifluoroacetate (90 mg) as an off-white solid. 5-(piperidin-4-yl)-2-(4-(trifluoromethyl)phenyl)benzo[d]oxazole 2,2,2-trifluoroacetate (90 mg, 0.19 mmol) dissolved in DCM (15 ml). To this mixture added TEA (0.1 ml, 0.56 mmol) and stirred the reaction mixture at rt for 30 mins. Reaction mixture cooled to 0° C. and added isopropylchloro formate (46 mg, 0.38 mmol). This mixture was stirred at rt for 30 mins. Work up (DCM/H$_2$O) followed by evaporation of the DCM on rotavapour afforded crude. Crude was purified with combiflash using a gradient mixture of ethylacetate and petether (15:85) as eluent to afford the titled compound (30 mg) as an off-white solid. M.P.: 145-148° C. $^1$H-NMR ($\delta$ ppm, CDCl$_3$, 400 MHz): 8.36 (d, J 8.1, 2H), 7.78 (d, J 8.3, 2H), 7.62 (d, J 1.5, 1H), 7.54 (d, J 8.5, 1H), 7.29-7.21 (m, 1H), 4.96 (septet, 6.2, 1H), 4.31 (bs, 2H), 2.95-2.76 (m, 3H), 1.90 (d, J 12.7, 2H), 1.75-1.63 (m, 2H), 1.27 (d, J 6.2, 6H).

Example 78

Isopropyl 4-(2-p-tolylbenzo[d]oxazol-6-yl)piperidine-1-carboxylate

Intermediate 49 (40 mg, 0.14 mmol) was dissolved in DCM (10 ml) and added trifluooroacetic acid (0.15 ml) at 0° C. This mixture was stirred at rt for 3 h. After 3 h DCM was removed on rotavapour and the residue that obtained was washed with diethyl ether to obtain 6-(piperidin-4-yl)-2-p-tolylbenzo[d]oxazole 2,2,2-trifluoroacetate (40 mg). 6-(piperidin-4-yl)-2-p-tolylbenzo[d]oxazole 2,2,2-trifluoroacetate (40 mg, 0.1 mmol) was dissolved in DCM (10 ml) and added TEA (0.1 ml, 0.79 mmol) at 0° C. To the above mixture isopropylchloro formate (24 mg, 0.2 mmol) was added and stirred at rt for 15 mins. Workup (DCM/H$_2$O) followed by column purification on 60-120 mesh silica gel using EtOAc and Petether (2:8) as eluent afforded the titled compound (12 mg) as an off-white solid. $^1$H-NMR ($\delta$ ppm, CDCl$_3$, 400 MHz): 8.12 (d, J 8.2, 2H), 7.66 (d, J 8.2, 1H), 7.40 (d, J 1.2, 1H), 7.32 (d, J 8, 2H), 7.19 (dd, J 1.4, 8.2, 1H), 4.96 (septet, J 6.2, 1H), 4.32 (bs, 2H), 2.93-2.75 (m, 3H), 2.44 (s, 3H), 1.90 (d, J 13.4, 2H), 1.75-1.65 (m, 2H), 1.27 (d, J 6.2, 6H).

Example 79

3-{4-[2-(2-fluoro-4-(methylsulfonyl)phenyl)benzo[d]oxazol-5-yl]-5,6-dihydropyridin-1(2H)-ylsulfonyl}propan-1-ol Example 59 (200 mg, 0.42 mmol) was dissolved in DCM (30 ml) and added TFA (1.5 ml, 9.2 mmol). This mixture was stirred at rt for 3 h and DCM was removed on rotavapour to obtain a residue. Residue was co-distilled with diethyl ether to obtain 2-(2-fluoro-4-(methyl sulfonyl)phenyl)-5-(1,2,3,6-tetrahydropyridin-4-yl)benzo[d]oxazole 2,2,2-trifluoroacetate (210 mg). 2-(2-fluoro-4-(methylsulfonyl)phenyl)-5-(1,2,3,6-tetrahydropyridin-4-yl)benzo[d]oxazole 2,2,2-trifluoroacetate (200 mg, 0.4 mmol) was dissolved in DCM (10 ml) and added TEA (0.46 ml, 3.3 mmol). This mixture was stirred at rt for 30 mins. After 30 mins reaction mixture cooled to 0° C. and added ethyl 3-(chlorosulfonyl)propanoate (164 mg, 0.4 mmol). This reaction continued for 30 mins at rt. Work up (H$_2$O/DCM) followed by column purification on combiflash using a gradient mixture of EtOAc and Petether (45:55) as eluent afforded ethyl 2-{4-[2-(2-fluoro-4-(methylsulfonyl)phenyl]benzo[d]oxazol-5-yl}-5,6-dihydropyridin-1(2H)-ylsulfonyl)acetate (120 mg). Ethyl 2-{4-[2-(2-fluoro-4-(methylsulfonyl)phenyl]benzo[d]oxazol-5-yl}-5,6-dihydropyridin-1(2H)-ylsulfonyl)acetate (100 mg, 0.19 mmol) was dissolved in THF (5 ml) and added Lithiumaluminium hydride (14 mg, 0.38 mmol) at 0° C. This mixture was stirred at same temperature for 90 mins. After completion of the reaction, reaction mass quenched with 1N HCl (7 ml). Work up (DCM/H$_2$O) followed by purification on combiflash using a gradient mixture of EtOAc and Petether (80:20) as eluent afforded the titled compound (40 mg) as a white solid. M.P.: 184-186° C. $^1$H-NMR ($\delta$ ppm, CDCl$_3$, 400 MHz): 8.48 (t, J 8.1, 1H), 8.06 (dd, J 1.6, 10.1, 1H), 8.00-7.94 (m, 2H), 7.84 (d, J 8.6, 1H), 7.63 (dd, J 1.8, 8.5, 1H), 6.29 (s, 1H), 4.64 (t, J 5.3, 1H), 3.94 (d, J 2.9, 2H), 3.50-3.42 (m, 4H), 3.36 (s, 3H), 3.18-3.10 (m, 2H), 2.70-2.62 (m, 2H), 1.88-1.80 (m, 2H).

Example 80

3-{4-[2-(2-fluoro-4-(methylsulfonyl)phenyl)benzo[d]oxazol-5-yl]piperidin-1-ylsulfonyl}propan-1-ol Example 61 (0.2 g, 0.41 mmol) was dissolved in DCM and added TEA (0.33 g, 3.3 mmol). This mixture was stirred at rt for 30 mins. After 30 mins reaction mixture cooled to 0° C. and added ethyl 3-(chlorosulfonyl)propanoate (245 mg, 1.2 mmol). This reaction continued for 30 mins at rt. Work up (H₂O/DCM) followed by column purification on combiflash using a gradient mixture of EtOAc and Petether (65:35) as eluent afforded ethyl 2-{4-[2-(2-fluoro-4-(methylsulfonyl)phenyl)benzo[d]oxazol-5-yl]piperidin-1-ylsulfonyl}acetate. Ethyl 2-{4-[2-(2-fluoro-4-(methylsulfonyl)phenyl)benzo[d]oxazol-5-yl]piperidin-1-ylsulfonyl}acetate (100 mg, 0.19 mmol) was dissolved in THF (5 ml) and added Lithiumaluminium hydride (14 mg, 0.37 mmol) at 0° C. This mixture was stirred at same temperature for 90 mins. After completion of the reaction, reaction mass quenched with 1N HCl (7 ml). Work up (DCM/H₂O) followed by purification on combiflash using a gradient mixture of EtOAc and Petether (65:35) as eluent afforded the titled compound (120 mg) as an off-white solid. M.P.: 204-206° C. ¹H-NMR (δ ppm, DMSO-d₆, 400 MHz): 8.47 (t, J 8.03, 1H), 8.06 (dd, J 1.6, 10.1, 1H), 7.97 (dd, J 1.6, 8.2, 1H), 7.82-7.75 (m, 2H), 7.43 (dd, J 1.5, 8.6, 1H), 4.66 (t, J 5.3, 1H), 3.74 (d, J 12.1, 2H), 3.50 (q, J 6.1, 2H), 3.38 (s, 3H), 3.12-3.06 (m, 2H), 2.98-2.80 (m, 3H), 1.96-1.90 (m, 2H), 1.88-1.81 (m, 2H), 1.79-1.69 (m, 2H).

Example 81

3-{4-[2-(2-fluoro-4-(methylsulfonyl)phenyl)benzo[d]oxazol-5-yl]piperidin-1-ylsulfonyl}propan-1-ol Example 61 (150 mg, and 0.31 mmol) and 2-Chloro-5-fluoropyrimidine (44 mg, 0.34 mmol) were dissolved in isopropanol (20 ml). To this mixture DiPEA (0.45 ml) was added and heated to 90° C. for 12 h. Isopropanol was removed on rotavapour to obtain a residue. Residue was purified by combiflash using a gradient mixture of EtOAc and Petether (38:62) as eluent to afford the titled compound (30 mg) as an off-white solid. M. P.: 220-222° C. MS (m/z): 471.2 [M+H]⁺.

Example 82

Tert-butyl 4-[2-(4-carbamoyl-3-fluorophenyl)benzo[d]oxazol-5-yl]piperidine-1-carboxylate Intermediate 52 (40 mg, 0.1 mmol), 2-fluoro-4-(4,4,5,5-tetramethyl-1,3,2-dioxaborolan-2-yl)benzamide (30 mg, 0.12 mmol) and KF (18 mg, 0.3 mmol) were dissolved in a mixture of DMF (1 ml) and water (0.4 ml). This mixture was purged with N₂ for 30 mins. Pd(dppf)Cl₂.CH₂Cl₂ was added to the above mixture and again purged with N₂ for 30 mins. This reaction mixture was heated to 90° C. for 12 h. Work up (EtOAc and H₂O) followed by purification on combiflash using a gradient mixture of EtOAc and Petether (55:45) as eluent afforded the titled compound (3 mg) as an Off-White solid. MS (m/z): 439.5 [M+H]⁺.

Example 83

2-[2-fluoro-4-(methylsulfonyl)phenyl]-5-[4-(3-isopropyl-1,2,4-oxadiazol-5-yl)piperidin-1-yl]benzo[d]oxazole Intermediate 28 (150 mg, 0.41 mmol), 3-isopropyl-5-(piperidin-4-yl)-1,2,4-oxadiazole hydrochloride (96 mg, 0.5 mmol), K₂CO₃ (59 mg, 0.43 mmol), CuCl (2 mg, 0.02 mmol), acetyl acetone (5 mg, 0.05 mmol) were dissolved in NMP (1 ml). This reaction mixture was stirred at 130° C. for 16 h under N₂ atmosphere. Work up (EtOAc/H₂O) followed by purification on combiflash using a gradient mixture of EtOAc and Petether (30:70) as eluent afforded the titled compound (25 mg) as a pale-yellow solid. M. P.: 206-209° C. ¹H-NMR (δ ppm, CDCl₃, 400 MHz): 8.26 (d, J 8.2, 1H), 7.97 (d, J 1.4, 1H), 7.69 (d, J 1.4, 1H), 7.63 (dd, J 1.5, 8.2, 1H), 7.56-7.48 (m, 2H), 3.49-3.39 (m, 2H), 3.15-3.04 (m, 5H), 3.03-2.93 (m, 2H), 2.25-2.16 (m, 4h), 1.36 (d, J 7, 6H).

Example 84

Tert-butyl 4-{2-[4-(trifluoromethyl)phenyl]benzo[d]oxazol-6-yl}piperidine-1-carboxylate Following the general procedure, tert-butyl 4-[2-(4-(trifluoromethyl)phenyl]benzo[d]oxazol-6-yl)-5,6-dihydropyridine-1(2H)-carboxylate (260 mg) was prepared from intermediate 55 (420 mg, 1.08 mmol) and tert-butyl 4-(trifluoromethylsulfonyloxy)-5,6-dihydropyridine-1(2H)-carboxylate (358 mg, 1.08 mmol). tert-butyl 4-[2-(4-(trifluoromethyl)phenyl]benzo[d]oxazol-6-yl)-5,6-dihydropyridine-1(2H)-carboxylate (260 mg, 0.58 mmol) was dissolved in methanol (8 ml) and added Pd/C (5%) (520 mg). This mixture was stirred under H₂ pressure (6.5 kg) for 12 h. Combined methanol fractions were evaporated on rotavapour to obtain the crude. Crude was purified on combiflash using a gradient mixture of EtOAc and Petether (1:9) as eluent to afford the titled compound (150 mg) as a white solid. M. P.: 174-179° C. MS (m/z): 446.46 [M+H]⁺.

Example 85

Isopropyl 4-{2-[2-fluoro-4-(methylsulfonyl)phenyl]benzo[d]oxazol-5-yl}piperazine-1-carboxylate Intermediate 28 (490 mg, 1.32 mmol), N-Benzylpiprazine (280 mg, 1.6 mmol), K₂CO₃ (190 mg, 1.4 mmol), CuCl (6.5 mg, 0.05 mmol), acetyl acetone (17 mg, 0.12 mmol) were dissolved in NMP (2 ml). This reaction mixture was stirred at 130° C. for 15 h under N₂ atmosphere. Work up (EtOAc/H₂O) followed by column purification on 60-120 mesh silica gel using a gradient mixture of EtOAc and Petether (1:1) as eluent afforded 5-(4-benzylpiperazin-1-yl)-2-[2-fluoro-4-(methylsulfonyl)phenyl]benzo[d]oxazole (250 mg) as a yellow solid. 5-(4-Benzylpiperazin-1-yl)-2-[2-fluoro-4-(methylsulfonyl)phenyl]benzo[d]oxazole (130 mg, 0.28 mmol) dissolved in DCM (15 ml) and added isopropylchloro formate (102 mg, 0.84 mmol). This mixture was stirred at reflux for 18 h. Work up (DCM/H₂O) followed by purification of the crude by column chromatography on 230-400 mesh silica gel using a gradient mixture of EtOAc and Petether (30:70) as eluent afforded the titled compound (25 mg) as a pale-yellow solid. M.P.: 231-234° C. ¹H-NMR (δ ppm, CDCl₃, 400 MHz): 8.28 (d, J 8.7, 1H), 7.96 (d, J 1.6, 1H), 7.68-7.64 (m, 2H), 7.57-7.47 (m, 2H), 4.95 (septet, J 6.2, 1H), 3.71-3.63 (m, 4H), 3.12-3.06 (m, 4H), 1.26 (d, J 6.2, 6H).

Example 86

Tert-butyl 4-{2-[4-(trifluoromethyl)phenyl]oxazolo[5,4-b]pyridin-6-yl}-5,6-dihydropyridine-1(2H)-carboxylate Following the general procedure-1, the titled compound (230 mg) was obtained from intermediate 58 (500 mg, 1.28 mmol) and tert-butyl 4-(trifluoromethylsulfonyloxy)-5,6-dihydropyridine-1(2H)-carboxylate (467 mg, 1.4 mmol) as an off-white solid. M.P.: 207-212° C. ¹H-NMR (δ ppm, CDCl₃, 400 MHz): 8.44-8.38 (m, 3H), 8.04 (d, J 2.2, 1H), 7.82 (d, J 8.3, 2H), 6.13 (bs, 1H), 4.14 (d, J 2.6, 2H), 3.70 (t, J 5.6, 2H), 2.59 (bs, 2H), 1.50 (s, 9H).

Example 87

Tert-butyl 4-{2-[4-(trifluoromethyl)phenyl]oxazolo[5,4-b]pyridin-6-yl}piperidine-1-carboxylate Tert-butyl 4-{2-[4-(trifluoromethyl)phenyl]oxazolo[5,4-b]pyridin-6-yl}-5,6-dihydropyridine-1(2H)-carboxylate (170 mg, 0.38 mmol) was dissolved in methanol (10 ml) and added Pd/C (5%) (283 mg). This mixture was stirred under $H_2$ pressure (6.5 kg) for 12 h. Combined methanol fractions were evaporated on rotavapour to obtain the crude. Crude was purified on combiflash using a gradient mixture of EtOAc and Petether (1:9) as eluent to afford the titled compound (35 mg) as a white solid. M. P.: 184-188° C. $^1$H-NMR (δ ppm, $CDCl_3$, 400 MHz): 8.40 (d, J 8.1, 2H), 8.27 (d, J 2, 1H), 7.93 (d, J 2, 1H), 7.81 (d, J 8.3, 2H), 4.31 (d, J 13.5, 2H), 2.91-2.81 (m, 3H), 1.91 (d, J 12.9, 2H), 1.78-1.62 (m, 2H), 1.50 (s, 9H).

Biological Assay

The biological properties of the compounds of this invention may be confirmed by a number of biological assays. The biological assays which can be been carried out with the compounds of the invention are exemplified below.

A. In Vitro Cyclic AMP Assay:

cAMP measurements were done using a Cisbio dynamic 2 HTRF kit (Cisbio, Bedford, Mass.) according to the manufacturer's protocol. Briefly, HEK293 cells (0.2×10$^6$/well) were plated in a 24 well plate and incubated overnight at 37° C. Cells were transfected with either empty vector DNA or human GPR119 expression plasmid DNA using Lipofectamine 2000 (Invitrogen). After 24 h, transfected cells were harvested, counted and plated at 1000 cells/5 ul in a black 384 welled small volume plate. Cells were treated with desired concentrations of compounds and incubated for 60 min at room temperature. Lysis buffer containing cAMP-d2 and cryptate conjugate were added and incubated for 1 h. HRTF ratio was measured on a microplate reader (BMG Labtech., Germany) at an excitation wavelength of 337 nm and emission wavelengths of 665 and 620 nm with an integration time of 400 μsec. Data were analyzed using Graphpad Prism (Graphpad software; San Diego Calif.) for $EC_{50}$ determination.

Results:

The results are as given in Table I as % Induction@ 10 μM, Table II as % Induction@ 10 μM and EC 50 in nM B. In Vitro Mouse GPR 119 Cyclic AMP Assay:

cAMP measurements were done using a Cisbio dynamic 2 HTRF kit (Cisbio, Bedford, Mass.) according to the manufacturer's protocol. HEK293 Cells were stably transfected with Mouse GPR119 expression plasmid DNA using Lipofectamine 2000 (Invitrogen) and maintained in culture. Cells were harvested, counted and plated at 1000 cells/5 ul in a black 384 welled small volume plate. Cells were treated with desired concentrations of compounds and incubated for 60 min at room temperature. Lysis buffer containing cAMP-d2 and cryptate conjugate were added and incubated for 1 h. HRTF ratio was measured on a microplate reader (BMG Labtech., Germany) at an excitation wavelength of 337 nm and emission wavelengths of 665 and 615 nm with an integration time of 400 μsec. Data were analyzed using Graphpad Prism (Graphpad software; San Diego Calif.) for $EC_{50}$ determination. For example example 12 showed an EC 50 of <25 nM C. In Vitro HIT-T15 Cyclic AMP Assay:

cAMP measurements were done using a Cisbio dynamic 2 HTRF kit (Cisbio, Bedford, Mass.) according to the manufacturer's protocol. Briefly, HIT-T15 cells were harvested, counted and plated at 4000 cells/5 ul PBS-BSA solution in a black 384 welled small volume plate. Cells were treated with desired concentrations of compounds and incubated for 60 min at room temperature. Lysis buffer containing cAMP-d2 and cryptate conjugate were added and incubated for 1 h. HRTF ratio was measured on a microplate reader (BMG Labtech., Germany) at an excitation wavelength of 337 nm and emission wavelengths of 665 and 615 nm with an integration time of 400 μsec. Data were analyzed using Graphpad Prism (Graphpad software; San Diego Calif.) for $EC_{50}$ determination. For instance example 12 showed an EC 50 of <25 nM D. In Vitro HIT-T15 Insulin Assay:

Insulin measurements were done using a Ultra Sensitive Insulin ELISA kit (Crystal Chem Inc, USA) according to the manufacturer's protocol. Briefly, 2.5×10$^5$ HIT-15 cells/well were plated in 24 well plate and incubator for 24 hours. Next day, media was replaced with DMEM-3 mM Glucose with 10% Horse Serum, 2.5% FBS, 1% pen-strep and further incubated for 24 h. Cells were treated with desired concentrations of compounds and incubated for 60 min at room temperature. Supernatant was collected, centrifuged and soup added to the pre-coated strips followed by ELISA. The absorbance was measured at 450 and 630 nM. Data were analyzed using Graphpad Prism (Graphpad software; San Diego Calif.) for $EC_{50}$ determination.

TABLE I

| COMPOUND | Induction | EC50* |
|---|---|---|
| EXAMPLE-1 | 55.35 | ND |
| EXAMPLE-2 | 35.78 | ND |
| EXAMPLE-3 | 35.44 | ND |
| EXAMPLE-4 | 74.19 | A |
| EXAMPLE-5 | 40.98 | ND |
| EXAMPLE-6 | 73.22 | A+ |
| EXAMPLE-7 | 62.63 | A |
| EXAMPLE-8 | 66.72 | A+ |
| EXAMPLE-9 | 46.83 | ND |
| EXAMPLE-10 | 59.24 | C |
| EXAMPLE-11 | 70.09 | ND |
| EXAMPLE-12 | 82.95 | A++ |
| EXAMPLE-13 | 68.17 | B |
| EXAMPLE-14 | 68.59 | A+ |
| EXAMPLE-15 | 77.69 | B |
| EXAMPLE-16 | 43.71 | ND |
| EXAMPLE-17 | 41.47 | ND |
| EXAMPLE-18 | 36.44 | ND |
| EXAMPLE-19 | 37.17 | ND |
| EXAMPLE-20 | 73.88 | A+ |
| EXAMPLE-21 | 59.02 | A |
| EXAMPLE-22 | 64.55 | ND |
| EXAMPLE-23 | 69.56 | A+ |
| EXAMPLE-24 | 67.48 | A++ |
| EXAMPLE-25 | 63.39 | ND |
| EXAMPLE-26 | 73.99 | ND |
| EXAMPLE-27 | 46.54 | ND |
| EXAMPLE-28 | 45.37 | ND |
| EXAMPLE-29 | 78.62 | A+ |
| EXAMPLE-30 | 62.20 | C |
| EXAMPLE-31 | 80.38 | A++ |
| EXAMPLE-32 | 63.93 | A |
| EXAMPLE-33 | 10.61 | ND |
| EXAMPLE-34 | — | ND |
| EXAMPLE-35 | 0.28 | ND |
| EXAMPLE-36 | 4.83 | ND |
| EXAMPLE-37 | 6.56 | ND |
| EXAMPLE-38 | 16.59 | ND |
| EXAMPLE-39 | 27.49 | ND |
| EXAMPLE-40 | 21.87 | ND |
| EXAMPLE-41 | — | ND |
| EXAMPLE-42 | 78.40 | A+ |
| EXAMPLE-43 | 48.77 | ND |
| EXAMPLE-44 | 64.79 | A+ |
| EXAMPLE-45 | 56.43 | ND |

TABLE I-continued

| COMPOUND | Induction | EC50* |
|---|---|---|
| EXAMPLE-46 | 53.02 | ND |
| EXAMPLE-47 | 33.13 | ND |
| EXAMPLE-48 | 26.66 | ND |
| EXAMPLE-49 | 32.86 | ND |
| EXAMPLE-50 | 38.68 | ND |
| EXAMPLE-51 | 38.73 | ND |
| EXAMPLE-52 | 68.36 | B |
| EXAMPLE-53 | 39.87 | ND |

ND: Not done;
A++: ≤25 nM;
A+: >25 to ≤50 nM;
A: >50 to ≤100 nM;
B: >100 to ≤500 nM;
C: >500 to ≤1000 nM;
*Emax varies between 65 to 80%.

TABLE II

| COMPOUND | Induction | EC50* |
|---|---|---|
| EXAMPLE-56 | 38.53 | ND |
| EXAMPLE-57 | 47.05 | ND |
| EXAMPLE-58 | 32.25 | ND |
| EXAMPLE-59 | 63.76 | ND |
| EXAMPLE-60 | 72.78 | A+ |
| EXAMPLE-61 | 29.77 | ND |
| EXAMPLE-62 | 59.34 | B |
| EXAMPLE-63 | 56.57 | ND |
| EXAMPLE-64 | 75.03 | A++ |
| EXAMPLE-65 | 32.09 | ND |
| EXAMPLE-66 | 18.89 | ND |
| EXAMPLE-67 | 73.03 | A+ |
| EXAMPLE-68 | 72.69 | ND |
| EXAMPLE-69 | 71.83 | A+ |
| EXAMPLE-70 | 64.66 | A++ |
| EXAMPLE-71 | 76.63 | A++ |
| EXAMPLE-72 | 81.57 | A++ |
| EXAMPLE-73 | 46.02 | C |
| EXAMPLE-74 | 14.69 | ND |
| EXAMPLE-75 | 57.49 | ND |
| EXAMPLE-76 | 74.90 | A |
| EXAMPLE-77 | 80.37 | A |
| EXAMPLE-78 | 59.36 | ND |
| EXAMPLE-79 | 46.17 | ND |
| EXAMPLE-80 | 26.39 | ND |
| EXAMPLE-81 | 42.96 | ND |
| EXAMPLE-82 | ND | ND |
| EXAMPLE-83 | 57.64 | ND |
| EXAMPLE-84 | 13.17 | ND |
| EXAMPLE-85 | ND | ND |
| EXAMPLE-86 | ND | ND |
| EXAMPLE-87 | 47.29 | ND |

ND: Not done;;
A++: ≤25 nM;
A+: >25 to ≤50 nM;
A: >50 & <250 nM;
B: <500 nM;
C: >500 to ≤1000 nM;
*Emax varies between 65 to 80%.

E: Oral Glucose Tolerance Test (OGTT) in C57Bl/6J Mice:

Results of the OGTT not only diagnose diabetes but can determine if a subject has impaired fasting glucose (IFG) or impaired glucose tolerance (IGT). Having either of these conditions indicates a significantly increased risk of developing diabetes in the future.

Figure 2:
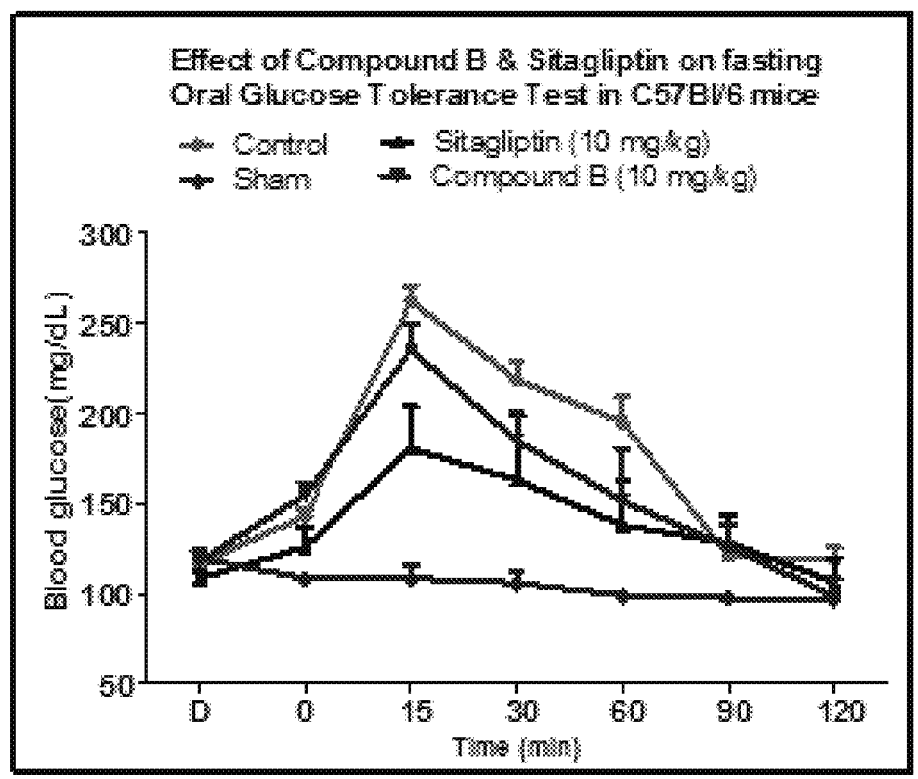
FIG. 2 is a graph of blood glucose over time in C57BI/6J mice according to the oral glucose tolerance test (Biological Assay Procedure E) before and after oral administration of vehicle (control), compound A (Example 42 @ 10 mg/kg), or sitagliptin (10 mg/kg @ 10 mg/kg).

After the quarantine period, 6 hr fasted animals were randomized and divided into various groups depending on their blood glucose levels. Test compounds or standard drug (sitagliptin) was prepared as a suspension in a vehicle consisting of 0.5% methylcellulose and Tween 80 as a suspending agent. The standard drug, Compound A (example-64), Compound B (example-42) or vehicle were administered by oral gavage in a volume of 10 mL/kg. 1 h after the test compounds, standard drug and vehicle administration, blood was sampled from the tail vein of mice at time 0 min (baseline) and at 30, 60, 90 and 120 min after an oral glucose load of 2.0 g/kg of body weight. Food, but not water, was withheld from the cages during the course of experiment. The area under curve (AUC) of experimental animals was compared with that of vehicle-treated control group. The results are shown in FIGS. 1 and 2 and are discussed below.

Results:

Compound A and Sitagliptin dosed as single agents lowered $AUC_{glucose}$ by 24% and 59%, respectively, and Compound B and sitagliptin dosed as single agents lowered $AUC_{glucose}$ by 22 and 50%, respectively.

F: Intraperitoneal Glucose Tolerance Test (IPGTT) in C57Bl/6J Mice:

After the quarantine period, 6 hr fasted animals are to be randomized and divided into various groups depending on their blood glucose levels. Test compound or standard drug is to be prepared as a suspension in a vehicle consisting of 0.5% methylcellulose in which Tween 80 as a suspending agent. The compound or vehicle is to be administered by oral gavage in a volume of 10 mL/kg. 1 h after drug or vehicle administration, blood is to be sampled from the tail vein of mice at time 0 min (baseline) and at 30, 60, 90 and 120 min after intraperitoneal administration of glucose solution of 2.0 g/kg of body weight. Food, but not water is to be withheld from the cages during the course of experiment. The area under curve (AUC) of experimental animals will be compared with that of vehicle-treated control group.

G: Oral Glucose Tolerance Test (OGTT) in Streptozotocin & Nicotinamide Induced Type 2 Diabetes in CD-1 Mice:

After the quarantine period, animals are to be randomized and divided into various groups depending on their body weights and animals are to be administered with nicotinamide (100 mg/kg) and streptozotocin (150 mg/kg) by intraperitoneally to induce diabetes. Sham control mice are to be intraperitoneally administered with physiological saline. Two weeks later, the diabetic mice were grouped to provide similar mean non-fasting blood glucose levels in each group, 6 hr fasted animals are to be randomized and divided into various groups depending on their blood glucose levels. Test compound or standard drug is to be prepared as a suspension in a vehicle consisting of 0.5% methylcellulose in which Tween 80 as a suspending agent. The compound or vehicle is to be administered by oral gavage in a volume of 10 mL/kg. 1 h after drug or vehicle administration, blood is to be sampled from the tail vein of mice at time 0 min (baseline) and at 30, 60, 90 and 120 min after an oral glucose load of 2.0 g/kg of body weight. Food, but not water is to be withheld from the cages during the course of experiment. The area under curve (AUC) of experimental animals will be compared with that of vehicle-treated control group.

H: Sub-Acute Treatment of Test Compound in Streptozotocin & Nicotinamide Induced Type 2 Diabetes in CD-1 Mice:

After the quarantine period, animals are to be randomized and divided into various groups depending on their body weights and animals are to be administered with nicotinamide (100 mg/kg) and streptozotocin (150 mg/kg) by intraperitoneally to induce diabetes. Sham control mice are to be intraperitoneally administered with physiological saline. Two weeks later, the diabetic mice are to be grouped to provide similar mean non-fasting blood glucose levels in each group, on day 0, fasted animals are to be randomized and divided into various groups depending on their blood glucose levels. Test compound or standard drug is to be prepared as a suspension in a vehicle consisting of 0.5% methylcellulose in which Tween 80 as a suspending agent. The compound or vehicle is to be administered by oral gavage in a volume of 10 mL/kg. 1 h after drug or vehicle administration, blood is to be sampled from the tail vein of mice at time 0 min (baseline) and at 30, 60, 90 and 120 min after an oral glucose load of 2.0 g/kg of body weight. Food, but not water is to be withheld from the cages during the course of experiment. The area under curve (AUC) of experimental animals will be compared with that of vehicle-treated control group. After conducting the OGTT on day 0, the treatment will be continued for 14 days, on day 14, 6 hr fasted animals will be used for the same OGTT procedure. After conducting the OGTT, blood samples will be collected from the animals and analysed for the lipid profile, insulin, and GLP-1 levels.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications and patent and/or patent applications cited in this application are herein incorporated by reference to the same extent as if each individual publication or patent application was specifically and individually indicated to be incorporated herein by reference.

We claim:
1. A compound of formula (A-I), (A-II), (B-I), (B-II), (B-III) and (B-IV):

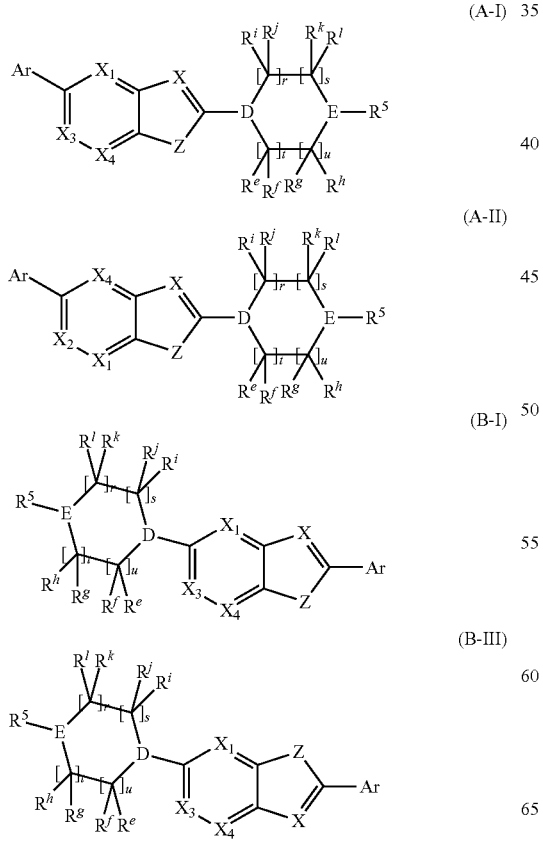

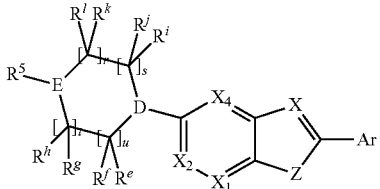

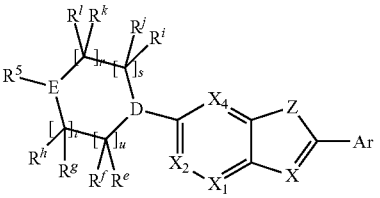

or a tautomer, stereoisomer, enantiomer, diastereomer, salt, or N-oxide thereof, wherein Ar is selected from substituted or unsubstituted aryl, substituted or unsubstituted heteroaryl or $Cy^1$;

$X^1$ is $CR^1$ or N; $X^2$ is $CR^2$ or N; $X^3$ is $CR^3$ or N; and $X^4$ is $CR^4$ or N;

X is CR or N;

Z is CO, O or $S(O)_q$;

$Cy^1$ is selected from substituted or unsubstituted cycloalkyl or substituted or unsubstituted heterocyclic group;

each occurrence of R, $R^2$, and $R^3$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, $-OR^a$, $-S(=O)_q-R^a$, $-NR^aR^b$, $-C(=Y)-R^a$, $-CR^aR^b-C(=Y)-R^a$, $-CR^aR^b-Y-CR^aR^b-$, $-C(=Y)-NR^aR^b-$, $-NR^a-C(=Y)-NR^aR^b-$, $-S(=O)_q-NR^aR^b-$, $-NR^a-S(=O)_q-NR^aR^b-$, and $-NR^a-NR^aR^b-$;

each occurrence of $R^1$ and $R^4$ may be same or different and is independently selected from hydrogen, nitro, hydroxy, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, $-OR^a$, $-S(=O)_q-R^a$, $-NR^aR^b$, $-C(=Y)-R^a$, $-CR^aR^b-C(=Y)-R^a$, $-CR^aR^b-Y-CR^aR^b-$, $-C(=Y)-NR^aR^b-$, $-NR^a-C(=Y)-NR^aR^b-$, $-S(=O)_q-NR^aR^b-$, $-NR^a-S(=O)_q-NR^aR^b-$, and $-NR^a-NR^aR^b$;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, NR$^c$ or S;
each occurrence of R$^c$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl;
each occurrence of Y is independently selected from O, S, and NR$^a$; and
each occurrence of q independently represents 0, 1 or 2;
D and E are independently selected from CH or N;
R$^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —OR$^a$, —OR$^a$C(O) NR$^a$R$^b$, —OR$^a$C(O)OR$^b$-, —OC(O)R$^a$, —OC(O) NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$; with the proviso that when R$^5$ is —SO$_2$R$^a$, then R$^a$ is not unsubstituted alkyl;
each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and
each occurrence of R$^e$, R$^f$, R$^g$, R$^h$, R$^j$, R$^k$ and R$^l$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl; or any two of R$^e$, R$^f$, R$^g$, R$^h$, R$^j$, R$^k$, R$^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl); and
each of r, s, t and u is 0, 1 or 2 with the proviso that r+s+t+u≠0.

2. A compound of formula (A-III) and (A-IV):

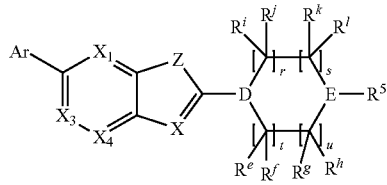

(A-III)

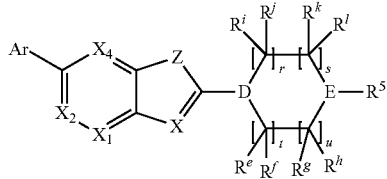

(A-IV)

or a tautomer, stereoisomer, enantiomer, diastereomer, salt, or N-oxide thereof, wherein
Ar is selected from substituted or unsubstituted aryl, substituted or unsubstituted heteroaryl or Cy$^1$;
X$^1$ is CR$^1$ or N; X$^2$ is CR$^2$ or N; X$^3$ is CR$^3$ or N; and X$^4$ is CR$^4$ or N;
X is CR or N;
Z is CO, O or S(O)$_q$;
Cy$^1$ is selected from substituted or unsubstituted cycloalkyl or substituted or unsubstituted heterocyclic group;
each occurrence of R, R$^2$, and R$^3$ may be same or different and is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, substituted or unsubstituted C$_{3-6}$ cycloalkenyl, OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$-;
each occurrence of R$^1$ and R$^4$ may be same or different and is independently selected from hydrogen, nitro, hydroxy, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, substituted or unsubstituted C$_{3-6}$ cycloalkenyl, OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$-;
each occurrence of R$^a$ and R$^b$ may be same or different and are independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl, or when two R$^a$ and/or R$^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^c$ or S;

each occurrence of R$^c$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl;

each occurrence of Y is independently selected from O, S, and NR$^a$; and each occurrence of q independently represents 0, 1 or 2;

D and E are independently selected from CH or N;

R$^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —SO$_2$NR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and each occurrence of R$^e$, R$^f$, R$^g$, R$^h$, R$^j$, R$^k$ and R$^l$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl; or any two of R$^e$, R$^f$, R$^g$, R$^h$, R$^j$, R$^k$, R$^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl); and each of r, s, t and u is 0, 1 or 2 with the proviso that r+s+t+u≠0, a) that for compound of formula (A-III), wherein Z is O or S and X$_4$ is N or CR$^4$ then Ar cannot be

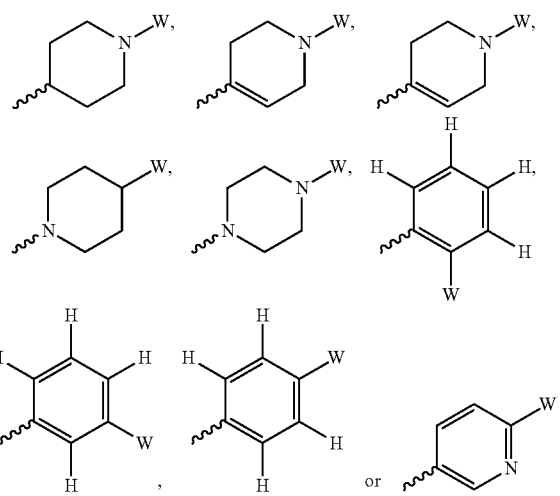

b) that for compound of formula (A-IV) wherein Z is O or S and X$_1$ is N or CR$^1$ then Ar cannot be

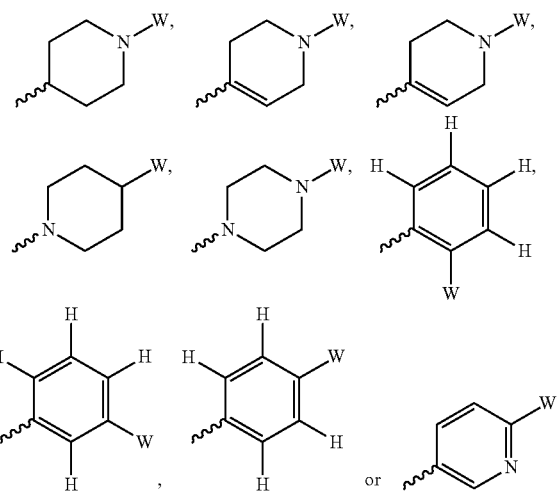

wherein

R$^1$ and R$^4$ is as defined above for compound of formula (A);

W is S(=O)$_2$—R$^1$, S(=O)$_2$—NR$_{1a}$R$_1$, —C(=O)—R$_1$, —C(=O)—O—R$_1$, —C(=O)—NR$_{1a}$R$_1$, —NR$_{1a}$—S(=O)$_2$—R$_1$, halo, or a 4 to 10-membered optionally substituted heteroaryl, which contains 1-4 heteroatoms selected from N, O, and S;

R$_{1a}$, at each occurrence, is independently hydrogen or (C$_1$-C$_8$)alkyl; and R$_1$ is optionally substituted (C$_1$-C$_6$)-alkyl, optionally substituted (C$_2$-C$_6$)-alkenyl, optionally substituted (C$_2$-C$_6$)- alkynyl, optionally substituted $(C_3-C_{12})$-cycloalkyl, optionally substituted $(C_1-C_{10})$aryl, a 4 to 10-membered optionally substituted heteroaryl, which contains 1-4 heteroatoms selected from N, O, and S; or a 4 to 10-membered heterocyclyl, which contains 1-4 heteroatoms selected from N, O, and S.

3. A compound of formula (A-I), (A-II), (B-I), (B-II), (B-III) and (B-IV):

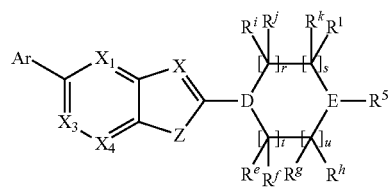
(A-I)

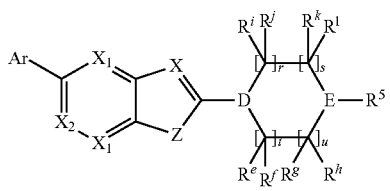
(A-II)

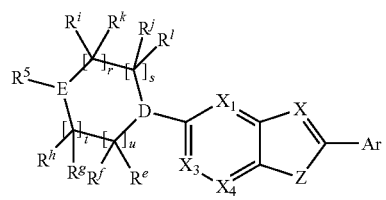
(B-I)

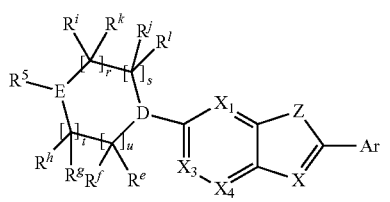
(B-III)

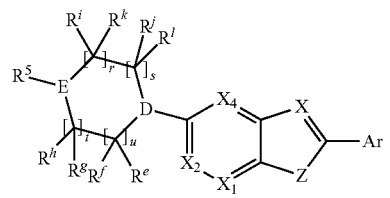
(B-II)

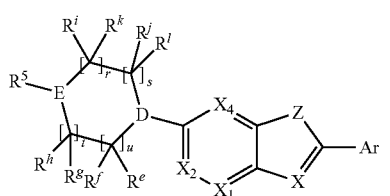
(B-IV)

or a tautomer, stereoisomer, enantiomer, diastereomer, salt, or N-oxide thereof, wherein Ar is selected from

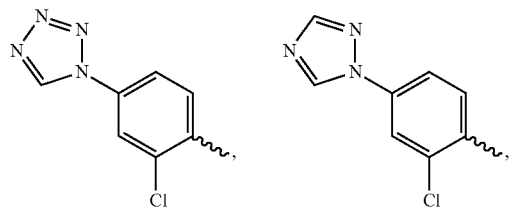

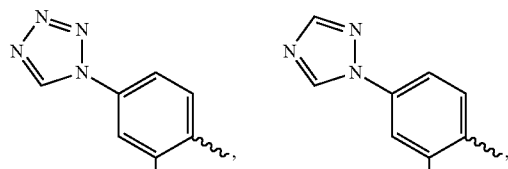

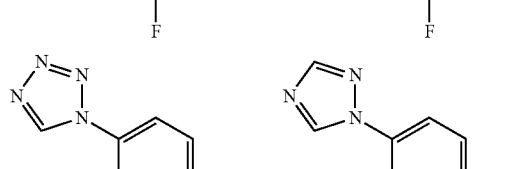

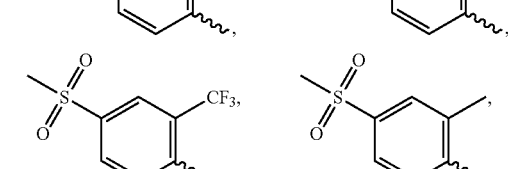

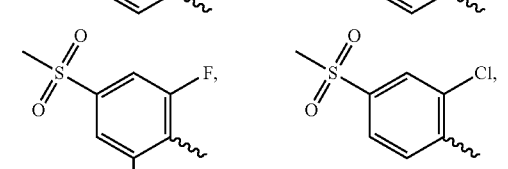

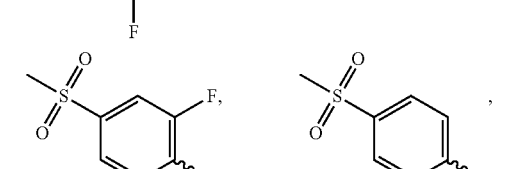

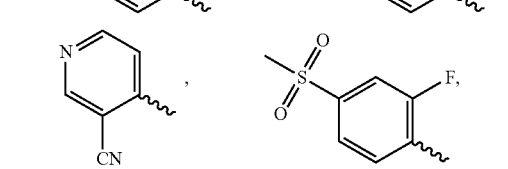

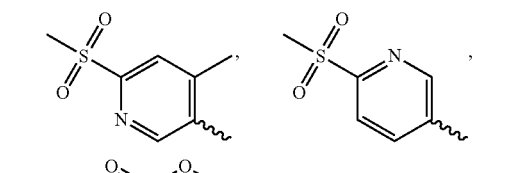

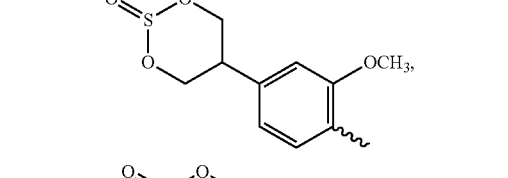

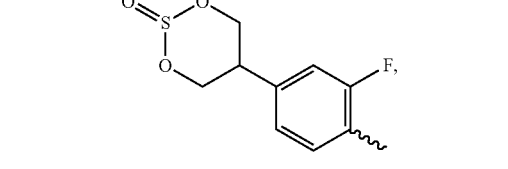

-continued

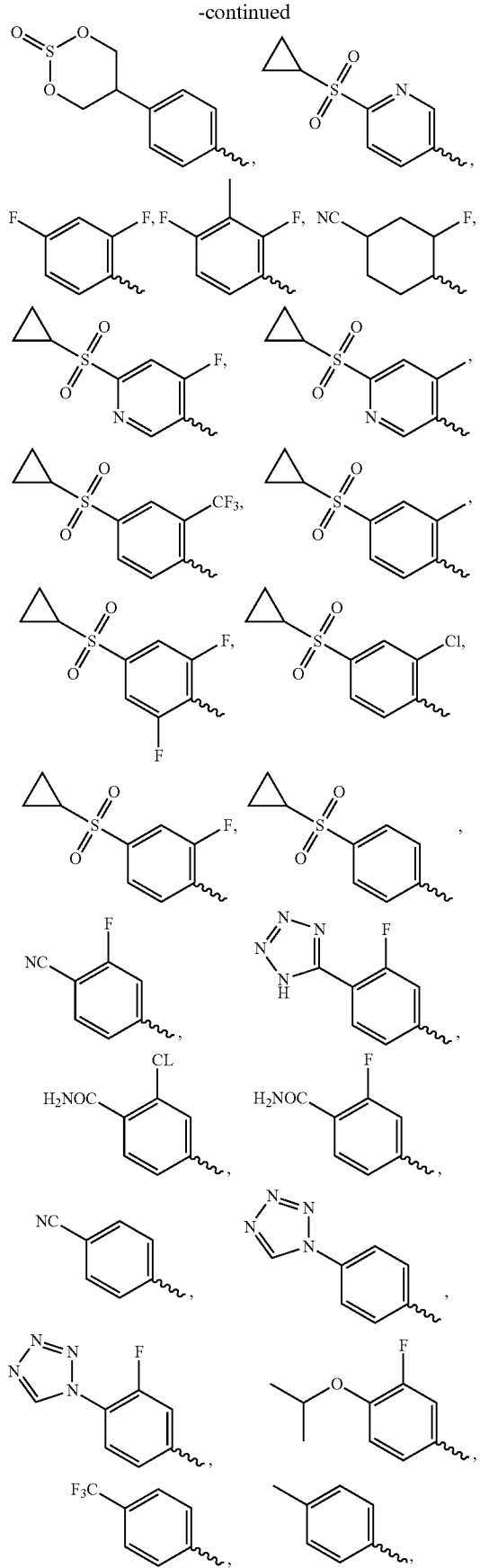

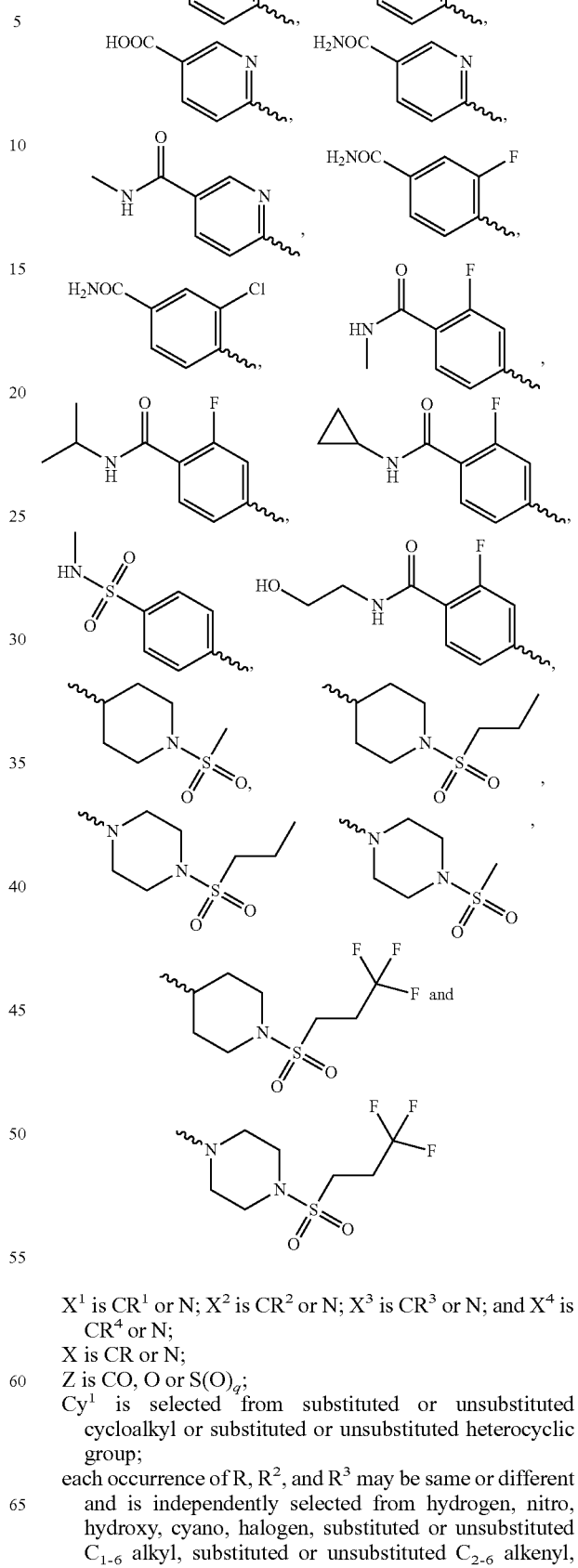

$X^1$ is $CR^1$ or N; $X^2$ is $CR^2$ or N; $X^3$ is $CR^3$ or N; and $X^4$ is $CR^4$ or N;

X is CR or N;

Z is CO, O or $S(O)_q$;

$Cy^1$ is selected from substituted or unsubstituted cycloalkyl or substituted or unsubstituted heterocyclic group;

each occurrence of R, $R^2$, and $R^3$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —$OR^a$, —$S(=O)_q$—$R^a$, —$NR^aR^b$, —$C(=Y)$—$R^a$, —$CR^aR^b$—$C(=Y)$—$R^a$, —$CR^aR^b$—Y—$CR^aR^b$-, —$C(=Y)$—$NR^aR^b$-, —$NR^a$—$C(=Y)$—$NR^aR^b$-, —$S(=O)_q$—$NR^aR^b$-, —$NR^a$—$S(=O)_q$—$NR^aR^b$-, and —$NR^a$—$NR^aR^b$-;

each occurrence of $R^1$ and $R^4$ may be same or different and is independently selected from hydrogen, nitro, hydroxy, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —$OR^a$, —$S(=O)_q$—$R^a$, —$NR^aR^b$, —$C(=Y)$—$R^a$, —$CR^aR^b$—$C(=Y)$—$R^a$, —$CR^aR^b$—Y—$CR^aR^b$-, —$C(=Y)$—$NR^aR^b$-, —$NR^a$—$C(=Y)$—$NR^aR^b$-, —$S(=O)_q$—$NR^aR^b$-, —$NR^a$—$S(=O)_q$—$NR^aR^b$-, and —$NR^a$—$NR^aR^b$;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of Y is independently selected from O, S, and $NR^a$; and each occurrence of q independently represents 0, 1 or 2;

D and E are independently selected from CH or N;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^a$, —$C(O)R^a$, —$C(S)R^a$, —$C(O)NR^aR^b$, —$C(O)ONR^aR^b$, —$NR^aR^b$, —$NR^aCONR^aR^b$, —$N(R^a)SOR^b$, —$N(R^a)SO_2R^b$, -(=N—$N(R^a)R^b$), —$NR^aC(O)OR^b$, —$NR^aC(O)R^b$-, —$NR^aC(S)R^b$ —$NR^aC(S)NR^aR^b$, —$SONR^aR^b$-, —$SO_2NR^aR^b$-, —$OR^a$, —$OR^aC(O)NR^aR^b$, —$OR^aC(O)OR^b$-, —OC(O)$R^a$, —$OC(O)NR^aR^b$, —$R^aNR^bC(O)R^a$, —$R^aOR^b$, —$R^aC(O)OR^b$, —$R^aC(O)NR^aR^b$, —$R^aC(O)R^b$, —$R^aOC(O)R^b$, —$SR^a$, —$SOR^a$, —$SO_2R^a$, and —$ONO_2$;

each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —$ONO_2$, or any two of $R^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and each occurrence of $R^e$, $R^f$, $R^g$, $R^h$, $R^j$, $R^k$ and $R^l$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl; or any two of $R^e$, $R^f$, $R^g$, $R^h$, $R^j$, $R^k$, $R^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl); and each of r, s, t and u is 0, 1 or 2 with the proviso that r+s+t+u≠0.

4. A compound of claim 1, wherein Z is, O or S.

5. A compound of claim 1, wherein $X^1$ is $CR^1$ or N, and $R^1$ is H or Halogen.

6. A compound of claim 1, wherein $X^2$ in compound of formula (A), (A-II), (A-IV), (B), (B-II) or (B-IV) is CH.

7. A compound of claim 1, wherein $X^3$ in compound of formula (A), (A-II), (A-IV), (B), (B-II) or (B-IV) is CH.

8. A compound of claim 1, wherein $X^4$ is $CR^4$ or N, and $R^4$ is H or Halogen.

9. A compound of claim 1, wherein X is CR or N.

10. A compound of formula (A-I), (A-II), (B-I), (B-II), (B-M) and (B-IV):

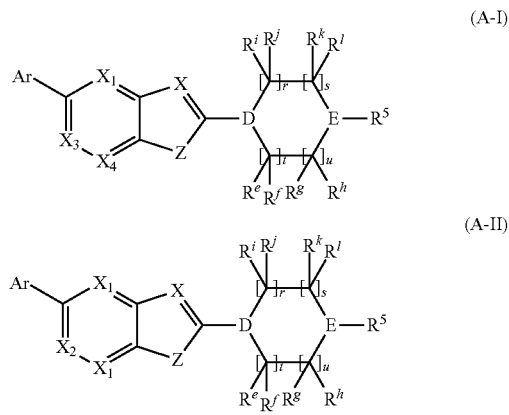

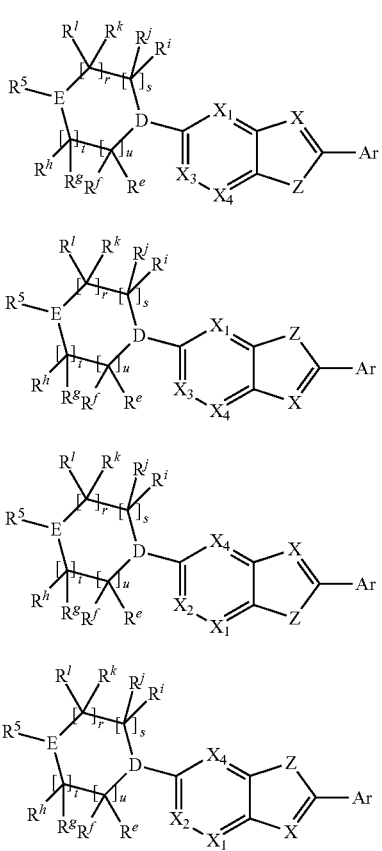
(B-I)
(B-II)
(B-II)
(B-IV)
(B-II) (B-IV)
or a tautomer, stereoisomer, enantiomer, diastereomer, salt, or N-oxide thereof, wherein
Ar is selected from substituted or unsubstituted aryl, substituted or unsubstituted heteroaryl or Cy$^1$;
$X^1$ is CR$^1$ or N; $X^2$ is CR$^2$ or N; $X^3$ is CR$^3$ or N; and $X^4$ is CR$^4$ or N;
X is CR or N;
Z is CO, O or S(O)$_q$;
Cy$^1$ is selected from
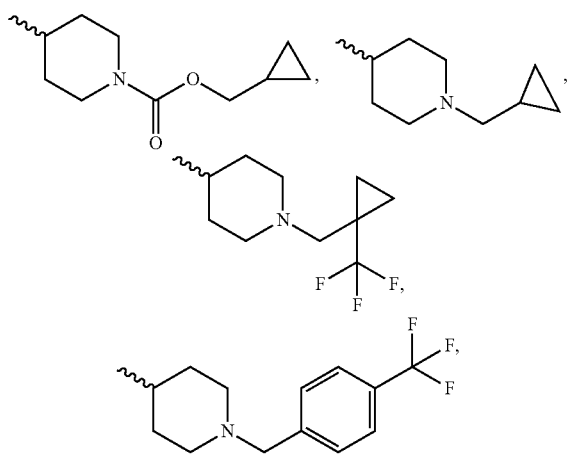
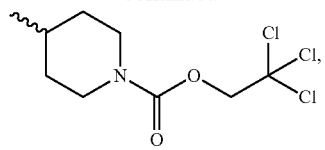
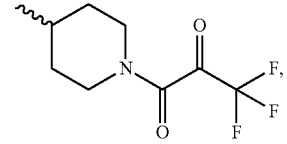
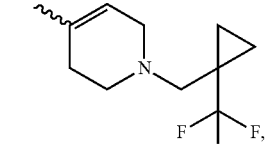
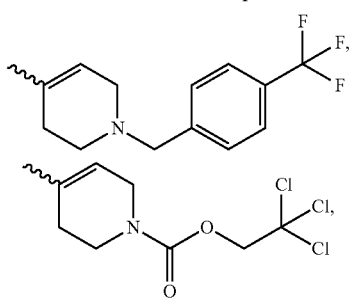
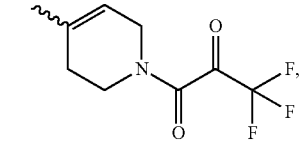
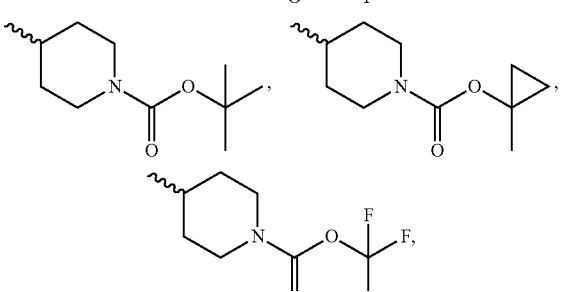
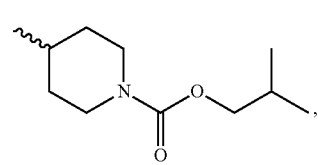
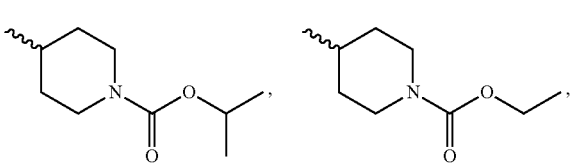

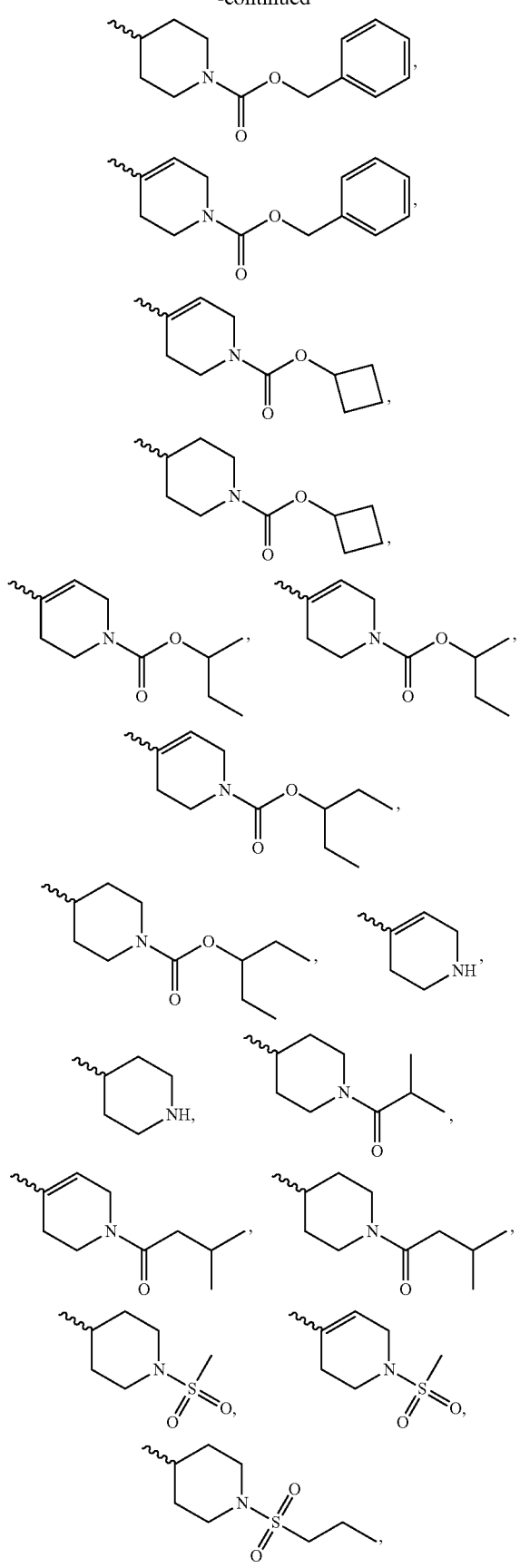
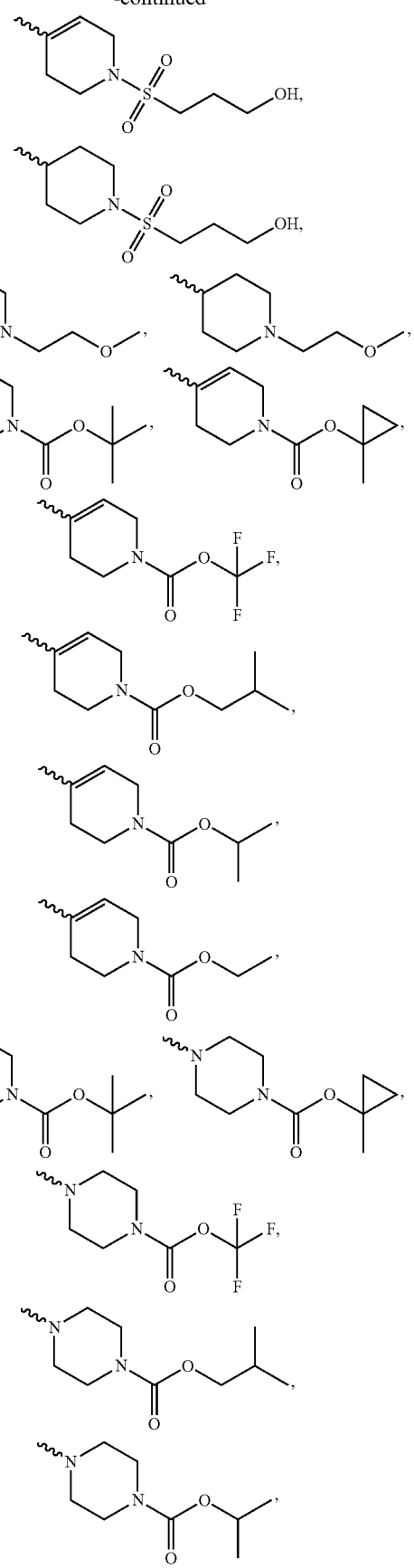

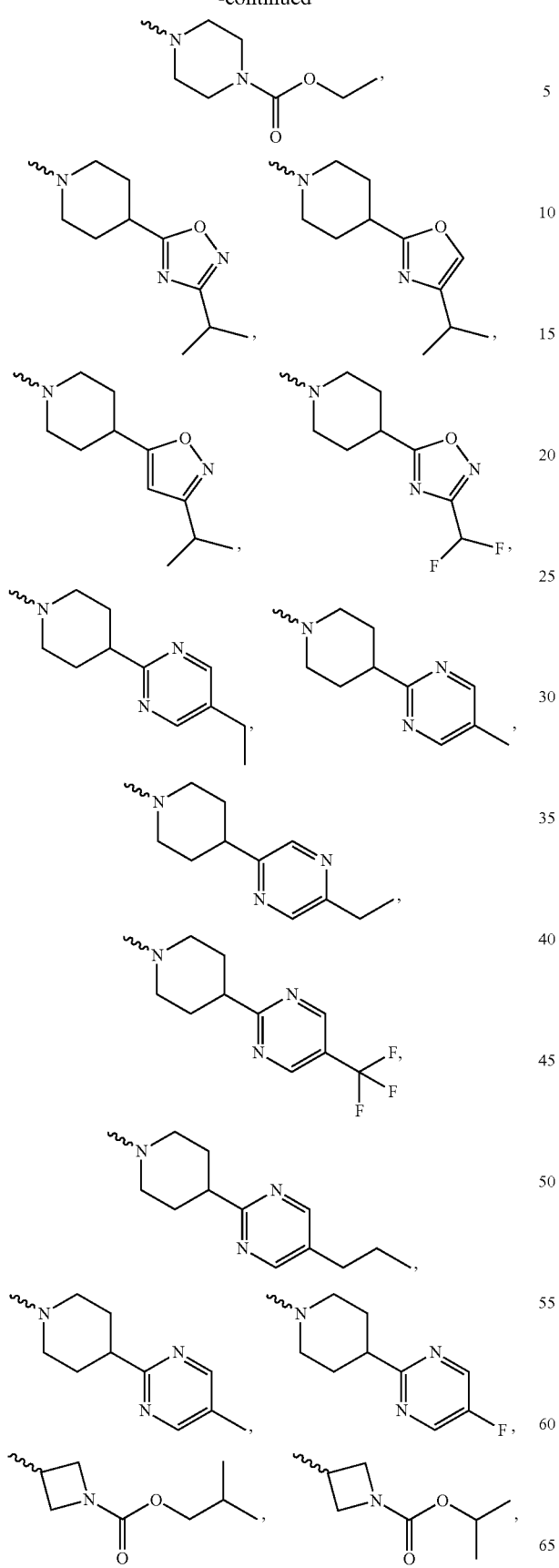
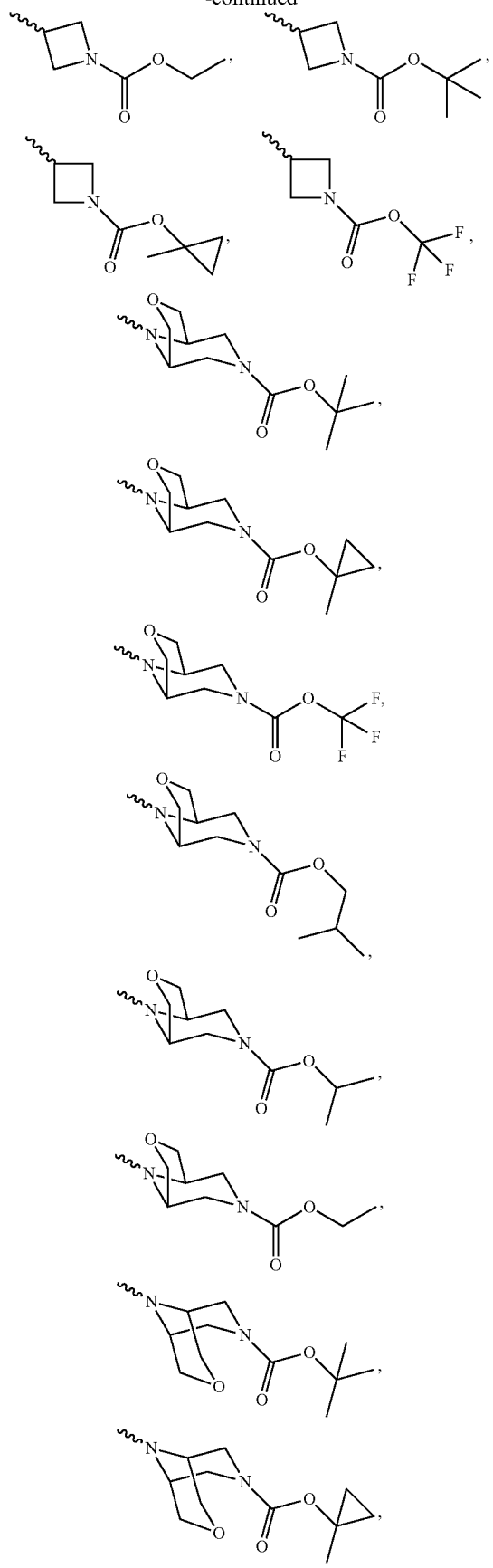

-continued

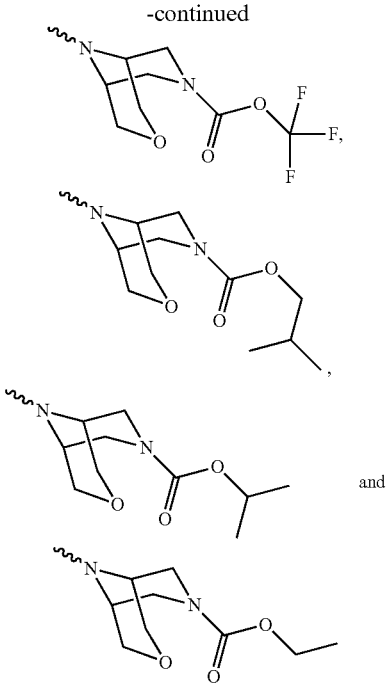

and each occurrence of R, $R^2$, and $R^3$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, $-OR^a$, $-S(=O)_q-R^a$, $-NR^aR^b$, $-C(=Y)-R^a$, $-CR^aR^b-C(=Y)-R^a$, $-CR^aR^b-Y-CR^aR^b-$, $-C(=Y)-NR^aR^b-$, $-NR^a-C(=Y)-NR^aR^b-$, $-S(=O)_q-NR^aR^b-$, $-NR^a-S(=O)_q-NR^aR^b-$, and $-NR^a-NR^aR^b-$;

each occurrence of $R^1$ and $R^4$ may be same or different and is independently selected from hydrogen, nitro, hydroxy, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, $OR^a$, $-S(=O)_q-R^a$, $-NR^aR^b$, $-C(=Y)-R^a$, $-CR^aR^b-C(=Y)-R^a$, $-CR^aR^b-Y-CR^aR^b-$, $-C(=Y)-NR^aR^b-$, $-NR^a-C(=Y)-NR^aR^b-$, $-S(=O)_q-NR^aR^b-$, $-NR^a-S(=O)_q-NR^aR^b-$, and $-NR^a-NR^aR^b$;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of Y is independently selected from O, S, and NR$^a$; and each occurrence of q independently represents 0, 1 or 2;

D and E are independently selected from CH or N;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, $-COOR^a$, $-C(O)R^a$, $-C(S)R^a$, $-C(O)NR^aR^b$, $-C(O)ONR^aR^b$, $-NR^aR^b$, $-NR^aCONR^aR^b$, $-N(R^a)SOR^b$, $-N(R^a)SO_2R^b$, $-(=N-N(R^a)R^b)$, $-NR^aC(O)OR^b$, $-NR^aC(O)R^b$-, $-NR^aC(S)R^b$ $-NR^aC(S)NR^aR^b$, $-SONR^aR^b$-, $-OR^a$, $-OR^aC(O)NR^aR^b$, $-OR^aC(O)OR^b$-, $-OC(O)R^a$, $-OC(O)NR^aR^b$, $-R^aNR^bC(O)R^a$, $-R^aOR^b$, $-R^aC(O)OR^b$, $-R^aC(O)NR^aR^b$, $-R^aC(O)R^b$, $-R^aOC(O)R^b$, $-SR^a$, $-SOR^a$, $-SO_2R^a$ and $-ONO_2$ with the proviso that when $R^5$ is $-SO_2R^a$, then $R^a$ is not unsubstituted alkyl;

each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and $-ONO_2$, or any two of $R^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR');

each occurrence of $R^e$, $R^f$, $R^g$, $R^h$, $R^j$, $R^k$ and $R^l$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl; or any two of $R^e$, $R^f$, $R^g$, $R^h$, $R^j$, $R^k$, $R^l$ may be joined to form (i) a substituted or unsubstituted, saturated or unsaturated 3-14 membered ring, which may optionally include one or more heteroatoms which may be the same or different and are selected from O, NR'

(where R' is H or alkyl) or S, or (ii) an oxo (=O), thio (=S) or imino (=NR') (where R' is H or alkyl); and each of r, s, t and u is 0, 1 or 2 with the proviso that r+s+t+u≠0.

11. A compound of formula (A-IA), (A-IIA), (B-IA), (B-IIA), (B-IIIA) or (B-IVA):

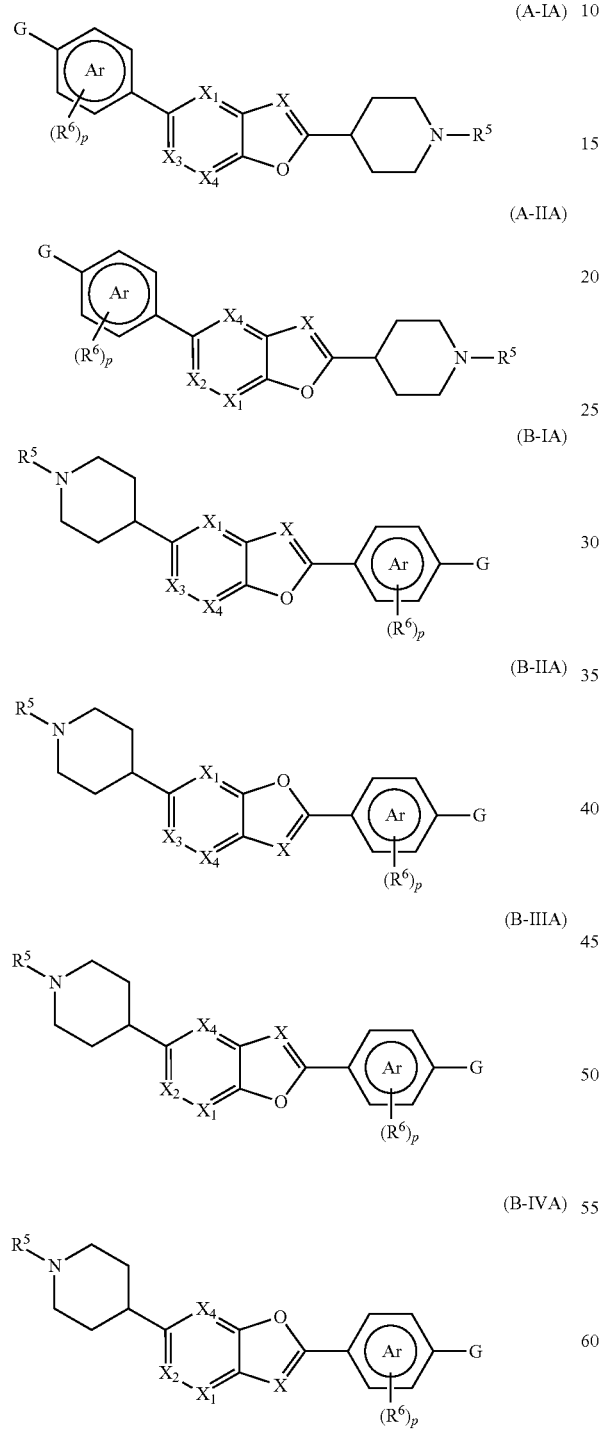

or a tautomer, stereoisomer, enantiomer, diastereomer, salt, or N-oxide thereof, wherein
Ar is

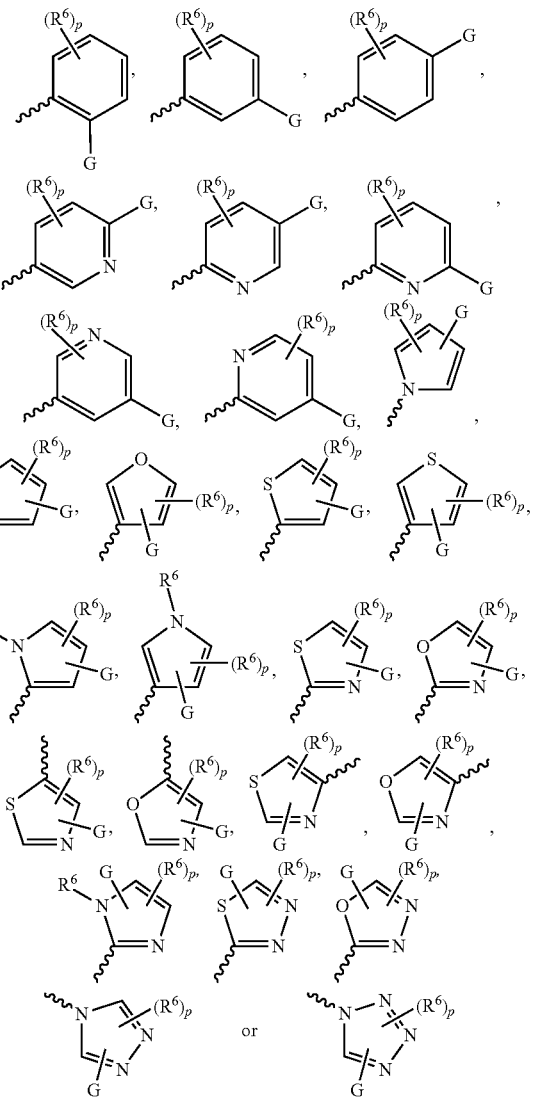

G is independently selected from

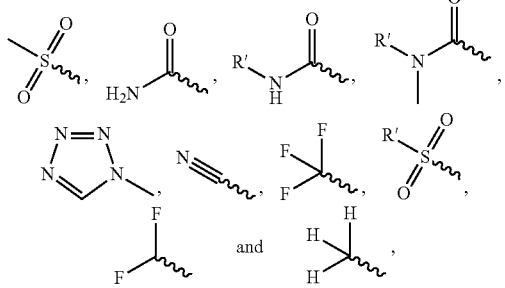

R' is substituted or unsubstituted alkyl, substituted or unsubstituted alkoxy, substituted or unsubstituted alkenyl, substituted or unsubstituted alkynyl or substituted or unsubstituted cycloalkyl;

$X^1$ is $CR^1$ or N; $X^2$ is $CR^2$ or N; $X^3$ is $CR^3$ or N and $X^4$ is $CR^4$ or N;

X is CR or N;

each occurrence of R, $R^1$, $R^2$, $R^3$ and $R^4$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —$OR^a$, —$S(=O)_q$—$R^a$, —$NR^aR^b$, —$C(=Y)$—$R^a$, —$CR^aR^b$—$C(=Y)$—$R^a$, —$CR^aR^b$—Y—$CR^aR^b$-, —$C(=Y)$—$NR^aR^b$-, —$NR^a$—$C(=Y)$—$NR^aR^b$-, —$S(=O)_q$—$NR^aR^b$-, —$NR^a$—$S(=O)_q$—$NR^aR^b$-, and —$NR^a$—$NR^aR^b$-;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of Y is independently selected from O, S, and $NR^a$; and each occurrence of q independently represents 0, 1 or 2;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^a$, —$C(O)R^a$, —$C(S)R^a$, —$C(O)NR^aR^b$, —$C(O)ONR^aR^b$, —$NR^aR^b$, —$NR^aCONR^aR^b$, —$N(R^a)SOR^b$, —$N(R^a)SO_2R^b$, -(=N—$N(R^a)R^b$), —$NR^aC(O)OR^b$, —$NR^aC(O)R^b$-, —$NR^aC(S)R^b$ —$NR^aC(S)NR^aR^b$, —$SONR^aR^b$-, —$SO_2NR^aR^b$-, —$OR^a$, —$OR^aC(O)NR^aR^b$, —$OR^aC(O)$ $OR^b$-, —$OC(O)R^a$, —$OC(O)NR^aR^b$, —$R^aNR^bC(O)R^a$, —$R^aOR^b$, —$R^aC(O)OR^b$, —$R^aC(O)NR^aR^b$, —$R^aC(O)R^b$, —$R^aOC(O)R^b$, —$SR^a$, —$SO_2R^a$, and —$ONO_2$; each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —$ONO_2$, or any two of $R^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and $R^6$ is selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^a$, —$C(O)R^a$, —$C(S)R^a$, —$C(O)NR^aR^b$, —$C(O)ONR^aR^b$, —$NR^aR^b$, —$NR^aCONR^aR^b$, —$N(R^a)SOR^b$, —$N(R^a)SO_2R^b$, -(=N—$N(R^a)R^b$), —$NR^aC(O)OR^b$, —$NR^aC(O)R^b$-, —$NR^aC(S)R^b$ —$NR^aC(S)NR^aR^b$, —$SONR^aR^b$-, —$SO_2NR^aR^b$-, —$OR^a$, —$OR^aC(O)NR^aR^b$, —$OR^aC(O)OR^b$-, —$OC(O)R^a$, —$OC(O)NR^aR^b$, —$R^aNR^bC(O)R^a$, —$R^aOR^b$, —$R^aC(O)OR^b$, —$R^aC(O)NR^aR^b$, —$R^aC(O)R^b$, —$R^aOC(O)R^b$, —$SR^a$, —$SOR^a$, —$SO_2R^a$, and —$ONO_2$;

each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —$ONO_2$; and p is 0, 1, 2, 3 or 4.

12. A compound of formula (A-IIIA) or (A-IVA)

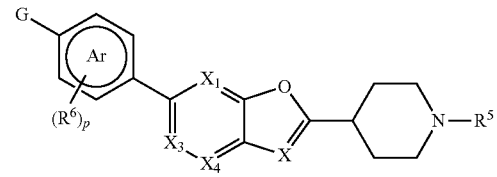

(A-IIIA)

-continued (A-IVA)

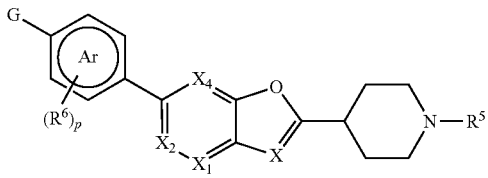

wherein
Ar is

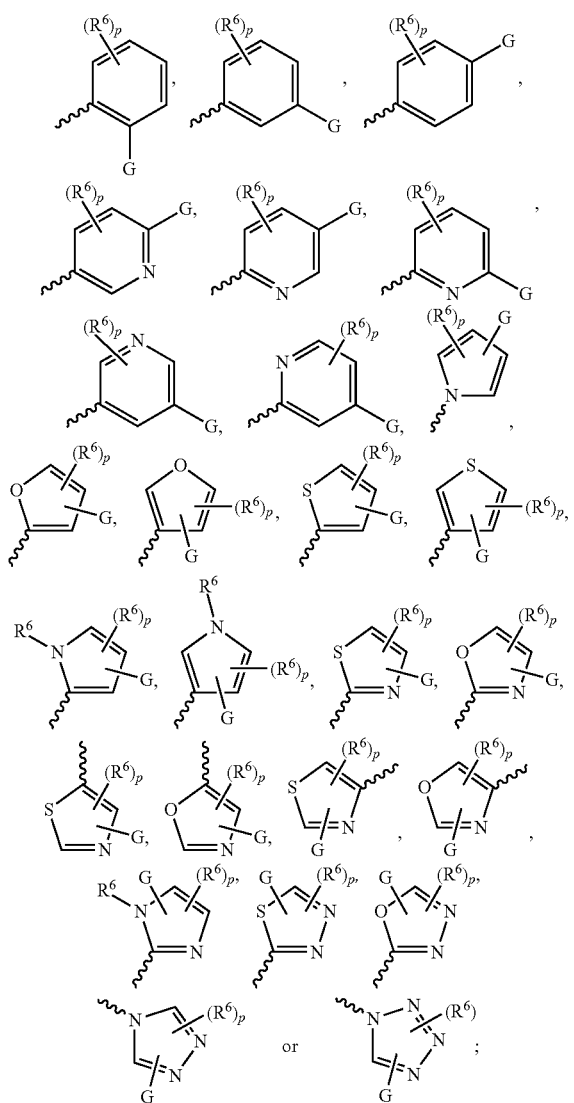

G is independently selected from

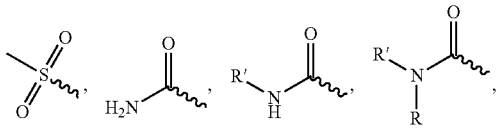

-continued

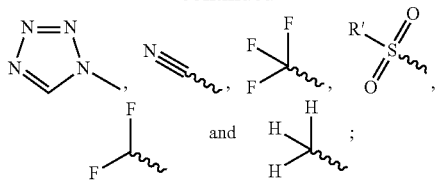

R' is substituted or unsubstituted alkyl, substituted or unsubstituted alkoxy, substituted or unsubstituted alkenyl, substituted or unsubstituted alkynyl or substituted or unsubstituted cycloalkyl.

$X^1$ is $CR^1$ or N; $X^2$ is $CR^2$ or N; $X^3$ is $CR^3$ or N and $X^4$ is $CR^4$ or N;

X is CR or N;

each occurrence of R, $R^1$, $R^2$, $R^3$ and $R^4$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —$OR^a$, —$S(=O)_q$—$R^a$, —$NR^aR^b$, —$C(=Y)$—$R^a$, —$CR^aR^b$—$C(=Y)$—$R^a$, —$CR^aR^b$—Y—$CR^aR^b$-, —$C(=Y)$—$NR^aR^b$-, —$NR^a$—$C(=Y)$—$NR^aR^b$-, —$S(=O)_q$—$NR^aR^b$-, —$NR^a$—$S(=O)_q$—$NR^aR^b$-, and —$NR^a$—$NR^aR^b$-;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of Y is independently selected from O, S, and $NR^a$; and each occurrence of q independently represents 0, 1 or 2;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —$COOR^a$, —$C(O)R^a$, —$C(S)R^a$, —$C(O)NR^aR^b$, —$C(O)ONR^aR^b$, —$NR^aR^b$, —$NR^aCONR^aR^b$, —N(R$^a$)SOR$^b$, —N(R$^a$)SO$_2$R$^b$, -(=N—N(R$^a$)R$^b$),
—NR$^a$C(O)OR$^b$, —NR$^a$C(O)R$^b$-, —NR$^a$C(S)R$^b$
—NR$^a$C(S)NR$^a$R$^b$, —SONR$^a$R$^b$-, —SO$_2$NR$^a$R$^b$-,
—OR$^a$, —OR$^a$C(O)NR$^a$R$^b$, —OR$^a$C(O)OR$^b$-, —OC
(O)R$^a$, —OC(O)NR$^a$R$^b$, —R$^a$NR$^b$C(O)R$^a$, —R$^a$OR$^b$,
—R$^a$C(O)OR$^b$, —R$^a$C(O)NR$^a$R$^b$, —R$^a$C(O)R$^b$,
—R$^a$OC(O)R$^b$, —SR$^a$, —SOR$^a$, —SO$_2$R$^a$, and
—ONO$_2$;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and R$^6$ is selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —SO$_2$NR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$;

p is 0, 1, 2, 3 or 4, with the proviso
a) that for compound of formula (A-IIIA), wherein Z is O or S and X$_4$ is N or CR$^4$ then Ar-G cannot be

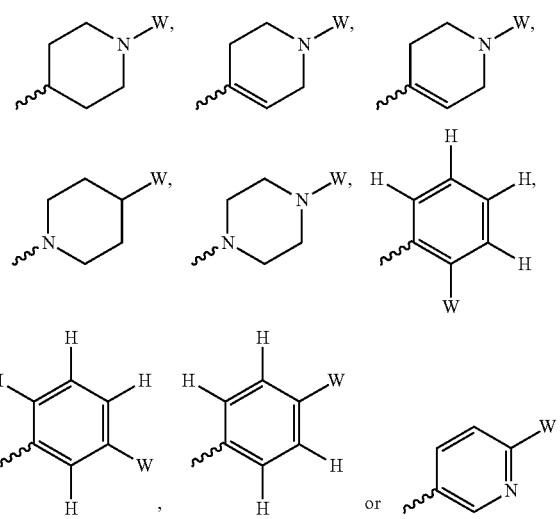

b) that for compound of formula (A-IVA) wherein Z is O or S and X$_1$ is N or CR$^1$ then Ar-G cannot be

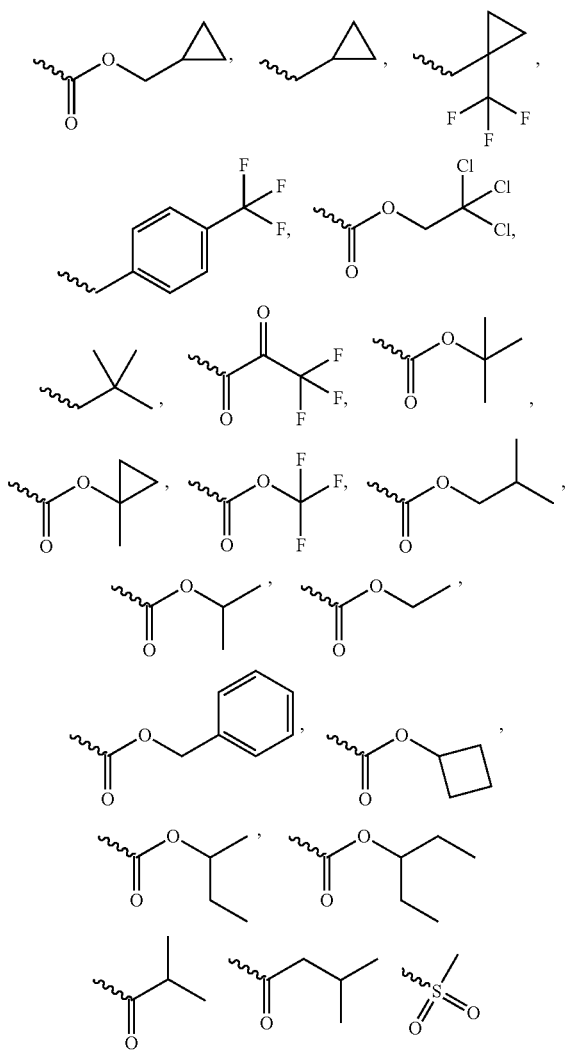

-continued

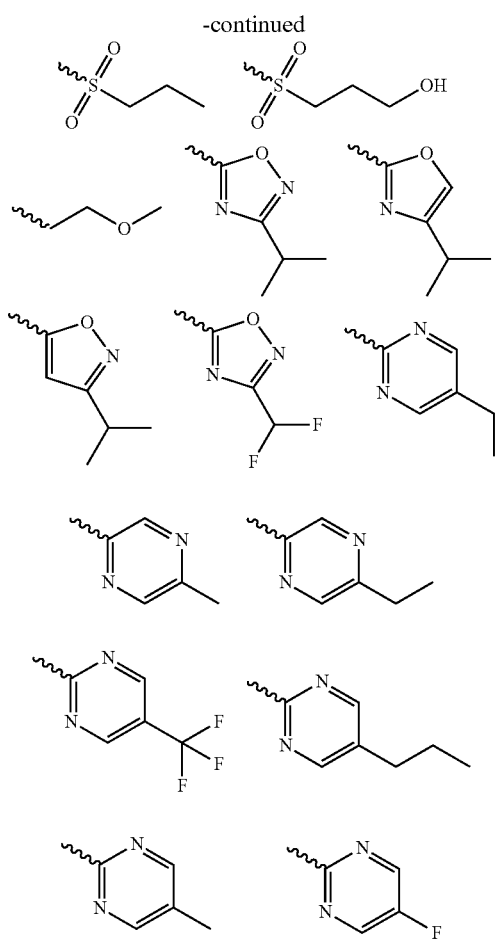

wherein

R[1] and R[4] is as defined above for compound of formula (A)

W is $S(=O)_2-R^1$, $S(=O)_2-NR_{1a}R_1$, $-C(=O)-R_1$, $-C(=O)-O-R_1$, $-C(=O)-NR_{1a}R_1$, $-NR_{1a}-S(=O)_2-R^1$, halo, or a 4 to 10-membered optionally substituted heteroaryl, which contains 1-4 heteroatoms selected from N, O, and S;

$R_{1a}$, at each occurrence, is independently hydrogen or $(C_1-C_8)$alkyl;

$R_1$ is optionally substituted $(C_1-C_6)$-alkyl, optionally substituted $(C_2-C_6)$-alkenyl, optionally substituted $(C_2-C_6)$-alkynyl, optionally substituted $(C_3-C_{12})$-cycloalkyl, optionally substituted $(C_1-C_{10})$aryl, a 4 to 10-membered optionally substituted heteroaryl, which contains 1-4 heteroatoms selected from N, O, and S; or a 4 to 10-membered heterocyclyl, which contains 1-4 heteroatoms selected from N, O, and S.

13. A compound of claim 11 wherein $X^1$ is $CR^1$ or N and R[1] is H or Halogen.

14. A compound of claim 11, wherein $X^2$ in compound of formula (A-IIA), (A-IVA), (B-IIA) or (B-IVA) is CH.

15. A compound of claim 11, wherein $X^3$ in compound of formula (A-IA), (A-IIIA), (B-IA) or (B-IIIA) is CH.

16. A compound of claim 11, wherein $X^4$ is $CR^4$ or N, and R[4] is H or Halogen.

17. A compound of claim 11, wherein X is CR or N.

18. A compound of claim 11, wherein R[5] is selected from

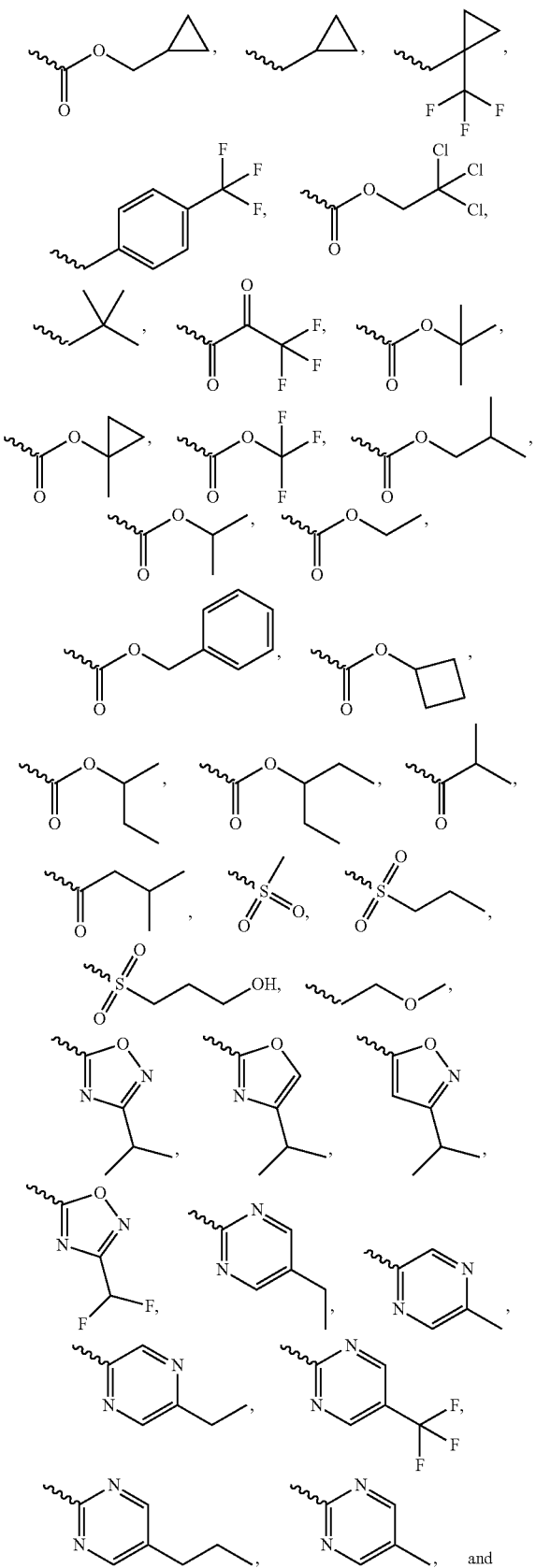

-continued

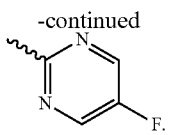
F.

19. A compound of claim 18, wherein $R^5$ is —C(O)OC(CH$_3$)$_3$ or —C(O)OCH(CH$_3$)$_2$.

20. A compound of claim 11, wherein p is 0 or 1.

21. A compound of claim 11, wherein $R^6$ is halogen, substituted or unsubstituted alkyl or —OR$^a$; wherein R$^a$ is substituted or unsubstituted alkyl.

22. A compound of claim 21, wherein $R^6$ is —F, —CH$_3$, —CF$_3$ or —OCH$_3$.

23. A compound of claim 11, wherein Ar-G is selected from

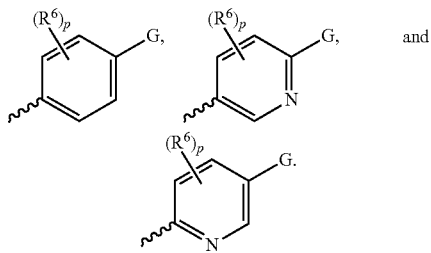

24. A compound of claim 23, wherein G is independently selected from

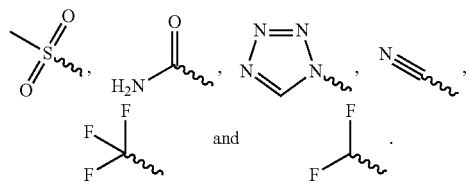

25. A compound of claim 23, wherein $X^1$ is CH or CF; X is N or CH and Z is S or O.

26. A compound of claim 25 wherein $X^1$ is CH or CF; X is N or CH and Z is O.

27. A compound of formula (A-IB) and (A-IIB)

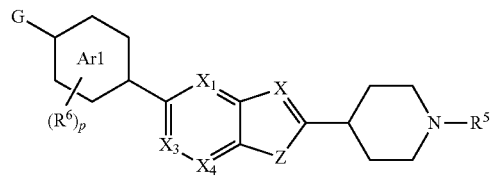
(A-IB)

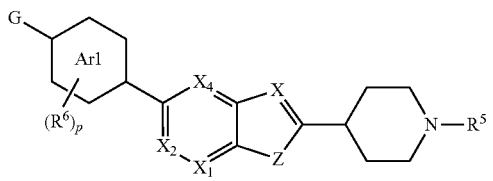
(A-IIB)

or a tautomer, stereoisomer, enantiomer, diastereomer, salt, or N-oxide thereof,
wherein
Z is O or S;
Ar1-G is

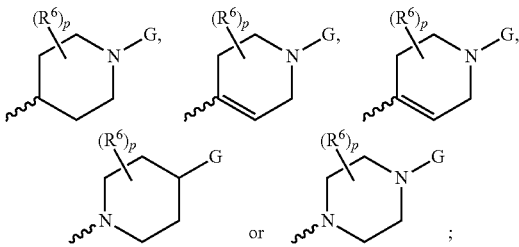

p is 0, 1-7 or 8;
G is selected from

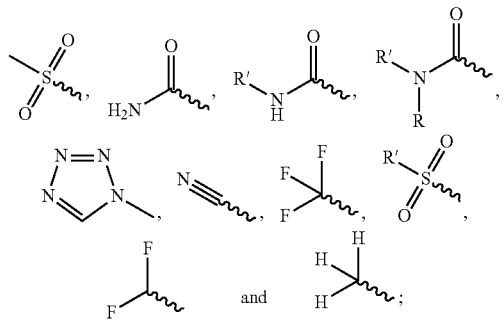

R' is substituted or unsubstituted alkyl, substituted or unsubstituted alkoxy, substituted or unsubstituted alkenyl, substituted or unsubstituted alkynyl or substituted or unsubstituted cycloalkyl;

$X^1$ is $CR^1$ or N; $X^2$ is $CR^2$ or N; $X^3$ is $CR^3$ or N and $X^4$ is $CR^4$ or N;

X is CR or N;

each occurrence of R, $R^1$, $R^2$, $R^3$ and $R^4$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$-;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)

$NR^aR^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —SO$_2$NR$^a$R$^b$-, —OR$^a$, —OR$^a$C(O)NR$^a$R$^b$, —OR$^a$C(O) OR$^b$-, —OC (O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$;

$R^6$ is selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —SO$_2$NR$^a$R$^b$-, —OR$^a$, —OR$^a$C(O) NR$^a$R$^b$, —OR$^a$C(O)OR$^b$-, —OC(O)R$^a$, —OC(O) NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$;

each occurrence of Y is independently selected from O, S, and NR$^a$;

each occurrence of q independently represents 0, 1 or 2;

each occurrence of R$^a$ and R$^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two R$^a$ and/or R$^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^c$ or S;

each occurrence of R$^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR').

28. A compound of formula (A-IIIB) and (A-IVB)

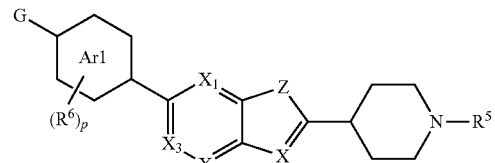

(A-IIIB)

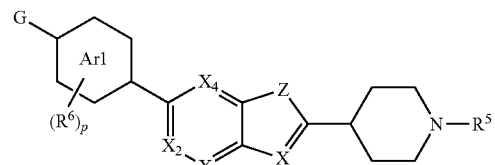

(A-IVB)

or a tautomer, stereoisomer, enantiomer, diastereomer, salt, or N-oxide thereof, wherein Z is O or S;

Ar1-G is

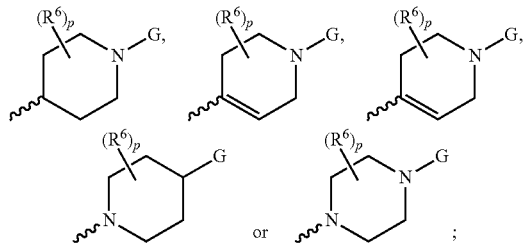

p is 0, 1-7 or 8;

G is selected from

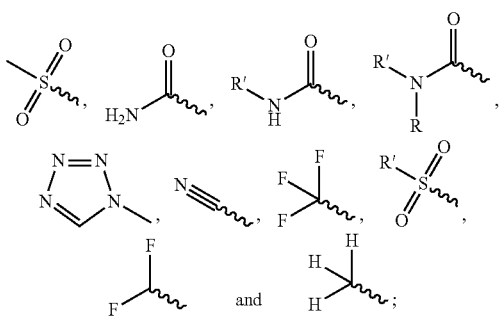

R' is substituted or unsubstituted alkyl, substituted or unsubstituted alkoxy, substituted or unsubstituted alkenyl, substituted or unsubstituted alkynyl or substituted or unsubstituted cycloalkyl;

$X^1$ is CR$^1$ or N; $X^2$ is CR$^2$ or N; $X^3$ is CR$^3$ or N and $X^4$ is CR$^4$ or N;

X is CR or N;

each occurrence of R, $R^1$, $R^2$, and $R^3$ and $R^4$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, $-OR^a$, $-S(=O)_q-R^a$, $-NR^aR^b$, $-C(=Y)-R^a$, $-CR^aR^b-C(=Y)-R^a$, $-CR^aR^b-Y-CR^aR^b-$, $-C(=Y)-NR^aR^b-$, $-NR^a-C(=Y)-NR^aR^b-$, $-S(=O)_q-NR^aR^b-$, $-NR^a-S(=O)_q-NR^aR^b-$, and $-NR^a-NR^aR^b-$;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, $-COOR^a$, $-C(O)R^a$, $-C(S)R^a$, $-C(O)NR^aR^b$, $-C(O)ONR^aR^b$, $-NR^aR^b$, $-NR^aCONR^aR^b$, $-N(R^a)SOR^b$, $-N(R^a)SO_2R^b$, $-(=N-N(R^a)R^b)$, $-NR^aC(O)OR^b$, $-NR^aC(O)R^b-$, $-NR^aC(S)R^b$ $-NR^aC(S)NR^aR^b$, $-SONR^aR^b-$, $-SO_2NR^aR^b-$, $-OR^a$, $-OR^aC(O)NR^aR^b$, $-OR^aC(O)OR^b-$, $-OC(O)R^a$, $-OC(O)NR^aR^b$, $-R^aNR^bC(O)R^a$, $-R^aOR^b$, $-R^aC(O)OR^b$, $-R^aC(O)NR^aR^b$, $-R^aC(O)R^b$, $-R^aOC(O)R^b$, $-SR^a$, $-SOR^a$, $-SO_2R^a$, and $-ONO_2$;

$R^6$ is selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, $-COOR^a$, $-C(O)R^a$, $-C(S)R^a$, $-C(O)NR^aR^b$, $-C(O)ONR^aR^b$, $-NR^aR^b$, $-NR^aCONR^aR^b$, $-N(R^a)SOR^b$, $-N(R^a)SO_2R^b$, $-(=N-N(R^a)R^b)$, $-NR^aC(O)OR^b$, $-NR^aC(O)R^b-$, $-NR^aC(S)R^b$ $-NR^aC(S)NR^aR^b$, $-SONR^aR^b-$, $-SO_2NR^aR^b-$, $-OR^a$, $-OR^aC(O)NR^aR^b$, $-OR^aC(O)OR^b-$, $-OC(O)R^a$, $-OC(O)NR^aR^b$, $-R^aNR^bC(O)R^a$, $-R^aOR^b$, $-R^aC(O)OR^b$, $-R^aC(O)NR^aR^b$, $-R^aC(O)R^b$, $-R^aOC(O)R^b$, $-SR^a$, $-SOR^a$, $-SO_2R^a$, and $-ONO_2$;

each occurrence of Y is independently selected from O, S, and $NR^a$;

each occurrence of q independently represents 0, 1 or 2;

each occurrence of $R^a$ and $R^b$ may be same or different and are independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form (i) an oxo (=O), thio (=S) or imino (=$NR^d$), or (ii) a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of $R^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and $-ONO_2$, or any two of $R^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and with the proviso a) that for compound of formula (A-IIIB), wherein Z is O or S and $X_4$ is N or $CR^4$ then Ar1-G cannot be

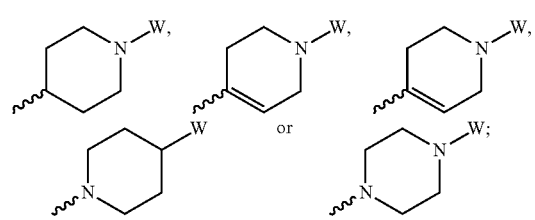

b) that for compound of formula (A-IVB) wherein Z is O or S and $X_1$ is N or $CR^1$ then Ar1-G cannot be

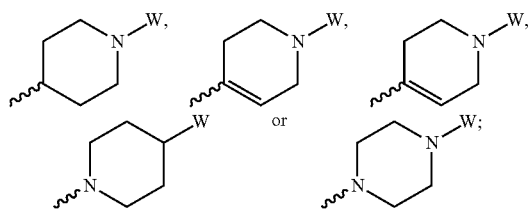

wherein $R^1$ and $R^4$ is as defined above for compound of formula (A)

W is $S(=O)_2-R^1$, $S(=O)_2-NR_{1a}R_1$, $-C(=O)-R_1$, $-C(=O)-O-R_1$, $-C(=O)-NR_{1a}R_1$, $-NR_{1a}-S(=O)_2-R_1$, halo, or a 4 to 10-membered optionally substituted heteroaryl, which contains 1-4 heteroatoms selected from N, O, and S;

$R_{1a}$, at each occurrence, is independently hydrogen or $(C_1-C_8)$alkyl; and $R_1$ is optionally substituted $(C_1-C_6)$-alkyl, optionally substituted $(C_2-C_6)$-alkenyl, optionally substituted $(C_2-C_6)$-alkynyl, optionally substituted $(C_3-C_{12})$-cycloalkyl, optionally substituted $(C_1-C_{10})$aryl, a 4- to 10-membered optionally substituted heteroaryl, which contains 1-4 heteroatoms selected from N, O, and S; or a 4 to 10-membered heterocyclyl, which contains 1-4 heteroatoms selected from N, O, and S.

29. A compound selected from

2-[1-(5-Ethylpyrimidin-2-yl)piperidin-4-yl]-5-[2-fluoro-4-(methylsulfonyl)phenyl]-1H-benzo[d]imidazole;

Tert-butyl 4-{5-[2-fluoro-4-(methylsulfonyl)phenyl]-1H-benzo[d]imidazol-2-yl}piperidine-1-carboxylate;

2-[1-(5-ethylpyrimidin-2-yl)piperidin-4-yl]-5-[2-fluoro-4-(methylsulfonyl)phenyl]benzo[d]oxazole;

Tert-butyl 4-{5-[2-fluoro-4-(methylsulfonyl)phenyl]benzo[d]oxazol-2-yl}piperidine-1-carboxylate;

Tert-butyl 4-{5-[2-fluoro-4-(methylsulfonyl)phenyl]-1-methyl-1H-benzo[d]imidazol-2-yl}piperidine-1-carboxylate;

Tert-butyl 4-{6-[2-fluoro-4-(methylsulfonyl)phenyl]benzo[d]oxazol-2-yl}piperidine-1-carboxylate;

Isopropyl 4-{5-[2-fluoro-4-(methylsulfonyl)phenyl]benzo[d]oxazol-2-yl}piperidine-1-carboxylate;

Tert-butyl 4-{7-fluoro-5-[2-fluoro-4-(methylsulfonyl)phenyl]benzo[d]oxazol-2-yl}piperidine-1-carboxylate;

Tert-butyl 4-[5-(4-cyanophenyl)benzo[d]oxazol-2-yl]piperidine-1-carboxylate;

Tert-butyl 4-{5-[3-fluoro-4-(methylsulfonyl)phenyl]benzo[d]oxazol-2-yl}piperidine-1-carboxylate;

Tert-butyl 4-{5-[4-(1H-tetrazol-1-yl)phenyl]benzo[d]oxazol-2-yl}piperidine-1-carboxylate;

Tert-butyl 4-{5-[2-fluoro-4-(1H-tetrazol-1-yl)phenyl]benzo[d]oxazol-2-yl}piperidine-1-carboxylate;

Tert-butyl 4-{5-[4-(trifluoromethyl)phenyl]benzo[d]oxazol-2-yl}piperidine-1-carboxylate;

Isopropyl 4-{5-[2-fluoro-4-(1H-tetrazol-1-yl)phenyl]benzo[d]oxazol-2-yl}piperidine-1-carboxylate;

Tert-butyl 4-{5-[3-fluoro-4-(1H-tetrazol-1-yl)phenyl]benzo[d]oxazol-2-yl}piperidine-1-carboxylate;

2-[1-(5-ethylpyrimidin-2-yl)piperidin-4-yl]-5-[2-fluoro-4-(1H-tetrazol-1-yl)phenyl]benzo[d]oxazole;

Tert-butyl 4-[5-(4-cyano-3-fluorophenyl)benzo[d]oxazol-2-yl]piperidine-1-carboxylate;

Isopropyl 4-{5-[3-fluoro-4-(1H-tetrazol-1-yl)phenyl]benzo[d]oxazol-2-yl}piperidine-1-carboxylate;

Tert-butyl 4-{5-[3-fluoro-4-(1H-tetrazol-5-yl)phenyl]benzo[d]oxazol-2-yl}piperidine-1-carboxylate;

Tert-butyl 4-[5-(4-carbamoyl-3-chlorophenyl)benzo[d]oxazol-2-yl]piperidine-1-carboxylate;

Tert-butyl 4-[5-(4-carbamoyl-3-fluorophenyl)benzo[d]oxazol-2-yl]piperidine-1-carboxylate;

Tert-butyl 4-[5-(3-fluoro-4-isopropoxyphenyl)benzo[d]oxazol-2-yl]piperidine-1-carboxylate;

Cyclobutyl 4-{5-[2-fluoro-4-(1H-tetrazol-1-yl)phenyl]benzo[d]oxazol-2-yl}piperidine-1-carboxylate;

Sec-butyl 4-{5-[2-fluoro-4-(1H-tetrazol-1-yl)phenyl]benzo[d]oxazol-2-yl}piperidine-1-carboxylate;

Pentan-3-yl 4-{5-[2-fluoro-4-(1H-tetrazol-1-yl)phenyl]benzo[d]oxazol-2-yl}piperidine-1-carboxylate;

5-[2-fluoro-4-(1H-tetrazol-1-yl)phenyl]-2-(piperidin-4-yl)benzo[d]oxazole;

Isopropyl 4-{5-[4-(trifluoromethyl)phenyl]benzo[d]oxazol-2-yl}piperidine-1-carboxylate;

Isopropyl 4-[5-(4-formylphenyl)benzo[d]oxazol-2-yl]piperidine-1-carboxylate;

Isopropyl 4-{5-[4-(difluoromethyl)phenyl]benzo[d]oxazol-2-yl}piperidine-1-carboxylate;

Isopropyl 4-[5-(4-carbamoyl-3-chlorophenyl)benzo[d]oxazol-2-yl]piperidine-1-carboxylate;

Isopropyl 4-[5-(4-carbamoyl-3-fluorophenyl)benzo[d]oxazol-2-yl]piperidine-1-carboxylate;

1-{4-[5-(2-fluoro-4-(1H-tetrazol-1-yl)phenyl)benzo[d]oxazol-2-yl]piperidin-1-yl}-2-methylpropan-1-one;

Isopropyl 4-{6-[4-(difluoromethyl)phenyl]benzo[d]oxazol-2-yl}piperidine-1-carboxylate;

6-{2-[1-(isopropoxycarbonyl)piperidin-4-yl]benzo[d]oxazol-5-yl}nicotinic acid;

5-[2-fluoro-4-(1H-tetrazol-1-yl)phenyl]-2-[1-(methylsulfonyl)piperidin-4-yl]benzo[d]oxazole;

Isopropyl 4-[5-(5-carbamoylpyridin-2-yl)benzo[d]oxazol-2-yl]piperidine-1-carboxylate;

Isopropyl 4-[5-(4-carbamoyl-2-fluorophenyl)benzo[d]oxazol-2-yl]piperidine-1-carboxylate;

Isopropyl 4-[5-(4-carbamoyl-2-chlorophenyl)benzo[d]oxazol-2-yl]piperidine-1-carboxylate;

2-Fluoro-4-{2-[1-(3-methylbutanoyl)piperidin-4-yl]benzo[d]oxazol-5-yl}benzamide;

1-{4-[5-(2-fluoro-4-(1H-tetrazol-1-yl)phenyl)benzo[d]oxazol-2-yl]piperidin-1-yl}-3-methylbutan-1-one;

5-[2-fluoro-4-(1H-tetrazol-1-yl)phenyl]-2-[1-(2-methoxyethyl)piperidin-4-yl]benzo[d]oxazole;

Isopropyl 4-{5-[3-fluoro-4-(methylcarbamoyl)phenyl]benzo[d]oxazol-2-yl}piperidine-1-carboxylate;

2-Fluoro-4-[2-(1-isobutyrylpiperidin-4-yl)benzo[d]oxazol-5-yl]benzamide;

Isopropyl 4-[6-(4-carbamoyl-3-fluorophenyl)benzo[d]oxazol-2-yl]piperidine-1-carboxylate;

Isopropyl 4-{5-[3-fluoro-4-(2-hydroxyethylcarbamoyl)phenyl]benzo[d]oxazol-2-yl}piperidine-1-carboxylate;

Isopropyl 4-{5-[3-fluoro-4-(isopropylcarbamoyl)phenyl]benzo[d]oxazol-2-yl}piperidine-1-carboxylate;

Isopropyl 4-{5-[4-(N-methylsulfamoyl)phenyl]benzo[d]oxazol-2-yl}piperidine-1-carboxylate;

Isopropyl 4-{5-[6-(methylcarbamoyl)pyridin-3-yl]benzo[d]oxazol-2-yl}piperidine-1-carboxylate;

Isopropyl 4-{5-[3-methyl-4-(methylcarbamoyl)phenyl]benzo[d]oxazol-2-yl}piperidine-1-carboxylate;

Isopropyl 4-{5-[4-(cyclopropylcarbamoyl)-3-fluorophenyl]benzo[d]oxazol-2-yl}piperidine-1-carboxylate;

2-Fluoro-4-{2-[1-(5-fluoropyrimidin-2-yl)piperidin-4-yl]benzo[d]oxazol-5-yl}benzamide;

Tert-butyl 4-[5-(4-carbamoyl-3-fluorophenyl)benzofuran-2-yl]-5,6-dihydropyridine-1(2H)-carboxylate;

2-fluoro-4-{2-[1-(propylsulfonyl)piperidin-4-yl]benzo[d]oxazol-5-yl}benzamide;

Tert-butyl 4-{2-[2-fluoro-4-(methylsulfonyl)phenyl]-1H-benzo[d]imidazol-5-yl}-5,6-dihydropyridine-1(2H)-carboxylate;

Tert-butyl 4-{2-[2-fluoro-4-(methylsulfonyl)phenyl]-1H-benzo[d]imidazol-5-yl}piperidine-1-carboxylate;

5-[1-(5-ethylpyrimidin-2-yl)piperidin-4-yl]-2-[2-fluoro-4-(methylsulfonyl)phenyl]-1H-benzo[d]imidazole;

Tert-butyl 4-{2-[2-fluoro-4-(methylsulfonyl)phenyl]benzo[d]oxazol-5-yl}-5,6-dihydropyridine-1(2H)-carboxylate;

Tert-butyl 4-{2-[2-fluoro-4-(methylsulfonyl)phenyl]benzo[d]oxazol-5-yl}piperidine-1-carboxylate;

2-[2-fluoro-4-(methylsulfonyl)phenyl]-5-(piperidin-4-yl)benzo[d]oxazole 2,2,2-trifluoro acetate;

5-[1-(5-ethylpyrimidin-2-yl)piperidin-4-yl]-2-[2-fluoro-4-(methylsulfonyl)phenyl]benzo[d]oxazole;
Tert-butyl 4-{7-fluoro-2-[2-fluoro-4-(methylsulfonyl)phenyl]benzo[d]oxazol-5-yl}piperidine-1-carboxylate;
Isopropyl 4-{2-[2-fluoro-4-(methylsulfonyl)phenyl]benzo[d]oxazol-5-yl}piperidine-1-carboxylate;
Tert-butyl 4-{2-[2-fluoro-4-(methylsulfonyl)phenyl]benzo[d]thiazol-6-yl}-5,6-dihydropyridine-1(2H)-carboxylate;
Tert-butyl 4-{2-[2-fluoro-4-(methylsulfonyl)phenyl]benzo[d]thiazol-5-yl}-5,6-dihydropyridine-1(2H)-carboxylate;
Tert-butyl 4-{2-[2-fluoro-4-(methylsulfonyl)phenyl]benzo[d]oxazol-6-yl}piperidine-1-carboxylate;
Tert-butyl 4-{2-[2-fluoro-4-(methylsulfonyl)phenyl]benzo[d]thiazol-5-yl}piperidine-1-carboxylate;
Ethyl 4-{2-[2-fluoro-4-(methylsulfonyl)phenyl]benzo[d]oxazol-5-yl}piperidine-1-carboxylate;
Tert-butyl 4-{2-[4-(trifluoromethyl)phenyl]benzo[d]oxazol-5-yl}piperidine-1-carboxylate;
Isopropyl 4-{2-[2-fluoro-4-(methylsulfonyl)phenyl]benzo[d]oxazol-6-yl}piperidine-1-carboxylate;
Ethyl 4-{2-[2-fluoro-4-(methylsulfonyl)phenyl]benzo[d]oxazol-6-yl}piperidine-1-carboxylate;
Ethyl 4-{2-[2-fluoro-4-(methylsulfonyl)phenyl]benzo[d]oxazol-6-yl}piperidine-1-carboxylate;
Benzyl 4-{2-[2-fluoro-4-(methylsulfonyl)phenyl]benzo[d]oxazol-5-yl}piperidine-1-carboxylate;
Isobutyl 4-{2-[2-fluoro-4-(methylsulfonyl)phenyl]benzo[d]oxazol-5-yl}piperidine-1-carboxylate;
Isopropyl 4-{2-[2-fluoro-4-(methylsulfonyl)phenyl]benzo[d]thiazol-6-yl}piperidine-1-carboxylate;
Isopropyl 4-{2-[4-(trifluoromethyl)phenyl]benzo[d]oxazol-5-yl}piperidine-1-carboxylate;
Isopropyl 4-(2-p-tolylbenzo[d]oxazol-6-yl)piperidine-1-carboxylate;
3-{4-[2-(2-fluoro-4-(methylsulfonyl)phenyl)benzo[d]oxazol-5-yl]-5,6-dihydropyridin-1(2H)-ylsulfonyl}propan-1-ol;
3-{4-[2-(2-fluoro-4-(methylsulfonyl)phenyl)benzo[d]oxazol-5-yl]piperidin-1-ylsulfonyl}propan-1-ol;
3-{4-[2-(2-fluoro-4-(methylsulfonyl)phenyl)benzo[d]oxazol-5-yl]piperidin-1-ylsulfonyl}propan-1-ol;
Tert-butyl 4-[2-(4-carbamoyl-3-fluorophenyl)benzo[d]oxazol-5-yl]piperidine-1-carboxylate;
2-[2-fluoro-4-(methylsulfonyl)phenyl]-5-[4-(3-isopropyl-1,2,4-oxadiazol-5-yl)piperidin-1-yl]benzo[d]oxazole;
Tert-butyl 4-{2-[4-(trifluoromethyl)phenyl]benzo[d]oxazol-6-yl}piperidine-1-carboxylate
Isopropyl 4-{2-[2-fluoro-4-(methylsulfonyl)phenyl]benzo[d]oxazol-5-yl}piperazine-1-carboxylate;
Tert-butyl 4-{2-[4-(trifluoromethyl)phenyl]oxazolo[5,4-b]pyridin-6-yl}-5,6-dihydropyridine-1(2H)-carboxylate;
Tert-butyl 4-{2-[4-(trifluoromethyl)phenyl]oxazolo[5,4-b]pyridin-6-yl}piperidine-1-carboxylate;
and pharmaceutically acceptable salts thereof.

30. A pharmaceutical composition, comprising a compound of claim 1 and a pharmaceutically acceptable carrier.

31. The pharmaceutical composition of claim 30, further comprising one or more additional therapeutic agents and mixtures thereof.

32. A compound of formula (A-I), (A-II), (B-I), (B-II), (B-III) and (B-IV):

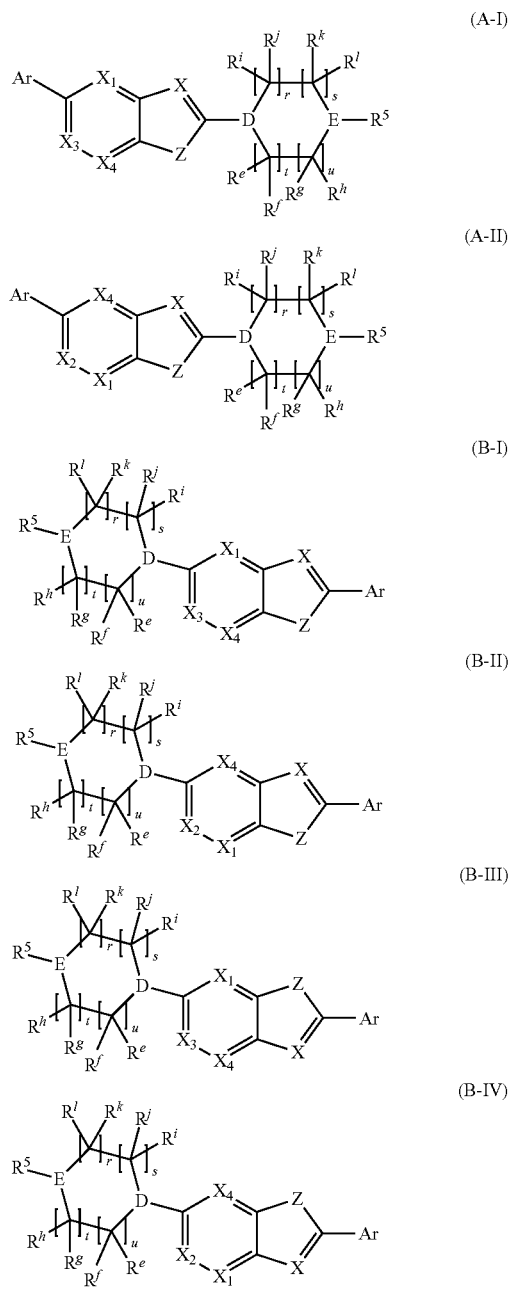

or a tautomer, stereoisomer, enantiomer, diastereomer, salt, or N-oxide thereof,
wherein
Ar is selected from substituted or unsubstituted aryl, substituted or unsubstituted heteroaryl or $Cy^1$;
$X^1$ is $CR^1$ or N; $X^2$ is $CR^2$ or N; $X^3$ is $CR^3$ or N; and $X^4$ is $CR^4$ or N;
X is N;
Z is CO, O or $S(O)_q$;
$Cy^1$ is selected from substituted or unsubstituted cycloalkyl or substituted or unsubstituted heterocyclic group;
each occurrence of R, $R^2$, and $R^3$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, substituted or unsubstituted C$_{3-6}$ cycloalkenyl, —OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$-;

each occurrence of R$^1$ and R$^4$ may be same or different and is independently selected from hydrogen, nitro, hydroxy, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, substituted or unsubstituted C$_{3-6}$ cycloalkenyl, OR a, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$;

each occurrence of R$^a$ and R$^b$ may be same or different and are independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl, or when two R$^a$ and/or R$^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^c$ or S;

each occurrence of R$^c$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl;

each occurrence of Y is independently selected from O, S, and NR$^a$; and each occurrence of q independently represents 0, 1 or 2;

D and E are independently selected from CH or N;

R$^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$, and —ONO$_2$;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR'); and each occurrence of R$^e$, R$^f$, R$^g$, R$^h$, R$^j$, R$^k$ and R$^l$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl; or any two of R$^e$, R$^f$, R$^g$, R$^h$, R$^j$, R$^k$, R$^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl); and each of r, s, t and u is 0, 1 or 2 with the proviso that r+s+t+u≠0.

33. A compound of formula (A-I), (A-II), (B-I), (B-II), (B-III) and (B-IV):

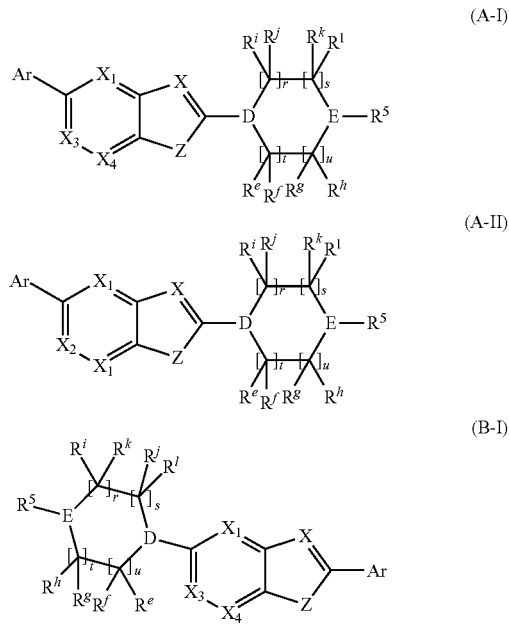

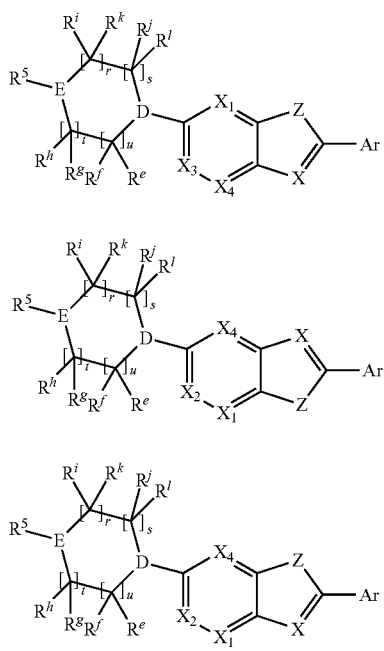
or a tautomer, stereoisomer, enantiomer, diastereomer, salt, or N-oxide thereof,
wherein
Ar is selected from substituted or unsubstituted aryl, substituted or unsubstituted heteroaryl or $Cy^1$;
$X^1$ is $CR^1$ or N; $X^2$ is $CR^2$ or N; $X^3$ is $CR^3$ or N; and $X^4$ is $CR^4$ or N;
X is N;
Z is CO, O or $S(O)_q$;
$Cy^1$ is selected from
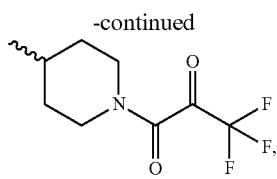
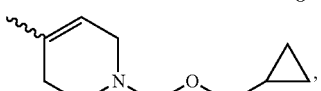
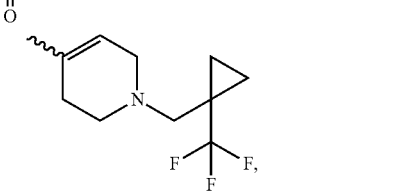
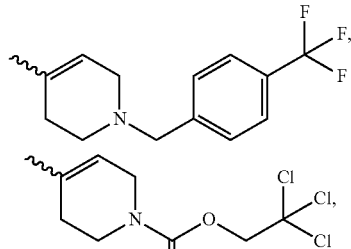
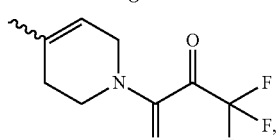
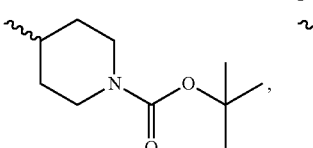
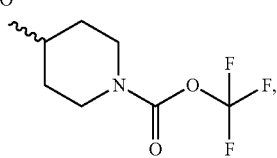
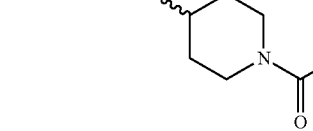
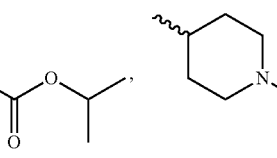
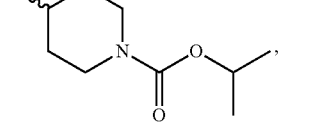
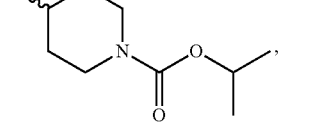
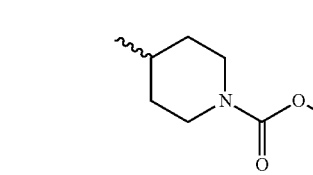
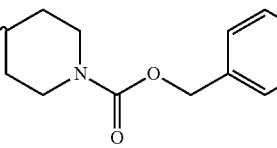
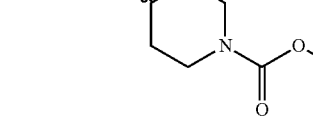
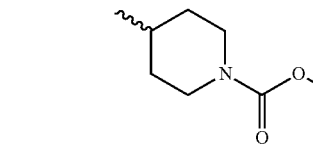

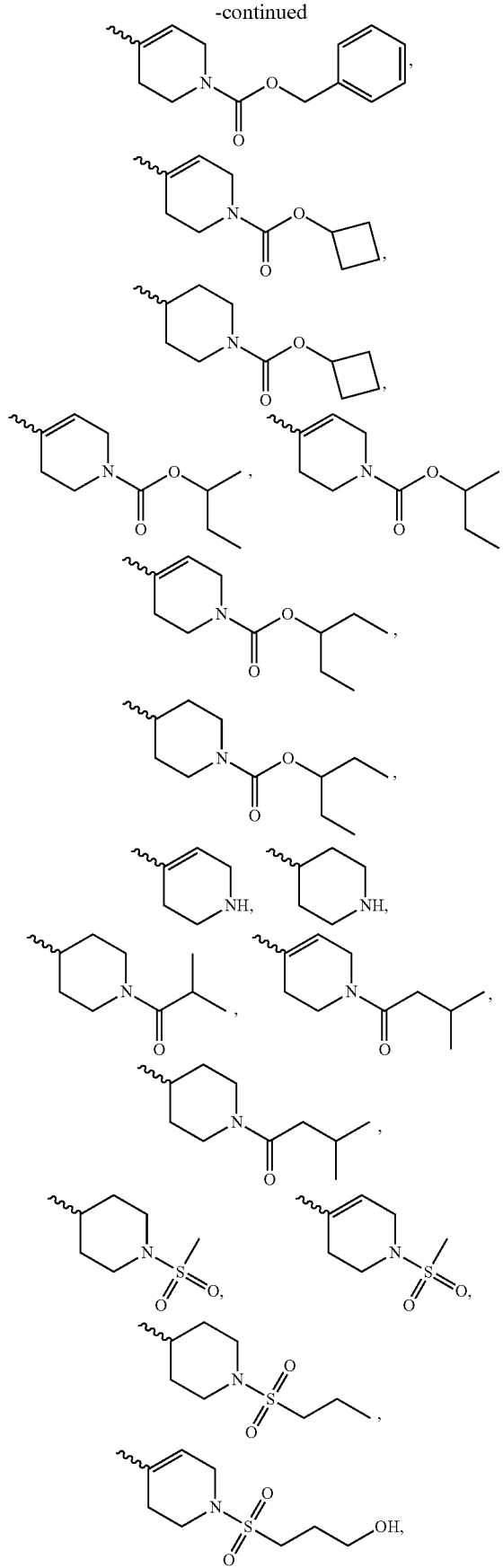
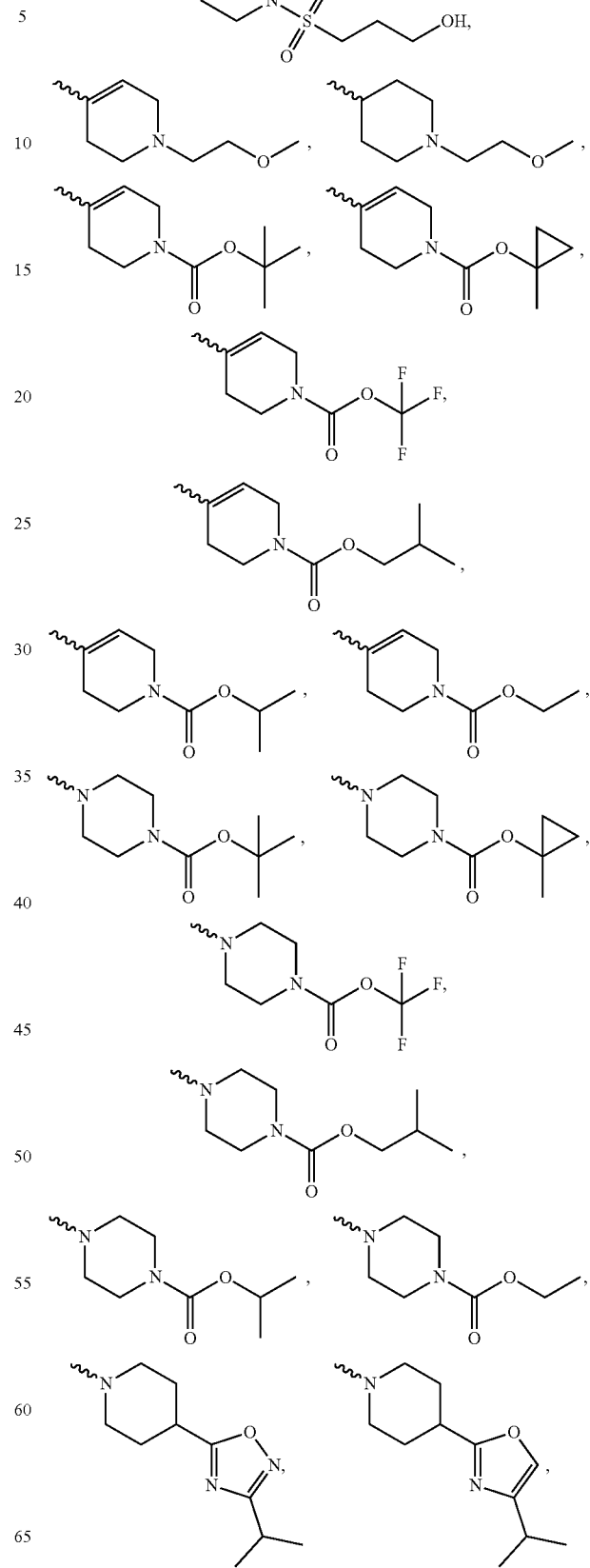

187
-continued

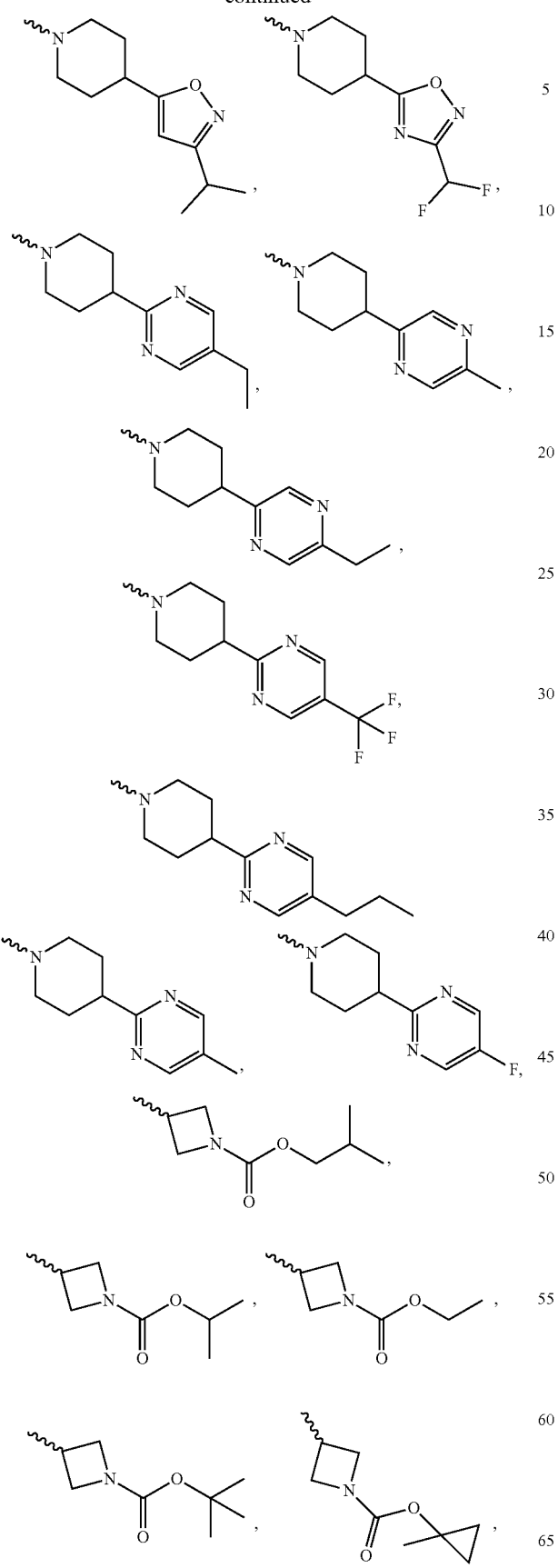

188
-continued

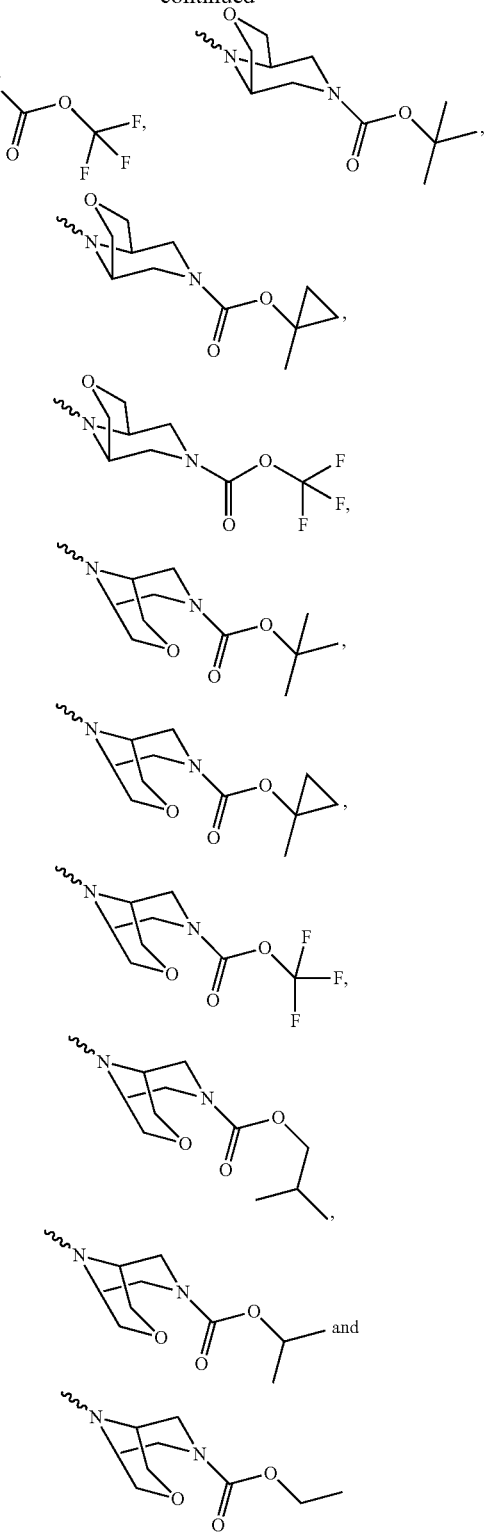

each occurrence of R, $R^2$, and $R^3$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl, —OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$-;

each occurrence of R$^1$ and R$^4$ may be same or different and is independently selected from hydrogen, nitro, hydroxy, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, substituted or unsubstituted C$_{3-6}$ cycloalkenyl, —OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$-, —C(=Y)—NR$^a$R$^b$-, —NR$^a$—C(=Y)—NR$^a$R$^b$-, —S(=O)$_q$—NR$^a$R$^b$-, —NR$^a$—S(=O)$_q$—NR$^a$R$^b$-, and —NR$^a$—NR$^a$R$^b$;

each occurrence of R$^a$ and R$^b$ may be same or different and are independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl, or when two R$^a$ and/or R$^b$ substituents are directly bound to a common atom, they may be joined to form (i) an oxo (=O), thio (=S) or imino (=NR$^d$), or (ii) a substituted or unsubstituted, saturated or unsaturated 3-10 member ring, which may optionally include one or more heteroatoms which may be same or different and are selected from O, NR$^c$ or S;

each occurrence of R$^c$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl;

each occurrence of Y is independently selected from O, S, and NR$^a$; and each occurrence of q independently represents 0, 1 or 2;

D and E are independently selected from CH or N;

R$^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^a$, —C(O)R$^a$, —C(S)R$^a$, —C(O)NR$^a$R$^b$, —C(O)ONR$^a$R$^b$, —NR$^a$R$^b$, —NR$^a$CONR$^a$R$^b$, —N(R$^a$)SOR$^b$, —N(R$^a$)SO$_2$R$^b$, -(=N—N(R$^a$)R$^b$), —NR$^a$C(O)OR$^b$, —NR$^a$C(O)R$^b$-, —NR$^a$C(S)R$^b$ —NR$^a$C(S)NR$^a$R$^b$, —SONR$^a$R$^b$-, —OR$^a$, —OR$^a$C(O)NR$^a$R$^b$, —OR$^a$C(O)OR$^b$-, —OC(O)R$^a$, —OC(O)NR$^a$R$^b$, —R$^a$NR$^b$C(O)R$^a$, —R$^a$OR$^b$, —R$^a$C(O)OR$^b$, —R$^a$C(O)NR$^a$R$^b$, —R$^a$C(O)R$^b$, —R$^a$OC(O)R$^b$, —SR$^a$, —SOR$^a$, —SO$_2$R$^a$ and —ONO$_2$;

each occurrence of R$^d$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocycicyalkyl, substituted or unsubstituted aryl, substituted or unsubstituted arylalkyl, substituted or unsubstituted heteroaryl, substituted or unsubstituted heteroarylalkyl, and —ONO$_2$, or any two of R$^d$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR');

each occurrence of R$^e$, R$^f$, R$^g$, R$^h$, R$^j$, R$^k$ and R$^l$ is independently selected from hydrogen, nitro, hydroxy, cyano, halogen, substituted or unsubstituted C$_{1-6}$ alkyl, substituted or unsubstituted C$_{2-6}$ alkenyl, substituted or unsubstituted C$_{2-6}$ alkynyl, substituted or unsubstituted C$_{3-6}$ cycloalkyl, substituted or unsubstituted C$_{3-6}$ cycloalkylalkyl, and substituted or unsubstituted C$_{3-6}$ cycloalkenyl; or any two of R$^e$, R$^f$, R$^g$, R$^h$, R$^j$, R$^k$, R$^l$ may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR') (where R' is H or alkyl); and each of r, s, t and u is 0, 1 or 2 with the proviso that r+s+t+u≠0.

* * * * *